US010647989B2

United States Patent
Kudithipudi et al.

(10) Patent No.: US 10,647,989 B2
(45) Date of Patent: May 12, 2020

(54) COMPOSITION AND METHODS FOR PRODUCING TOBACCO PLANTS AND PRODUCTS HAVING REDUCED TOBACCO-SPECIFIC NITROSAMINES (TSNAS)

(71) Applicant: Altria Client Services LLC, Richmond, VA (US)

(72) Inventors: Chengalrayan Kudithipudi, Midlothian, VA (US); Dongmei Xu, Glen Allen, VA (US); James Strickland, Richmond, VA (US)

(73) Assignee: Altria Client Services LLC, Richmond, VA (US)

( * ) Notice: Subject to any disclaimer, the term of this patent is extended or adjusted under 35 U.S.C. 154(b) by 118 days.

(21) Appl. No.: 15/727,523

(22) Filed: Oct. 6, 2017

(65) Prior Publication Data

US 2018/0119163 A1 May 3, 2018

Related U.S. Application Data

(60) Provisional application No. 62/405,607, filed on Oct. 7, 2016, provisional application No. 62/503,103, filed on May 8, 2017.

(51) Int. Cl.
 *C12N 15/82* (2006.01)
 *A24B 15/24* (2006.01)
 (Continued)

(52) U.S. Cl.
 CPC ......... *C12N 15/8243* (2013.01); *A01H 4/005* (2013.01); *A01H 4/008* (2013.01);
 (Continued)

(58) Field of Classification Search
 CPC .................................................. C12N 15/8243
 See application file for complete search history.

(56) References Cited

U.S. PATENT DOCUMENTS 4,516,590 A 5/1985 Teng
4,528,993 A 7/1985 Sensabaugh, Jr. et al.
(Continued)

FOREIGN PATENT DOCUMENTS

WO WO 1998/049350 A1 5/1998
WO WO 1999/007865 A1 2/1999
(Continued)

OTHER PUBLICATIONS

Dubos, Christian, et al. "MYB transcription factors in Arabidopsis." Trends in plant science 15.10 (2010): 573-581 (Year: 2010).*
(Continued)

*Primary Examiner* — Weihua Fan
(74) *Attorney, Agent, or Firm* — David R. Marsh; Arnold & Porter Kaye Scholer LLP

(57) ABSTRACT

The present disclosure provides approaches for reducing tobacco-specific nitrosamines (TSNAs) in tobacco. Some of these approaches include genetically engineering tobacco plants to increase one or more antioxidants, increase oxygen radical absorbance capacity (ORAC), or reduce nitrite. Also provided are methods and compositions for producing modified tobacco plants and tobacco products therefrom comprising reduced TSNAs.

26 Claims, 21 Drawing Sheets

Specification includes a Sequence Listing.

(51) Int. Cl.
| | |
|---|---|
| A24B 15/10 | (2006.01) |
| C12N 9/04 | (2006.01) |
| A01H 4/00 | (2006.01) |
| A24B 13/00 | (2006.01) |
| C07K 14/415 | (2006.01) |

(52) U.S. Cl.
CPC .............. *A24B 13/00* (2013.01); *A24B 15/10* (2013.01); *A24B 15/245* (2013.01); *C07K 14/415* (2013.01); *C12N 9/0006* (2013.01); *C12N 15/825* (2013.01); *C12N 15/8205* (2013.01); *C12N 15/8225* (2013.01)

(56) References Cited

U.S. PATENT DOCUMENTS

| | | |
|---|---|---|
| 4,660,577 A | 4/1987 | Sensabaugh, Jr. et al. |
| 4,732,856 A | 3/1988 | Federoff |
| 4,762,785 A | 8/1988 | Comai |
| 4,848,373 A | 7/1989 | Lenkey |
| 4,945,050 A | 7/1990 | Sanford et al. |
| 4,987,907 A | 1/1991 | Townend |
| 5,004,863 A | 4/1991 | Umbeck |
| 5,104,310 A | 4/1992 | Saltin |
| 5,141,131 A | 8/1992 | Miller, Jr. et al. |
| 5,149,645 A | 9/1992 | Hoekema et al. |
| 5,159,135 A | 10/1992 | Umbeck |
| 5,177,010 A | 1/1993 | Goldman et al. |
| 5,231,019 A | 7/1993 | Paszkowski et al. |
| 5,316,931 A | 5/1994 | Donson et al. |
| 5,372,149 A | 12/1994 | Roth et al. |
| 5,463,174 A | 10/1995 | Moloney et al. |
| 5,464,763 A | 11/1995 | Schilperoort et al. |
| 5,469,976 A | 11/1995 | Burchell |
| 5,491,081 A | 2/1996 | Webb |
| 5,563,055 A | 10/1996 | Townsend et al. |
| 5,565,350 A | 10/1996 | Kmiec |
| 5,589,367 A | 12/1996 | Donson et al. |
| 5,659,026 A | 8/1997 | Baszczynski et al. |
| 5,689,035 A | 11/1997 | Webb |
| 5,731,181 A | 3/1998 | Kmiec |
| 5,756,325 A | 3/1998 | Kmiec |
| 5,760,012 A | 6/1998 | Kmiec et al. |
| 5,789,156 A | 8/1998 | Bujard et al. |
| 5,795,972 A | 8/1998 | Kmiec |
| 5,814,618 A | 9/1998 | Bujard et al. |
| 5,866,785 A | 2/1999 | Donson et al. |
| 5,871,984 A | 2/1999 | Kmiec |
| 5,879,918 A | 3/1999 | Tomes et al. |
| 5,886,244 A | 3/1999 | Tomes et al. |
| 5,889,190 A | 3/1999 | Donson et al. |
| 5,889,191 A | 3/1999 | Turpen |
| 5,932,782 A | 8/1999 | Bidney |
| 5,981,840 A | 11/1999 | Zhao et al. |
| 6,072,050 A | 6/2000 | Bowen et al. |
| 8,124,851 B2 | 2/2012 | Dewey et al. |
| 8,319,011 B2 | 11/2012 | Xu et al. |
| 9,187,759 B2 | 11/2015 | Dewey et al. |
| 9,228,194 B2 | 1/2016 | Dewey et al. |
| 9,228,195 B2 | 1/2016 | Dewey et al. |
| 9,247,706 B2 | 2/2016 | Dewey et al. |
| 9,913,451 B2 * | 3/2018 | Dewey .................. C12N 9/0077 |
| 2004/0118422 A1 | 6/2004 | Lundin et al. |
| 2005/0178398 A1 | 8/2005 | Breslin et al. |
| 2006/0191548 A1 | 8/2006 | Strickland et al. |
| 2006/0212960 A1 * | 9/2006 | Nessler .............. C12N 15/8243 800/278 |
| 2006/0260014 A1 | 11/2006 | Li et al. |
| 2017/0233756 A1 | 8/2017 | Begemann et al. |

FOREIGN PATENT DOCUMENTS

| | | |
|---|---|---|
| WO | WO 2003/022081 A1 | 3/2003 |
| WO | WO 2004/041006 A1 | 5/2004 |
| WO | WO 2004/061098 A1 | 7/2004 |
| WO | WO 2010/069004 A1 | 6/2010 |
| WO | WO 2011/027315 A1 | 3/2011 |
| WO | WO 2013/064499 A1 | 5/2013 |

OTHER PUBLICATIONS

Gates, Daniel J., et al. "Diversification of R2R3-MYB transcription factors in the tomato family Solanaceae." Journal of molecular evolution 83.1-2 (2016): 26-37 (Year: 2016).*

Huang, Yu-Ji, et al. "Differential activation of anthocyanin biosynthesis in Arabidopsis and tobacco over-expressing an R2R3 MYB from Chinese bayberry." Plant Cell, Tissue and Organ Culture (PCTOC) 113.3 (2013): 491-499 (Year: 2013).*

Xie, De-Yu, et al. "Metabolic engineering of proanthocyanidins through co-expression of anthocyanidin reductase and the PAP1 MYB transcription factor." The Plant Journal 45.6 (2006): 895-907. (Year: 2006).*

Beetham et al., "A Tool for Functional Plant Genomics: Chimeric Rna/Dna Oligonucleotides Cause in vitro Gene-specific Mutations," *Proc. Natl. Acad. Sci.*, 96:8774-8778 (1999).

Bowman et al., "Revised North Carolina Grade Index for Flue-Cured Tobacco," *Tobacco Science*, 32:39-40 (1988).

Canevascini et al., "Tissue-Specific Expression and Promoter Analysis of the Tobacco ltp 1 Gene," *Plant Physiol.* 112(2):513-524 (1996).

Christensen et al., "Sequence Analysis and Transcriptional Regulation by Heat Shock of Polyubiquitin Transcripts from Maize," *Plant Mol. Biol.* 12:619-632 (1989).

Christensen et al., "Maize polyubiquitin genes: structure, thermal perturbation of expression and transcript splicing, and promoter activity following transfer to protoplasts by electroporation" *Plant Mol. Biol.* 18:675-689) (1992).

Christou et al., "Stable Transformation of Soybean Callus by DNA-Coated Gold Particles," *Plant Physiol.* 87:671-674 (1988).

Crossway et al., "Micromanipulation Techniques in Plant Biotechnology," *Biotechniques*, 4:320-334 (1986).

De Wet et al., "Exogenous Gene Transfer in Maize" *The Experimental Manipulation of Ovule Tissues*, ed. pp. 197-209 (1985).

D'Halluin et al., "Transgenic Maize Plants by Tissue Electroporation" *Plant Cell*, 4:1495-1505 (1992).

Estruch et al., "Transgenic Plants: An emerging approach to pest control," *Nat. Biotechnol.*15:137 (1997).

Fedoroff et al., "Cloning of the bronze locus in maize by a simple and generalized procedure using the transposable controlling element *Activator* (*Ac*)," *Proc. Natl. Acad. Sci.*, 81:3825-3829 (1984).

Finer et al., "Transformation of soybean via particle bombardment of embryogenic suspension culture tissue," In Vitro *Cell Dev. Biol.*, 27P: 175-182 (1991).

Gatz et al., "Regulation of a modified CaMV 35S promoter by the Tn 10-enclosed Tet repressor in transgenic tobacco," *Mol. Gen. Genet.*, 227:229-237 (1991).

Goldman et al., "Female sterile tobacco plants are produced by stigma-specific cell ablation," *EMBO Journal*, 13:2976-2984 (1994).

Guevara-Garcia et al., "Tissue-specific and wound-inducible pattern of expression of the mannopine synthase promoter is determined by the interaction between positive and negative cis-regulatory elements," *Plant J.*,4(3):495-505 (1993).

Hoekema et al., "A binary plant vector strategy based on separation of vir- and T-region of the *Agrobacterium tumefaciens* Ti-plasmid," *Nature*, 303(12):179-80 (1983).

International Search Report and Written Opinion dated Feb. 2, 2018 in corresponding International Application No. PCT/US20017/055618.

Kaeppler et al., "Silicon carbide fiber-mediated DNA delivery into plant cells," *Plant Cell Reports* 9:415-418 (1990).

Kaeppler et al., "Silicon carbide fiber-mediated stable transformation of plant cells," *Theor. Appl. Genet.* 84:560-566 (1992).

Kawamata et al., "Temporal and spatial pattern of expression of the pea Phenylalanine ammonia-lyase gene1 promoter in transgenic tobacco," *Plant Cell Physiol.* 38(7):792-803(1997).

Last et al., "pEmu: an improved promoter for gene expression in cereal cells," *Theor. Appl. Genet.* 81:581-588 (1991).

(56) References Cited

OTHER PUBLICATIONS

Matsuoka et al., "Tissue-specific light-regulated expression by the promoter of a $C_4$ gene, maize pyruvate, orthophosphate dikinases, in a $C_3$ plant, rice," *Proc Natl. Acad. Sci.* USA 90(20):9586-9590 (1993).
McCabe et al., "Stable transformation of soybean (glycine max) by particle acceleration," *Biotechnology* 6:923-926 (1988).
McCallum et al., "Targeted Screening for Induced Mutations," *Nat. Biotechnol.*, 18:455-457 (2000).
McNellis et al., "Glucocorticoid-inducible Expression of a Bacterial Avirulence Gene in Transgenic *Arabidopsis* Induces Hypersensitive Cell Death" *Plant J.* 14(2):247-257) (1998).
Miller et al., "Exported Abstract Records, A Grade Index for Type 22 and 23 Fire-Cured Tobacco," *Tobacco Intern.*, 192(2):55-57 (1990).
Odell et al., "Identification of DNA sequences required for activity of the cauliflower mosaic virus 35S promoter," *Nature*, 313:810-812 (1985).
Paszkowski et al., "Direct Gene Transfer to Plants," *EMBO J.* 3:2717-2722) (1984).
Porta et al., "Use of Viral Replicons for the Expression of Genes in Plants" *Molecular Biotechnology*, 5:209-221 (1996).
Riggs et al., "Stable Transformation of Tobacco by Electroporation: Evidence for Plasmid Concatenation," *Proc. Natl. Acad. Sci.*, 83:5602-5606) (1986).
Rinehart et al., "Tissue-Specific and Developmental Regulation of Cotton Gene *FbL2A*" *Plant Physiol.*, 112(3):1331-1341 (1996).
Russell et al., "Tissue-Specific Expression in Transgenic Maize of Four Endosperm Promoters from Maize and Rice," *Transgenic Res.* 6(2):157-168 (1997).
Schena et al., "A Steroid-inducible Gene Expression System for Plant Cells" *Proc. Natl. Acad. Sci.* 88:10421-10425 (1991).
Shillito et al., "Direct Gene Transfer to Protoplasts," *Meth. Enzymol.* 153:313-336 (1987).
Singh et al., "Cytological Charcterization of Transgenic Soybean," *Theor. Appl. Genet.* 96:319-324 (1998).
Tanaka, et al., "Studies on Biological Effects of Ion Beams on Lethality, Molecular Nature of Mutation, Mutation Rate, and Spectrum of Mutation Phenotype for Mutation Breeding in Higher Plants," *Radiat. Res.* 51:223-233 (2010).
Tomes et al., "Direct DNA Transfer into Intact Plant Cells Via Microprojectile Bombardment," *Plant Cell, Tissue, and Organ Culture*, Springer-Verlag ed. (1995).
Van Camp et al., "Tissue-Specific Activity of Two Manganese Superoxide Dismutase Promoters in Transgenic Tobacco," *Plant Physiol.* 112(2):525-535 (1996).
Velten et al., "Isolation of a Dual Plant Promoter Fragment from the Ti Plasmid of *Agrobacterium tumefaciens*" *EMBO J.* 3(12):2723-2730 (1984).
Verkerk, "Chimerism of the Tomato Plant After Seed Irradiation with Fast Neutrons," *Neth. J. Agric. Sci.* 19:197-203 (1971).
Weising et al., "Foreign Genes in Plants: Transfer, Structure, Expression, and Applications," *Ann. Rev. Genet.* 22:421-477 (1988).
Yamamoto et al., "The Promoter of a Pine Photosynthetic Gene Allows Expression of a jS-Glucuronidase Reporter Gene in Transgenic Rice Plants in a Light-Independent but Tissue-Specific Manner," *Plant Cell Physiol.* 35(5):773-778 (1994).
Yamamoto et al., "Light-responsive Elements of the Tobacco PSI-D Gene are Located Both Upstream and within the Transcribed Region," *Plant J.* 12(2):255-265 (1997).
Prouse et al., "Interactions between the R2R3-MYB Transcription Factor, AtMYB61, and Target DNA Binding Sites," *PLoS One* 2013, 8(5): e65132.

\* cited by examiner

Figure 6
Figure 6A
Nitrite (ppm)
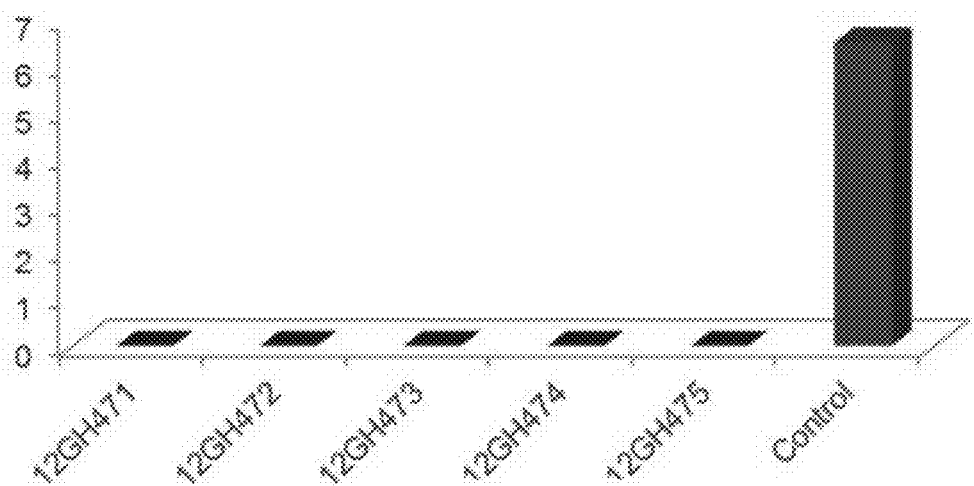
Figure 6B
Nitrate (ppm)
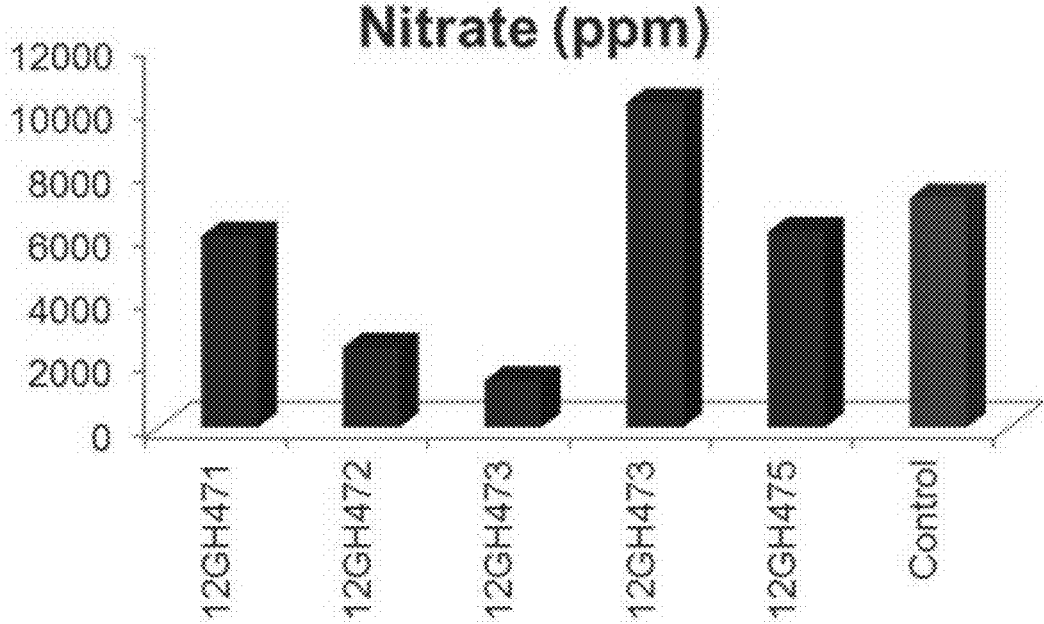

Figure 10
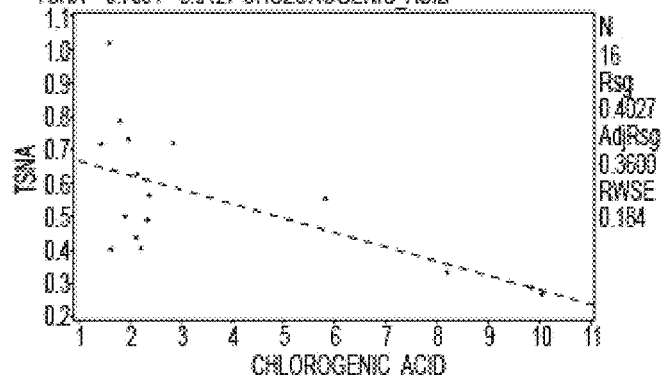
FIG. 10A
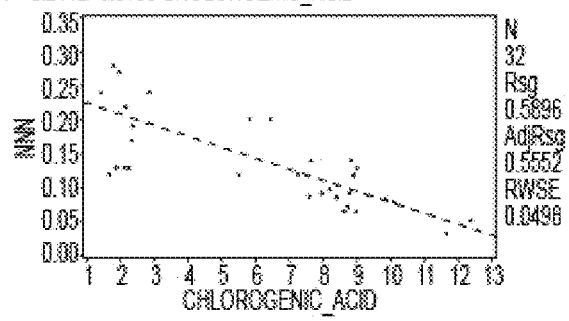
FIG. 10B
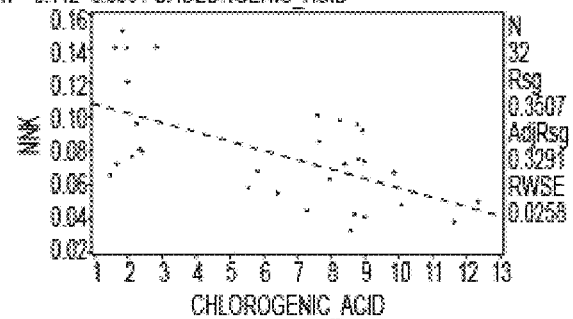
FIG. 10C

µmoles trolox/gram ical Composition of Tobacco", Wiernik et al., *Recent Adv. Tob. Sci*, (1995), 21, pp. 39-80. According to Wiernik et al., TSNAs are not present in significant quantities in growing tobacco plants or fresh cut tobacco (green tobacco), but are formed during the curing process. Bacterial populations which reside on the tobacco leaf are stated to largely cause the formation of nitrites from nitrate during curing and possibly affect the direct catalysis of the nitrosation of secondary amines at physiological pH values. The affected secondary amines include tobacco alkaloids, which form TSNAs when nitrosated.

COMPOSITION AND METHODS FOR PRODUCING TOBACCO PLANTS AND PRODUCTS HAVING REDUCED TOBACCO-SPECIFIC NITROSAMINES (TSNAS)

CROSS-REFERENCE TO RELATED APPLICATIONS

This application claims priority to U.S. Provisional Application No. 62/405,607, filed Oct. 7, 2016, and U.S. Provisional Application No. 62/503,103, filed May 8, 2017. Each of these U.S. Provisional Applications are incorporated by reference herein in their entireties.

INCORPORATION OF SEQUENCE LISTING

A sequence listing contained in the file named "P34473US02_SEQ.txt" which is 194,758 bytes (measured in MS-Windows®) and created on Oct. 31, 2017, comprises 63 sequences, is filed electronically herewith and incorporated by reference in its entirety.

FIELD

The present disclosure relates generally to methods for reducing tobacco specific nitrosamines (TSNAs) comprising modulating the levels of antioxidants, nitrite, or oxygen radical absorbance capacity (ORAC). Also provided are methods and compositions related to reducing or eliminating TSNAs in cured leaf from tobacco plants and products, their development via breeding or transgenic approaches, and production of tobacco products from those tobacco plants.

BACKGROUND

Tobacco-specific nitrosamines (TSNAs), such as N-nitrosonornicotine (NNN) and 4-(methylnitrosamino)-1-(3-pyridyl)-1-butanone (NNK), can be found in smokeless tobacco; mainstream smoke; and side stream smoke of cigarettes. It has been reported that air-cured and flue-cured tobacco contain tobacco-specific nitrosamines. See, "Effect of Air-Curing on the Chem Prior reports suggest several approaches to reduce TSNA levels. For example, WO2003/022081 proposed methods for reducing tobacco-specific nitrosamine (TSNA) content in cured tobacco by increasing the levels of antioxidants in the tobacco prior to harvesting. Specifically, WO2003/022081 proposed root pruning of the tobacco plant prior to harvesting; severing the xylem tissue of the tobacco plant prior to harvesting; and administering antioxidants and/or chemicals which increase antioxidants to the tobacco plant after harvesting. Despite previous attempts and proposals, simpler, more uniform, more economical and non-labor-intensive methods are desirable for reducing TSNA levels in cured tobacco leaf. Here, the inventors address this need by providing methods and compositions for reducing TSNAs by manipulating antioxidant levels via, inter alia, modification of genes involved in antioxidant biosynthesis or regulation thereof.

SUMMARY

In one aspect, the present disclosure provides cured tobacco leaf from a modified tobacco plant described here, where the cured tobacco leaf comprises a reduced level of one or more tobacco-specific nitrosamines (TSNAs) and further comprises an increased level of one or more antioxidants, wherein said reduced and increased levels are compared to cured tobacco leaf from a control tobacco plant of the same variety when grown and cured under comparable conditions.

In another aspect, the present disclosure provides a tobacco product comprising or made from cured leaf from a modified tobacco plant described here.

In one aspect, the present disclosure provides cured tobacco leaf from a modified tobacco plant comprising a reduced level of one or more tobacco-specific nitrosamines (TSNAs) and further comprising an increased level of one or more antioxidants, wherein said reduced and increased levels are compared to cured tobacco leaf from a control tobacco plant of the same variety when grown and cured under comparable conditions.

In another aspect, the present disclosure provides cured tobacco leaf from a modified tobacco plant comprising a reduced level of one or more tobacco-specific nitrosamines (TSNAs) and further comprising a reduced level of nitrite, wherein said reduced levels are compared to cured tobacco leaf from a control tobacco plant of the same variety when grown and cured under comparable conditions.

In one aspect, the present disclosure provides a modified tobacco plant or cured tobacco leaf from a modified tobacco plant comprising a reduced level of one or more tobacco-specific nitrosamines (TSNAs) and further comprising an increased level of oxygen radical absorbance capacity (ORAC), and wherein said reduced and increased levels are compared to a control tobacco plant or cured tobacco leaf from a control tobacco plant of the same variety when grown and cured under comparable conditions.

In another aspect, the present disclosure provides a seed giving rise to a modified tobacco plant described here.

In one aspect, the present disclosure provides a method comprising: planting a seed; and growing from the seed a modified tobacco plant described here.

In another aspect, the present disclosure provides a method comprising preparing a tobacco product using cured tobacco leaf from a modified tobacco plant described here.

In one aspect, the present disclosure provides a method of reducing the level of one or more TSNAs in cured tobacco leaf from a tobacco plant, said method comprising increasing the level of one or more antioxidants in said tobacco plant by expressing a biosynthetic enzyme, a regulatory transcription factor, a transporter, a catabolic enzyme, or a combination thereof, for said one or more antioxidants.

In another aspect, the present disclosure provides a method for producing a tobacco plant comprising: crossing at least one tobacco plant of a first tobacco variety with at least one tobacco plant of a second tobacco variety, wherein said at least one tobacco plant of said first tobacco variety is a modified tobacco plant described here; and selecting for a progeny tobacco plant capable of producing cured tobacco leaf comprising reduced levels of one or more tobacco-specific nitrosamines (TSNAs) and further comprising one or more traits selected from the group consisting of: a reduced level of nitrite, an increased level of oxygen radical absorbance capacity (ORAC), and an increased level of one or more antioxidants; wherein said reduced or increased level is compared to a control tobacco plant or cured tobacco leaf from a control tobacco plant of the same cross grown and cured under comparable conditions.

In one aspect, the present disclosure provides a method for reducing the level of one or more TSNAs in cured tobacco leaf or a tobacco product made therefrom, the method comprising increasing the level of one or more antioxidants in a tobacco plant via a transgene encoding or directly modulating an antioxidant biosynthetic enzyme, a regulatory transcription factor of an antioxidant, an antioxidant transporter, an antioxidant metabolic enzyme, or a combination thereof; and reducing the level of one or more TSNAs in cured tobacco leaf from the tobacco plant or a tobacco product made from the cured tobacco leaf.

In one aspect, the present disclosure provides a method for reducing the level of one or more TSNAs in cured tobacco leaf or a tobacco product made therefrom, the method comprising increasing the level of one or more antioxidants in a tobacco plant via a genetic modification in an endogenous gene, wherein the endogenous gene encodes an antioxidant biosynthetic enzyme, a regulatory transcription factor of an antioxidant, an antioxidant transporter, an antioxidant metabolic enzyme, or a combination thereof; and reducing the level of one or more TSNAs in cured tobacco leaf from the tobacco plant or a tobacco product made from the cured tobacco leaf.

In one aspect, the present disclosure provides a method for manufacturing a tobacco product, the method comprising obtaining cured tobacco leaf comprising a transgene or comprising a genetic modification in an endogenous gene, and further comprising an increased level of one or more antioxidants compared to a control cured tobacco leaf lacking the transgene or the genetic modification, wherein an endogenous gene encodes an antioxidant biosynthetic enzyme, a regulatory transcription factor of an antioxidant, an antioxidant transporter, an antioxidant metabolic enzyme, or a combination thereof, wherein the transgene encodes or directly modulates an antioxidant biosynthetic enzyme, a regulatory transcription factor of an antioxidant, an antioxidant transporter, an antioxidant metabolic enzyme, or a combination thereof; and producing a tobacco product from cured tobacco leaf, wherein the tobacco product comprises a reduced level of one or more TSNAs relative to a control tobacco product prepared from a control cured tobacco leaf.

In one aspect, the present disclosure provides a method for preparing cured tobacco leaf, the method comprising growing a tobacco plant comprising a transgene or a genetic modification in an endogenous gene, and further comprising an increased level of one or more antioxidants compared to a control tobacco plant lacking the transgene or the genetic modification, wherein an endogenous gene encodes an antioxidant biosynthetic enzyme, a regulatory transcription factor of an antioxidant, an antioxidant transporter, an antioxidant metabolic enzyme, or a combination thereof, wherein the transgene encodes or directly modulates an antioxidant biosynthetic enzyme, a regulatory transcription factor of an antioxidant, an antioxidant transporter, an antioxidant metabolic enzyme, or a combination thereof; and preparing cured leaf from a tobacco plant, wherein cured leaf comprises a reduced level of one or more TSNAs relative to a control cured leaf from a control tobacco plant not comprising the transgene or the genetic modification.

In one aspect, the present disclosure provides cured leaf of a modified tobacco plant, wherein cured leaf comprises a reduced level of one or more tobacco-specific nitrosamines (TSNAs) and further comprises an increased level of one or more antioxidants and a reduced nitrite level, wherein reduced and increased levels are compared to a control cured leaf of an unmodified tobacco plant of the same variety when grown and cured under comparable conditions, wherein the modification comprises a transgene or a genetic modification in an endogenous gene, wherein a transgene or an endogenous gene encodes an antioxidant biosynthetic enzyme, a regulatory transcription factor of an antioxidant, an antioxidant transporter, an antioxidant metabolic enzyme, or a combination thereof; wherein the modified tobacco plant does not comprise a transgene overexpressing an *Arabidopsis* PAP1 protein.

BRIEF DESCRIPTION OF THE SEQUENCES

SEQ ID NOs: 1 to 23 and 47 to 52 are amino acid sequences of selected genes that are involved in antioxidant production. SEQ ID NOs: 24 to 46 and 53 to 58 are corresponding nucleic acid sequences that encode SEQ ID NOs: 1 to 23, and 47 to 52. SEQ ID NOs:59 to 63 are polynucleotides encoding recombinant DNA molecules comprising cisgenic promoters, coding regions, and terminators.

BRIEF DESCRIPTION OF THE DRAWINGS

FIG. 6: Nitrite and Nitrate levels in AtPAP1 overexpression plants. FIG. 6A: Nitrite levels in AtPAP1 overexpression plants are reduced compared to controls. FIG. 6B: Nitrate levels in AtPAP1 overexpression plants are not consistently different from controls.

DETAILED DESCRIPTION

Figure 1:
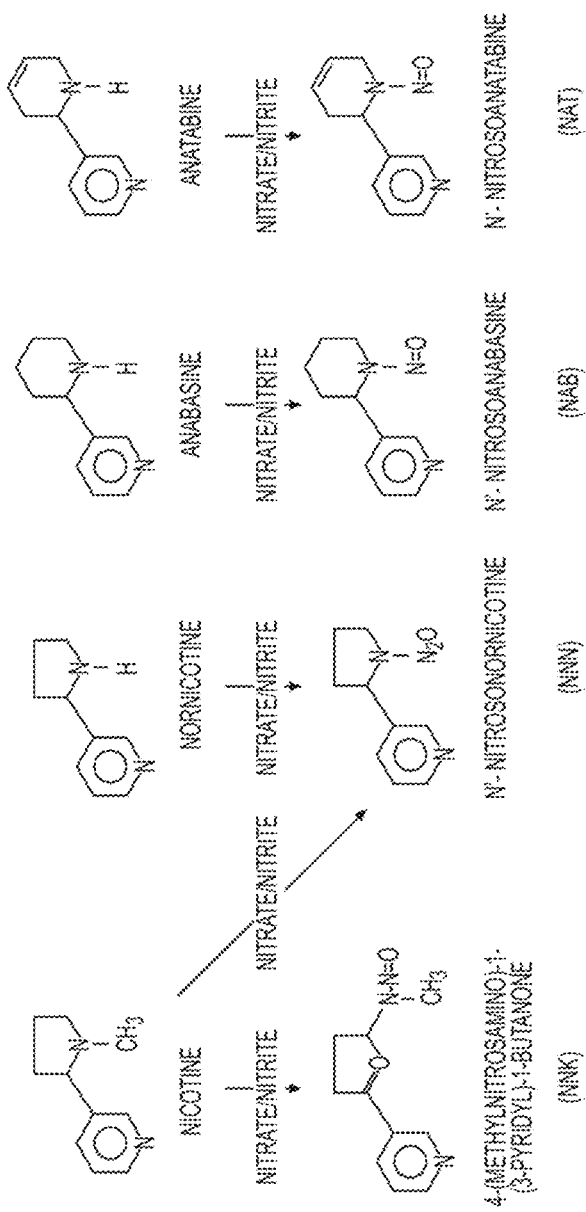
FIG. 1: TSNAs are formed when alkaloids nitrosinate in the presence of nitrite.

Unless defined otherwise, technical and scientific terms used herein have the same meaning as commonly understood by one of ordinary skill in the art. One skilled in the art will recognize many methods can be used in the practice of the present disclosure. Indeed, the present disclosure is in no way limited to the methods and materials described. For purposes of the present disclosure, the following terms are defined below.

Any references cited herein, including, e.g., all patents, published patent applications, and non-patent publications, are incorporated by reference in their entirety.

As used herein, the singular form "a," "an," and "the" include plural references unless the context clearly dictates otherwise. For example, the term "a compound" or "at least one compound" may include a plurality of compounds, including mixtures thereof.

The term "about" is used herein to mean approximately, roughly, around, or in the region of. When the term "about" is used in conjunction with a numerical range, it modifies that range by extending the boundaries above and below the numerical values set forth by 10%.

As used herein, a tobacco plant can be from any plant from the *Nicotiana tabacum* genus including, but not limited to *Nicotiana tabacum tabacum*; *Nicotiana tabacum amplexicaulis* PI 271989; *Nicotiana tabacum benthamiana* PI 555478; *Nicotiana tabacum bigelovii* PI 555485; *Nicotiana tabacum debneyi*; *Nicotiana tabacum excelsior* PI 224063; *Nicotiana tabacum glutinosa* PI 555507; *Nicotiana tabacum goodspeedii* PI 241012; *Nicotiana tabacum gossei* PI 230953; *Nicotiana tabacum hesperis* PI 271991; *Nicotiana tabacum knightiana* PI 555527; *Nicotiana tabacum maritima* PI 555535; *Nicotiana tabacum megalosiphon* PI 555536; *Nicotiana tabacum nudicaulis* PI 555540; *Nicotiana tabacum paniculata* PI 555545; *Nicotiana tabacum plumbaginifolia* PI 555548; *Nicotiana tabacum repanda* PI 555552; *Nicotiana tabacum rustica*; *Nicotiana tabacum suaveolens* PI 230960; *Nicotiana tabacum sylvestris* PI 555569; *Nicotiana tabacum tomentosa* PI 266379; *Nicotiana tabacum tomentosiformis*; and *Nicotiana tabacum trigonophylla* PI 555572.

In one aspect, this disclosure provides methods and compositions related to modified tobacco plants, seeds, plant components, plant cells, and products made from modified tobacco plants, seeds, plant parts, and plant cells. In one aspect, a modified seed provided herein gives rise to a modified plant provided herein. In one aspect, a modified plant, seed, plant component, plant cell, or plant genome provided herein comprises a recombinant DNA construct provided herein. In another aspect, cured tobacco material or tobacco products provided herein comprise modified tobacco plants, plant components, plant cells, or plant genomes provided herein.

As used herein, "modified" refers to plants, seeds, plant components, plant cells, and plant genomes that have been subjected to mutagenesis, genome editing, genetic transformation, or a combination thereof.

In one aspect, the present disclosure provides a modified tobacco plant capable of producing cured tobacco leaf comprising a reduced level of one or more tobacco-specific nitrosamines (TSNAs) and further comprising an increased level of one or more antioxidants, wherein the reduced and increased levels are compared to a control tobacco plant or cured leaf from a control tobacco plant of the same variety when grown and cured under comparable conditions. In one aspect, a reduced level of one or more TSNAs is less than 50% of the level of the one or more TSNAs in cured leaf from a control plant. In another aspect, a modified tobacco plant further comprises an increased level of oxygen radical absorbance capacity (ORAC) compared to a control tobacco plant when grown and cured under comparable conditions. In a further aspect, cured leaf from a modified tobacco plant comprises a reduced level of nitrite compared to cured leaf from a control tobacco plant when grown and cured under comparable conditions.

In another aspect, cured leaf from a modified tobacco plant comprises a reduced level of total TSNAs compared to the cured leaf from a control tobacco plant when grown and cured under comparable conditions. In one aspect, reduced one or more TSNAs are selected from the group consisting of N'-nitrosonornicotine (NNN), 4-methylnitrosoamino-1-(3-pyridyl)-1-butanone (NNK), N'-nitrosoanatabine (NAT) N'-nitrosoanabasine (NAB), and any combination thereof. In one aspect, the level of total TSNAs or an individual TSNA is measured based on a freeze-dried cured leaf sample using liquid chromatograph with tandem mass spectrometry (LC/MS/MS).

In one aspect, the present disclosure provides cured leaf from a modified tobacco plant comprising a reduced level of 4-methylnitrosoamino-1-(3-pyridyl)-1-butanone (NNK) compared to cured leaf from a control tobacco plant of the same variety when grown and cured under comparable conditions. In one aspect, a reduced level of NNK is less than 50% of the level of the NNK in cured leaf from a control plant. In one aspect, a modified tobacco plant or cured leaf from a modified tobacco plant further comprises an increased level of one or more antioxidants compared to a control tobacco plant or cured tobacco leaf from a control plant of the same variety when grown and cured under comparable conditions. In another aspect, a modified tobacco plant or cured leaf from a modified tobacco plant further comprises an increased level of oxygen radical absorbance capacity (ORAC) compared to a control tobacco or cured tobacco leaf from a control plant when grown and cured under comparable conditions. In a further aspect, cured leaf from a modified tobacco plant comprises a reduced level of nitrite compared to cured leaf from a control tobacco plant when grown and cured under comparable conditions. The role of nitrite in the formation is nitrosamines and TSNAs is linked to the reduction of nitrate by the activity of bacteria during the curing process. Nitrite is believed to generate nitrosating compounds which then react with secondary amines such as the tobacco alkaloids nicotine, nornicotine, anabasine, and anatabine to form TSNAs. Reducing the amount of nitrite and therefore the nitrosation of tobacco alkaloids, the production of TSNAs can be prevented during the curing process.

In one aspect, a modified tobacco plant or cured leaf from a modified tobacco plant comprises an increased level of one or more antioxidants selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin.

In another aspect, a modified tobacco plant or cured leaf from a modified tobacco plant comprises an increased level of one or more antioxidants selected from the group consisting of Delphnidin, Cyanidin, Procyanidin, Prodelphinidin, Hesperetin, Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C.

In one aspect, a modified tobacco plant or cured leaf from a modified tobacco plant comprises an antioxidant that is undetectable in the control plant or leaf. In another aspect, a modified tobacco plant or cured leaf from a modified tobacco plant comprises an antioxidant that does not exist in the control plant.

In another aspect, the present disclosure provides cured leaf from a modified tobacco plant comprising a reduced level of one or more tobacco-specific nitrosamines (TSNAs) and further comprising a reduced level of nitrite, wherein the reduced levels are compared to cured leaf from a control tobacco plant of the same variety when grown and cured under comparable conditions. In another aspect, a modified tobacco plant or cured leaf from a modified tobacco plant further comprises an increased level of oxygen radical absorbance capacity (ORAC) compared to the control tobacco plant or cured leaf from the control tobacco plant when grown and cured under comparable conditions.

In a further aspect, the present disclosure provides a modified tobacco plant capable of producing cured leaf comprising a reduced level of one or more tobacco-specific nitrosamines (TSNAs) and further comprising an increased level of oxygen radical absorbance capacity (ORAC), and wherein the reduced and increased levels are compared to a control tobacco plant or cured leaf from a control tobacco plant of the same variety when grown and cured under comparable conditions.

In one aspect, a reduced or increased level is within about 10%, within about 20%, within about 30%, within about 40%, within about 50%, within about 60%, within about 70%, within about 80%, within about 90%, within about 92%, within about 94%, within about 95%, within about 96%, within about 97%, within about 98%, or within about 99% lower or higher than the level in a control tobacco plant or cured leaf from a control tobacco plant when grown and cured under comparable conditions.

In another aspect, a reduced or increased level is within about 1 fold, within about 2 folds, within about 3 folds, within about 4 folds, within about 5 folds, within about 6 folds, within about 7 folds, within about 8 folds, within about 9 folds, within about 10 folds, within about 15 folds, within about 20 folds, within about 25 folds, or within about 30 folds lower or higher than the level in a control tobacco plant or cured leaf from a control tobacco plant when grown and cured under comparable conditions.

In one aspect, a reduced or increased level is at least about 10%, at least about 20%, at least about 30%, at least about 40%, at least about 50%, at least about 60%, at least about 70%, at least about 80%, at least about 90%, at least about 92%, at least about 94%, at least about 95%, at least about 96%, at least about 97%, at least about 98%, or at least about 99% lower or higher than the level in a control tobacco plant or cured leaf from a control tobacco plant when grown and cured under comparable conditions.

In another aspect, a reduced or increased level is at least about 1 fold, at least about 2 folds, at least about 3 folds, at least about 4 folds, at least about 5 folds, at least about 6 folds, at least about 7 folds, at least about 8 folds, at least about 9 folds, at least about 10 folds, at least about 15 folds, at least about 20 folds, at least about 25 folds, or at least about 30 folds lower or higher than the level in a control tobacco plant or cured leaf from a control tobacco plant when grown and cured under comparable conditions.

In one aspect, a reduced or increased level is about 10%, about 20%, about 30%, about 40%, about 50%, about 60%, about 70%, about 80%, about 90%, about 92%, about 94%, about 95%, about 96%, about 97%, about 98%, or about 99% lower or higher than the level in a control tobacco plant or cured leaf from a control tobacco plant when grown and cured under comparable conditions.

In another aspect, a reduced or increased level is about 1 fold, about 2 folds, about 3 folds, about 4 folds, about 5 folds, about 6 folds, about 7 folds, about 8 folds, about 9 folds, about 10 folds, about 15 folds, about 20 folds, about 25 folds, or about 30 folds lower or higher than the level in a control tobacco plant or cured leaf from a control tobacco plant when grown and cured under comparable conditions.

In one aspect, a reduced or increased level is about 1-2 folds, about 2-3 folds, about 3-4 folds, about 4-5 folds, about 5-6 folds, about 6-7 folds, about 7-8 folds, about 8-9 folds, about 9-10 folds, about 10-15 folds, about 15-20 folds, about 20-25 folds, about 25-30 folds, or about 30-50 folds lower or higher than the level in a control tobacco plant or cured leaf from a control tobacco plant when grown and cured under comparable conditions.

In another aspect, a reduced or increased level is about 1-10 folds, about 2-10 folds, about 3-10 folds, about 4-10 folds, about 5-10 folds, about 6-10 folds, about 7-10 folds, about 8-10 folds, about 9-10 folds, about 10-50 folds, about 15-50 folds, about 20-50 folds, about 25-50 folds, or about 30-50 folds lower or higher than the level in a control tobacco plant or cured leaf from a control tobacco plant when grown and cured under comparable conditions.

In one aspect, cured leaf from a modified tobacco plant produces or comprises less than 2, less than 1.8, less than 1.5, less than 1.2, less than 1.0, less than 0.8, less than 0.6, less than 0.4, less than 0.3, less than 0.2, less than 0.15, less than 0.1, or less than 0.05 ppm total TSNAs. In one aspect, cured leaf from a modified tobacco plant comprises between 2 and 0.05, between 1.8 and 0.05, between 1.5 and 0.05, between 1.2 and 0.05, between 1.0 and 0.05, between 0.8 and 0.05, between 0.6 and 0.05, between 0.4 and 0.05, between 0.3 and 0.05, between 0.2 and 0.05, between 0.15 and 0.05, or between 0.1 and 0.05 ppm total TSNAs. In one aspect, cured leaf from a modified tobacco plant comprises between 2 and 0.05, between 1.8 and 0.1, between 1.5 and 0.15, between 1.2 and 0.2, between 1.0 and 0.3, between 0.8 and 0.4, or between 0.6 and 0.5 ppm total TSNAs.

In one aspect, cured leaf from a modified tobacco plant comprises or produces less than 0.08 ppm NNK, wherein the level of the NNK level is measured based on a freeze-dried cured leaf sample using liquid chromatograph with tandem mass spectrometry (LC/MS/MS).

As used herein, "comparable conditions" refers to similar environmental conditions, agronomic practices, and/or curing process for growing or curing tobacco and making meaningful comparisons between two or more plant genotypes so that neither environmental conditions nor agronomic practices (including curing process) would contribute to, or explain, any differences observed between the two or more plant genotypes. Environmental conditions include, for example, light, temperature, water, humidity, and nutrition (e.g., nitrogen and phosphorus). Agronomic practices include, for example, seeding, clipping, undercutting, transplanting, topping, suckering, and curing. See Chapters 4B and 4C of Tobacco, Production, Chemistry and Technology, Davis & Nielsen, eds., Blackwell Publishing, Oxford (1999), pp. 70-103.

As used herein, a "reduced" or "increased" level refers to a statistically significant change (reduction or increase) from a reference point. As used herein, "statistically significant" refers to a p-value of less than 0.05, a p-value of less than 0.025, a p-value of less than 0.01, or a p-value of less than 0.001 when using an appropriate measure of statistical significance (e.g., a one-tailed two sample t-test).

As used herein, a "control plant" refers to a comparator plant that is an unmodified tobacco plant of the same variety or a tobacco plant having no transgene of interest, depending on the context or the purpose of the control plant. Control tobacco plants and plants of interest are grown and cured under comparable conditions.

In one aspect, a modified tobacco plant provided herein has similar or higher leaf yield compared to a control tobacco plant when grown and cured under comparable conditions. In an aspect, leaf yield is selected from the group consisting of fresh yield, dry yield, and cured yield. In one aspect, a modified tobacco plant provided herein produces a leaf yield mass within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% compared to a control tobacco plant when grown and cured under comparable conditions. In another aspect, a modified tobacco plant provided herein produces a leaf yield mass at least 0.25%, 0.5%, 1%, 2.5%, 5%, 10%, 15%, 20%, 25%, 30%, 40%, 50%, 60%, 70%, 80%, 90%, 100%, or more than 100% higher compared to a control tobacco plant when grown and cured under comparable conditions. In another aspect, a modified tobacco plant provided herein produces a leaf yield mass 0.25%-100%, 0.5%-100%, 1%-100%, 2.5%-100%, 5%-100%, 10%-100%, 15%-100%, 20%-100%, 25%-100%, 30%-100%, 40%-100%, 50%-100%, 60%-100%, 70%-100%, 80%-100%, 90%-100%, 100%-200%, 100%-175%, 100%-150%, 100%-125%, 0.25%-50%, 0.5%-50%, 1%-50%, 2.5%-50%, 5%-50%, 10%-50%, 15%-50%, 20%-50%, 25%-50%, 30%-50%, 40%-50%, 50%-200%, 50%-175%, 50%-150%, 50%-125%, 0.25%-25%, 0.5%-25%, 1%-25%, 2.5%-25%, 5%-25%, 10%-25%, 15%-25%, 20%-25%, 25%-200%, 25%-175%, 25%-150%, or 25%-125% higher compared to a control tobacco plant when grown and cured under comparable conditions.

In one aspect, a modified tobacco plant provided herein has a similar or comparable plant height compared to a control tobacco plant when grown and cured under comparable conditions. In one aspect, a modified tobacco plant provided herein comprises a height within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% compared to a control tobacco plants when grown and cured under comparable conditions. In another aspect, a modified tobacco plant provided herein comprises a height 0.25%, 0.5%, 1%, 2.5%, 5%, 10%, 15%, 20%, 25%, 30%, 40%, 50%, 60%, 70%, 80%, 90%, 100%, or more than 100% taller compared to a control tobacco plant when grown and cured under comparable conditions. In another aspect, a modified tobacco plant comprises a height 0.25%-100%, 0.5%-100%, 1%-100%, 2.5%-100%, 5%-100%, 10%-100%, 15%-100%, 20%-100%, 25%-100%, 30%-100%, 40%-100%, 50%-100%, 60%-100%, 70%-100%, 80%-100%, 90%-100%, 100%-200%, 100%-175%, 100%-150%, 100%-125%, 0.25%-50%, 0.5%-50%, 1%-50%, 2.5%-50%, 5%-50%, 10%-50%, 15%-50%, 20%-50%, 25%-50%, 30%-50%, 40%-50%, 50%-200%, 50%-175%, 50%-150%, 50%-125%, 0.25%-25%, 0.5%-25%, 1%-25%, 2.5%-25%, 5%-25%, 10%-25%, 15%-25%, 20%-25%, 25%-200%, 25%-175%, 25%-150%, or 25%-125% taller compared to a control tobacco plant when grown and cured under comparable conditions.

In one aspect, a modified tobacco plant provided herein produces leaf that has a similar or higher USDA grade index value compared to a control tobacco plant when grown and cured under comparable conditions. In one aspect, a modified tobacco plant provided herein produces leaf with a USDA grade index value within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% compared to a control tobacco plant when grown and cured under comparable conditions. In one aspect, a modified tobacco plant provided herein is capable of producing leaf having a USDA grade index value of 55 or more, 60 or more, 65 or more, 70 or more, 75 or more, 80 or more, 85 or more, 90 or more, or 95 or more. In one aspect, a modified tobacco plant provided herein produces leaf with a USDA grade index value at least 1, 2, 3, 4, 5, 6, 7, 8, 9, 10, 12, 13, 14, 15, 16, 17, 18, 19, 20, 21, 22, 23, 24, 25, 26, 27, 28, 29, 30, 35, 40, 45, 50, or more than 50 units higher compared to a control tobacco plant when grown and cured under comparable conditions. In one aspect, a modified tobacco plant provided herein produces leaf with a USDA grade index value 1-50, 1-45, 1-40, 1-35, 1-30, 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, 1-2, 2-50, 2-45, 2-40, 2-35, 2-30, 2-29, 2-28, 2-27, 2-26, 2-25, 2-24, 2-23, 2-22, 2-21, 2-20, 2-19, 2-18, 2-17, 2-16, 2-15, 2-14, 2-13, 2-12, 2-11, 2-10, 2-9, 2-8, 2-7, 2-6, 2-5, 2-4, 2-3, 3-50, 3-45, 3-40, 3-35, 3-30, 3-29, 3-28, 3-27, 3-26, 3-25, 3-24, 3-23, 3-22, 3-21, 3-20, 3-19, 3-18, 3-17, 3-16, 3-15, 3-14, 3-13, 3-12, 3-11, 3-10, 3-9, 3-8, 3-7, 3-6, 3-5, 3-4, 4-50, 4-45, 4-40, 4-35, 4-30, 4-29, 4-28, 4-27, 4-26, 4-25, 4-24, 4-23, 4-22, 4-21, 4-20, 4-19, 4-18, 4-17, 4-16, 4-15, 4-14, 4-13, 4-12, 4-11, 4-10, 4-9, 4-8, 4-7, 4-6, 4-5, 5-50, 5-45, 5-40, 5-35, 5-30, 5-29, 5-28, 5-27, 5-26, 5-25, 5-24, 5-23, 5-22, 5-21, 5-20, 5-19, 5-18, 5-17, 5-16, 5-15, 5-14, 5-13, 5-12, 5-11, 5-10, 5-9, 5-8, 5-7, 5-6, 10-50, 10-40, 10-30, 10-20, 20-50, 20-30, 20-40, or 20-30 units higher compared to a control tobacco plant when grown and cured under comparable conditions.

Tobacco grades are evaluated based on factors including, but not limited to, the leaf stalk position, leaf size, leaf color, leaf uniformity and integrity, ripeness, texture, elasticity, sheen (related with the intensity and the depth of coloration of the leaf as well as the shine), hygroscopicity (the faculty of the tobacco leaf to absorb and to retain the ambient moisture), and green nuance or cast. Leaf grade can be determined, for example, using an Official Standard Grade published by the Agricultural Marketing Service of the US Department of Agriculture (7 U.S.C. § 511). See, e.g., Official Standard Grades for Burley Tobacco (U.S. Type 31 and Foreign Type 93), effective Nov. 5, 1990 (55 F.R. 40645); Official Standard Grades for Flue-Cured Tobacco (U.S. Types 11, 12, 13, 14 and Foreign Type 92), effective Mar. 27, 1989 (54 F.R. 7925); Official Standard Grades for Pennsylvania Seedleaf Tobacco (U.S. Type 41), effective Jan. 8, 1965 (29 F.R. 16854); Official Standard Grades for Ohio Cigar-Leaf Tobacco (U.S. Types 42, 43, and 44), effective Dec. 8, 1963 (28 F.R. 11719 and 28 F.R. 11926); Official Standard Grades for Wisconsin Cigar-Binder Tobacco (U.S. Types 54 and 55), effective Nov. 20, 1969 (34 F.R. 17061); Official Standard Grades for Wisconsin Cigar-Binder Tobacco (U.S. Types 54 and 55), effective Nov. 20, 1969 (34 F.R. 17061); Official Standard Grades for Georgia and Florida Shade-Grown Cigar-Wrapper Tobacco (U.S. Type 62), Effective April 1971. A USDA grade index value can be determined according to an industry accepted grade index. See, e.g., Bowman et al, *Tobacco Science*, 32:39-40 (1988); Legacy Tobacco Document Library (Bates Document #523267826-523267833, Jul. 1, 1988, Memorandum on the Proposed Burley Tobacco Grade Index); and Miller et al., 1990, *Tobacco Intern.*, 192:55-57 (all foregoing references are incorporated by inference in their entirety). Alternatively, leaf grade can be determined via hyper-spectral imaging. See e.g., WO 2011/027315 (published on Mar. 10, 2011, and incorporated by inference in its entirety).

In one aspect, a modified tobacco plant provided herein comprises tobacco leaf with reduced total TSNAs and further comprises one or more desirable or enhanced properties, e.g., inhibited or reduced sucker growth prior to or after topping. In one aspect, a modified plant provided herein comprises fewer total suckers, smaller suckers, or both compared to a control plant lacking such modification when grown and cured under comparable conditions. In one aspect, smaller suckers of a modified plant provided herein comprise reduced mass, reduced length, reduced diameter, or a combination thereof compared to suckers of a control plant grown and cured under comparable conditions.

Unless specified otherwise, measurements of the level of total TSNAs, individual TSNA, total or individual alkaloid, total or individual antioxidant, leaf yield, or leaf grade index values mentioned herein for cured leaf from a tobacco plant, variety, cultivar, or line refer to average measurements, including, for example, an average of multiple leaves (e.g., 2, 3, 4, 5, 6, 7, 8, 9, 10, 11, 12, 13, 14, 15, 16, 17, 18, 19, or 20 or more leaves) of a single plant or an average measurement from a population of tobacco plants from a single variety, cultivar, or line. A population of tobacco plants or a collection of tobacco leaf for determining an average measurement (e.g., fresh weight or leaf grading) can be of any size, for example, 5, 10, 15, 20, 25, 30, 35, 40, or 50. Industry-accepted standard protocols are followed for determining average measurements or grade index values.

In one aspect, a modified tobacco plant or leaf provided here has a similar leaf chemistry profile compared to a control plant when grown and cured under comparable conditions. Without being limiting, a leaf chemistry profile can comprise the amount of alkaloids (e.g., nicotine, nornicotine, anabasine, anatabine), malic acid, and reducing sugars (e.g., dextrose), or a combination thereof in a tobacco plant or tobacco leaf. In one aspect, a modified plant or leaf provided herein comprises a total alkaloids level within about 90%, within about 80%, within about 70%, within about 60%, within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the total alkaloids level of a control plant when grown and cured under comparable conditions. In one aspect, a modified plant or leaf provided herein comprises a nicotine level within about 90%, within about 80%, within about 70%, within about 60%, within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the nicotine level of a control plant when grown and cured under comparable conditions. In one aspect, a modified plant or leaf provided herein comprises a nornicotine level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the nornicotine level of a control plant when grown and cured under comparable conditions. In one aspect, a modified plant or leaf provided herein comprises an anabasine level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the anabasine level of a control plant when grown and cured under comparable conditions. In one aspect, a modified plant or leaf provided herein comprises an anatabine level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the anatabine level of a control plant when grown and cured under comparable conditions. In one aspect, a modified plant or leaf provided herein comprises a malic acid level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the malic acid level of a control plant when grown and cured under comparable conditions. In one aspect, a modified plant or leaf provided herein comprises a reducing sugars level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the reducing sugars level of a control plant when grown and cured under comparable conditions. In one aspect, a modified plant or leaf provided herein comprises a dextrose level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the dextrose level of a control plant when grown and cured under comparable conditions.

In one aspect, a plant component provided herein includes, but is not limited to, a leaf, a stem, a root, a seed, a flower, pollen, an anther, an ovule, a pedicel, a fruit, a meristem, a cotyledon, a hypocotyl, a pod, an embryo, endosperm, an explant, a callus, a tissue culture, a shoot, a cell, and a protoplast. In further aspects, this disclosure provides tobacco plant cells, tissues, and organs that are not reproductive material and do not mediate the natural reproduction of the plant. In another aspect, this disclosure also provides tobacco plant cells, tissues, and organs that are reproductive material and mediate the natural reproduction of the plant. In another aspect, this disclosure provides tobacco plant cells, tissues, and organs that cannot maintain themselves via photosynthesis. In another aspect, this disclosure provides somatic tobacco plant cells. Somatic cells, contrary to germline cells, do not mediate plant reproduction.

Provided cells, tissues and organs can be from seed, fruit, leaf, cotyledon, hypocotyl, meristem, embryos, endosperm, root, shoot, stem, pod, flower, inflorescence, stalk, pedicel, style, stigma, receptacle, petal, sepal, pollen, anther, filament, ovary, ovule, pericarp, phloem, and vascular tissue. In another aspect, this disclosure provides a tobacco plant chloroplast. In a further aspect, this disclosure provides an epidermal cell, a stomata cell, a leaf hair (trichome), a root hair, or a storage root. In another aspect, this disclosure provides a tobacco protoplast.

Skilled artisans understand that tobacco plants naturally reproduce via seeds, not via asexual reproduction or vegetative propagation. In one aspect, this disclosure provides tobacco endosperm. In another aspect, this disclosure provides a tobacco endosperm cell. In a further aspect, this disclosure provides a male or female sterile tobacco plant, which cannot reproduce without human intervention.

In one aspect, a modified plant, seed, plant part, or plant cell provided herein comprises one or more non-naturally occurring mutations. In one aspect, a mutation provided herein suppresses TSNA levels in cured leaf from a tobacco plant. Types of mutations provided herein include, for example, substitutions (point mutations), deletions, insertions, duplications, and inversions. Such mutations are desirably present in the coding region of a gene; however, mutations in a promoter or other regulatory region, an intron, an intron-exon boundary, or an untranslated region of a gene may also be desirable.

In one aspect, a modified tobacco plant comprises one or more mutations or modifications capable of providing the reduced level of one or more TSNAs. In another aspect, one or more mutations are further capable of providing one or more traits selected from the group consisting of: i. a reduced level of nitrite, ii. an increased level of oxygen radical absorbance capacity (ORAC), and iii. an increased level of one or more antioxidants; wherein the reduced or increased level is compared to a control tobacco plant or cured leaf from a control tobacco plant when grown and cured under comparable. In one aspect, a mutation comprises a mutation type selected from the group consisting of an insertion, a deletion, an inversion, a duplication, a substitution, and a combination thereof.

In one aspect, a modified tobacco plant comprises one or more mutations or modifications capable of activating one or more genes encoding a biosynthetic enzyme, a regulatory transcription factor, a transporter, a catabolic enzyme, or a combination thereof, for one or more antioxidants. In another aspect, one or more mutations or modifications are in one or more genes encoding a biosynthetic enzyme, a regulatory transcription factor, a transporter, a catabolic enzyme, or a combination thereof, for one or more antioxidants selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin. In a further aspect, one or more mutations or modifications are in one or more genes encoding a biosynthetic enzyme, a regulatory transcription factor, a transporter, a catabolic enzyme, or a combination thereof, for one or more antioxidants selected from the group consisting of Delphnidin, Cyanidin, Procyanidin, Prodelphinidin, Hesperetin, Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C.

In one aspect, a modified tobacco plant of the present specification comprises tobacco leaves with increased levels of anthocyanins. In a further aspect, a modified tobacco plant with increased levels of anthocyanins further comprises leaves that have a purple or crimson visual appearance. In one aspect, a modified tobacco plant of the present specification comprises tobacco leaves with increased levels of antioxidants and without increased levels of anthocyanins. In a further aspect, a modified tobacco plant comprising increased levels of antioxidants and without increased levels of anthocyanins further comprises leaves with a visual appearance similar to an unmodified tobacco plant.

As used herein, a "biosynthetic enzyme" refers to a protein that functions in the synthesis of antioxidants, alkaloids, TSNAs, nitrite, nitrate, Chlorogenic Acid or other proteins affecting the activity or stability of antioxidants, alkaloids, TSNAs, nitrite, nitrate or Chlorogenic Acid. These proteins catalyze reactions that result in the transformation of one molecular structure into another structure as part of a biosynthesis pathway. Exemplary biosynthetic enzymes include but are limited to Anthocyanidin synthase2 (NtANS2), Dihyfroflavonol-4-reductase (NtDFR2), Shikimate O-hydroxycinnamoyl transferase (HCT) and Hydroxycinnamoyl CoA quinate Transferase (HQT). The activity of a biosynthetic enzyme effects the total concentration of different molecule species that compose a biosynthetic pathway.

As used herein, a "regulatory transcription factor" is a protein that binds a promoter element of a target gene to modulate the transcription of one or more genes involved in antioxidant biosynthesis, transport, catabolism, or other processes affecting the level of one or more antioxidants. Exemplary regulatory transcription factors include AtPAP1, NtPAP1, NtMYB3-like, NtJAF13, and AtTTG1. A regulatory transcription factor can bind DNA as part of a protein complex or individually. A regulatory transcription factor can have a single target or multiple targets and can bind different targets with varying affinities. The activity of a regulatory transcription factor can be to activate, repress, or attenuate transcription from a target loci.

As used herein, a "transport protein" can be a transmembrane protein that actively or passively moves molecules across a biological membrane. A transport protein can aid in the movement of ions, small molecules or macromolecules. A transport protein can be referred to as a transmembrane transporter, a transmembrane pump, an anion transport protein, a cation transport protein, or an escort protein. Transport proteins can also facilitate the movement of molecules or proteins in vesicles composed of biological membrane. A transport protein can be integrated into a biological membrane. A Transport protein can be anchored to a biological membrane via different modifications such as but not limited to myristolation, prenylation or palmitoylation.

In one aspect, a modified tobacco plant comprises one or more mutations in a gene encoding a polypeptide having at least 50%, 55%, 60%, 65%, 70%, 75%, 80%, 85%, 90%, 95%, 97%, 98%, 99%, or 100% identity to a sequence selected from the group consisting of SEQ ID No. 1 to 23 and 47 to 52. In another aspect, a modified tobacco plant comprises one or more mutations in a gene comprise a coding sequence having at least 50%, 55%, 60%, 65%, 70%, 75%, 80%, 85%, 90%, 95%, 97%, 98%, 99%, or 100% identity to a sequence selected from the group consisting of SEQ ID No. 24 to 46 and 53 to 58.

In one aspect, a modified plant, seed, plant component, plant cell, or plant genome provided herein comprises one or more transgenes. As used herein, a "transgene" refers to a polynucleotide that has been transferred into a genome by any method known in the art. In one aspect, a transgene is an exogenous polynucleotide. In one aspect, a transgene is an endogenous polynucleotide that is integrated into a new genomic locus where it is not normally found.

As used herein, "modified", in the context of plants, seeds, plant components, plant cells, and plant genomes, refers to a state containing changes or variations from their natural or native state. For instance, a "native transcript" of a gene refers to an RNA transcript that is generated from an unmodified gene. Typically, a native transcript is a sense transcript. Modified plants or seeds contain molecular changes in their genetic materials, including either genetic or epigenetic modifications. Typically, modified plants or seeds, or a parental or progenitor line thereof, have been subjected to mutagenesis, genome editing (e.g., without being limiting, via methods using site-specific nucleases), genetic transformation (e.g., without being limiting, via methods of *Agrobacterium* transformation or microprojectile bombardment), or a combination thereof. In one aspect, a modified plant provided herein comprises no non-plant genetic material or sequences. In yet another aspect, a modified plant provided herein comprises no interspecies genetic material or sequences. In one aspect, this disclosure provides methods and compositions related to modified plants, seeds, plant components, plant cells, and products made from modified plants, seeds, plant parts, and plant cells. In one aspect, a modified seed provided herein gives rise to a modified plant provided herein. In one aspect, a modified plant, seed, plant component, plant cell, or plant genome provided herein comprises a recombinant DNA construct or vector provided herein. In another aspect, a product provided herein comprises a modified plant, plant component, plant cell, or plant chromosome or genome provided herein. The present disclosure provides modified plants with desirable or enhanced properties, e.g., without being limiting, disease, insect, or pest tolerance (for example, virus tolerance, bacteria tolerance, fungus tolerance, nematode tolerance, arthropod tolerance, gastropod tolerance); herbicide tolerance; environmental stress resistance; quality improvements such as yield, nutritional enhancements, environmental or stress tolerances; any desirable changes in plant physiology, growth, development, morphology or plant product(s) including starch production, modified oils production, high oil production, modified fatty acid content, high protein production, fruit ripening, enhanced animal and human nutrition, biopolymer production, pharmaceutical peptides and secretable peptides production; improved processing traits; improved digestibility; low raffinose; industrial enzyme production; improved flavor; nitrogen fixation; hybrid seed production; and fiber production.

As used herein, "genome editing" or editing refers to targeted mutagenesis, insertion, deletion, inversion, substitution, or translocation of a nucleotide sequence of interest in a genome using a targeted editing technique. A nucleotide sequence of interest can be of any length, e.g., at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, at least 75, at least 100, at least 250, at least 500, at least 1000, at least 2500, at least 5000, at least 10,000, or at least 25,000 nucleotides. As used herein, a "targeted editing technique" refers to any method, protocol, or technique that allows the precise and/or targeted editing of a specific location in a genome (e.g., the editing is not random). Without being limiting, use of a site-specific nuclease is one example of a targeted editing technique. Another non-limiting example of a targeted editing technique is the use of one or more tether guide Oligos (tgOligos). As used herein, a "targeted edit" refers to a targeted mutagenesis, insertion, deletion, inversion, or substitution caused by a targeted editing technique. A nucleotide sequence of interest can be an endogenous genomic sequence or a transgenic sequence.

In one aspect, a "targeted editing technique" refers to any method, protocol, or technique that allows the precise and/or targeted editing of a specific location in a genome (e.g., the editing is not random). Without being limiting, use of a site-specific nuclease is one example of a targeted editing technique.

In one aspect, a targeted editing technique is used to edit an endogenous locus or an endogenous gene. In another aspect, a targeted editing technique is used to edit a transgene. As used herein, an "endogenous gene" or a "native copy" of a gene refers to a gene that originates from within a given organism, cell, tissue, genome, or chromosome. An "endogenous gene" or a "native copy" of a gene is a gene that was not previously modified by human action.

In one aspect, a modified tobacco plant described here comprises one or more mutations are introduced via a system selected from the group consisting of chemical mutagenesis, irradiation mutagenesis, transposon mutagenesis, *Agrobacterium*-mediated transformation, a meganuclease, a zinc-finger nuclease (ZFN), a transcription activator-like effector nuclease (TALEN), a clustered regularly-interspaced short palindromic repeats (CRISPR)/Cas9 system, a CRISPR/Cpf1 system, a CRISPR/Csm1 system, and a combination thereof (see, for example, U.S. Patent Application publication 2017/0233756).

In one aspect, methods provided herein are capable of producing a tobacco plant comprising a reduced level of one or more TSNAs using mutagenesis. Mutagenesis methods include, without limitation, chemical mutagenesis, for example, treatment of seeds with ethyl methylsulfate (EMS) (Hildering and Verkerk, In, The use of induced mutations in plant breeding. Pergamon Press, pp. 317-320, 1965); or UV-irradiation, X-rays, electron beams, ion beams (e.g., carbon ion beam, helium ion beam, neon ion beam), and fast neutron irradiation (see, for example, Verkerk, *Neth. J. Agric. Sci.* 19:197-203, 1971; Poehlman, Breeding Field Crops, Van Nostrand Reinhold, N.Y. (3.sup.rd ed.), 1987; and Tanaka, *J. Radiat. Res.* 51:223-233, 2010); transposon tagging (Fedoroff et al., 1984; U.S. Pat. Nos. 4,732,856 and 5,013,658); and T-DNA insertion methodologies (Hoekema et al., 1983; U.S. Pat. No. 5,149,645). EMS-induced mutagenesis consists of chemically inducing random point mutations over the length of a genome. Fast neutron mutagenesis consists of exposing seeds to neutron bombardment which causes large deletions through double stranded DNA breakage. Transposon tagging comprises inserting a transposon within an endogenous gene to reduce or eliminate expression of the gene.

In addition, a fast and automatable method for screening for chemically induced mutations, TILLING (Targeting Induced Local Lesions In Genomes), using denaturing HPLC or selective endonuclease digestion of selected PCR products is also applicable to the present disclosure. See, McCallum et al. (2000) *Nat. Biotechnol.* 18:455-457. Mutations that impact gene expression or that interfere with the function of genes provided herein can be determined using methods that are well known in the art. Insertional mutations in gene exons usually result in null-mutants. Mutations in conserved residues can be particularly effective in inhibiting the function of a protein.

The screening and selection of mutagenized tobacco plants can be through any methodologies known to those having ordinary skill in the art. Examples of screening and selection methodologies include, but are not limited to, Southern analysis, PCR amplification for detection of a polynucleotide, Northern blots, RNase protection, primer-extension, RT-PCR amplification for detecting RNA transcripts, Sanger sequencing, Next Generation sequencing technologies (e.g., Illumina, PacBio, Ion Torrent, 454) enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

In one aspect, a modified plant or plant genome provided herein is mutated or edited by a nuclease selected from the group consisting of a meganuclease, a zinc-finger nuclease (ZFN), a transcription activator-like effector nuclease (TALEN), a CRISPR/Cas9 nuclease, a CRISPR/Cpf1 nuclease, or a CRISPR/Csm1 nuclease. As used herein, "editing" or "genome editing" refers to targeted mutagenesis of at least 1, at least 2, at least 3, at least 4, at least 5, at least 6, at least 7, at least 8, at least 9, or at least 10 nucleotides of an endogenous plant genome nucleic acid sequence, or removal or replacement of an endogenous plant genome nucleic acid sequence. In one aspect, an edited nucleic acid sequence provided herein has at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% sequence identity with an endogenous nucleic acid sequence. In one aspect, an edited nucleic acid sequence provided herein has at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% sequence identity with a polynucleotide selected from the group consisting of SEQ ID NOs: 24 to 46 and 53 to 58, and fragments thereof. In another aspect, an edited nucleic acid sequence provided herein has at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% sequence identity with a polynucleotide encoding a polypeptide selected from the group consisting of SEQ ID NOs: 1 to 23 and 47 to 52.

Meganucleases, ZFNs, TALENs, CRISPR/Cas9, CRISPR/Csm1, and CRISPR/Cpf1 induce a double-strand DNA break at a target site of a genomic sequence that is then repaired by the natural processes of homologous recombination (HR) or non-homologous end-joining (NHEJ). Sequence modifications then occur at the cleaved sites, which can include deletions or insertions that result in gene disruption in the case of NHEJ, or integration of donor nucleic acid sequences by HR. In one aspect, a method provided herein comprises editing a plant genome with a nuclease provided herein to mutate at least 1, at least 2, at least 3, at least 4, at least 5, at least 6, at least 7, at least 8, at least 9, at least 10, or more than 10 nucleotides in the plant genome via HR with a donor polynucleotide. In one aspect, a mutation provided herein is caused by genome editing using a nuclease. In another aspect, a mutation provided herein is caused by non-homologous end-joining or homologous recombination.

In one aspect, a mutation provided herein provides a dominant mutant that activates the expression or activity of a gene of interest, e.g., a gene selected from the group consisting of a biosynthetic enzyme, a regulatory transcription factor, a transporter, a catabolic enzyme, or a combination thereof, for one or more antioxidants.

Meganucleases, which are commonly identified in microbes, are unique enzymes with high activity and long recognition sequences (>14 bp) resulting in site-specific digestion of target DNA. Engineered versions of naturally occurring meganucleases typically have extended DNA recognition sequences (for example, 14 to 40 bp). The engineering of meganucleases can be more challenging than that of ZFNs and TALENs because the DNA recognition and cleavage functions of meganucleases are intertwined in a single domain. Specialized methods of mutagenesis and high-throughput screening have been used to create novel meganuclease variants that recognize unique sequences and possess improved nuclease activity.

ZFNs are synthetic proteins consisting of an engineered zinc finger DNA-binding domain fused to the cleavage domain of the FokI restriction endonuclease. ZFNs can be designed to cleave almost any long stretch of double-stranded DNA for modification of the zinc finger DNA-binding domain. ZFNs form dimers from monomers composed of a non-specific DNA cleavage domain of FokI endonuclease fused to a zinc finger array engineered to bind a target DNA sequence.

The DNA-binding domain of a ZFN is typically composed of 3-4 zinc-finger arrays. The amino acids at positions −1, +2, +3, and +6 relative to the start of the zinc finger ∞-helix, which contribute to site-specific binding to the target DNA, can be changed and customized to fit specific target sequences. The other amino acids form the consensus backbone to generate ZFNs with different sequence specificities. Rules for selecting target sequences for ZFNs are known in the art.

The FokI nuclease domain requires dimerization to cleave DNA and therefore two ZFNs with their C-terminal regions are needed to bind opposite DNA strands of the cleavage site (separated by 5-7 bp). The ZFN monomer can cute the target site if the two-ZF-binding sites are palindromic. The term ZFN, as used herein, is broad and includes a monomeric ZFN that can cleave double stranded DNA without assistance from another ZFN. The term ZFN is also used to refer to one or both members of a pair of ZFNs that are engineered to work together to cleave DNA at the same site.

Without being limited by any scientific theory, because the DNA-binding specificities of zinc finger domains can in principle be re-engineered using one of various methods, customized ZFNs can theoretically be constructed to target nearly any gene sequence. Publicly available methods for engineering zinc finger domains include Context-dependent Assembly (CoDA), Oligomerized Pool Engineering (OPEN), and Modular Assembly.

TALENs are artificial restriction enzymes generated by fusing the transcription activator-like effector (TALE) DNA binding domain to a FokI nuclease domain. When each member of a TALEN pair binds to the DNA sites flanking a target site, the FokI monomers dimerize and cause a double-stranded DNA break at the target site. The term TALEN, as used herein, is broad and includes a monomeric TALEN that can cleave double stranded DNA without assistance from another TALEN. The term TALEN is also used to refer to one or both members of a pair of TALENs that work together to cleave DNA at the same site.

Transcription activator-like effectors (TALEs) can be engineered to bind practically any DNA sequence. TALE proteins are DNA-binding domains derived from various plant bacterial pathogens of the genus *Xanthomonas*. The X pathogens secrete TALEs into the host plant cell during infection. The TALE moves to the nucleus, where it recognizes and binds to a specific DNA sequence in the promoter region of a specific DNA sequence in the promoter region of a specific gene in the host genome. TALE has a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs.

Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity.

The relationship between amino acid sequence and DNA recognition of the TALE binding domain allows for designable proteins. Software programs such as DNA Works can be used to design TALE constructs. Other methods of designing TALE constructs are known to those of skill in the art. See Doyle et al., *Nucleic Acids Research* (2012) 40: W117-122; Cermak et al., *Nucleic Acids Research* (2011). 39:e82; and tale-nt.cac.cornell.edu/about.

A CRISPR/Cas9 system, CRISPR/Csm1, or a CRISPR/Cpf1 system are alternatives to the FokI-based methods ZFN and TALEN. The CRISPR systems are based on RNA-guided engineered nucleases that use complementary base pairing to recognize DNA sequences at target sites.

CRISPR/Cas9, CRISPR/Csm1, and a CRISPR/Cpf1 systems are part of the adaptive immune system of bacteria and archaea, protecting them against invading nucleic acids such as viruses by cleaving the foreign DNA in a sequence-dependent manner. The immunity is acquired by the integration of short fragments of the invading DNA known as spacers between two adjacent repeats at the proximal end of a CRISPR locus. The CRISPR arrays, including the spacers, are transcribed during subsequent encounters with invasive DNA and are processed into small interfering CRISPR RNAs (crRNAs) approximately 40 nt in length, which combine with the trans-activating CRISPR RNA (tracrRNA) to activate and guide the Cas9 nuclease. This cleaves homologous double-stranded DNA sequences known as protospacers in the invading DNA. A prerequisite for cleavage is the presence of a conserved protospacer-adjacent motif (PAM) downstream of the target DNA, which usually has the sequence 5-NGG-3 but less frequently NAG. Specificity is provided by the so-called "seed sequence" approximately 12 bases upstream of the PAM, which must match between the RNA and target DNA. Cpf1 acts in a similar manner to Cas9, but Cpf1 does not require a tracrRNA.

In still another aspect, a modified tobacco plant provided herein further comprises one or more mutations in one or more loci encoding a nicotine demethylase (e.g., CYP82E4, CYP82E5, CYP82E10) that confer reduced amounts of nornicotine (See U.S. Pat. Nos. 8,319,011; 8,124,851; 9,187,759; 9,228,194; 9,228,195; 9,247,706) compared to control plant lacking one or more mutations in one or more loci encoding a nicotine demethylase. In one aspect, a modified tobacco plant described herein further comprises reduced nicotine demethylase activity compared to a control plant when grown and cured under comparable conditions. In another aspect, a modified tobacco plant described herein further comprises a reduced level of total alkaloids compared to the control plant when grown and cured under comparable conditions. In another aspect, a tobacco plant provided herein further comprises one or more mutations in a Nic1 locus, a Nic2 locus, or both, which confer reduced amounts of nicotine compared to a control plant lacking one or more mutations in a Nic1 locus, a Nic2 locus, or both. In another aspect, a modified tobacco plant described herein further comprises a reduced level of nicotine compared to the control plant when grown and cured under comparable conditions. In a further aspect, a modified tobacco plant described herein comprises a substantially similar level of nicotine compared to the control plant when grown and cured under comparable conditions.

In one aspect, a modified tobacco plant described herein is a cisgenic plant. As used herein, "cisgenesis" or "cisgenic" refers to genetic modification of a plant, plant cell, or plant genome in which all components (e.g., promoter, donor nucleic acid, selection gene) have only plant origins (i.e., no non-plant origin components are used). In one aspect, a modified plant, plant cell, or plant genome provided herein is cisgenic. Cisgenic plants, plant cells, and plant genomes provided herein can lead to ready-to-use tobacco lines. In another aspect, a modified tobacco plant provided herein comprises no non-tobacco genetic material or sequences. In one aspect, a cisgenic construct of the present specification encodes a polynucleotide selected from the group consisting of Ubi4-P:PAP1-HSP-T (SEQ ID NO:59), Ubi4-P:NtAN2-HSP-T (SEQ ID NO:60), Tub-P:NtAN2-HSP-T (SEQ ID NO:61), Ubi4-P:NtAN2-HSP-T: Tub-P:NtAN2-HSP-T (SEQ ID NO:62), and Ubi4-P: NtAN1a-HSP-T:Tub-P:NtAN2-HSP-T (SEQ ID NO:63).

In one aspect, a modified tobacco plant described herein comprises one or more transgenes or recombinant DNA constructs capable of providing a reduced level of one or more TSNAs compared to a control plant without the one or more transgenes. In another aspect, a modified tobacco plant comprises one or more transgenes or recombinant DNA constructs further providing the one or more traits selected from the group consisting of: i. a reduced level of nitrite, ii. an increased level of oxygen radical absorbance capacity (ORAC), and iii. an increased level of one or more antioxidants; wherein the reduced or increased level is compared to a control tobacco plant when grown and cured under comparable.

In another aspect, a modified tobacco plant comprises one or more transgenes or recombinant DNA constructs encoding a biosynthetic enzyme, a regulatory transcription factor, a transporter, a catabolic enzyme, or a combination thereof, for one or more antioxidants selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin. In another aspect, a modified tobacco plant comprises one or more transgenes or recombinant DNA constructs encoding a biosynthetic enzyme, a regulatory transcription factor, a transporter, a catabolic enzyme, or a combination thereof, for one or more antioxidants selected from the group consisting of Delphnidin, Cyanidin, Procyanidin, Prodelphinidin, Hesperetin, Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C. In one aspect, one or more transgenes or recombinant DNA constructs encode a polypeptide having at least 50%, 55%, 60%, 65%, 70%, 75%, 80%, 85%, 90%, 95%, 97%, 98%, 99%, or 100% identity to a sequence selected from the group consisting of SEQ ID No. 1 to 23 and 47 to 52. In another aspect, one or more transgenes or recombinant DNA constructs encode a gene comprise a coding sequence having at least 50%, 55%, 60%, 65%, 70%, 75%, 80%, 85%, 90%, 95%, 97%, 98%, 99%, or 100% identity to a sequence selected from the group consisting of SEQ ID No. 24 to 46 and 53 to 58.

In one aspect, a recombinant DNA construct of the present disclosure comprises a promoter capable of driving gene transcription in a plant, operably linked to a polynucleotide encoding a polypeptide having at least 70%, at least 75%, at least 80%, at least 85%, at least 90%, at least 95%, at least 96%, at least 97%, at least 98%, at least 99% or 100% sequence identity to a polypeptide selected from the group consisting of SEQ ID NOs: 1 to 23 and 47 to 52. In one aspect, a recombinant DNA construct or expression cassette in a transgene provided herein comprises a promoter selected from the group consisting of a constitutive promoter, an inducible promoter, and a tissue-preferred promoter (for example, without being limiting, a leaf-specific promoter, a shoot-specific promoter, a root-specific promoter, or a meristem-specific promoter).

Exemplary constitutive promoters include the core promoter of the Rsyn7 promoter and other constitutive promoters disclosed in U.S. Pat. No. 6,072,050; the core CaMV 35S promoter (Odell et al. (1985) Nature 313:810-812); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J 3:2723-2730); ALS promoter (U.S. Pat. No. 5,659,026), and the like.

Exemplary chemical-inducible promoters include the tobacco PR-1a promoter, which is activated by salicylic acid. Other chemical-inducible promoters of interest include steroid-responsive promoters (see, for example, the glucocorticoid-inducible promoter in Schena et al. (1991) Proc. Natl. Acad. Sci. USA 88:10421-10425 and McNellis et al. (1998) Plant J. 14(2):247-257) and tetracycline-inducible promoters (see, for example, Gatz et al. (1991) Mol. Gen. Genet. 227:229-237, and U.S. Pat. Nos. 5,814,618 and 5,789,156). Additional exemplary promoters that can be used herein are those responsible for heat-regulated gene expression, light-regulated gene expression (for example, the pea rbcS-3A; the maize rbcS promoter; the chlorophyll alb-binding protein gene found in pea; or the Arabssu promoter), hormone-regulated gene expression (for example, the abscisic acid (ABA) responsive sequences from the Em gene of wheat; the ABA-inducible HVA1 and HVA22, and rd29A promoters of barley and *Arabidopsis*; and wound-induced gene expression (for example, of wunl), organ specific gene expression (for example, of the tuber-specific storage protein gene; the 23-kDa zein gene from maize described by; or the French bean (β-phaseolin gene), or pathogen-inducible promoters (for example, the PR-1, prp-1, or (β-1,3 glucanase promoters, the fungal-inducible wirla promoter of wheat, and the nematode-inducible promoters, TobRB7-5A and Hmg-1, of tobacco arid parsley, respectively).

Additional exemplary tissue-preferred promoters include those disclosed in Yamamoto et al. (1997) Plant J. 12(2): 255-265; Kawamata et al. (1997) Plant Cell Physiol. 38(7): 792-803; Hansen et al. (1997) Mol. Gen. Genet. 254(3):337-343; Russell et al. (1997) Transgenic Res. 6(2):157-168; Rinehart et al. (1996) Plant Physiol. 112(3):1331-1341; Van Camp et al. (1996) Plant Physiol. 112(2):525-535; Canevascini et al. (1996) Plant Physiol. 112(2):513-524; Yamamoto et al. (1994) Plant Cell Physiol. 35(5):773-778; Lam (1994) Results Probl. Cell Differ. 20:181-196; Orozco et al. (1993) Plant Mol. Biol. 23(6):1129-1138; Matsuoka et al. (1993) Proc Natl. Acad. Sci. USA 90(20):9586-9590; and Guevara-Garcia et al. (1993) Plant J. 4(3):495-505.

As used herein, "operably linked" refers to a functional linkage between two or more elements. For example, an operable linkage between a polynucleotide of interest and a regulatory sequence (e.g., a promoter) is a functional link that allows for expression of the polynucleotide of interest. Operably linked elements may be contiguous or non-contiguous.

In one aspect, a transgene provided herein comprises a heterologous or non-tobacco promoter or coding sequence. In another aspect, a transgene provided herein comprises a endogenous or tobacco-origin promoter or coding sequence. As used herein, "heterologous" refers to a sequence that originates from a foreign species, or, if from the same species, is substantially modified from its native form in composition and/or genomic locus by deliberate human intervention. The term also is applicable to nucleic acid constructs, also referred to herein as "polynucleotide constructs" or "nucleotide constructs." In this manner, a "heterologous" nucleic acid construct is intended to mean a construct that originates from a foreign species, or, if from the same species, is substantially modified from its native form in composition and/or genomic locus by deliberate human intervention. Heterologous nucleic acid constructs include, but are not limited to, recombinant nucleotide constructs that have been introduced into a plant or plant part thereof, for example, via transformation methods or subsequent breeding of a transgenic plant with another plant of interest.

In one aspect, a recombinant DNA construct, modified plant, seed, plant component, plant cell, or plant genome provided herein comprises a heterologous promoter operably linked to a polynucleotide encoding a polypeptide having at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a polypeptide selected from the group consisting of SEQ ID NOs: 24 to 46 and 53 to 58.

Enhancer elements are regions of DNA that can be bound by proteins to activate RNA transcription. In one aspect, a promoter sequence used herein is operably linked to an enhancer element. In one aspect, an enhancer element provided herein is a CsVMV promoter.

Also provided herein are the transformation of tobacco plants with recombinant constructs or expression cassettes described herein using any suitable transformation methods known in the art. Methods for introducing polynucleotide sequences into tobacco plants are known in the art and include, but are not limited to, stable transformation methods, transient transformation methods, and virus-mediated methods. "Stable transformation" refers to transformation where the nucleotide construct of interest introduced into a plant integrates into a genome of the plant and is capable of being inherited by the progeny thereof "Transient transformation" is intended to mean that a sequence is introduced into the plant and is only temporally expressed or is only transiently present in the plant.

In one aspect, methods and compositions provided herein comprise the introduction of one or more polynucleotides into one or more plant cells. In one aspect, a plant genome provided herein is modified to include an introduced polynucleotide or recombinant DNA construct. As used herein, "plant genome" refers to a nuclear genome, a mitochondrial genome, or a plastid (e.g., chloroplast) genome of a plant cell. In another aspect, a polynucleotide provided herein is integrated into an artificial chromosome. In one aspect, an artificial chromosome comprising a polynucleotide provided herein is integrated into a plant cell.

In one aspect, transgenes provided herein comprise a recombinant DNA construct. In one aspect, recombinant DNA constructs or expression cassettes provided herein can comprise a selectable marker gene for the selection of transgenic cells. Selectable marker genes include, but are not limited to, genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, triazolopyrimidines, sulfonylurea (e.g., chlorsulfuron and sulfometuron methyl), and 2,4-dichlorophenoxyacetate (2,4-D). Additional selectable markers include phenotypic markers such as β-galactosidase and fluorescent proteins such as green fluorescent protein (GFP).

In one aspect, methods and compositions provided herein comprise a vector. As used herein, the terms "vector" or "plasmid" are used interchangeably and refer to a circular, double-stranded DNA molecule that is physically separate from chromosomal DNA. In one aspect, a plasmid or vector used herein is capable of replication in vivo. A "transformation vector," as used herein, is a plasmid that is capable of transforming a plant cell. In an aspect, a plasmid provided herein is a bacterial plasmid. In another aspect, a plasmid provided herein is an *Agrobacterium* Ti plasmid or derived from an *Agrobacterium* Ti plasmid.

In one aspect, a plasmid or vector provided herein is a recombinant vector. As used herein, the term "recombinant vector" refers to a vector formed by laboratory methods of genetic recombination, such as molecular cloning. In another aspect, a plasmid provided herein is a synthetic plasmid. As used herein, a "synthetic plasmid" is an artificially created plasmid that is capable of the same functions (e.g., replication) as a natural plasmid (e.g., Ti plasmid). Without being limited, one skilled in the art can create a synthetic plasmid de novo via synthesizing a plasmid by individual nucleotides, or by splicing together nucleic acid molecules from different pre-existing plasmids.

Vectors are commercially available or can be produced by recombinant DNA techniques routine in the art. A vector containing a nucleic acid can have expression elements operably linked to such a nucleic acid, and further can include sequences such as those encoding a selectable marker (e.g., an antibiotic resistance gene). A vector containing a nucleic acid can encode a chimeric or fusion polypeptide (i.e., a polypeptide operatively linked to a heterologous polypeptide, which can be at either the N-terminus or C-terminus of the polypeptide). Representative heterologous polypeptides are those that can be used in purification of the encoded polypeptide (e.g., 6×His tag, glutathione S-transferase (GST)).

Suitable methods of introducing polynucleotides (e.g., transgenes, recombinant vectors, recombinant DNA constructs, expression constructs) into plant cells of the present disclosure include microinjection (Crossway et al. (1986) *Biotechniques* 4:320-334), electroporation (Shillito et al. (1987) *Meth. Enzymol.* 153:313-336; Riggs et al. (1986) *Proc. Natl. Acad. Sci. USA* 83:5602-5606), *Agrobacterium*-mediated transformation (U.S. Pat. Nos. 5,104,310, 5,149,645, 5,177,010, 5,231,019, 5,463,174, 5,464,763, 5,469,976, 4,762,785, 5,004,863, 5,159,135, 5,563,055, and 5,981,840), direct gene transfer (Paszkowski et al. (1984) *EMBO J.* 3:2717-2722), and ballistic particle acceleration (see, for example, U.S. Pat. Nos. 4,945,050, 5,141,131, 5,886,244, 5,879,918, and 5,932,782; Tomes et al. (1995) in *Plant Cell,*

*Tissue, and Organ Culture Fundamental Methods*, ed. Gamborg and Phillips (Springer-Verlag, Berlin); McCabe et al. (1988) *Biotechnology* 6:923-926). Also see Weissinger et al. (1988) *Ann. Rev. Genet.* 22:421-477; Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P: 175-182 (soybean); Singh et al. (1998) *Theor. Appl. Genet.* 96:319-324 (soybean); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation). In one aspect, a bacterial cell provided herein comprises a recombinant DNA construct or recombinant vector provided herein.

In another aspect, recombinant constructs or expression cassettes provided herein may be introduced into plants by contacting plants with a virus or viral nucleic acids. Generally, such methods involve incorporating an expression cassette of the present disclosure within a viral DNA or RNA molecule. It is recognized that promoters for use in the expression cassettes provided herein also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221.

Any plant tissue that can be subsequently propagated using clonal methods, whether by organogenesis or embryogenesis, may be transformed with a recombinant construct or an expression cassette provided herein. By "organogenesis" in intended the process by which shoots and roots are developed sequentially from meristematic centers. By "embryogenesis" is intended the process by which shoots and roots develop together in a concerted fashion (not sequentially), whether from somatic cells or gametes. Exemplary tissues that are suitable for various transformation protocols described herein include, but are not limited to, callus tissue, existing meristematic tissue (e.g., apical meristems, axillary buds, and root meristems) and induced meristem tissue (e.g., cotyledon meristem and hypocotyl meristem), hypocotyls, cotyledons, leaf disks, pollen, embryos, and the like.

It is understood that any modified tobacco plant of the present disclosure can further comprise additional agronomically desirable traits, for example, by transformation with a genetic construct or transgene using a technique known in the art. Without limitation, an example of a desired trait is herbicide resistance, pest resistance, disease resistance, high yield, high grade index value, curability, curing quality, mechanical harvestability, holding ability, leaf quality, height, plant maturation (e.g., early maturing, early to medium maturing, medium maturing, medium to late maturing, or late maturing), stalk size (e.g., a small, medium, or a large stalk), or leaf number per plant (e.g., a small (e.g., 5-10 leaves), medium (e.g., 11-15 leaves), or large (e.g., 16-21) number of leaves), or any combination. In one aspect, tobacco plants capable of producing cured leaf with reduced TSNA or seeds provided herein comprise one or more transgenes expressing one or more insecticidal proteins, such as, for example, a crystal protein of *Bacillus thuringiensis* or a vegetative insecticidal protein from *Bacillus cereus*, such as VIP3 (see, for example, Estruch et al. (1997) *Nat. Biotechnol.* 15:137). In another aspect, tobacco plants provided herein further comprise an introgressed trait conferring resistance to brown stem rot (U.S. Pat. No. 5,689,035) or resistance to cyst nematodes (U.S. Pat. No. 5,491,081).

The level and/or activity of polypeptides provided herein may be modulated by employing a polynucleotide that is not capable of directing, in a transformed plant, the expression of a protein or an RNA. For example, the polynucleotides of the invention may be used to design polynucleotide constructs that can be employed in methods for altering or mutating a genomic nucleotide sequence in an organism. Such polynucleotide constructs include, but are not limited to, RNA:DNA vectors, RNA:DNA mutational vectors, RNA:DNA repair vectors, mixed-duplex oligonucleotides, self-complementary RNA:DNA oligonucleotides and recombinogenic oligonucleobases. Such nucleotide constructs and methods of use are known in the art. See, U.S. Pat. Nos. 5,565,350; 5,731,181; 5,756,325; 5,760,012; 5,795,972 and 5,871,984; each of which is incorporated herein by reference as if set forth in its entirety. See also, International Patent Application Publication Nos. WO 98/149350, WO 99/107865 and WO 99/125921; and Beetham et al. (1999) Proc. Natl. Acad. Sci. USA 96:8774-8778; each of which is incorporated herein by reference as if set forth in its entirety.

The present disclosure also provides compositions and methods for inhibiting the expression or function of one or more polypeptides that suppress, directly or indirectly, the production or accumulation of one or more antioxidants in a plant, particularly plants of the *Nicotiana tabacum* genus, including tobacco plants of various commercial varieties.

In one aspect, inhibition of the expression of one or more polypeptides provided herein may be obtained by RNA interference (RNAi) by expression of a transgene capable of producing an inhibitory sequence provided herein. In one aspect, RNAi comprises expressing a non-coding RNA. As used herein, a "non-coding RNA" is selected from the group consisting of a microRNA (miRNA), a small interfering RNA (siRNA), a trans-acting siRNA (ta-siRNA), a transfer RNA (tRNA), a ribosomal RNA (rRNA), an intron, a hairpin RNA (hpRNA), and an intron-containing hairpin RNA (ihpRNA). In one aspect, a single non-coding RNA provided herein inhibits the expression of at least 1, at least 2, at least 3, at least 4, at least 5, at least 6, at least 7, at least 8, at least 9, at least 10, or more than 10 polypeptides. In one aspect, a non-coding RNA provided herein is stably transformed into a plant genome. In another aspect, a non-coding RNA provided herein is transiently transformed into a plant genome.

As used herein, the terms "suppress," "inhibit," "inhibition," "inhibiting", and "downregulation" are defined as any method known in the art or described herein that decreases the expression or function of a gene product (e.g., an mRNA, a protein, a non-coding RNA). "Inhibition" can be in the context of a comparison between two cells, for example, a modified cell versus a control cell. Inhibition of expression or function of a gene product can also be in the context of a comparison between plant cells, organelles, organs, tissues, or plant components within the same plant or between different plants, and includes comparisons between developmental or temporal stages within the same plant or plant component or between plants or plant components. "Inhibition" includes any relative decrement of function or production of a gene product of interest, up to and including complete elimination of function or production of that gene product. The term "inhibition" encompasses any method or composition that down-regulates translation and/or transcription of the target gene product or functional activity of the target gene product. "Inhibition" need not comprise complete elimination of expression of a gene product. In an aspect, a gene product in a modified cell provided herein comprises expression that is at least 1%, at least 2%, at least 3%, at least 4%, at least 5%, at least 10%, at least 20%, at least 25%, at least 30%, at least 40%, at least 50%, at least 60%, at least 70%, at least 80%, at least 90%, at least 95%, or 100% lower than the expression of the gene product in a control cell. In another aspect, a gene product in a modified cell provided herein comprises expression that is between 1% and 100%, between 1% and 95%, between 1% and 90%, between 1% and 80%, between 1% and 70%, between 1% and 60%, between 1% and 50%, between 1% and 40%, between 1% and 30%, between 1% and 25%, between 1% and 20%, between 1% and 15%, between 1% and 10%, between 1% and 5%, between 5% and 25%, between 5% and 50%, between 5% and 75%, between 5% and 100%, between 10% and 25%, between 10% and 50%, between 10% and 75%, between 10% and 100%, between 25% and 50%, between 25% and 75%, between 25% and 100%, or between 50% and 100% lower than the expression of the gene product in a control cell.

As used herein, a "target site" refers to a location of a polynucleotide sequence that is bound to and cleaved by a site-specific nuclease introducing a double stranded break into the nucleic acid backbone. In another aspect a target site comprises at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 29, or at least 30 consecutive nucleotides. In another aspect, a target site provided herein is at least 10, at least 20, at least 30, at least 40, at least 50, at least 75, at least 100, at least 125, at least 150, at least 200, at least 250, at least 300, at least 400, or at least 500 nucleotides. In one aspect a site-specific nuclease binds to a target site. In another aspect a site-specific nuclease binds to a target site via a guiding non-coding RNA (i.e., such as, without being limiting, a CRISPR RNA or single-guide RNA (both described in detail below)). In one aspect, a non-coding RNA provided herein is complementary to a target site. It will be appreciated that perfect complementarity is not required for a non-coding RNA to bind to a target site; at least 1, at least 2, at least 3, at least 4, or at least 5, at least 6, at least 7 or at least 8 mismatches between a target site and a non-coding RNA can be tolerated. As used herein, a "target region" or a "targeted region" refers to a polynucleotide sequence that is desired to be modified. In one aspect, a "target region," "targeted region," or a "target gene" is flanked by two or more, three or more, four or more, five or more, six or more, seven or more, eight or more, nine or more, or ten or more target sites. A "target gene" refers to a polynucleotide sequence encoding a gene that is desired to be modified or from which transcript expression is desired to be modulated. In one aspect, a polynucleotide sequence comprising a target gene further comprises one or more target sites. In another aspect, a transgene is said to be targeting a target site or a target gene. In another aspect, a target region comprises one or more, two or more, three or more, four or more, five or more, six or more, seven or more, eight or more, nine or more, or ten or more target genes. Without being limiting, in one aspect a target region can be subject to deletion or inversion. As used herein, "flanked" when used to describe a target region, refers to two or more target sites physically surrounding the target region, with one target site on each side of the target region.

As used herein, in the context of a transgene "directly modulating" or "directly modulates" refers to inducing a change in the transcript or protein level of a target gene by an agent produced by the transgene and sharing sufficient homology with at least a portion of the target gene. Direct modulation can result in a change in transcriptional activity, transcript stability, transcript constitution, or transcript expression level which can either increase or decrease the number of transcripts available for translation and can either increase or decrease the number of protein molecules.

A target site can be positioned in a polynucleotide sequence encoding a leader, an enhancer, a transcriptional start site, a promoter, a 5'-UTR, an exon, an intron, a 3'-UTR, a polyadenylation site, or a termination sequence. It will be appreciated that a target site can be also be positioned upstream or downstream of a sequence encoding a leader, an enhancer, a transcriptional start site, a promoter, a 5'-UTR, an exon, an intron, a 3'-UTR, a polyadenylation site, or a termination sequence. In one aspect, a target site is positioned within 10, within 20, within 30, within 40, within 50, within 75, within 100, within 125, within 150, within 200, within 250, within 300, within 400, within 500, within 600, within 700, within 800, within 900, within 1000, within 1250, within 1500, within 2000, within 2500, within 5000, within 10,000, or within 25,000 nucleotides of a polynucleotide encoding a leader, an enhancer, a transcriptional start site, a promoter, a 5'-UTR, an exon, an intron, a 3'-UTR, a polyadenylation site, a gene, or a termination sequence.

As used herein, "upstream" refers to a nucleic acid sequence that is positioned before the 5' end of a linked nucleic acid sequence. As used herein, "downstream" refers to a nucleic acid sequence is positioned after the 3' end of a linked nucleic acid sequence. As used herein, "5'" refers to the start of a coding DNA sequence or the beginning of an RNA molecule. As used herein, "3'" refers to the end of a coding DNA sequence or the end of an RNA molecule. It will be appreciated that an "inversion" refers to reversing the orientation of a given polynucleotide sequence. For example, if the sample sequence 5'-ATGATC-3' is inverted it will read 5'-CTAGTA-3' in reverse orientation. Additionally, the sample sequence 5'-ATGATC-3' is considered to be in "opposite orientation" to the sample sequence 5'-CTAGTA-3'.

The term "inhibitory sequence" encompasses any polynucleotide or polypeptide sequence capable of inhibiting the expression or function of a gene in a plant, such as full-length polynucleotide or polypeptide sequences, truncated polynucleotide or polypeptide sequences, fragments of polynucleotide or polypeptide sequences, variants of polynucleotide or polypeptide sequences, sense-oriented nucleotide sequences, antisense-oriented nucleotide sequences, the complement of a sense- or antisense-oriented nucleotide sequence, inverted regions of nucleotide sequences, hairpins of nucleotide sequences, double-stranded nucleotide sequences, single-stranded nucleotide sequences, combinations thereof, and the like. The term "polynucleotide sequence" includes sequences of RNA, DNA, chemically modified nucleic acids, nucleic acid analogs, combinations thereof, and the like.

Inhibitory sequences are designated herein by the name of the target gene product. Thus, as a non-limiting example, an "gene X inhibitory sequence" refers to an inhibitory sequence that is capable of inhibiting the expression of a gene X locus in a plant, for example, at the level of transcription and/or translation, or which is capable of inhibiting the function of a gene product. When the phrase "capable of inhibiting" is used in the context of a transgene containing polynucleotide inhibitory sequence, it is intended to mean that the inhibitory sequence itself exerts the inhibitory effect; or, where the inhibitory sequence encodes an inhibitory nucleotide molecule (for example, hairpin RNA, miRNA, or double-stranded RNA polynucleotides), or encodes an inhibitory polypeptide (e.g., a polypeptide that inhibits expression or function of the target gene product), following its transcription (for example, in the case of an inhibitory sequence encoding a hairpin RNA, miRNA, or double-stranded RNA polynucleotide) or its transcription and translation (in the case of an inhibitory sequence encoding an inhibitory polypeptide), the transcribed or translated product, respectively, exerts the inhibitory effect on the target gene product (e.g., inhibits expression or function of the target gene product).

An inhibitory sequence provided herein can be a sequence triggering gene silencing via any silencing pathway or mechanism known in the art, including, but not limited to, sense suppression/co-suppression, antisense suppression, double-stranded RNA (dsRNA) interference, hairpin RNA interference and intron-containing hairpin RNA interference, amplicon-mediated interference, ribozymes, small interfering RNA, artificial or synthetic microRNA, and artificial trans-acting siRNA.

One aspect of the present application relates to methods of screening and selecting cells for targeted edits and methods of selecting cells comprising targeted edits. Nucleic acids can be isolated using various techniques. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

Also provided herein is cured tobacco material made from tobacco leaf, tobacco plants, or plant components provided herein. "Curing" is the aging process that reduces moisture and brings about the destruction of chlorophyll giving tobacco leaf a golden color and by which starch is converted to sugar. Cured tobacco therefore has a higher reducing sugar content and a lower starch content compared to harvested green leaf. In one aspect, tobacco plants or plant components provided herein can be cured using conventional means, e.g., flue-cured, barn-cured, fire-cured, air-cured or sun-cured. See, for example, Tso (1999, Chapter 1 in Tobacco, Production, Chemistry and Technology, Davis & Nielsen, eds., Blackwell Publishing, Oxford) for a description of different types of curing methods. Cured tobacco is usually aged in a wooden drum (e.g., a hogshead) or cardboard cartons in compressed conditions for several years (e.g., two to five years), at a moisture content ranging from 10% to about 25%. See, U.S. Pat. Nos. 4,516,590 and 5,372,149. Cured and aged tobacco then can be further processed. Further processing includes conditioning the tobacco under vacuum with or without the introduction of steam at various temperatures, pasteurization, and fermentation. Fermentation typically is characterized by high initial moisture content, heat generation, and a 10 to 20% loss of dry weight. See, for example, U.S. Pat. Nos. 4,528,993, 4,660,577, 4,848,373, 5,372,149; U.S. Publication No. 2005/0178398; and Tso (1999, Chapter 1 in Tobacco, Production, Chemistry and Technology, Davis & Nielsen, eds., Blackwell Publishing, Oxford). Cured, aged, and fermented tobacco can be further processed (e.g., cut, shredded, expanded, or blended). See, for example, U.S. Pat. Nos. 4,528,993; 4,660,577; and 4,987,907. In one aspect, the cured tobacco material of the present disclosure is flue-cured, sun-cured, air-cured, or fire-cured.

Tobacco material obtained from modified tobacco lines, varieties or hybrids of the present disclosure can be used to make tobacco products. As used herein, "tobacco product" is defined as any product made or derived from tobacco that is intended for human use or consumption. In an aspect, a tobacco product provided herein comprises cured components from a modified tobacco plant provided herein. In another aspect, a tobacco product provided herein comprises cured tobacco leaf from a modified tobacco plant provided herein.

Tobacco products provided herein include, without limitation, cigarette products (e.g., cigarettes, bidi cigarettes, kreteks), cigar products (e.g., cigars, cigar wrapping tobacco, cigarillos), pipe tobacco products, products derived from tobacco, tobacco-derived nicotine products, smokeless tobacco products (e.g., moist snuff, dry snuff, snus, chewing tobacco, moist smokeless tobacco, fine cut chewing tobacco, long cut chewing tobacco, pouched chewing tobacco), films, chewables (e.g., gum), lozenges, dissolving strips, tabs, tablets, shaped parts, gels, consumable units, insoluble matrices, hollow shapes, reconstituted tobacco, expanded tobacco, and the like. See, for example, U.S. Patent Publication No. US 2006/0191548.

As used herein, "cigarette" refers a tobacco product having a "rod" and "filler". The cigarette "rod" includes the cigarette paper, filter, plug wrap (used to contain filtration materials), tipping paper that holds the cigarette paper (including the filler) to the filter, and all glues that hold these components together. The "filler" includes (1) all tobaccos, including but not limited to reconstituted and expanded tobacco, (2) non-tobacco substitutes (including but not limited to herbs, non-tobacco plant materials and other spices that may accompany tobaccos rolled within the cigarette paper), (3) casings, (4) flavorings, and (5) all other additives (that are mixed into tobaccos and substitutes and rolled into the cigarette).

In one aspect, this disclosure provides nicotine derived from and a method of producing nicotine from a modified tobacco plant provided herein for use in a product.

In one aspect, a method provided herein comprises preparing a tobacco product using cured tobacco leaf from a modified tobacco plant provided herein.

As used herein, "reconstituted tobacco" refers to a part of tobacco filler made from tobacco dust and other tobacco scrap material, processed into sheet form and cut into strips to resemble tobacco. In addition to the cost savings, reconstituted tobacco is very important for its contribution to cigarette taste from processing flavor development using reactions between ammonia and sugars.

As used herein, "expanded tobacco" refers to a part of tobacco filler which is processed through expansion of suitable gases so that the tobacco is "puffed" resulting in reduced density and greater filling capacity. It reduces the weight of tobacco used in cigarettes.

Tobacco products derived from plants of the present disclosure also include cigarettes and other smoking articles, particularly those smoking articles including filter elements, where the rod of smokeable material includes cured tobacco within a tobacco blend. In an aspect, a tobacco product of the present disclosure is selected from the group consisting of a cigarillo, a non-ventilated recess filter cigarette, a vented recess filter cigarette, a bidi cigarette, a cigar, snuff, pipe tobacco, cigar tobacco, cigarette tobacco, chewing tobacco, leaf tobacco, hookah tobacco, shredded tobacco, and cut tobacco. In another aspect, a tobacco product of the present disclosure is a smokeless tobacco product. Smokeless tobacco products are not combusted and include, but not limited to, chewing tobacco, moist smokeless tobacco, snus, and dry snuff. Chewing tobacco is coarsely divided tobacco leaf that is typically packaged in a large pouch-like package and used in a plug or twist. Moist smokeless tobacco is a moist, more finely divided tobacco that is provided in loose form or in pouch form and is typically packaged in round cans and used as a pinch or in a pouch placed between an adult tobacco consumer's cheek and gum. Snus is a heat treated smokeless tobacco. Dry snuff is finely ground tobacco that is placed in the mouth or used nasally. In a further aspect, a tobacco product of the present disclosure is selected from the group consisting of loose leaf chewing tobacco, plug chewing tobacco, moist snuff, and nasal snuff. In yet another aspect, a tobacco product of the present disclosure is selected from the group consisting of an electronically heated cigarette, an e-cigarette, an electronic vaporing device.

The present disclosure further provides a method for manufacturing a tobacco product comprising tobacco material from tobacco plants provided herein. In one aspect, methods provided herein comprise conditioning aged tobacco material made from tobacco plants provided herein to increase its moisture content from between about 12.5% and about 13.5% to about 21%, blending the conditioned tobacco material to produce a desirable blend. In one aspect, the method of manufacturing a tobacco product provided herein further comprises casing or flavoring the blend. Generally, during the casing process, casing or sauce materials are added to blends to enhance their quality by balancing the chemical composition and to develop certain desired flavor characteristics. Further details for the casing process can be found in *Tobacco Production, Chemistry and Technology*, Edited by L. Davis and M. Nielsen, Blackwell Science, 1999.

Tobacco material provided herein can be also processed using methods including, but not limited to, heat treatment (e.g., cooking, toasting), flavoring, enzyme treatment, expansion and/or curing. Both fermented and non-fermented tobaccos can be processed using these techniques. Examples of suitable processed tobaccos include dark air-cured, dark fire cured, burley, flue cured, and cigar filler or wrapper, as well as the products from the whole leaf stemming operation. In one aspect, tobacco fibers include up to 70% dark tobacco on a fresh weight basis. For example, tobacco can be conditioned by heating, sweating and/or pasteurizing steps as described in U.S. Publication Nos. 2004/0118422 or 2005/0178398.

Tobacco material provided herein can be subject to fermentation. Fermenting typically is characterized by high initial moisture content, heat generation, and a 10 to 20% loss of dry weight. See, e.g., U.S. Pat. Nos. 4,528,993; 4,660,577; 4,848,373; and 5,372,149. In addition to modifying the aroma of the leaf, fermentation can change either or both the color and texture of a leaf. Also during the fermentation process, evolution gases can be produced, oxygen can be taken up, the pH can change, and the amount of water retained can change. See, for example, U.S. Publication No. 2005/0178398 and Tso (1999, Chapter 1 in Tobacco, Production, Chemistry and Technology, Davis & Nielsen, eds., Blackwell Publishing, Oxford). Cured, or cured and fermented tobacco can be further processed (e.g., cut, expanded, blended, milled or comminuted) prior to incorporation into the oral product. The tobacco, in some cases, is long cut fermented cured moist tobacco having an oven volatiles content of between 48 and 50 weight percent prior to mixing with a copolymer and, optionally, flavorants and other additives.

In one aspect, tobacco material provided herein can be processed to a desired size. In certain aspects, tobacco fibers can be processed to have an average fiber size of less than 200 micrometers. In one aspect, tobacco fibers are between 75 and 125 micrometers. In another aspect, tobacco fibers are processed to have a size of 75 micrometers or less. In one aspect, tobacco fibers include long cut tobacco, which can be cut or shredded into widths of about 10 cuts/inch up to about 110 cuts/inch and lengths of about 0.1 inches up to about 1 inch. Double cut tobacco fibers can have a range of particle sizes such that about 70% of the double cut tobacco fibers falls between the mesh sizes of −20 mesh and 80 mesh.

Tobacco material provided herein can be processed to have a total oven volatiles content of about 10% by weight or greater; about 20% by weight or greater; about 40% by weight or greater; about 15% by weight to about 25% by weight; about 20% by weight to about 30% by weight; about 30% by weight to about 50% by weight; about 45% by weight to about 65% by weight; or about 50% by weight to about 60% by weight. Those of skill in the art will appreciate that "moist" tobacco typically refers to tobacco that has an oven volatiles content of between about 40% by weight and about 60% by weight (e.g., about 45% by weight to about 55% by weight, or about 50% by weight). As used herein, "oven volatiles" are determined by calculating the percentage of weight loss for a sample after drying the sample in a pre-warmed forced draft oven at 110° C. for 3.25 hours. An oral product can have a different overall oven volatiles content than the oven volatiles content of the tobacco fibers used to make the oral product. The processing steps described herein can reduce or increase the oven volatiles content.

In one aspect, tobacco plants, seeds, plant components, plant cells, and plant genomes provided herein are from a tobacco type selected from the group consisting of flue-cured tobacco, sun-cured tobacco, air-cured tobacco, dark air-cured tobacco, and dark fire-cured tobacco. In another aspect, tobacco plants, seeds, plant components, plant cells, and plant genomes provided herein are from a tobacco type selected from the group consisting of Burley tobacco, Maryland tobacco, bright tobacco, Virginia tobacco, Oriental tobacco, Turkish tobacco, dark tobacco, and Galpão tobacco. In one aspect, a tobacco plant or seed provided herein is a hybrid plant or seed. As used herein, a "hybrid" is created by crossing two plants from different varieties or species, such that the progeny comprises genetic material from each parent. Skilled artisans recognize that higher order hybrids can be generated as well. For example, a first hybrid can be made by crossing Variety C with Variety D to create a C×D hybrid, and a second hybrid can be made by crossing Variety E with Variety F to create an E×F hybrid. The first and second hybrids can be further crossed to create the higher order hybrid (C×D)×(E×F) comprising genetic information from all four parent varieties.

Flue-cured tobaccos (also called Virginia or bright tobaccos) amount to approximately 40% of world tobacco production. Flue-cured tobaccos are often also referred to as "bright tobacco" because of the golden-yellow to deep-orange color it reaches during curing. Flue-cured tobaccos have a light, bright aroma and taste. Flue-cured tobaccos are generally high in sugar and low in oils. Major flue-cured tobacco growing countries are Argentina, Brazil, China, India, Tanzania and the U.S. In one aspect, modified tobacco plants or seeds provided herein are in a flue-cured tobacco background selected from the group consisting of CC 13, CC 27, CC 33, CC35, CC 37, CC 65, CC 67, CC 700, GF 318, GL 338, GL 368, GL 939, K 346, K 399, K326, NC 102, NC 196, NC 291, NC 297, NC 299, NC 471, NC 55, NC 606, NC 71, NC 72, NC 92, PVH 1118, PVH 1452, PVH 2110, SPEIGHT 168, SPEIGHT 220, SPEIGHT 225, SPEIGHT 227, SPEIGHT 236, and any variety essentially derived from any one of the foregoing varieties. In another aspect, modified tobacco plants or seeds provided herein are in a flue-cured tobacco background selected from the group consisting of Coker 48, Coker 176, Coker 371-Gold, Coker 319, Coker 347, GL 939, K 149, K326, K 340, K 346, K 358, K 394, K 399, K 730, NC 27NF, NC 37NF, NC 55, NC 60, NC 71, NC 72, NC 82, NC 95, NC 297, NC 606, NC 729, NC 2326, McNair 373, McNair 944, Ox 207, Ox 414 NF, Reams 126, Reams 713, Reams 744, RG 8, RG 11, RG 13, RG 17, RG 22, RG 81, RG H4, RG H51, Speight H-20, Speight G-28, Speight G-58, Speight G-70, Speight G-108, Speight G-111, Speight G-117, Speight 168, Speight 179, Speight NF-3, Va 116, Va 182, and any variety essentially derived from any one of the foregoing varieties. See WO 2004/041006 A1. In further aspects, modified tobacco plants, seeds, hybrids, varieties, or lines provided herein are in any flue cured background selected from the group consisting of K326, K346, and NC196.

Air-cured tobaccos include Burley, Maryland, and dark tobaccos. The common factor is that curing is primarily without artificial sources of heat and humidity. Burley tobaccos are light to dark brown in color, high in oil, and low in sugar. Burley tobaccos are air-cured in barns. Major Burley growing countries are Argentina, Brazil, Italy, Malawi, and the U.S. Maryland tobaccos are extremely fluffy, have good burning properties, low nicotine and a neutral aroma. Major Maryland growing countries include the U.S. and Italy. In one aspect, modified tobacco plants or seeds provided herein are in a Burley tobacco background selected from the group consisting of Clay 402, Clay 403, Clay 502, Ky 14, Ky 907, Ky 910, Ky 8959, NC 2, NC 3, NC 4, NC 5, NC 2000, TN 86, TN 90, TN 97, R 610, R 630, R 711, R 712, NCBH 129, HB4488PLC, PD 7319LC, Bu 21×Ky 10, HB04P, Ky 14×L 8, Kt 200, Newton 98, Pedigo 561, Pf561 and Va 509. In further aspects, modified tobacco plants, seeds, hybrids, varieties, or lines provided herein are in any Burley background selected from the group consisting of TN 90, KT 209, KT 206, KT212, and HB 4488. In another aspect, modified tobacco plants or seeds provided herein are in a Maryland tobacco background selected from the group consisting of Md 10, Md 40, Md 201, Md 609, Md 872 and Md 341.

Dark air-cured tobaccos are distinguished from other types primarily by its curing process which gives dark air-cured tobacco its medium- to dark-brown color and distinct aroma. Dark air-cured tobaccos are mainly used in the production of smokeless tobacco products including chewing tobacco and snuff. In one aspect, modified tobacco plants or seeds provided herein are in a dark air-cured tobacco background selected from the group consisting of Sumatra, Jatim, Dominican Cubano, Besuki, One sucker, Green River, Virginia sun-cured, and Paraguan Passado.

Dark fire-cured tobaccos are generally cured with low-burning wood fires on the floors of closed curing barns. Dark fire-cured tobaccos are used for making pipe blends, cigarettes, chewing tobacco, snuff and strong-tasting cigars. Major growing regions for dark fire-cured tobaccos are Tennessee, Kentucky, and Virginia, USA. In one aspect, modified tobacco plants or seeds provided herein are in a dark fire-cured tobacco background selected from the group consisting of Narrow Leaf Madole, Improved Madole, Tom Rosson Madole, Newton's VH Madole, Little Crittenden, Green Wood, Little Wood, Small Stalk Black Mammoth, DT 508, DT 518, DT 592, KY 171, DF 911, DF 485, TN D94, TN D950, VA 309, and VA 359.

Oriental tobaccos are also referred to as Greek, aroma and Turkish tobaccos due to the fact that they are typically grown in eastern Mediterranean regions such as Turkey, Greece, Bulgaria, Macedonia, Syria, Lebanon, Italy, and Romania. The small plant and leaf size, characteristic of today's Oriental varieties, as well as its unique aroma properties are a result of the plant's adaptation to the poor soil and stressful climatic conditions in which it develop over many past centuries. In one aspect, modified tobacco plants or seeds provided herein are in an Oriental tobacco background selected from the group consisting of Izmir, Katerini, Samsun, Basma and Krumovgrad, Trabzon, Thesalian, Tasova, Sinop, Izmit, Hendek, Edirne, Semdinli, Adiyanman, Yayladag, Iskenderun, Duzce, Macedonian, Mavra, Prilep, Bafra, Bursa, Bucak, Bitlis, Balikesir, and any variety essentially derived from any one of the foregoing varieties.

In one aspect, modified tobacco plants, seeds, hybrids, varieties, or lines provided herein are essentially derived from or in the genetic background of BU 64, CC 101, CC 200, CC 13, CC 27, CC 33, CC 35, CC 37, CC 65, CC 67, CC 301, CC 400, CC 500, CC 600, CC 700, CC 800, CC 900, CC 1063, Coker 176, Coker 319, Coker 371 Gold, Coker 48, CU 263, DF911, Galpão, GL 26H, GL 338, GL 350, GL 395, GL 600, GL 737, GL 939, GL 973, GF 157, GF 318, RJR 901, HB 04P, K 149, K 326, K 346, K 358, K394, K 399, K 730, NC 196, NC 37NF, NC 471, NC 55, NC 92, NC2326, NC 95, NC 925, PVH 1118, PVH 1452, PVH 2110, PVH 2254, PVH 2275, VA 116, VA 119, KDH 959, KT 200, KT204LC, KY 10, KY 14, KY 160, KY 17, KY 171, KY 907, KY 907LC, KTY14×L8 LC, Little Crittenden, McNair 373, McNair 944, male sterile KY 14×L8, Narrow Leaf Madole, MS KY171, Narrow Leaf Madole (phph), MS Narrow Leaf Madole, MS TND950, PD 7302LC, PD 7305LC, PD 7309LC, PD 7312LC, PD 7318LC, PD 7319LC, MSTKS 2002, TKF 2002, TKF 6400, TKF 4028, TKF 4024, KT206LC, KT209LC, KT210LC, KT212LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, 'Perique', PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN90LC, TN 97, TN97LC, TN D94, TN D950, a TR (Tom Rosson) Madole, VA 309, VA 359, or any commercial tobacco variety according to standard tobacco breeding techniques known in the art.

All foregoing mentioned specific varieties of dark air-cured, Burley, Maryland, dark fire-cured, or Oriental type are only listed for exemplary purposes. Any additional dark air-cured, Burley, Maryland, dark fire-cured, or Oriental varieties are also contemplated in the present application.

Also provided herein are populations of tobacco plants described herein. In one aspect, a population of tobacco plants provided herein has a planting density of between about 5,000 and about 8000, between about 5,000 and about 7,600, between about 5,000 and about 7,200, between about 5,000 and about 6,800, between about 5,000 and about 6,400, between about 5,000 and about 6,000, between about 5,000 and about 5,600, between about 5,000 and about 5,200, between about 5,200 and about 8,000, between about 5,600 and about 8,000, between about 6,000 and about 8,000, between about 6,400 and about 8,000, between about 6,800 and about 8,000, between about 7,200 and about 8,000, or between about 7,600 and about 8,000 plants per acre. In another aspect, a population of tobacco plants provided herein is in a soil type with low to medium fertility.

Also provided herein are containers of seeds from tobacco plants described herein. A container of tobacco seeds of the present disclosure may contain any number, weight, or volume of seeds. For example, a container can contain at least, or greater than, about 100, at least, or greater than, about 200, at least, or greater than, about 300, at least, or greater than, about 400, at least, or greater than, about 500, at least, or greater than, about 600, at least, or greater than, about 700, at least, or greater than, about 800, at least, or greater than, about 900, at least, or greater than, about 1000, at least, or greater than, about 1500, at least, or greater than, about 2000, at least, or greater than, about 2500, at least, or greater than, about 3000, at least, or greater than, about 3500, at least, or greater than, or about 4000 or more seeds. Alternatively, the container can contain at least, or greater than, about 1 ounce, at least, or greater than, about 5 ounces, at least, or greater than, about 10 ounces, at least, or greater than, about 1 pound, at least, or greater than, about 2 pounds, at least, or greater than, about 3 pounds, at least, or greater than, about 4 pounds, at least, or greater than, about 5 pounds or more seeds. Containers of tobacco seeds may be any container available in the art. By way of non-limiting example, a container may be a box, a bag, a packet, a pouch, a tape roll, a tube, or a bottle.

The present disclosure also provides methods for breeding tobacco lines, cultivars, or varieties comprising cured leaf with reduced or eliminated TSNAs (and, optionally, also comprising increased antioxidants or decreased nitrite). Breeding can be carried out via any known procedures. DNA fingerprinting, SNP mapping, haplotype mapping or similar technologies may be used in a marker-assisted selection (MAS) breeding program to transfer or breed a desirable trait or allele into a tobacco plant. For example, a breeder can create segregating populations in an $F_2$ or backcross generation using $F_1$ hybrid plants provided herein or further crossing the $F_1$ hybrid plants with other donor plants with an agronomically desirable genotype. Plants in the $F_2$ or backcross generations can be screened for a desired agronomic trait or a desirable chemical profile using one of the techniques known in the art or listed herein. Depending on the expected inheritance pattern or the MAS technology used, self-pollination of selected plants before each cycle of backcrossing to aid identification of the desired individual plants can be performed. Backcrossing or other breeding procedure can be repeated until the desired phenotype of the recurrent parent is recovered. In one aspect, a recurrent parent in the present disclosure can be a flue-cured variety, a Burley variety, a dark air-cured variety, a dark fire-cured variety, or an Oriental variety. In another aspect, a recurrent parent can be a modified tobacco plant, line, or variety. Other breeding techniques can be found, for example, in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N.Y., incorporated herein by reference in their entirety.

Results of a plant breeding program using modified tobacco plants described herein includes useful lines, cultivars, varieties, progeny, inbreds, and hybrids of the present disclosure. As used herein, the term "variety" refers to a population of plants that share constant characteristics which separate them from other plants of the same species. A variety is often, although not always, sold commercially. While possessing one or more distinctive traits, a variety is further characterized by a very small overall variation between individuals within that variety. A "pure line" variety may be created by several generations of self-pollination and selection, or vegetative propagation from a single parent using tissue or cell culture techniques. A variety can be essentially derived from another line or variety. As defined by the International Convention for the Protection of New Varieties of Plants (Dec. 2, 1961, as revised at Geneva on Nov. 10, 1972; on Oct. 23, 1978; and on Mar. 19, 1991), a variety is "essentially derived" from an initial variety if: a) it is predominantly derived from the initial variety, or from a variety that is predominantly derived from the initial variety, while retaining the expression of the essential characteristics that result from the genotype or combination of genotypes of the initial variety; b) it is clearly distinguishable from the initial variety; and c) except for the differences which result from the act of derivation, it conforms to the initial variety in the expression of the essential characteristics that result from the genotype or combination of genotypes of the initial variety. Essentially derived varieties can be obtained, for example, by the selection of a natural or induced mutant, a somaclonal variant, a variant individual from plants of the initial variety, backcrossing, or transformation. A first tobacco variety and a second tobacco variety from which the first variety is essentially derived, are considered as having essentially identical genetic background. A "line" as distinguished from a variety most often denotes a group of plants used non-commercially, for example in plant research. A line typically displays little overall variation between individuals for one or more traits of interest, although there may be some variation between individuals for other traits.

In one aspect, the present disclosure provides a method of producing a tobacco plant comprising crossing at least one tobacco plant of a first tobacco variety with at least one tobacco plant of a second tobacco variety, where the at least one tobacco plant of the first tobacco variety comprising one or more desired traits, e.g., comprising a reduced level of one or more tobacco-specific nitrosamines (TSNAs) in cured leaf and further comprising one or more traits selected from the group consisting of: a reduced level of nitrite, an increased level of oxygen radical absorbance capacity (ORAC), and an increased level of one or more antioxidants, wherein said reduced or increased level is compared to a control tobacco plant of the same cross grown and cured under comparable conditions; and selecting for progeny tobacco plants that exhibit the one or more desired traits. In one aspect, a first tobacco variety provided herein comprises modified tobacco plants. In another aspect, a second tobacco variety provided herein comprises modified tobacco plants. In one aspect, a first or second tobacco variety is male sterile. In another aspect, a first or second tobacco variety is cytoplasmically male sterile. In another aspect, a first or second tobacco variety is female sterile. In one aspect, a first or second tobacco variety is an elite variety. In another aspect, a first or second tobacco variety is a hybrid.

In one aspect, the present disclosure provides a method of introgressing one or more transgenes or mutations into a tobacco variety, the method comprising: (a) crossing a first tobacco variety comprising one or more transgenes or mutations provided herein with a second tobacco variety without the one or more transgenes or mutations to produce one or more progeny tobacco plants; (b) genotyping the one or more progeny tobacco plants for the one or more transgenes or mutations; and (c) selecting a progeny tobacco plant comprising the one or more transgenes or mutations. In another aspect, these methods further comprise backcrossing the selected progeny tobacco plant with the second tobacco variety. In further aspects, these methods further comprise: (d) crossing the selected progeny plant with itself or with the second tobacco variety to produce one or more further progeny tobacco plants; and (e) selecting a further progeny tobacco plant comprising the one or more transgenes or mutations. In one aspect, the second tobacco variety is an elite variety.

In one aspect, the present disclosure provides a method of growing a population of modified tobacco plants disclosed herein, where the method comprises planting a population of tobacco seeds comprising one or more mutations, one or more transgenes, or both as described herein, where the one or more modified tobacco plants or cured leaf of one or more modified tobacco plants comprise a reduced level of one or more TSNAs and further comprises one or more traits selected from the group consisting of an increased level of one or more antioxidants, an increased level of oxygen radical absorbance capacity (ORAC), and a reduced level of nitrite, wherein said reduced or increased level is compared to control tobacco plants or cured leaf of a control tobacco plant of the same variety when grown and cured under comparable conditions.

In one aspect, the present disclosure provides a method of growing a modified tobacco plant described herein comprising planting a modified tobacco seed described herein; and growing the modified tobacco plant from the seed. In an aspect, growing comprises germinating a seed. In another aspect, growing comprises placing a seedling in soil, agar, agar-based media, or a hydroponics system. In another aspect, growing comprises providing a seed or plant with water, light (e.g., artificial light, sunlight), fertilizer, a rooting media, or a combination thereof. In an aspect, growing can take place indoors (e.g., a greenhouse) or outdoors (e.g., a field). In one aspect, growing comprises placing a seed or a plant in a container.

In one aspect, this disclosure provides a method for manufacturing a modified seed, comprising introducing a recombinant DNA construct provided herein into a plant cell; screening a population of plant cells for the recombinant DNA construct; selecting one or more plant cells from the population; generating one or more modified plants from the one or more plant cells; and collecting one or more modified seeds from the one or more modified plants.

As used herein, "locus" is a chromosome region where a polymorphic nucleic acid, trait determinant, gene, or marker is located. The loci of this disclosure comprise one or more polymorphisms in a population; e.g., alternative alleles are present in some individuals. As used herein, "allele" refers to an alternative nucleic acid sequence at a particular locus. The length of an allele can be as small as 1 nucleotide base, but is typically larger. For example, a first allele can occur on one chromosome, while a second allele occurs on a second homologous chromosome, e.g., as occurs for different chromosomes of a heterozygous individual, or between different homozygous or heterozygous individuals in a population. As used herein, a chromosome in a diploid plant is "hemizygous" when only one copy of a locus is present. For example, an inserted transgene is hemizygous when it only inserts into one sister chromosome (i.e., the second sister chromosome does not contain the inserted transgene).

In one aspect, a modified plant, seed, plant component, plant cell, or plant genome is homozygous for a transgene provided herein. In another aspect, a modified plant, seed, plant component, plant cell, or plant genome is heterozygous for a transgene provided herein. In one aspect, a modified plant, seed, plant component, plant cell, or plant genome is hemizygous for a transgene provided herein. In one aspect, a modified plant, seed, plant component, plant cell, or plant genome is homozygous for a mutation provided herein. In another aspect, a modified plant, seed, plant component, plant cell, or plant genome is heterozygous for a mutation provided herein. In one aspect, a modified plant, seed, plant component, plant cell, or plant genome is hemizygous for a mutation provided herein.

As used herein, "introgression" or "introgress" refers to the transmission of a desired allele of a genetic locus from one genetic background to another.

As used herein, "crossed" or "cross" means to produce progeny via fertilization (e.g. cells, seeds or plants) and includes crosses between different plants (sexual) and self-fertilization (selfing).

As used herein, "backcross" and "backcrossing" refer to the process whereby a progeny plant is repeatedly crossed back to one of its parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. The initial cross gives rise to the $F_1$ generation. The term "$BC_1$" refers to the second use of the recurrent parent, "$BC_2$" refers to the third use of the recurrent parent, and so on. In one aspect, a backcross is performed repeatedly, with a progeny individual of each successive backcross generation being itself backcrossed to the same parental genotype.

As used herein, "elite variety" means any variety that has resulted from breeding and selection for superior agronomic performance.

As used herein, "selecting" or "selection" in the context of breeding refer to the act of picking or choosing desired individuals, normally from a population, based on certain pre-determined criteria.

In one aspect, tobacco plants provided herein are hybrid plants. Hybrids can be produced by preventing self-pollination of female parent plants (e.g., seed parents) of a first variety, permitting pollen from male parent plants of a second variety to fertilize the female parent plants, and allowing $F_1$ hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by male sterility (MS), or transgenic male sterility where a transgene inhibits microsporogenesis and/or pollen formation, or self-incompatibility. Female parent plants containing MS are particularly useful. In aspects in which the female parent plants are MS, pollen may be harvested from male fertile plants and applied manually to the stigmas of MS female parent plants, and the resulting $F_1$ seed is harvested. Additionally, female sterile plants can also be used to prevent self-fertilization.

Plants can be used to form single-cross tobacco $F_1$ hybrids. Pollen from a male parent plant is manually transferred to an emasculated female parent plant or a female parent plant that is male sterile to form $F_1$ seed. Alternatively, three-way crosses can be carried out where a single-cross $F_1$ hybrid is used as a female parent and is crossed with a different male parent. As another alternative, double-cross hybrids can be created where the $F_1$ progeny of two different single-crosses are themselves crossed. Self-incompatibility can be used to particular advantage to prevent self-pollination of female parents when forming a double-cross hybrid.

In one aspect, a tobacco variety provided herein is male sterile. In another aspect, a tobacco variety provided herein is cytoplasmic male sterile (CMS). Male sterile tobacco plants may be produced by any method known in the art. Methods of producing male sterile tobacco are described in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N.Y. 761 pp. In another aspect, a tobacco variety provided herein is female sterile. As a non-limiting example, female sterile plants can be made by mutating the STIG1 gene. See, for example, Goldman et al. 1994, *EMBO Journal* 13:2976-2984.

As used herein, the term "sequence identity" or "identity" in the context of two polynucleotide or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity."

The use of the term "polynucleotide" is not intended to limit the present disclosure to polynucleotides comprising DNA. Those of ordinary skill in the art will recognize that polynucleotides and nucleic acid molecules can comprise ribonucleotides and combinations of ribonucleotides and deoxyribonucleotides. Such deoxyribonucleotides and ribonucleotides include both naturally occurring molecules and synthetic analogues. The polynucleotides of the present disclosure also encompass all forms of sequences including, but not limited to, single-stranded forms, double-stranded forms, hairpins, stem-and-loop structures, and the like.

As used herein, the term "polypeptide" refers to a chain of at least two covalently linked amino acids.

Nucleic acid molecules, polypeptides, or proteins provided herein can be isolated or substantially purified. An "isolated" or "purified" nucleic acid molecule, polypeptide, protein, or biologically active portion thereof, is substantially or essentially free from components that normally accompany or interact with the polynucleotide or protein as found in its naturally occurring environment. For example, an isolated or purified polynucleotide or protein is substantially free of other cellular material, or culture medium when produced by recombinant techniques, or substantially free of chemical precursors or other chemicals when chemically synthesized. In another aspect, an isolated polypeptide provided herein is substantially free of cellular material in preparations having less than about 30%, less than about 20%, less than about 10%, less than about 5%, or less than about 1% (by dry weight) of chemical precursors or non-protein-of-interest chemicals. Fragments of the disclosed polynucleotides and polypeptides encoded thereby are also encompassed by the present invention. Fragments of a polynucleotide may encode polypeptide fragments that retain the biological activity of the native polypeptide. Alternatively, fragments of a polynucleotide that are useful as hybridization probes or PCR primers using methods known in the art generally do not encode fragment polypeptides retaining biological activity. Fragments of a polynucleotide provided herein can range from at least about 20 nucleotides, about 50 nucleotides, about 70 nucleotides, about 100 nucleotides, about 150 nucleotides, about 200 nucleotides, about 250 nucleotides, about 300 nucleotides, and up to the full-length polynucleotide encoding the polypeptides of the invention, depending on the desired outcome.

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

In one aspect, this disclosure provides methods of detecting in plant cells one or more recombinant nucleic acids and polypeptides described here. Without being limiting, nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, N.Y.).

Polypeptides can be detected using antibodies. Techniques for detecting polypeptides using antibodies include enzyme linked immunosorbent assays (ELISAs), Western blots, immunoprecipitations and immunofluorescence. An antibody provided herein can be a polyclonal antibody or a monoclonal antibody. An antibody having specific binding affinity for a polypeptide provided herein can be generated using methods well known in the art. An antibody provided herein can be attached to a solid support such as a microtiter plate using methods known in the art.

Detection (e.g., of an amplification product, of a hybridization complex, of a polypeptide) can be accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

In one aspect, the present disclosure also provides a method of reducing the level of one or more TSNAs in cured leaf from a tobacco plant, the method comprising increasing the level of one or more antioxidants in the tobacco plant by expressing a biosynthetic enzyme, a regulatory transcription factor, a transporter, a catabolic enzyme, or a combination thereof, for the one or more antioxidants. In another aspect, a method comprises expressing a gene promoting the production or accumulation of one or more antioxidants are selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin. In a further aspect, a method comprises expressing a gene promoting the production or accumulation of one or more antioxidants are selected from the group consisting of Delphnidin, Cyanidin, Procyanidin, Prodelphinidin, Hesperetin, Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C. In one aspect, a method does not substantially reduce the level of total alkaloids in the tobacco plant. In another aspect, a method does not substantially reduce the level of nicotine in the tobacco plant.

In one aspect, the present disclosure provides a method for reducing the level of one or more TSNAs in cured tobacco leaf or a tobacco product made therefrom, the method comprising increasing the level of one or more antioxidants in a tobacco plant via a transgene encoding or directly modulating an antioxidant biosynthetic enzyme, a regulatory transcription factor of an antioxidant, an antioxidant transporter, an antioxidant metabolic enzyme, or a combination thereof; and reducing the level of one or more TSNAs in cured tobacco leaf from the tobacco plant or a tobacco product made from the cured tobacco leaf. In another aspect of a method described herein, the level of one or more TSNAs reduces by at least 50%, by at least 45%, by at least 40%, by at least 35%, by at least 30%, by at least 25%, by at least 20%, by at least 15%, by at least 10%, or by at least 5%, compared to cured leaf from a control tobacco plant not comprising a transgene. In a further aspect of a method described herein, cured leaf of the modified tobacco plant produces or comprises less than 2, less than 1.9, less than 1.8, less than 1.7, less than 1.6, less than 1.5, less than 1.4, less than 1.3, less than 1.2, less than 1.1, less than 1.0, less than 0.9, less than 0.8, less than 0.7, less than 0.6, less than 0.5, less than 0.4, less than 0.3, less than 0.2, less than 0.15, less than 0.1, or less than 0.05 ppm total TSNAs. In a further aspect of a method described herein, cured leaf of the modified tobacco plant comprises between 2 and 0.05, between 1.9 and 0.05, between 1.8 and 0.05, between 1.7 and 0.05, between 1.6 and 0.05, between 1.5 and 0.05, between 1.4 and 0.05, between 1.3 and 0.05, between 1.2 and 0.05, between 1.1 and 0.05, between 1.0 and 0.05, between 0.9 and 0.05, between 0.8 and 0.05, between 0.7 and 0.05, between 0.6 and 0.05, between 0.5 and 0.05, between 0.4 and 0.05, between 0.3 and 0.05, between 0.2 and 0.05, between 0.15 and 0.05, or between 0.1 and 0.05 ppm total TSNAs. In a further aspect of a method described herein, cured leaf of the modified tobacco plant comprises between 2 and 0.05, between 1.8 and 0.1, between 1.5 and 0.15, between 1.2 and 0.2, between 1.0 and 0.3, between 0.8 and 0.4, or between 0.6 and 0.5 ppm total TSNAs. In a further aspect of a method described herein, one or more TSNAs are selected from the group consisting of N'-nitrosonornicotine (NNN), 4-methylnitrosoamino-1-(3-pyridyl)-1-butanone (NNK), N'-nitrosoanatabine (NAT), N'-nitrosoanabasine (NAB), and any combination thereof. In a further aspect of a method described herein, the TSNA reduction comprises a reduction of NNK. In a further aspect of a method described herein, the TSNA reduction consists of a reduction of NNK. In a further aspect of a method described herein, NNK is reduced below 0.08 parts per million, below 0.07 parts per million, below 0.06 parts per million, or below 0.05 parts per million, as measured in freeze-dried cured leaf samples using liquid chromatography with tandem mass spectrometry.

In another aspect of a method described herein, the tobacco plant comprises reduced nicotine demethylase activity compared to a control plant. In a further aspect of a method described herein, the tobacco plant comprises at least one mutation in a nicotine demethylase gene selected from the group consisting of CYP82E4, CYP82E5, CYP82E10, and a combination thereof. In another aspect of a method described herein, a method reduces nitrite levels in cured tobacco leaf comprising the transgene. In another aspect of a method described herein, a method increases the oxygen radical absorbance capacity level in cured tobacco leaf comprising the transgene. In another aspect of a method described herein, the one or more antioxidants that are increased in cured tobacco leaf comprising the transgene are selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin. In a further aspect of a method described herein, the one or more antioxidants that are increased in cured tobacco leaf comprising the transgene are selected from the group consisting of Delphnidin, Cyanidin, Procyanidin, Prodelphinidin, Hesperetin, Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C In a further aspect of a method described herein, a method does not substantially reduce the level of total alkaloids in a tobacco plant. In a further aspect of a method described herein, a method does not substantially reduce the level of nicotine in a tobacco plant. In an aspect of a method described herein, a transgene encodes or directly modulates a biosynthetic enzyme, a regulatory transcription factor, a transporter, a metabolic enzyme, or a combination thereof, for one or more antioxidants selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin. In a further aspect of a method described herein, a transgene encodes or directly modulates a biosynthetic enzyme, a regulatory transcription factor, a transporter, a metabolic enzyme, or a combination thereof, for one or more antioxidants selected from the group consisting of Delphnidin, Cyanidin, Procyanidin, Prodelphinidin, Hesperetin, Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C In another aspect of a method described herein, the transgene encodes a protein comprising a sequence having at least 50%, 55%, 60%, 65%, 70%, 75%, 80%, 85%, 90%, 95%, 97%, 98%, 99%, or 100% identity to a sequence selected from the group consisting of SEQ ID No. 1 to 23 and 47 to 52.

In one aspect, the present disclosure provides a method for reducing the level of one or more TSNAs in cured tobacco leaf or a tobacco product made therefrom, a method comprising increasing the level of one or more antioxidants in a tobacco plant via a genetic modification in an endogenous gene, wherein the endogenous gene encodes an antioxidant biosynthetic enzyme, a regulatory transcription factor of an antioxidant, an antioxidant transporter, an antioxidant metabolic enzyme, or a combination thereof; and reducing the level of one or more TSNAs in cured tobacco leaf from the tobacco plant or a tobacco product made from the cured tobacco leaf. In another aspect of a method described herein, the level of one or more TSNAs is reduced by at least 50%, by at least 45%, by at least 40%, by at least 35%, by at least 30%, by at least 25%, by at least 20%, by at least 15%, by at least 10%, or by at least 5%, compared to cured leaf from a control tobacco plant not comprising a transgene. In a further aspect of a method described herein, one or more TSNAs are selected from the group consisting of N'-nitrosonornicotine (NNN), 4-methylnitrosoamino-1-(3-pyridyl)-1-butanone (NNK), N'-nitrosoanatabine (NAT) N'-nitrosoanabasine (NAB), and any combination thereof. In further aspect of a method described herein, the TSNA reduction comprises a reduction of NNK. In a further aspect of a method described herein, the TSNA reduction consists of a reduction of NNK. In a further aspect of a method described herein, NNK is reduced below 0.08 parts per million as measured in freeze-dried cured leaf samples using liquid chromatography with tandem mass spectrometry.

In another aspect of a method described herein, a tobacco plant comprises reduced nicotine demethylase activity compared to a control plant. In a further aspect of a method described herein, a tobacco plant comprises at least one mutation in a nicotine demethylase gene selected from the group consisting of CYP82E4, CYP82E5, CYP82E10, and a combination thereof. In another aspect of a method described herein, a method reduces nitrite levels in cured tobacco leaf comprising a transgene. In another aspect of a method described herein, a method increases the oxygen radical absorbance capacity level in cured tobacco leaf comprising a transgene. In another aspect of a method described herein, a method increases the oxygen radical absorbance capacity level in cured tobacco leaf comprising a transgene. In another aspect of a method described herein, one or more increased antioxidants are tobacco native antioxidants. In another aspect of a method described herein, the one or more antioxidants that are increased in cured tobacco leaf comprising a transgene are selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin. In a further aspect of the method, the one or more antioxidants that are increased in cured tobacco leaf comprising the transgene are selected from the group consisting of Delphnidin, Cyanidin, Procyanidin, Prodelphinidin, Hesperetin, Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C.

In a further aspect of a method described herein, a method does not substantially reduce the level of total alkaloids in a tobacco plant. In a further aspect of a method described herein, a method does not substantially reduce the level of nicotine in a tobacco plant. In another aspect of a method described herein, an endogenous gene encodes a protein comprising a sequence having at least 50%, 55%, 60%, 65%, 70%, 75%, 80%, 85%, 90%, 95%, 97%, 98%, 99%, or 100% identity to a sequence selected from the group consisting of SEQ ID No. 1 to 23 and 47 to 52.

In one aspect, the present disclosure provides a method for manufacturing a tobacco product, the method comprising obtaining cured tobacco leaf comprising a transgene or comprising a genetic modification in an endogenous gene, and further comprising an increased level of one or more antioxidants compared to cured tobacco leaf control lacking a transgene or a genetic modification, wherein an endogenous gene encodes an antioxidant biosynthetic enzyme, a regulatory transcription factor of an antioxidant, an antioxidant transporter, an antioxidant metabolic enzyme, or a combination thereof, wherein a transgene encodes or directly modulates an antioxidant biosynthetic enzyme, a regulatory transcription factor of an antioxidant, an antioxidant transporter, an antioxidant metabolic enzyme, or a combination thereof; and producing a tobacco product from cured tobacco leaf, wherein a tobacco product comprises a reduced level of one or more TSNAs relative to a control tobacco product prepared from a control cured tobacco leaf. In another aspect of a method described herein, cured tobacco leaf comprises a transgene encoding or directly modulating an antioxidant biosynthetic enzyme, a regulatory transcription factor of an antioxidant, an antioxidant transporter, an antioxidant metabolic enzyme, or a combination thereof. In another aspect of a method described herein, cured tobacco leaf comprises a genetic modification in an antioxidant biosynthetic enzyme, a regulatory transcription factor of an antioxidant, an antioxidant transporter, an antioxidant metabolic enzyme, or a combination thereof.

In another aspect of a method described herein, the level of one or more TSNAs is reduced by at least 50%, by at least 45%, by at least 40%, by at least 35%, by at least 30%, by at least 25%, by at least 20%, by at least 15%, by at least 10%, or by at least 5%, compared to cured leaf from a control tobacco plant not comprising a transgene. In another aspect of a method described herein, the level of one or more TSNAs is reduced by at least 50%, by at least 45%, by at least 40%, by at least 35%, by at least 30%, by at least 25%, by at least 20%, by at least 15%, by at least 10%, or by at least 5%, compared to cured leaf from a control tobacco plant not comprising a genetic modification in an endogenous gene. In another aspect of a method described herein, cured tobacco leaf comprises a reduced nitrite level compared to a control plant without a transgene. In another aspect of a method described herein, the cured tobacco leaf comprises a reduced nitrite level compared to a control plant without a genetic modification in an endogenous gene.

In one aspect, the present disclosure provides a method for preparing cured tobacco leaf, the method comprising growing a tobacco plant comprising a transgene or a genetic modification in an endogenous gene, and further comprising an increased level of one or more antioxidants compared to a control cured tobacco leaf lacking a transgene or a genetic modification, wherein an endogenous gene encodes an antioxidant biosynthetic enzyme, a regulatory transcription factor of an antioxidant, an antioxidant transporter, an antioxidant metabolic enzyme, or a combination thereof, wherein a transgene encodes or directly modulates an antioxidant biosynthetic enzyme, a regulatory transcription factor of an antioxidant, an antioxidant transporter, an antioxidant metabolic enzyme, or a combination thereof; and preparing cured leaf from a tobacco plant, wherein cured leaf comprises a reduced level of one or more TSNAs relative to a control cured leaf from a control tobacco plant not comprising a transgene or a genetic modification. In another aspect of a method described herein, cured tobacco leaf comprises a transgene encoding or directly modulating an antioxidant biosynthetic enzyme, a regulatory transcription factor of an antioxidant, an antioxidant transporter, an antioxidant metabolic enzyme, or a combination thereof. In another aspect of a method described herein, cured tobacco leaf comprises a genetic modification in an antioxidant biosynthetic enzyme, a regulatory transcription factor of an antioxidant, an antioxidant transporter, an antioxidant metabolic enzyme, or a combination thereof.

In another aspect of a method described herein, the level of one or more TSNAs is reduced by at least 50%, by at least 45%, by at least 40%, by at least 35%, by at least 30%, by at least 25%, by at least 20%, by at least 15%, by at least 10%, or by at least 5%, compared to cured leaf from a control tobacco plant not comprising a transgene. In another aspect of a method described herein, the level of one or more TSNAs is reduced by at least 50%, by at least 45%, by at least 40%, by at least 35%, by at least 30%, by at least 25%, by at least 20%, by at least 15%, by at least 10%, or by at least 5%, compared to cured leaf from a control tobacco plant not comprising a genetic modification in an endogenous gene. In another aspect of a method described herein, cured tobacco leaf comprises a reduced nitrite level compared to a control plant without a transgene. In another aspect of a method described herein, cured tobacco leaf comprises a reduced nitrite level compared to a control plant without a genetic modification in an endogenous gene.

In one aspect, the present disclosure provides cured leaf of a modified tobacco plant, wherein cured leaf comprises a reduced level of one or more tobacco-specific nitrosamines (TSNAs) and further comprises an increased level of one or more antioxidants and a reduced nitrite level, wherein reduced and increased levels are compared to a control cured leaf of an unmodified tobacco plant of the same variety when grown and cured under comparable conditions, wherein a modification comprises a transgene or a genetic modification in an endogenous gene, wherein a transgene or an endogenous gene encodes an antioxidant biosynthetic enzyme, a regulatory transcription factor of an antioxidant, an antioxidant transporter, an antioxidant metabolic enzyme, or a combination thereof; wherein a modified tobacco plant does not comprise a transgene overexpressing an *Arabidopsis* PAP1 protein. In a further aspect of a method described herein, cured leaf of the modified tobacco plant produces or comprises less than 2, less than 1.9, less than 1.8, less than 1.7, less than 1.6, less than 1.5, less than 1.4, less than 1.3, less than 1.2, less than 1.1, less than 1.0, less than 0.9, less than 0.8, less than 0.7, less than 0.6, less than 0.5, less than 0.4, less than 0.3, less than 0.2, less than 0.15, less than 0.1, or less than 0.05 ppm total TSNAs. In a further aspect of a method described herein, cured leaf of the modified tobacco plant comprises between 2 and 0.05, between 1.9 and 0.05, between 1.8 and 0.05, between 1.7 and 0.05, between 1.6 and 0.05, between 1.5 and 0.05, between 1.4 and 0.05, between 1.3 and 0.05, between 1.2 and 0.05, between 1.1 and 0.05, between 1.0 and 0.05, between 0.9 and 0.05, between 0.8 and 0.05, between 0.7 and 0.05, between 0.6 and 0.05, between 0.5 and 0.05, between 0.4 and 0.05, between 0.3 and 0.05, between 0.2 and 0.05, between 0.15 and 0.05, or between 0.1 and 0.05 ppm total TSNAs. In a further aspect of a method described herein, cured leaf of the modified tobacco plant comprises between 2 and 0.05, between 1.8 and 0.1, between 1.5 and 0.15, between 1.2 and 0.2, between 1.0 and 0.3, between 0.8 and 0.4, or between 0.6 and 0.5 ppm total TSNAs. In a further aspect of a method described herein, one or more TSNAs are selected from the group consisting of N'-nitrosonornicotine (NNN), 4-methylnitrosoamino-1-(3-pyridyl)-1-butanone (NNK), N'-nitrosoanatabine (NAT) N'-nitrosoanabasine (NAB), and any combination thereof. In a further aspect of a method described herein, the TSNA reduction comprises a reduction of NNK. In a further aspect of a method described herein, the TSNA reduction consists of a reduction of NNK. In a further aspect of a method described herein, NNK is reduced below 0.08 parts per million, below 0.07 parts per million, below 0.06 parts per million, or below 0.05 parts per million, as measured in freeze-dried cured leaf samples using liquid chromatography with tandem mass spectrometry. In another aspect of a method described herein, a tobacco plant comprises reduced nicotine demethylase activity compared to a control plant. In a further aspect of a method described herein, a tobacco plant comprises at least one mutation in a nicotine demethylase gene selected from the group consisting of CYP82E4, CYP82E5, CYP82E10, and a combination thereof. In a further aspect of a method described herein, a method provides a tobacco product comprising cured leaf of a modified tobacco plant.

Having now generally described the disclosure, the same will be more readily understood through reference to the following examples that are provided by way of illustration, and are not intended to be limiting of the present disclosure, unless specified.

The following are exemplary embodiments of the present disclosure.

Embodiment 1

Cured leaf of a modified tobacco plant, wherein said cured leaf comprises a reduced level of one or more tobacco-specific nitrosamines (TSNAs) and further comprises an increased level of one or more antioxidants, wherein said reduced and increased levels are compared to a control cured leaf of an unmodified tobacco plant of the same variety when grown and cured under comparable conditions.

Embodiment 2

A tobacco product comprising the cured leaf of embodiment 1.

Embodiment 3

A tobacco product made from the cured leaf of any one of embodiments 1 or 2.

Embodiment 4

The cured leaf of any one of embodiments 1 to 3, wherein said one or more antioxidants are endogenous antioxidants.

Embodiment 5

The cured leaf of any one of embodiments 1 to 4, wherein said one or more antioxidants are not exogenous antioxidants administered, added, or introduced to said cured leaf or modified tobacco plant.

Embodiment 6

The cured leaf of any one of embodiments 1 to 5, wherein said one or more antioxidants are produced by said modified tobacco plant.

Embodiment 7

The cured leaf of any one of embodiments 1 to 6, wherein said one or more antioxidants are produced in vivo in said cured leaf.

Embodiment 8

The cured leaf of any one of embodiments 1 to 7, wherein said cured leaf comprises an increased level of oxygen radical absorbance capacity (ORAC) compared to said control cured leaf.

Embodiment 9

The cured leaf of any one of embodiments 1 to 8, wherein said modified tobacco plant comprises in a green leaf an increased level of oxygen radical absorbance capacity (ORAC) compared to said unmodified tobacco plant of the same variety when grown under comparable conditions.

Embodiment 10

The cured leaf of any one of embodiments 1 and 4 to 9, wherein said reduced or increased level is within about 10%, within about 20%, within about 30%, within about 40%, within about 50%, within about 60%, within about 70%, within about 80%, within about 90%, within about 92%, within about 94%, within about 95%, within about 96%, within about 97%, within about 98%, or within about 99% lower or higher than the level in said control cured leaf.

Embodiment 11

The cured leaf of any one of embodiments 1 and 4 to 10, wherein said reduced or increased level is within about 1 fold, within about 2 folds, within about 3 folds, within about 4 folds, within about 5 folds, within about 6 folds, within about 7 folds, within about 8 folds, within about 9 folds, within about 10 folds, within about 15 folds, within about 20 folds, within about 25 folds, or within about 30 folds lower or higher than the level in said control cured leaf.

Embodiment 12

The cured leaf of any one of embodiments 1 and 4 to 11, wherein said reduced or increased level is at least about 10%, at least about 20%, at least about 30%, at least about 40%, at least about 50%, at least about 60%, at least about 70%, at least about 80%, at least about 90%, at least about 92%, at least about 94%, at least about 95%, at least about 96%, at least about 97%, at least about 98%, or at least about 99% lower or higher than the level in said control cured leaf.

Embodiment 13

The cured leaf of any one of embodiments 1 and 4 to 12, wherein said reduced or increased level is at least about 1 fold, at least about 2 folds, at least about 3 folds, at least about 4 folds, at least about 5 folds, at least about 6 folds, at least about 7 folds, at least about 8 folds, at least about 9 folds, at least about 10 folds, at least about 15 folds, at least about 20 folds, at least about 25 folds, or at least about 30 folds lower or higher than the level in said control cured leaf.

Embodiment 14

The cured leaf of any one of embodiments 1 and 4 to 13, wherein said reduced or increased level is about 10%, about 20%, about 30%, about 40%, about 50%, about 60%, about 70%, about 80%, about 90%, about 92%, about 94%, about 95%, about 96%, about 97%, about 98%, or about 99% lower or higher than the level in said control cured leaf.

Embodiment 15

The cured leaf of any one of embodiments 1 and 4 to 14, wherein said reduced or increased level is about 1 fold, about 2 folds, about 3 folds, about 4 folds, about 5 folds, about 6 folds, about 7 folds, about 8 folds, about 9 folds, about 10 folds, about 15 folds, about 20 folds, about 25 folds, or about 30 folds lower or higher than the level in said control cured leaf.

Embodiment 16

The cured leaf of any one of embodiments 1 and 4 to 15, wherein said reduced or increased level is about 1-2 folds, about 2-3 folds, about 3-4 folds, about 4-5 folds, about 5-6 folds, about 6-7 folds, about 7-8 folds, about 8-9 folds, about 9-10 folds, about 10-15 folds, about 15-20 folds, about 20-25 folds, about 25-30 folds, or about 30-50 folds lower or higher than the level in said control cured leaf.

Embodiment 17

The cured leaf of any one of embodiments 1 and 4 to 16, wherein said reduced or increased level is about 1-10 folds, about 2-10 folds, about 3-10 folds, about 4-10 folds, about 5-10 folds, about 6-10 folds, about 7-10 folds, about 8-10 folds, about 9-10 folds, about 10-50 folds, about 15-50 folds, about 20-50 folds, about 25-50 folds, or about 30-50 folds lower or higher than the level in said control cured leaf.

Embodiment 18

The cured leaf of any one of embodiments 1 to 9, wherein said increased level of one or more antioxidants is from the modification in said modified tobacco plant.

Embodiment 19

The cured leaf of embodiment 18, wherein said modification in said modified tobacco plant comprises a tobacco genome mutation or a transgene.

Embodiment 20

The cured leaf of any one of embodiments 18 or 19, wherein said modification in said modified tobacco plant comprises a tobacco genome mutation in a gene encoding a biosynthetic enzyme, a regulatory transcription factor, a transporter, a catabolic enzyme, or a combination thereof, for one or more antioxidants selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin.

Embodiment 21

The cured leaf of any one of embodiments 18 to 20, wherein said modification in said modified tobacco plant comprises a tobacco genome mutation in a gene encoding a biosynthetic enzyme, a regulatory transcription factor, a transporter, a catabolic enzyme, or a combination thereof, for one or more antioxidants selected from the group consisting of Delphnidin, Cyanidin, Procyanidin, Prodelphinidin, Hesperetin, Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C.

Embodiment 22

The cured leaf of any one of embodiments 18 to 21, wherein said modification in said modified tobacco plant comprises a tobacco genome mutation in a gene encoding a protein comprising a sequence having at least 50%, 55%, 60%, 65%, 70%, 75%, 80%, 85%, 90%, 95%, 97%, 98%, 99%, or 100% identity to a sequence selected from the group consisting of SEQ ID No. 1 to 23 and 47 to 52.

Embodiment 23

The cured leaf of any one of embodiments 18 to 22, wherein said modification in said modified tobacco plant comprises a transgene encoding or directly modulating a biosynthetic enzyme, a regulatory transcription factor, a transporter, a catabolic enzyme, or a combination thereof, for one or more antioxidants selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin.

Embodiment 24

The cured leaf of any one of embodiments 18 to 23, wherein said modification in said modified tobacco plant comprises a transgene encoding or directly modulating a biosynthetic enzyme, a regulatory transcription factor, a transporter, a catabolic enzyme, or a combination thereof, for one or more antioxidants selected from the group consisting of Delphnidin, Cyanidin, Procyanidin, Prodelphinidin, Hesperetin, Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C.

Embodiment 25

The cured leaf of any one of embodiments 18 to 24, wherein said modification in said modified tobacco plant comprises a transgene encoding a protein comprising a sequence having at least 50%, 55%, 60%, 65%, 70%, 75%, 80%, 85%, 90%, 95%, 97%, 98%, 99%, or 100% identity to a sequence selected from the group consisting of SEQ ID No. 1 to 23 and 47 to 52.

Embodiment 26

The cured leaf of any one of embodiments 18 to 25, wherein said modification in said modified tobacco plant comprises a transgene that targets a gene comprising a sequence having at least 50%, 55%, 60%, 65%, 70%, 75%, 80%, 85%, 90%, 95%, 97%, 98%, 99%, or 100% identity to a sequence selected from the group consisting of SEQ ID No. 24 to 46 and 53 to 58.

Embodiment 27

The cured leaf of any one of embodiments 1 to 26, wherein said cured leaf comprises a reduced level of nitrite compared to said control cured leaf.

Embodiment 28

The cured leaf of any one of embodiments 1 to 27, wherein said cured leaf is flue-cured tobacco, air-cured burley tobacco, air-cured dark tobacco, fire-cured dark tobacco, or oriental tobacco.

Embodiment 29

Cured leaf from a modified tobacco plant comprising a reduced level of one or more tobacco-specific nitrosamines (TSNAs) and further comprising an increased level of one or more antioxidants, wherein said reduced and increased levels are compared to a control tobacco plant of the same variety when grown and cured under comparable conditions.

Embodiment 30

The cured leaf from a modified tobacco plant of embodiment 29, wherein said cured leaf from a modified tobacco plant comprises an increased level of oxygen radical absorbance capacity (ORAC) compared to said control tobacco plant when grown and cured undergrown and cured under comparable conditions.

Embodiment 31

The cured leaf from a modified tobacco plant of any one of embodiments 29 or 30, wherein said cured leaf from a modified tobacco plant comprises a reduced level of nitrite compared to said control tobacco plant when grown and cured under comparable conditions.

Embodiment 32

The cured leaf from a modified tobacco plant of any one of embodiments 29 to 31, wherein said cured leaf from a modified tobacco plant comprises a reduced level of total TSNAs compared to said control tobacco plant when grown and cured under comparable conditions.

Embodiment 33

The cured leaf from a modified tobacco plant of any one of embodiments 29 to 32, wherein said one or more antioxidants are tobacco endogenous antioxidants.

Embodiment 34

Cured leaf from a modified tobacco plant comprising a reduced level of one or more tobacco-specific nitrosamines (TSNAs) and further comprising a reduced level of nitrite, wherein said reduced levels are compared to cured leaf from a control tobacco plant of the same variety when grown and cured under comparable conditions.

Embodiment 35

The cured leaf from a modified tobacco plant of embodiment 34, wherein said cured leaf from a modified tobacco plant comprises an increased level of oxygen radical absorbance capacity (ORAC) compared to said control tobacco plant when grown and cured under comparable conditions.

Embodiment 36

Cured leaf from a modified tobacco plant comprising a reduced level of one or more tobacco-specific nitrosamines (TSNAs) and further comprising an increased level of oxygen radical absorbance capacity (ORAC), and wherein said reduced and increased levels are compared to cured leaf from a control tobacco plant of the same variety when grown and cured under comparable conditions.

Embodiment 37

The cured leaf from a modified tobacco plant of any one of embodiments 30, 35, or 36, wherein said increased level of oxygen radical absorbance capacity (ORAC) is based on a green leaf sample or cured leaf sample.

Embodiment 38

The cured leaf from a modified tobacco plant of any one of embodiments 29 to 37, wherein said one or more tobacco-specific nitrosamines (TSNAs) are selected from the group consisting of N'-nitrosonornicotine (NNN), 4-methylnitrosoamino-1-(3-pyridyl)-1-butanone (NNK), N'-nitrosoanatabine (NAT) N'-nitrosoanabasine (NAB), and any combination thereof.

Embodiment 39

The cured leaf from a modified tobacco plant of any one of embodiments 29 to 38, wherein said increased level of said one or more TSNAs is based on cured leaf sample.

Embodiment 40

The cured leaf from a modified tobacco plant of any one of embodiments 29 to 39, wherein the level of said one or more TSNAs is measured based on a freeze-dried cured leaf sample using liquid chromatograph with tandem mass spectrometry (LC/MS/MS).

Embodiment 41

The cured leaf from a modified tobacco plant of any one of embodiments 29 to 33, wherein said one or more antioxidants are selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin.

Embodiment 42

The cured leaf from a modified tobacco plant of any one of embodiments 29 to 33, wherein said one or more antioxidants are selected from the group consisting of Delphnidin, Cyanidin, Procyanidin, Prodelphinidin, Hesperetin, Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C.

Embodiment 43

The cured leaf from a modified tobacco plant of any one of embodiments 29 to 42, wherein said modified tobacco plant comprises an antioxidant that is undetectable in said cured leaf from a control plant.

Embodiment 44

The cured leaf of a modified tobacco plant of any one of embodiments 29 to 43, wherein said modified tobacco plant comprises an antioxidant that does not exist in said cured leaf from a control plant.

Embodiment 45

The cured leaf from a modified tobacco plant of any one of embodiments 29 to 44, wherein said cured leaf from a modified tobacco plant comprises one or more mutations capable of providing said reduced level of one or more TSNAs.

Embodiment 46

The cured leaf from a modified tobacco plant of embodiment 45, wherein said one or more mutations are further capable of providing one or more traits selected from the group consisting of:
A. a reduced level of nitrite,
B. an increased level of oxygen radical absorbance capacity (ORAC), and
C. an increased level of one or more antioxidants;
D. wherein said reduced or increased level is compared to said cured leaf of a control tobacco plant when grown and cured under comparable.

Embodiment 47

The cured leaf from a modified tobacco plant of any one of embodiments 45 or 46, wherein said one or more mutations comprise a mutation type selected from the group consisting of an insertion, a deletion, an inversion, a duplication, a substitution, and a combination thereof.

Embodiment 48

The cured leaf from a modified tobacco plant of any one of embodiments 45 to 47, wherein said one or more mutations are capable of activating one or more genes encoding a biosynthetic enzyme, a regulatory transcription factor, a transporter, a catabolic enzyme, or a combination thereof, for one or more antioxidants.

Embodiment 49

The cured leaf from a modified tobacco plant of any one of embodiments 45 to 48, wherein said one or more mutations are in one or more genes encoding a biosynthetic enzyme, a regulatory transcription factor, a transporter, a catabolic enzyme, or a combination thereof, for one or more antioxidants selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin.

Embodiment 50

The cured leaf from a modified tobacco plant of any one of embodiments 45 to 49, wherein said one or more mutations are in one or more genes encoding a biosynthetic enzyme, a regulatory transcription factor, a transporter, a catabolic enzyme, or a combination thereof, for one or more antioxidants selected from the group consisting of Delphnidin, Cyanidin, Procyanidin, Prodelphinidin, Hesperetin, Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C.

Embodiment 51

The cured leaf from a modified tobacco plant of any one of embodiments 45 to 50, wherein said one or more mutations are introduced via a system selected from the group consisting of chemical mutagenesis, irradiation mutagenesis, transposon mutagenesis, *Agrobacterium*-mediated transformation, protoplast transformation, electroporation, ballistic transformation, a meganuclease, a zinc-finger nuclease (ZFN), a transcription activator-like effector nuclease (TALEN), a clustered regularly-interspaced short palindromic repeats (CRISPR)/Cas9 system, a CRISPR/Cpf1 system, a CRISPR/Csm1 system, and a combination thereof.

Embodiment 52

The modified tobacco plant of any one of embodiments 45 to 51, one or more mutations are in a gene encoding a polypeptide having at least 50%, 55%, 60%, 65%, 70%, 75%, 80%, 85%, 90%, 95%, 97%, 98%, 99%, or 100% identity to a sequence selected from the group consisting of SEQ ID No. 1 to 23 and 47 to 52.

Embodiment 53

The modified tobacco plant of any one of embodiments 45 to 52, one or more mutations are in a gene comprise a coding sequence having at least 50%, 55%, 60%, 65%, 70%, 75%, 80%, 85%, 90%, 95%, 97%, 98%, 99%, or 100% identity to a sequence selected from the group consisting of SEQ ID No. 24 to 46 and 53 to 58.

Embodiment 54

The modified tobacco plant of any one of embodiments 29 to 44, wherein said modified tobacco plant comprises one or more transgenes capable of providing said reduced level of one or more TSNAs in cured leaf.

Embodiment 55

The cured leaf from a modified tobacco plant of embodiment 54, wherein said one or more transgenes further cause said one or more traits selected from the group consisting of:

A. a reduced level of nitrite,
B. an increased level of oxygen radical absorbance capacity (ORAC), and
C. an increased level of one or more antioxidants;
D. wherein said reduced or increased level is compared to said cured leaf from a control tobacco plant when grown and cured under comparable.

Embodiment 56

The modified tobacco plant of any one of embodiments 54 or 55, wherein said one or more transgenes comprises a promoter selected from the group consisting of a constitutive promoter, an inducible promoter, and a tissue-preferred promoter.

Embodiment 57

The modified tobacco plant of any one of embodiments 54 to 56, wherein said one or more transgenes comprises a leaf-specific promoter, a shoot-specific promoter, or a root-specific promoter.

Embodiment 58

The modified tobacco plant of any one of embodiments 54 to 57, wherein said one or more transgenes encode a biosynthetic enzyme, a regulatory transcription factor, a transporter, a catabolic enzyme, or a combination thereof, for one or more antioxidants selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin.

Embodiment 59

The modified tobacco plant of any one of embodiments 54 to 58, wherein said one or more transgenes encode a biosynthetic enzyme, a regulatory transcription factor, a transporter, a catabolic enzyme, or a combination thereof, for one or more antioxidants selected from the group consisting of Delphnidin, Cyanidin, Procyanidin, Prodelphinidin, Hesperetin, Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C.

Embodiment 60

The modified tobacco plant of any one of embodiments 54 to 59, wherein said one or more transgenes encodes one or more polypeptides having at least 50%, 55%, 60%, 65%, 70%, 75%, 80%, 85%, 90%, 95%, 97%, 98%, 99%, or 100% identity to a sequence selected from the group consisting of SEQ ID No. 1 to 23 and 47 to 52.

Embodiment 61

The modified tobacco plant of any one of embodiments 54 to 60, wherein said one or more transgenes targets one or more endogenous genes having at least 50%, 55%, 60%, 65%, 70%, 75%, 80%, 85%, 90%, 95%, 97%, 98%, 99%, or 100% identity to a sequence selected from the group consisting of SEQ ID No. 24 to 46 and 53 to 58.

Embodiment 62

The modified tobacco plant of any one of embodiments 54 to 61, wherein said one or more transgenes comprises one or more polynucleotide sequences encoding one or more polypeptides having at least 50%, 55%, 60%, 65%, 70%, 75%, 80%, 85%, 90%, 95%, 97%, 98%, 99%, or 100% identity to a sequence selected from the group consisting of SEQ ID No. 1 to 23 and 47 to 52.

Embodiment 63

The modified tobacco plant of any one of embodiments 54 to 62, wherein said one or more transgenes comprise a sequence having at least 50%, 55%, 60%, 65%, 70%, 75%, 80%, 85%, 90%, 95%, 97%, 98%, 99%, or 100% identity to a sequence selected from the group consisting of SEQ ID No. 24 to 46 and 53 to 58.

Embodiment 64

The modified tobacco plant of any one of embodiments 54 to 63, wherein said one or more transgenes comprise a sequence having at least 50%, 55%, 60%, 65%, 70%, 75%, 80%, 85%, 90%, 95%, 97%, 98%, 99%, or 100% identity to a sequence selected from the group consisting of SEQ ID No. 24 to 46 and 53 to 58.

Embodiment 65

The modified tobacco plant of any one of embodiments 54 to 64, wherein said modified tobacco plant is a cis-genic plant.

Embodiment 66

The modified tobacco plant of any one of embodiments 29 to 65, wherein said modified tobacco plant has a similar or higher leaf yield compared to said control tobacco plant when grown and cured under comparable conditions.

Embodiment 67

The modified tobacco plant of embodiment 66, wherein said higher leaf yield is at least 0.5%, 1%, 2.5%, 5%, 10%, 15%, or at least 20% higher.

Embodiment 68

The modified tobacco plant of any one of embodiments 29 to 66, wherein said modified tobacco plant has a similar plant height compared to said control tobacco plant when grown and cured under comparable conditions.

Embodiment 69

The modified tobacco plant of embodiment 68, wherein said similar plant height is within 1%, 5%, 10%, 20%, or 25%.

Embodiment 70

The modified tobacco plant of any one of embodiments 29 to 68, wherein said modified tobacco plant has a similar cured leaf chemistry profile compared to said control tobacco plant when grown and cured under comparable conditions.

Embodiment 71

The modified tobacco plant of any one of embodiments 29 to 68, wherein said modified tobacco plant produces cured leaf that has a similar or higher USDA grade index value compared to cured leaf from said control tobacco plant when grown and cured under comparable conditions.

Embodiment 72

The modified tobacco plant of embodiment 45 or 54, wherein said modified tobacco plant is homozygous for said one or more transgenes or said one or more mutations.

Embodiment 73

The modified tobacco plant of any one of embodiments 45, 54, or 72, wherein said modified tobacco plant is hemizygous for said one or more transgenes or said one or more mutations.

Embodiment 74

The modified tobacco plant of any one of embodiments 45, 54, 72, or 73, wherein said modified tobacco plant is heterozygous for said one or more transgenes or said one or more mutations.

Embodiment 75

The modified tobacco plant of any one of embodiments 29 to 74, wherein said modified tobacco plant further comprises reduced nicotine demethylase activity compared to said control plant when grown and cured under comparable conditions.

Embodiment 76

The modified tobacco plant of embodiment 75, wherein said tobacco plant comprises at least one mutation in a nicotine demethylase gene selected from the group consisting of CYP82E4, CYP82E5, CYP82E10, and a combination thereof.

Embodiment 77

The cured leaf from a modified tobacco plant of any one of embodiments 29 to 75, wherein said modified tobacco plant further comprises a reduced level of total alkaloids compared to said cured leaf from a control plant when grown and cured under comparable conditions.

Embodiment 78

The cured leaf from a modified tobacco plant of any one of embodiments 29 to 77, wherein said modified tobacco plant further comprises a substantially similar level of total alkaloids compared to said cured leaf from a control plant when grown and cured under comparable conditions.

Embodiment 79

The cured leaf from a modified tobacco plant of any one of embodiments 29 to 78, wherein said modified tobacco plant further comprises a reduced level of nicotine compared to said cured leaf from a control plant when grown and cured under comparable conditions.

Embodiment 80

The cured leaf from a modified tobacco plant of any one of embodiments 29 to 79, wherein said modified tobacco plant further comprises a substantially similar level of nicotine compared to said cured leaf from a control plant when grown and cured under comparable conditions.

Embodiment 81

The modified tobacco plant of embodiment any one of embodiments 29 to 80, wherein said modified plant is selected from the group consisting of a flue-cured variety, a Burley variety, a Maryland variety, a dark variety, and an Oriental variety.

Embodiment 82

The modified tobacco plant of any one of embodiments 29 to 81, wherein said modified tobacco plant is selected from the group consisting a BU 64 plant, a CC 101 plant, a CC 200 plant, a CC 13 plant, a CC 27 plant, a CC 33 plant, a CC 35 plant, a CC 37 plant, a CC 65 plant, a CC 67 plant, a CC 301 plant, a CC 400 plant, a CC 500 plant, CC 600 plant, a CC 700 plant, a CC 800 plant, a CC 900 plant, a CC 1063 plant, a Coker 176 plant, a Coker 319 plant, a Coker 371 Gold plant, a Coker 48 plant, a CU 263 plant, a DF911 plant, a Galpao plant, a GL 26H plant, a GL 338 plant, a GL 350 plant, a GL 395 plant, a GL 600 plant, a GL 737 plant, a GL 939 plant, a GL 973 plant, a GF 157 plant, a GF 318 plant, an RJR 901 plant, an HB 04P plant, a K 149 plant, a K 326 plant, a K 346 plant, a K 358 plant, a K394 plant, a K 399 plant, a K 730 plant, an NC 196 plant, an NC 37NF plant, an NC 471 plant, an NC 55 plant, an NC 92 plant, an NC2326 plant, an NC 95 plant, an NC 925 plant, a PVH 1118 plant, a PVH 1452 plant, a PVH 2110 plant, a PVH 2254 plant, a PVH 2275 plant, a VA 116 plant, a VA 119 plant, a KDH 959 plant, a KT 200 plant, a KT204LC plant, a KY 10 plant, a KY 14 plant, a KY 160 plant, a KY 17 plant, a KY 171 plant, a KY 907 plant, a KY 907LC plant, a KTY14×L8 LC plant, a Little Crittenden plant, a McNair 373 plant, a McNair 944 plant, a male sterile KY 14×L8 plant, a Narrow Leaf Madole plant, a MS KY171 plant, a Narrow Leaf Madole (phph) plant, a MS Narrow Leaf Madole plant, a MS TND950 plant, a PD 7302LC plant, a PD 7305LC plant, a PD 7309LC plant, a PD 7312LC plant, a PD 7318LC plant, a PD 7319LC plant, a MSTKS 2002 plant, a TKF 2002 plant, a TKF 6400 plant, a TKF 4028 plant, a TKF 4024 plant, a KT206LC plant, a KT209LC plant, a KT210LC plant, a KT212LC plant, an NC 100 plant, an NC 102 plant, an NC 2000 plant, an NC 291 plant, an NC 297 plant, an NC 299 plant, an NC 3 plant, an NC 4 plant, an NC 5 plant, an NC 6 plant, an NC7 plant, an NC 606 plant, an NC 71 plant, an NC 72 plant, an NC 810 plant, an NC BH 129 plant, an NC 2002 plant, a Neal Smith Madole plant, an OXFORD 207 plant, a 'Perique' plant, a PVH03 plant, a PVH09 plant, a PVH19 plant, a PVH50 plant, a PVH51 plant, an R 610 plant, an R 630 plant, an R 7-11 plant, an R 7-12 plant, an RG 17 plant, an RG 81 plant, an RG H51 plant, an RGH 4 plant, an RGH 51 plant, an RS 1410 plant, a Speight 168 plant, a Speight 172 plant, a Speight 179 plant, a Speight 210 plant, a Speight 220 plant, a Speight 225 plant, a Speight 227 plant, a Speight 234 plant, a Speight G-28 plant, a Speight G-70 plant, a Speight H-6 plant, a Speight H20 plant, a Speight NF3 plant, a TI 1406 plant, a TI 1269 plant, a TN 86 plant, a TN86LC plant, a TN 90 plant, a TN90LC plant, a TN 97 plant, a TN97LC plant, a TN D94 plant, a TN D950 plant, a TR (Tom Rosson) Madole plant, a VA 309 plant, and a VA 359 plant.

Embodiment 83

The modified tobacco plant of any one of embodiments 29 to 82, wherein said modified tobacco plant is a hybrid.

Embodiment 84

The modified tobacco plant of any one of embodiments 29 to 83, wherein said modified tobacco plant is male sterile or cytoplasmically male sterile (CMS).

Embodiment 85

The modified tobacco plant of any one of embodiments 29 to 84, wherein said modified tobacco plant is female sterile.

Embodiment 86

The cured tobacco leaf or modified tobacco plant of any one of embodiments 29 to 85, wherein said reduced or increased level is within about 10%, within about 20%, within about 30%, within about 40%, within about 50%, within about 60%, within about 70%, within about 80%, within about 90%, within about 92%, within about 94%, within about 95%, within about 96%, within about 97%, within about 98%, or within about 99% lower or higher than the level in said control cured tobacco leaf or tobacco plant when grown and cured under comparable conditions.

Embodiment 87

The cured tobacco leaf or modified tobacco plant of any one of embodiments 29 to 86, wherein said reduced or increased level is within about 1 fold, within about 2 folds, within about 3 folds, within about 4 folds, within about 5 folds, within about 6 folds, within about 7 folds, within about 8 folds, within about 9 folds, within about 10 folds, within about 15 folds, within about 20 folds, within about 25 folds, or within about 30 folds lower or higher than the level in said control cured tobacco leaf or tobacco plant when grown and cured under comparable conditions.

Embodiment 88

The cured tobacco leaf or modified tobacco plant of any one of embodiments 29 to 87, wherein said reduced or increased level is at least about 10%, at least about 20%, at least about 30%, at least about 40%, at least about 50%, at least about 60%, at least about 70%, at least about 80%, at least about 90%, at least about 92%, at least about 94%, at least about 95%, at least about 96%, at least about 97%, at least about 98%, or at least about 99% lower or higher than the level in said control cured tobacco leaf or tobacco plant when grown and cured under comparable conditions.

Embodiment 89

The cured tobacco leaf or modified tobacco plant of any one of embodiments 29 to 88, wherein said reduced or increased level is at least about 1 fold, at least about 2 folds, at least about 3 folds, at least about 4 folds, at least about 5 folds, at least about 6 folds, at least about 7 folds, at least about 8 folds, at least about 9 folds, at least about 10 folds, at least about 15 folds, at least about 20 folds, at least about 25 folds, or at least about 30 folds lower or higher than the level in said control cured tobacco leaf or tobacco plant when grown and cured under comparable conditions.

Embodiment 90

The cured tobacco leaf or modified tobacco plant of any one of embodiments 29 to 89, wherein said reduced or increased level is about 10%, about 20%, about 30%, about 40%, about 50%, about 60%, about 70%, about 80%, about 90%, about 92%, about 94%, about 95%, about 96%, about 97%, about 98%, or about 99% lower or higher than the level in said control cured tobacco leaf or tobacco plant when grown and cured under comparable conditions.

Embodiment 91

The cured tobacco leaf or modified tobacco plant of any one of embodiments 29 to 90, wherein said reduced or increased level is about 1 fold, about 2 folds, about 3 folds, about 4 folds, about 5 folds, about 6 folds, about 7 folds, about 8 folds, about 9 folds, about 10 folds, about 15 folds, about 20 folds, about 25 folds, or about 30 folds lower or higher than the level in said control cured tobacco leaf or tobacco plant when grown and cured under comparable conditions.

Embodiment 92

The cured tobacco leaf or modified tobacco plant of any one of embodiments 29 to 91, wherein said reduced or increased level is about 1-2 folds, about 2-3 folds, about 3-4 folds, about 4-5 folds, about 5-6 folds, about 6-7 folds, about 7-8 folds, about 8-9 folds, about 9-10 folds, about 10-15 folds, about 15-20 folds, about 20-25 folds, about 25-30 folds, or about 30-50 folds lower or higher than the level in said control cured tobacco leaf or tobacco plant when grown and cured under comparable conditions.

Embodiment 93

The cured tobacco leaf or modified tobacco plant of any one of embodiments 29 to 92, wherein said reduced or increased level is about 1-10 folds, about 2-10 folds, about 3-10 folds, about 4-10 folds, about 5-10 folds, about 6-10 folds, about 7-10 folds, about 8-10 folds, about 9-10 folds, about 10-50 folds, about 15-50 folds, about 20-50 folds, about 25-50 folds, or about 30-50 folds lower or higher than the level in said cured tobacco leaf or control tobacco plant when grown and cured under comparable conditions.

Embodiment 94

A tobacco leaf of the modified tobacco plant of any one of embodiments 29 to 93.

Embodiment 95

The tobacco leaf of embodiment 94, wherein said tobacco leaf is cured tobacco leaf.

Embodiment 96

The tobacco leaf of any one of embodiments 94 or 95, wherein said cured tobacco leaf is air-cured, fire-cured, sun-cured, or flue-cured.

Embodiment 97

The cured tobacco leaf of any one of embodiments 94 to 96 comprising less than 2 ppm total TSNAs, wherein the level of said total TSNAs is measured based on a freeze-dried cured leaf sample using liquid chromatograph with tandem mass spectrometry (LC/MS/MS).

Embodiment 98

The cured tobacco leaf of any one of embodiments 94 to 97, wherein said cured tobacco leaf comprises less than 2, less than 1.8, less than 1.5, less than 1.2, less than 1.0, less than 0.8, less than 0.6, less than 0.4, less than 0.3, less than 0.2, less than 0.15, less than 0.1, or less than 0.05 ppm total TSNAs.

Embodiment 99

The cured tobacco leaf of any one of embodiments 94 to 98, wherein said cured tobacco leaf comprises between 2 and 0.05, between 1.8 and 0.05, between 1.5 and 0.05, between 1.2 and 0.05, between 1.0 and 0.05, between 0.8 and 0.05, between 0.6 and 0.05, between 0.4 and 0.05, between 0.3 and 0.05, between 0.2 and 0.05, between 0.15 and 0.05, or between 0.1 and 0.05 ppm total TSNAs.

Embodiment 100

The cured tobacco leaf of any one of embodiments 94 to 99, wherein said cured tobacco leaf comprises between 2 and 0.05, between 1.8 and 0.1, between 1.5 and 0.15, between 1.2 and 0.2, between 1.0 and 0.3, between 0.8 and 0.4, or between 0.6 and 0.5 ppm total TSNAs.

Embodiment 101

The cured tobacco leaf of any one of embodiments 94 to 100, comprising less than 0.08 ppm 4-methylnitrosoamino-1-(3-pyridyl)-1-butanone (NNK), wherein the level of said total TSNAs is measured based on a freeze-dried cured leaf sample using liquid chromatograph with tandem mass spectrometry (LC/MS/MS).

Embodiment 102

A tobacco product comprising cured leaf from the modified tobacco plant of any one of embodiments 29 to 85.

Embodiment 103

The tobacco product of embodiment 102, wherein said tobacco product is selected from the group consisting of a cigarette, a kretek, a bidi cigarette, a cigar, a cigarillo, a non-ventilated cigarette, a vented recess filter cigarette, pipe tobacco, snuff, snus, chewing tobacco, moist smokeless tobacco, fine cut chewing tobacco, long cut chewing tobacco, pouched chewing tobacco product, gum, a tablet, a lozenge, an e-liquid for a vaping device, and a dissolving strip.

Embodiment 104

A seed giving rise to the modified tobacco plant of any one of embodiments 29 to 85.

Embodiment 105

A method comprising:
A. planting the seed of embodiment 104; and
B. growing a tobacco plant from said seed.

Embodiment 106

A method comprising preparing a tobacco product using cured tobacco leaf from the modified tobacco plant of any one of embodiments 29 to 85.

Embodiment 107

A method of reducing the level of one or more TSNAs in cured leaf from a tobacco plant, said method comprising increasing the level of one or more antioxidants in said tobacco plant by expressing a biosynthetic enzyme, a regulatory transcription factor, a transporter, a catabolic enzyme, or a combination thereof, for said one or more antioxidants.

Embodiment 108

The method of embodiment 107, wherein said one or more antioxidants are selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin.

Embodiment 109

The method of any one of embodiment s 107 or 108, wherein said one or more antioxidants are selected from the group consisting of Delphnidin, Cyanidin, Procyanidin, Prodelphinidin, Hesperetin, Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C.

Embodiment 110

The method of any one of embodiment s 107 to 109, wherein said method does not substantially reduce the level of total alkaloids in said cured leaf from a tobacco plant.

Embodiment 111

The method of one of embodiment s 107 to 110, wherein said method does not substantially reduce the level of nicotine in said cured leaf from a tobacco plant.

Embodiment 112

A method for producing a tobacco plant comprising:
A. crossing at least one tobacco plant of a first tobacco variety with at least one tobacco plant of a second tobacco variety, wherein said at least one tobacco plant of said first tobacco variety is the modified tobacco plant of any one of embodiments 29 to 93; and
B. selecting for cured leaf from a progeny tobacco plant comprising a reduced level of one or more tobacco-specific nitrosamines (TSNAs) and further comprising one or more traits selected from the group consisting of
  i. a reduced level of nitrite,
  ii. an increased level of oxygen radical absorbance capacity (ORAC), and
  iii. an increased level of one or more antioxidants;
  iv. wherein said reduced or increased level is compared to cured leaf from a control tobacco plant of the same cross grown and cured under comparable conditions.

EXAMPLES

Example 1. Plant Transformation

Figure 2:
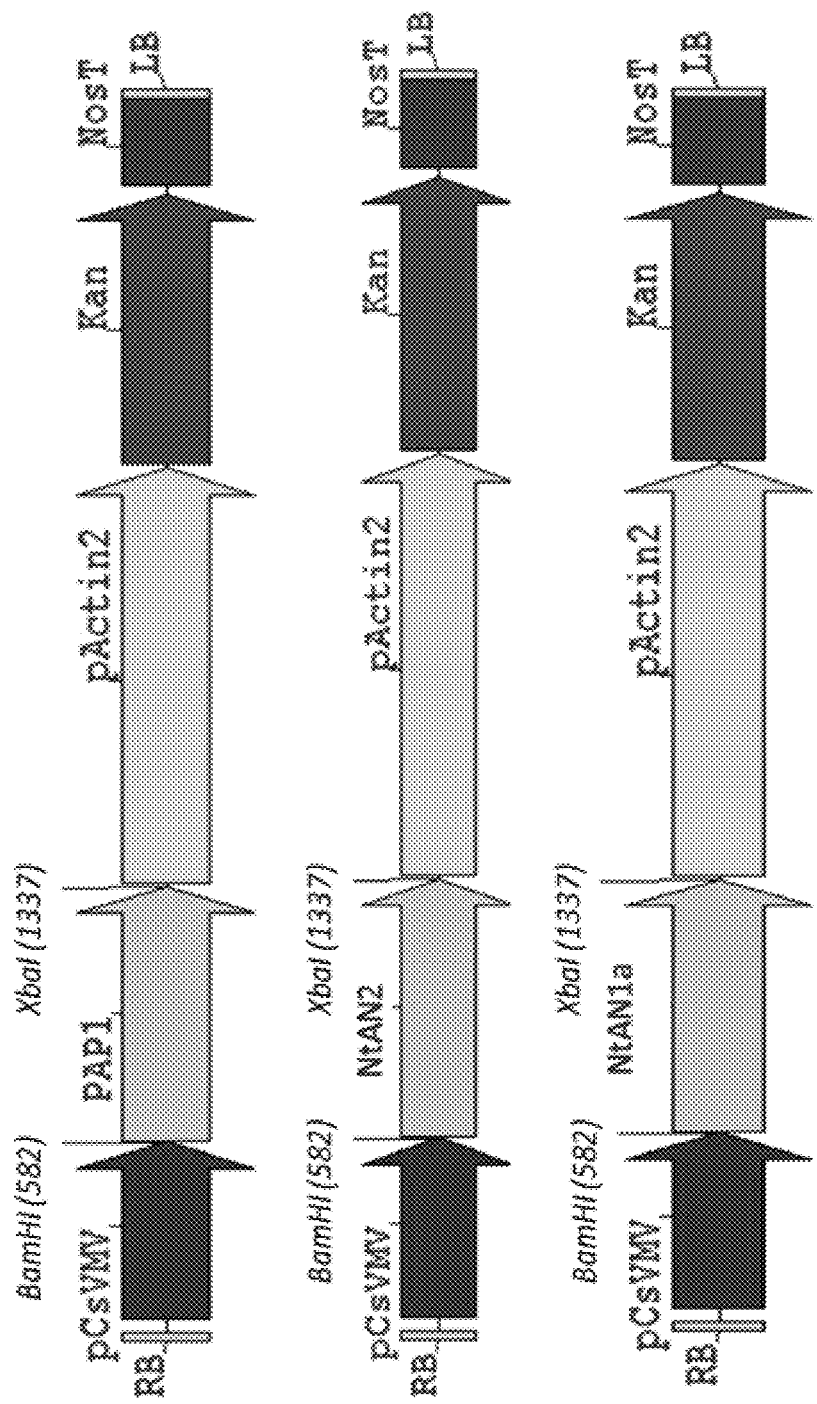
FIG. 2: Cloning of AtPAP1, NtAN2, and NtAN1 into 45-2-7 binary vector.

Tobacco plants overexpressing a gene of interest are generated via *Agrobacterium*-mediated transformation. An expression vector, p45-2-7 (FIG. 2), is used as a backbone to generate multiple transformation vectors. p45-2-7 contains a CsVMV promoter, a NOS terminator, and a cassette comprising a kanamycin selection marker (NPT II) operably linked to an Actin2 promoter and a NOS terminator. Nucleic acid vectors comprising transgenes of interest are introduced into tobacco leaf discs via *Agrobacterium* transformation. See, for example, Mayo et al., 2006, *Nat Protoc.* 1:1105-11 and Horsch et al., 1985, *Science* 227:1229-1231.

Narrow Leaf Madole (NLM) tobacco plants are grown in Magenta™ GA-7 boxes and leaf discs are cut and placed into Petri plates. *Agrobacterium tumefaciens* cells comprising a transformation vector are collected by centrifuging a 20 mL cell suspension in a 50 mL centrifuge tube at 3500 RPM for 10 minutes. The supernatant is removed and the *Agrobacterium tumefaciens* cell pellet is re-suspended in 40 mL liquid re-suspension medium. Tobacco leaf, avoiding the midrib, are cut into eight 0.6 cm discs with a #15 razor blade and placed upside down in a Petri plate. A thin layer of Murashige & Skoog with B5 vitamins liquid re-suspension medium is added to the Petri plate and the leaf discs are poked uniformly with a fine point needle. About 25 mL of the *Agrobacterium tumefaciens* suspension is added to the Petri plate and the leaf discs are incubated in the suspension for 10 minutes.

Leaf discs are transferred to co-cultivation Petri plates (½ MS medium) and discs are placed upside down in contact with filter paper overlaid on the co-cultivation TOM medium (MS medium with 20 g/L sucrose; 1 mg/L indole-3-acetic acid; and 2.5 mg/L 6-benzyl aminopurine (BAP)). The Petri plate is sealed with parafilm prior to incubation in dim light (60-80 mE/ms) with 18 hours on, 6 hours off photoperiods at 24 degrees Celsius for three days. After incubation, leaf discs are transferred to regeneration/selection TOM K medium Petri plates (TOM medium plus 300 mg/L kanamycin). Leaf discs are sub-cultured bi-weekly to fresh TOM K medium in dim light with 18 hours on, 6 hours off photoperiods at 24 degrees Celsius until shoots become excisable. Shoots from leaf are removed with forceps and inserted in MS basal medium with 100 mg/L kanamycin. Shoots on MS basal medium with 100 mg/L kanamycin are incubated at 24 degrees Celsius with 18 hours on, 6 hours off photoperiods with high intensity lighting (6080 mE/ms) to induce rooting.

When plantlets containing both shoots and roots grow large enough (e.g., reach approximately half the height of a Magenta™ GA-7 box), they are transferred to soil. Established seedlings are transferred to a greenhouse for further analysis and to set seed. Control plants are either NLM plants that have not been transformed or NLM plants that have been transformed with an empty p45-2-7 vector.

Example 2. AtPAP1 Overexpressing Plants Comprise Reduced TSNAs

Figure 3:
FIG. 3: A control plant (left) exhibits a similar growth profile compared AtPAP1 overexpression plants (right). AtPAP1 plants exhibit a purple color due to anthocyanin accumulation.

Tobacco plants overexpressing AtPAP1 are generated via *Agrobacterium*-mediated transformation. AtPAP1, comprising SEQ ID NO:46, is incorporated into an overexpression vector and transformed into tobacco as described in Example 1. After transformation, established seedlings are transferred to a greenhouse for further analysis and to set seed. Transformed plants are developmentally similar to control plants except that they exhibit a purple color due to anthocyanin accumulation as shown in FIG. 3.

The effect of AtPAP1 overexpression on TSNA levels is determined for five T1 AtPAP1 overexpression lines (six plants each) after cultivation in the greenhouse. At flowering, the plants are topped. After four to six weeks, plants are harvested and leaf is cured in PGC chambers. Cured leaf samples are freeze dried and crushed to 1 mm.

Figures 4, 4A:
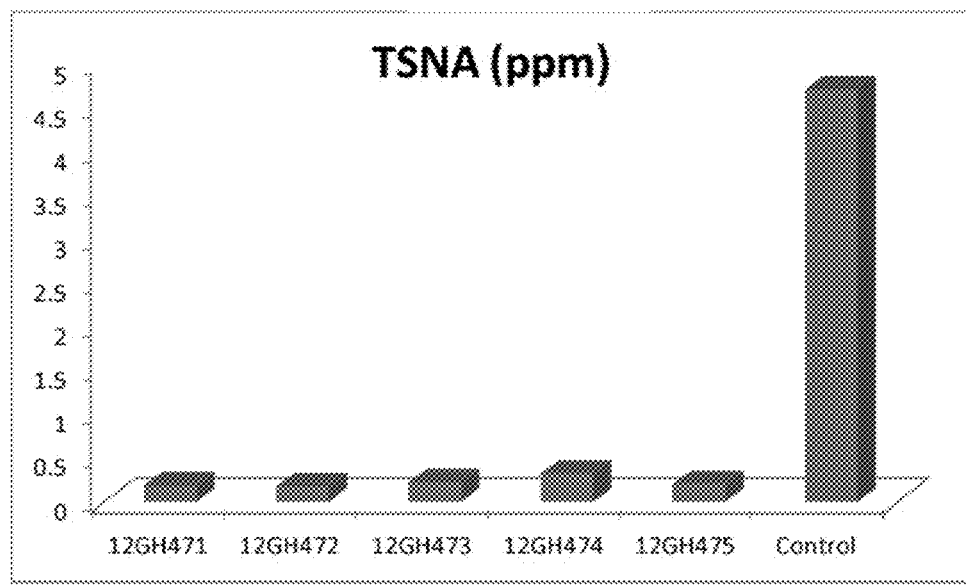
FIG. 4: TSNA reduction in five AtPAP1 overexpression lines.
FIG. 4A: total TSNAs are reduced in AtPAP1 overexpression lines.
Figure 4B:
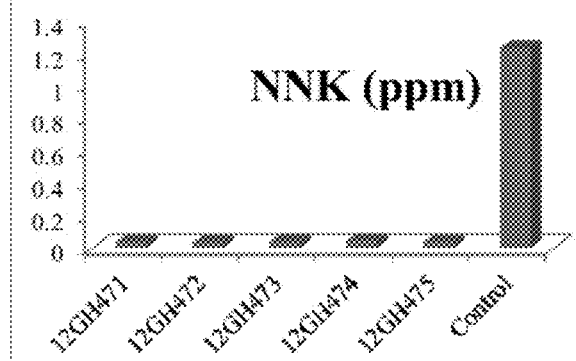
FIG. 4B: NNN levels are reduced in AtPAP1 overexpression lines compared to controls.
Figure 4C:
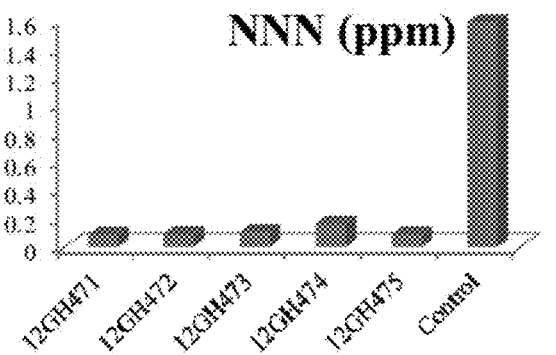
FIG. 4C: NNK levels are reduced in AtPAP1 overexpression lines compared to controls.
Figure 4D:
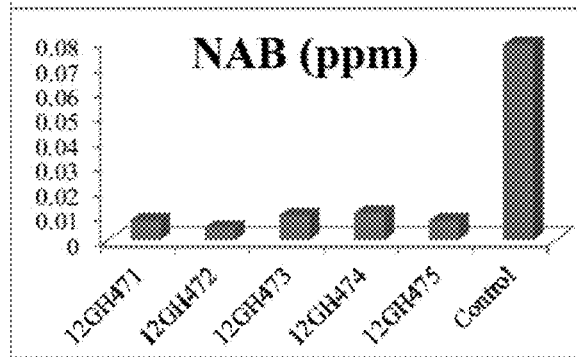
FIG. 4D: NAB levels are reduced in AtPAP1 overexpression lines compared to controls.
Figure 4E:
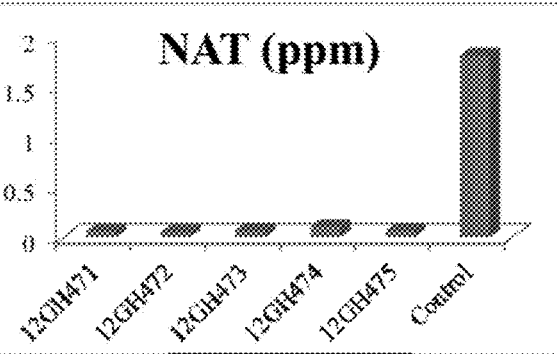
FIG. 4E: NAT levels are reduced in AtPAP1 overexpression lines compared to controls.

The amounts of four TSNAs are measured: N'-nitrosonornicotine (NNN), 4-methylnitrosoamino-1-(3-pyridyl)-1-butanone (NNK), N'-nitrosoanatabine (NAT) and N'-nitrosoanabasine (NAB) are measured. For TSNA analysis, 750 mg of crushed, freeze-dried leaf is added to 30 mls of 10 mM ammonium acetate. After incubation in a shaker for 30 minutes, approximately 4 mls of sample is transferred into disposable culture tubes containing 0.25 ml of concentrated ammonium hydroxide. The sample is vortexed briefly and 1.5 mls is added to a prewashed and conditioned extraction cartridge with a flow rate of 1 to 2 drops per second. Analytes are eluted from the sample using 1.5 mls of 70:30 methanol with 0.1% acetic acid. Samples are analyzed using liquid chromatography with tandem mass spectrometry (LC/MS/MS). Measurements of NNN, NNK, NAB, and NAT in AtPAP1 overexpressing plants is shown in Table 1. Total TSNA levels are considerably reduced in AtPAP1 plants as shown in FIG. 4A. Considerable reductions in NNK levels (FIG. 4B), NNN levels (FIG. 4C), NAB levels (FIG. 4D), and NAT levels (FIG. 4E) are also observed.

Example 3. AtPAP1 Overexpressing Plants Exhibit Increased Oxygen Radical Absorbance Capacity The effect of AtPAP1 overexpression on oxidative capacity is determined for five T1 AtPAP1 overexpression lines (six plants each) after cultivation in the greenhouse. Oxygen Radical Absorbance Capacity (ORAC) is measured to determine antioxidant activity in AtPAP1 overexpressing plants. Quenching of a Progallol Red (PGR) florescent probe is used to determine the ORAC measurement according to manufactures instruction (BioTek, Winooski, Vt.). Antioxidants are extracted from crushed tissue samples with a methanol/HCL extraction buffer (6/1, v/v). The samples are incubated for 30 minutes at 37° C. in a reaction mixture containing 75 mM phosphate buffer, pH 7.4, and 5 µM PGR. After incubation, 37° C. AAPH solution is added to the reaction mixture to a final concentration of 10 mM. Controls with all the solution components, but without the tissue samples, are used for comparison.

Figure 5:
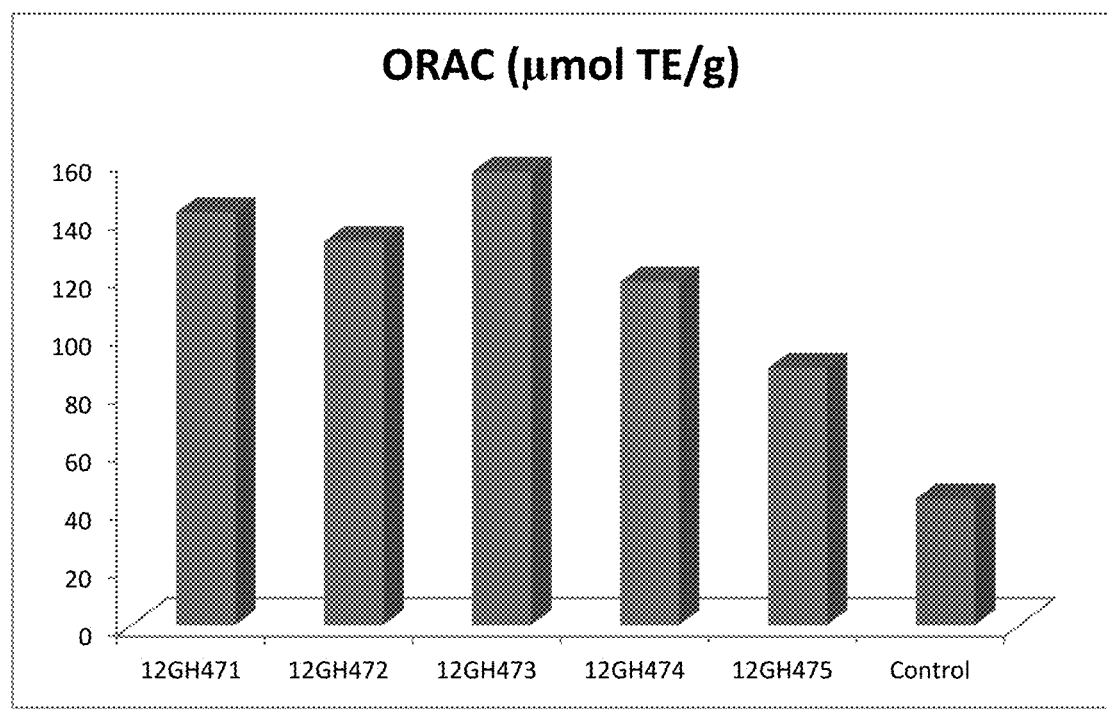
FIG. 5: Oxygen radical absorbance capacity (ORAC) values in AtPAP1 overexpression plants are increased compared to controls.

Reaction and control samples are shaken and the absorption (A) is recorded every 30 seconds for 180 minutes. The kinetic values are recorded as $A/A_{time0}$. ORAC scores are determined based on the Area Under Curve (AUC) values determined scores from the sample and blank. ORAC scores are assessed for all time-points until the $A/A_{time0}$ reaches a value of 0.2 using MicroCal Origin (R17.0, Boston, Mass.). ORAC values are recorded in FIG. 5 demonstrating increased ORAC values in AtPAP1 overexpression lines.

Example 4. Alkaloid Levels in Tobacco Plants Expressing AtPAP1

The effect of AtPAP1 overexpression on total alkaloid levels is determined for five T1 AtPAP1 overexpression lines (six plants each) after cultivation in the greenhouse. The levels of the alkaloids nicotine, nornicotine, anatabine, and anabasine are determined with Gas Chromatography followed by Mass Spectrometry (GC-MS). For example, measurement of anatabine is performed by mixing one gram of cured leaf tissue with 10 mls of 2N NaOH, followed by incubation at room temperature for fifteen minutes. Anatabine is then extracted by addition of 50 mls of 0.04% quinolone (w/v) dissolved in methyl-tert-butyl ether followed by rotation on a linear shaker for three hours. After phase separation, alkaloid levels are determined using an Agilent 6890 Gas Chromatograph and an Agilent 5973N Mass Spectrometer. The results of measurements for the alkaloids nicotine, nornicotine, anatabine, and anabasine are recorded in Table 2.

TABLE 1

TSNA levels in AtPAP1 overexpression plants are reduced compared to controls.

| Plant ID | Variety | NNN (ppm) | NNK (ppm) | NAB (ppm) | NAT (ppm) | Total TSNA (ppm) | % TSNA Reduction |
|---|---|---|---|---|---|---|---|
| 12GH471 | t-NL Madole LC T821 (PAP1 OEX) | 0.087 | 0.035 | 0.008 | 0.059 | 0.189 | 95.98 |
| 12GH472 | t-NL Madole LC T824 (PAP1 OEX) | 0.091 | 0.031 | 0.005 | 0.048 | 0.175 | 96.28 |
| 12GH473 | t-NL Madole LC T827 (PAP1 OEX) | 0.105 | 0.037 | 0.01 | 0.069 | 0.221 | 95.30 |
| 12GH474 | t-NL Madole LC T827 (PAP1 OEX) | 0.164 | 0.043 | 0.011 | 0.103 | 0.321 | 93.18 |
| 12GH475 | t-NL Madole LC T836 (PAP1 OEX) | 0.089 | 0.036 | 0.008 | 0.067 | 0.2 | 95.75 |
| Control | NL Madole | 1.581 | 1.232 | 0.079 | 1.812 | 4.704 | — |

TABLE 2

Alkaloid levels in AtPAP1 overexpressing plants are mildly reduced compared to controls.

| Plant ID | Variety | Nicotine (% by wt) | Nornicotine (% by wt) | Anabasine (% by wt) | Anatabine (% by wt) |
|---|---|---|---|---|---|
| 12GH471 | t-NL Madole LC T821 (PAP1 OEX) | 3.679 | 0.046 | 0.009 | 0.038 |
| 12GH472 | t-NL Madole LC T824 (PAP1 OEX) | 3.009 | 0.089 | 0.008 | 0.034 |
| 12GH473 | t-NL Madole LC T827 (PAP1 OEX) | 4.323 | 0.073 | 0.011 | 0.048 |
| 12GH474 | t-NL Madole LC T827 (PAP1 OEX) | 4.609 | 0.052 | 0.009 | 0.037 |
| 12GH475 | t-NL Madole LC T836 (PAP1 OEX) | 3.329 | 0.036 | 0.008 | 0.034 |
| Control | NL Madole | 5.921 | 0.09 | 0.014 | 0.074 |

Example 5. AtPAP1 Overexpressing Plants Comprise Reduced Nitrite

The effect of AtPAP1 overexpression on nitrite and nitrate levels is determined for five T1 AtPAP1 overexpression lines (six plants each) after cultivation in the greenhouse. Cured leaf Samples are prepared as in Example 2 for LC/MS/MS and tested. Nitrite and nitrate levels as shown in FIG. 6A and FIG. 6B. The overexpression of AtPAP1 reduces the level of nitrite but not nitrate.

Figure 7:
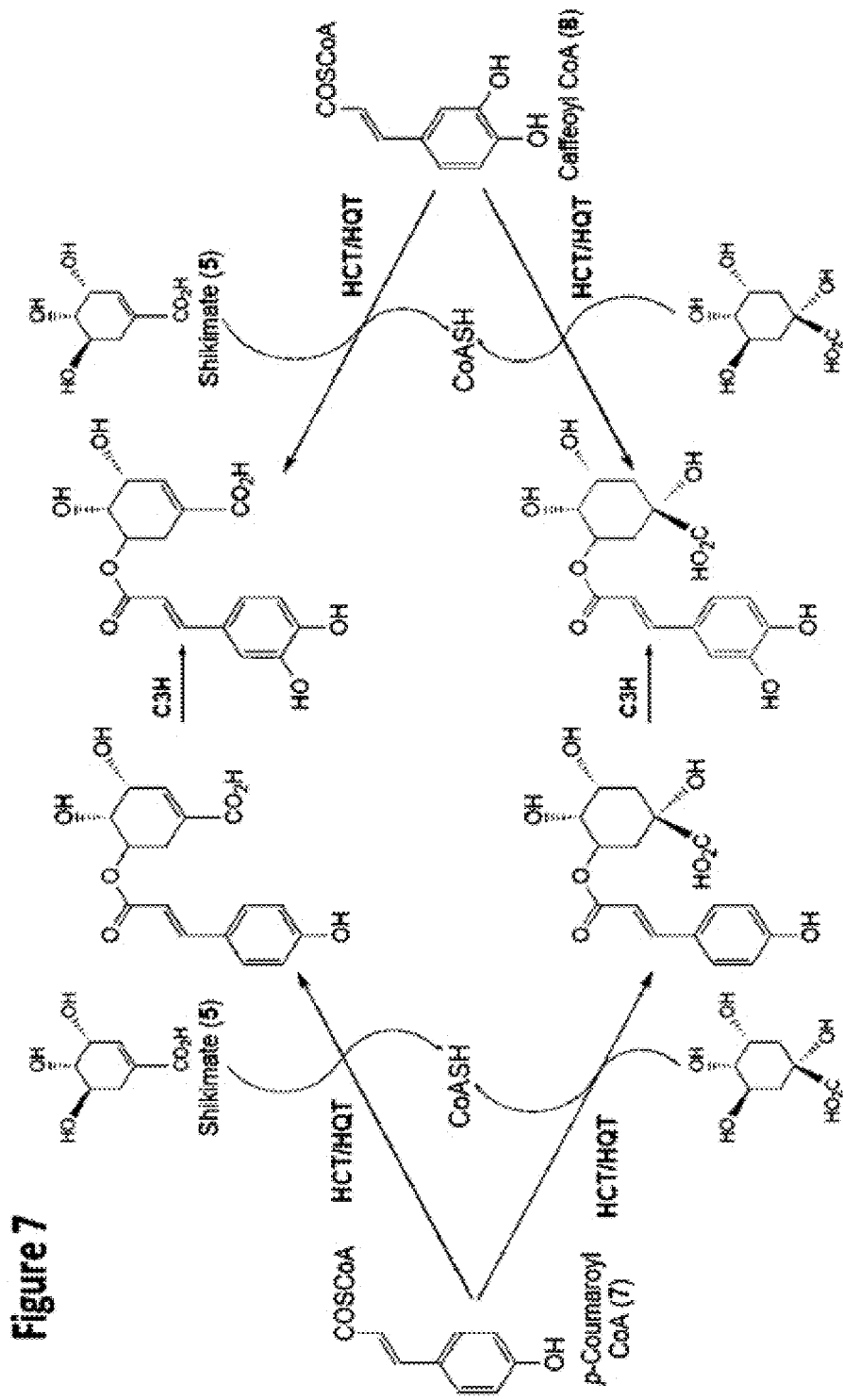
FIG. 7: HCT and HQT function in the biosynthetic pathway of Chlorogenic Acid.
Figure 8:
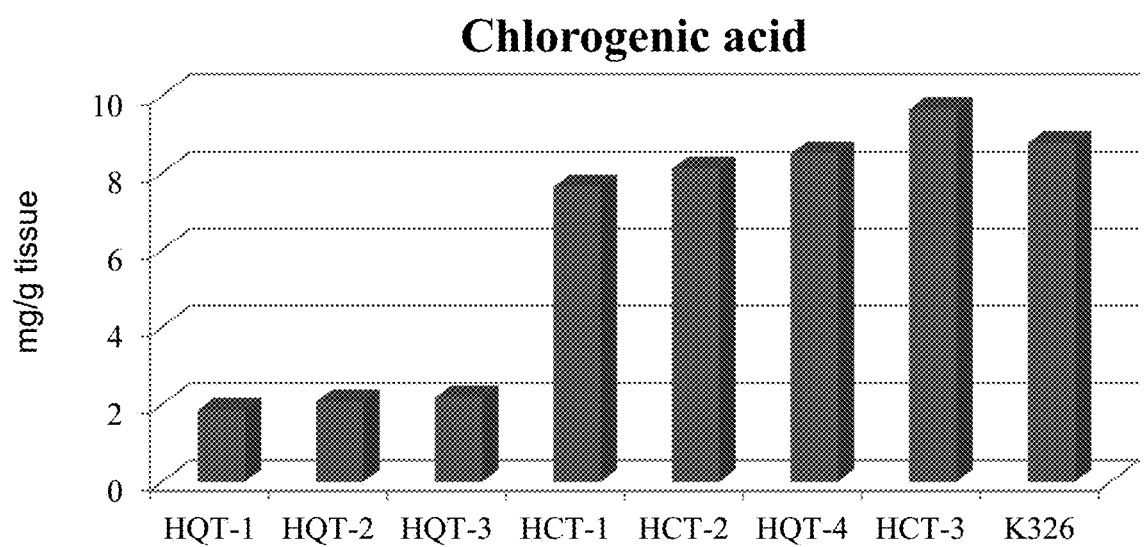
FIG. 8: Chlorogenic Acid levels are reduced in 3 of 4 HQT RNAi lines but not in HCT RNAi lines.
Figure 9:
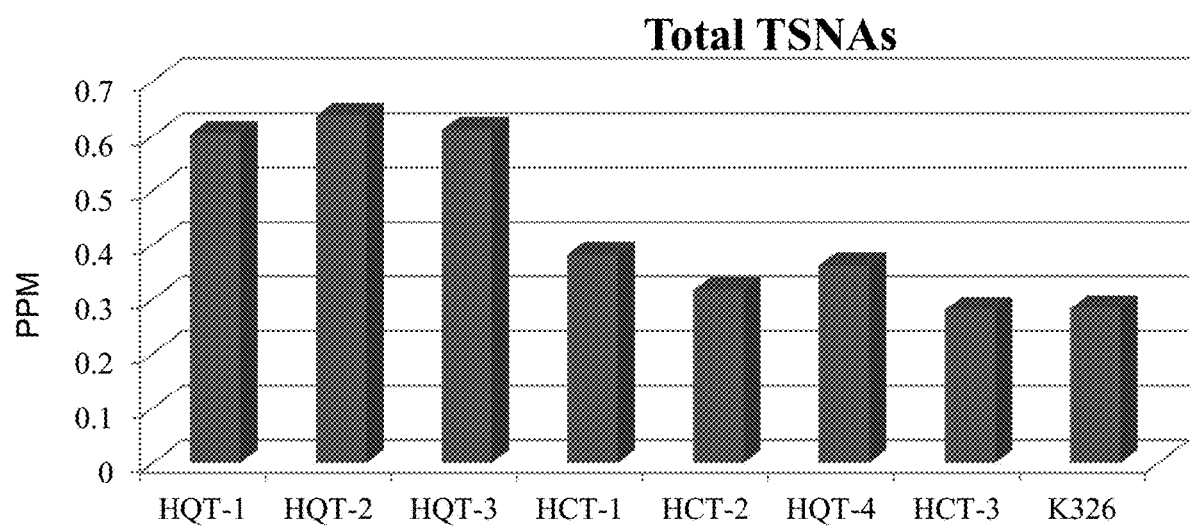
FIG. 9: Total TSNAs are increased in the 3 HQT RNAi lines with decreased Chlorogenic Acid levels.
Figure 10D:
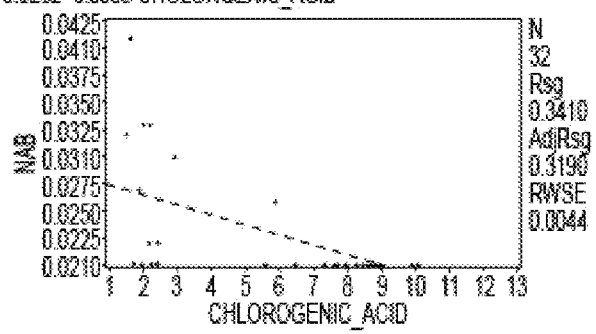
FIG. 10: Accumulation of Chlorogenic Acid is inversely correlated with TSNA levels. A negative correlation is observed between CGA levels and total TSNA levels as shown in Table 4 and FIG. 10A. This correlation is also observed between CGA levels and individual TSNAs NNN (FIG. 10B), NNK (FIG. 10C), NAB (FIG. 10D), and NAA (FIG. 10E).
Figure 10E:
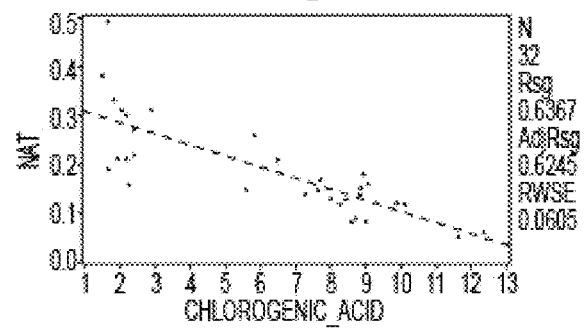
Figure 11:
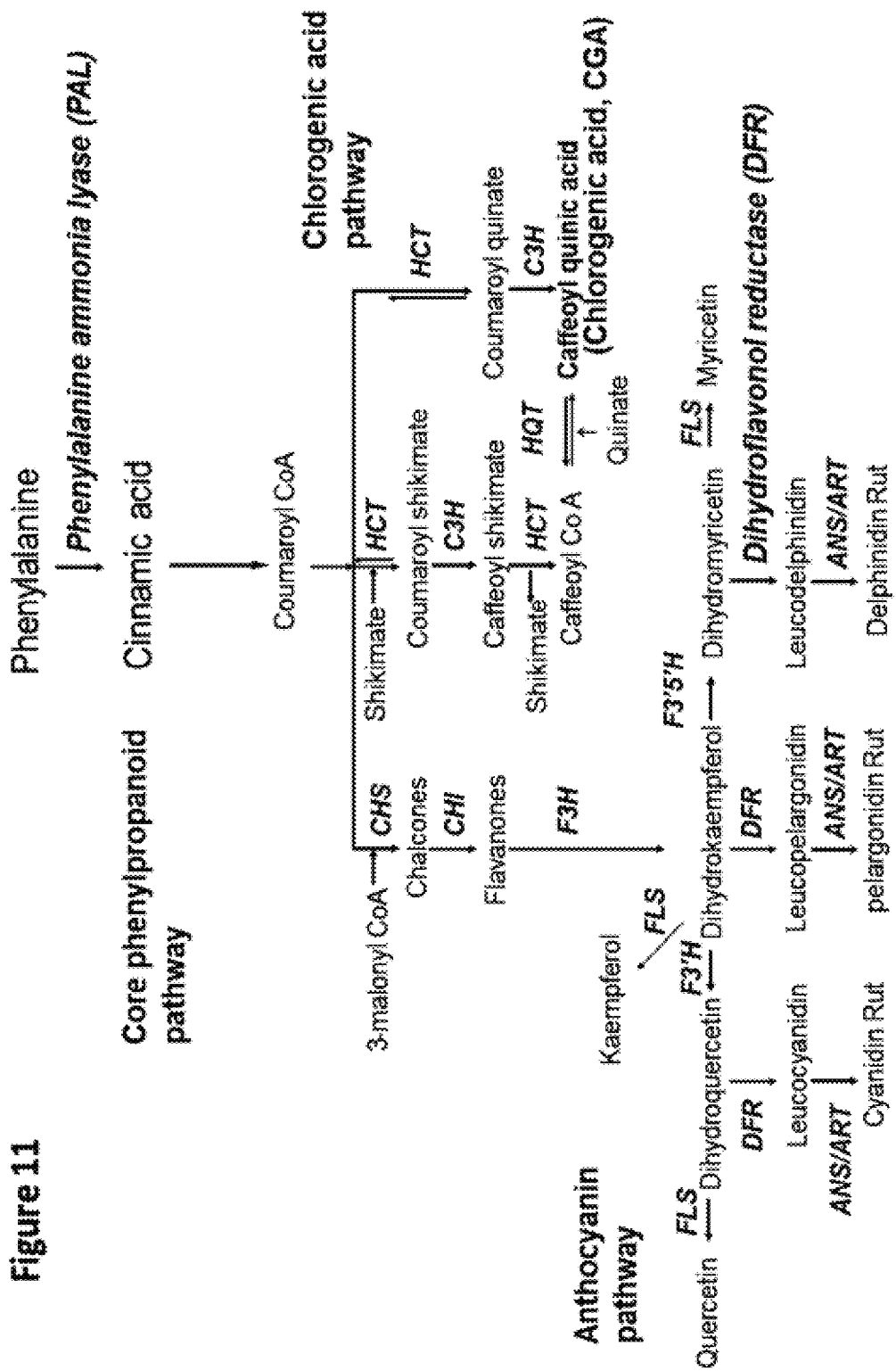
FIG. 11: The phenylpropanoid pathway can be targeted to reduce TSNA levels in tobacco by increasing antioxidant levels.
Figure 12:
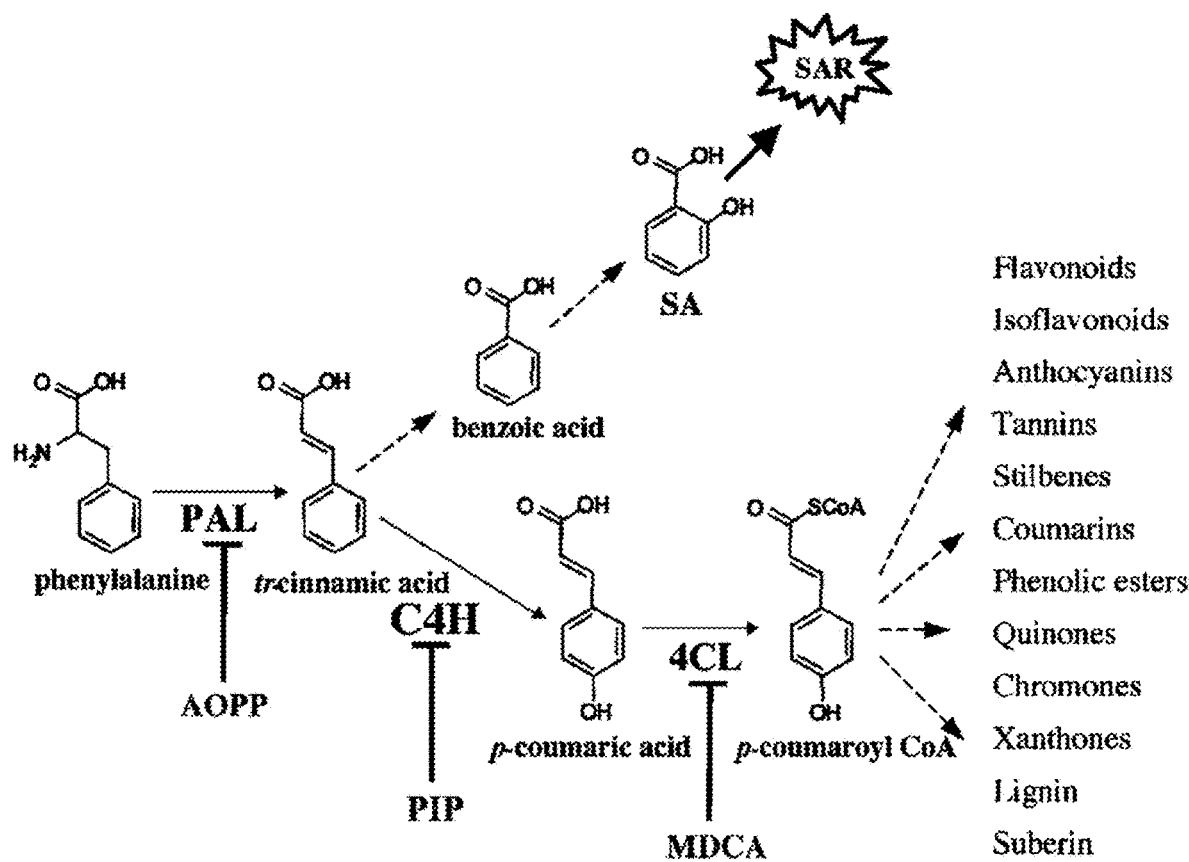
FIG. 12: The phenylpropanoid pathway leads to the biosynthesis of many antioxidants.

Example 6. Reduced Chlorogenic Acid in Tobacco Leaf Correlates with Elevated TSNA Levels The level of additional antioxidants are modulated to further demonstrate a negative correlation between antioxidants and TSNAs. Reduction of Chlorogenic acid (CGA) levels results in an increase in total TSNAs and total alkaloids. CGA or Caffeoyl quinate is generated from Caffeoyl CoA or p-Coumaroyl CoA through the activity of hydroxycinnamoyl-CoA quinate hydroxycinnamoyl transferase (HQT) and hydroxycinnamoyl-CoA shikimate/quinate hydroxycinnamoyl transferase (HCT) (Payyavula et al., 2015, Plant Biotechnology Journal, Hoffmann et al., 2004, The Plant Cell, FIG. 7). The activity of these enzymes is reduced in tobacco by silencing HCT and HQT with RNAi. Silencing HQT and HCT results in a reduction of CGA as shown in FIG. 8 and an increase in total TSNAs as shown in FIG. 9.

Transformation vectors comprising RNAi constructs are designed to inhibit the expression of tobacco genes that promote the conversion of Caffeoyl CoA or p-Coumaroyl CoA to CGA. Modified tobacco plants and control tobacco plants are created and grown as described in Example 1. Cured leaf samples from the modified tobacco plants are prepared for evaluation of TSNAs, alkaloids, and nitrite/nitrate as described in Examples 2, 4 and 5. Alkaloid levels show mild modulations as shown in Table 3. A negative correlation is observed between CGA levels and TSNA levels, as well as the levels of individual TSNAs (NNN, NNK, NAB, and NNA) as shown in FIG. 10A-E and Table 4. Nitrite levels are unchanged and nitrate levels show reductions compared to controls (Table 4).

TABLE 3

Alkaloid and CGA levels in HCT and HQT RNAi lines.

| | | Nicotine (% by wt) | Nornicotine (% by wt) | Myosmine (% by wt) | Anabasine (% by wt) | Anatabine (% by wt) | CGA (mg/g) |
|---|---|---|---|---|---|---|---|
| K326 | HQT-1 | 3.90 | 0.10775 | 0.007918 | 0.0217 | 0.109775 | 1.8525 |
| K326 | HQT-2 | 4.10 | 0.112275 | 0.006815 | 0.022825 | 0.106125 | 2.07 |
| K326 | HQT-3 | 4.04 | 0.115 | 0.006995 | 0.021025 | 0.103175 | 2.17 |
| K326 | HCT-1 | 3.59 | 0.095625 | 0.006978 | 0.018425 | 0.091025 | 7.6375 |
| K326 | HCT-2 | 3.45 | 0.083525 | 0.005678 | 0.0178 | 0.085525 | 8.1075 |
| K326 | HQT-4 | 3.93 | 0.0972 | 0.00643 | 0.01985 | 0.10085 | 8.5025 |
| K326 | HCT-3 | 3.28 | 0.07795 | 0.006198 | 0.0154 | 0.074925 | 9.65 |
| K326 | Control | 3.45 | 0.09165 | 0.007213 | 0.018575 | 0.094975 | 8.775 |

TABLE 4

TSNA, CGA, Nitrite and Nitrate levels in HQT and HCT RNAi plants.

| | | LL NNN (ppm) | LL NNK (ppm) | LL NAB (ppm) | LL NAT (ppm) | LL TSNA (ppm) | LL Nitrite (ppm) | LL Nitrate (ppm) | CGA (mg/g) |
|---|---|---|---|---|---|---|---|---|---|
| K326 | HQT-1 | 0.205 | 0.08425 | 0.02675 | 0.2875 | 0.6035 | 0.245 | 3192.5 | 1.8525 |
| K326 | HQT-2 | 0.2175 | 0.09825 | 0.0285 | 0.2925 | 0.63675 | 0.2 | 3257.5 | 2.07 |
| K326 | HQT-3 | 0.195 | 0.1265 | 0.02475 | 0.265 | 0.61125 | 0.22 | 2685 | 2.17 |
| K326 | HCT-1 | 0.13325 | 0.0635 | 0.02 | 0.165 | 0.38175 | 0.2 | 3285 | 7.6375 |

TABLE 4-continued

TSNA, CGA, Nitrite and Nitrate levels in HQT and HCT RNAi plants.

| | | LL NNN (ppm) | LL NNK (ppm) | LL NAB (ppm) | LL NAT (ppm) | LL TSNA (ppm) | LL Nitrite (ppm) | LL Nitrate (ppm) | CGA (mg/g) |
|---|---|---|---|---|---|---|---|---|---|
| K326 | HCT-2 | 0.0955 | 0.07025 | 0.02 | 0.13075 | 0.3165 | 0.2225 | 3202.5 | 8.1075 |
| K326 | HQT-4 | 0.11475 | 0.07 | 0.0215 | 0.155 | 0.36125 | 0.215 | 2655 | 8.5025 |
| K326 | HCT-3 | 0.088 | 0.0635 | 0.02 | 0.1085 | 0.28 | 0.2525 | 2945.5 | 9.65 |
| K326 | Control | 0.0885 | 0.0575 | 0.02 | 0.1165 | 0.2825 | 0.2 | 1862.5 | 8.775 |

Example 7: Increased Antioxidant Capacity in Field Grown AtPAP1 Overexpressing Plants A Ferric Reducing Antioxidant Power (FRAP) analysis is conducted on field grown tobacco plants overexpressing AtPAP1. AtPAP1 overexpression constructs are transformed into TN90 and Narrow Leaf Madole (NLM) tobacco plants as described in Example 1. Modified and unmodified control plants are grown in a field under standard field conditions. Plants are topped at flowering and leaves for analysis are collected harvest stage (4 weeks) later. At least five plants from two independent transgenic events in both the TN90 background and the NLM background and at least five plants from unmodified TN90 and NLM plants are sampled and tested. 10 mg of freeze dried leaf is taken into an Eppendorf tube and 1500 μl of 80% ethanol is added and sonicated for 10 minutes. After centrifuge, 5-10 μl of supernatant is used to measure antioxidant capacity.

The Ferric Reducing Antioxidant Power (FRAP) method is based on the reduction of complexes of 2,4,6-tripyridyl-s-triazine (TPTZ) with ferric chloride hexahydrate (FeCl3.6H2O) which forms blue ferrous complexes after its reduction (Benzie & Strain, 1996, Analytical Biochemistry, 239, 70-76). Three solutions are used for the assay: Solution 1) 10 mmol·L-1 solution of TPTZ (0.07802 g/25 mL), in 40 mM of hydrochloric acid; Solution 2) 20 mM solution of ferric chloride hexahydrate (0.13513 g/25 mL) in ACS water; Solution 3) 20 mM acetate buffer, pH 3.6 (weight of sodium acetate trihydrate is 0.27216 g in 100 mL ACS water, adjusted to the desired pH using HCl). These three solutions (TPTZ, FeCl3, acetate buffer) are mixed in a 1:1:10 ratio. A 245 μL volume of the mixed solution is pipetted into a plastic cuvette with subsequent addition of a 5 μL sample (gallic acid, Trolox®). Absorbance is measured at primary λ, 593 nm wavelength. Different concentrations of Trolox® was used to make a standard curve and samples are compared to standard curve. Total antioxidants are calculated using the following equation $$\text{Antioxidants(nmol/mg)} = \frac{\textit{nmoles present in the sample} \times \text{total sample extraction volume}}{\text{total wt of the sample} \times \text{volume used for measurement}}$$

Figure 13:
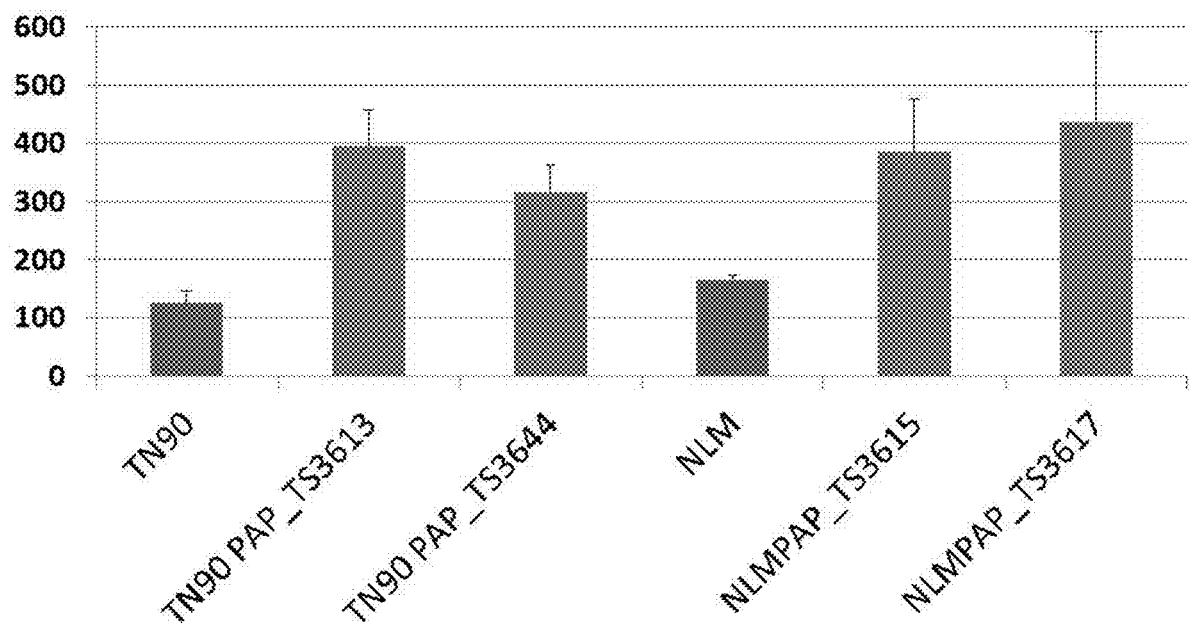
FIG. 13: Overexpression of AtPAP1 in TN90 and Narrow Leaf Madole (NLM) results in increased antioxidant capacity as measured using a FRAP assay. Measurements from leaves from at least five plants are averaged together for unmodified TN90 and NLM, two independent lines overexpressing AtPAP1 in TN90, and two independent lines overexpressing AtPAP1 in NLM are tested using a FRAP assay. Both independent lines overexpressing AtPAP1 in TN90 exhibit a highly significant increase in average antioxidant capacity (P<0.01) compared to unmodified TN90 plants. Both independent lines overexpressing AtPAP1 in NLM exhibit a highly significant increase in average antioxidant capacity (P<0.01) compared to unmodified NLM plants.

Modified tobacco plants overexpressing AtPAP1 show a significantly increased antioxidant capacity as measured by FRAP analysis compared to the unmodified controls (P<0.01) (FIG. 13).

Example 8. Secondary Metabolite Accumulation in Field Grown AtPAP1 Overexpressing Plants A secondary metabolite accumulation analysis is conducted on greenhouse grown AtPAP1 overexpressing plants. AtPAP1 overexpression constructs are transformed into Narrow Leaf Madole (NLM) tobacco plants as described in Example 1. Modified and unmodified control plants are grown in a greenhouse under standard conditions. Plants are topped at flowering and leaves for analysis are collected two weeks later from two independently modified NLM plants (D1 and D2) and one unmodified NLM plant. A set of Benzenoids, Flavonoids, and Phenylpropanoids show significantly increased levels in modified plants compared to unmodified plants (P<0.01) (See Table 5).

TABLE 5

Secondary metabolite accumulation in 35:AtPAP1 overexpressing Narrow Leaf Madole tobacco plants. D1 and D2 represent individual plants from independently transformed lines and DC represents an unmodified control plant.

| Pathway | Biochemical Name | D1/DC | D2/DC | D1 | D2 | DC |
|---|---|---|---|---|---|---|
| Benzenoids | protocatechuic acid-3-glucoside | 109.21* | 101.57* | 5.56 | 5.17 | 0.05 |
| | 4-hydroxybenzoate | 12.26* | 11.42* | 1.37 | 1.27 | 0.11 |
| | gentisic acid-5-glucoside | 5.98* | 6.23* | 2.16 | 2.25 | 0.36 |
| | salicylate-glucoside | 5.09** | 5.85* | 0.95 | 1.10 | 0.19 |
| | benzoyl-O-glucose | 4.62* | 4.6* | 0.27 | 0.27 | 0.06 |
| | salicylate | 2.22* | 2.81* | 0.63 | 0.80 | 0.28 |
| | benzoate | 1.49 | 2.07* | 0.52 | 0.72 | 0.35 |
| Flavonoids | rutinose | 99.63* | 93.99* | 41.90 | 39.52 | 0.42 |
| | naringenin | 5.26* | 3.79* | 1.19 | 0.86 | 0.23 |
| | quercetin 3-galactoside | 2.54 | 3.11 | 0.14 | 0.17 | 0.05 |
| Phenylpropanoids | coumaroylquinate (4) | 92.06* | 45.21* | 21.81 | 10.71 | 0.24 |
| | coumaroylquinate (2) | 16.17* | 12.87* | 10.70 | 8.52 | 0.66 |
| | chlorogenate | 9.15* | 6.59* | 7.55 | 5.44 | 0.83 |
| | vanillate | 5.95* | 7.25* | 0.39 | 0.47 | 0.06 |
| | cryptochlorogenic acid | 4.74* | 3.93* | 2.18 | 1.80 | 0.46 |
| | coumaroylquinate (5) | 5.74* | 5.86* | 5.44 | 5.55 | 0.95 |
| | coumaroylquinate (3) | 3.2* | 2.99* | 2.32 | 2.17 | 0.72 |

TABLE 5-continued

Secondary metabolite accumulation in 35:AtPAP1 overexpressing Narrow Leaf Madole tobacco plants. D1 and D2 represent individual plants from independently transformed lines and DC represents an unmodified control plant.

| Pathway | Biochemical Name | D1/DC | D2/DC | D1 | D2 | DC |
|---|---|---|---|---|---|---|
| | dihydroferulic acid | 2.45** | 2.57* | 0.74 | 0.78 | 0.30 |
| | vanillin | 2.37* | 1.82** | 0.77 | 0.60 | 0.33 |

Highly significant differences as compared to the unmodified control plant (P < 0.01) are indicated with *.
Significant differences as compared to the unmodified control plant (P < 0.05) are indicated with **.

Example 9. Expression of Additional Genes to Modulate TSNA Levels

Transformation vectors and modified tobacco plants are generated to overexpress full-length coding sequences from tobacco genes (e.g., SEQ ID NOs: 24-42, 44, 45, and 53 to 58) or non-tobacco origin genes (e.g., SEQ ID NOs: 43 and 46) that promote or are involved in the production or accumulation of one or more antioxidants (see Table 6). The overexpression of transcription factors that promote or are involved in the production or accumulation of one or more antioxidants is described below. Nucleotide (Table 7) and protein (Table 8) identity scores are shown comparing the transcription factors used in this study. Exemplary genes and their sequences are listed in the sequence listing and Table 9.

Figure 14:
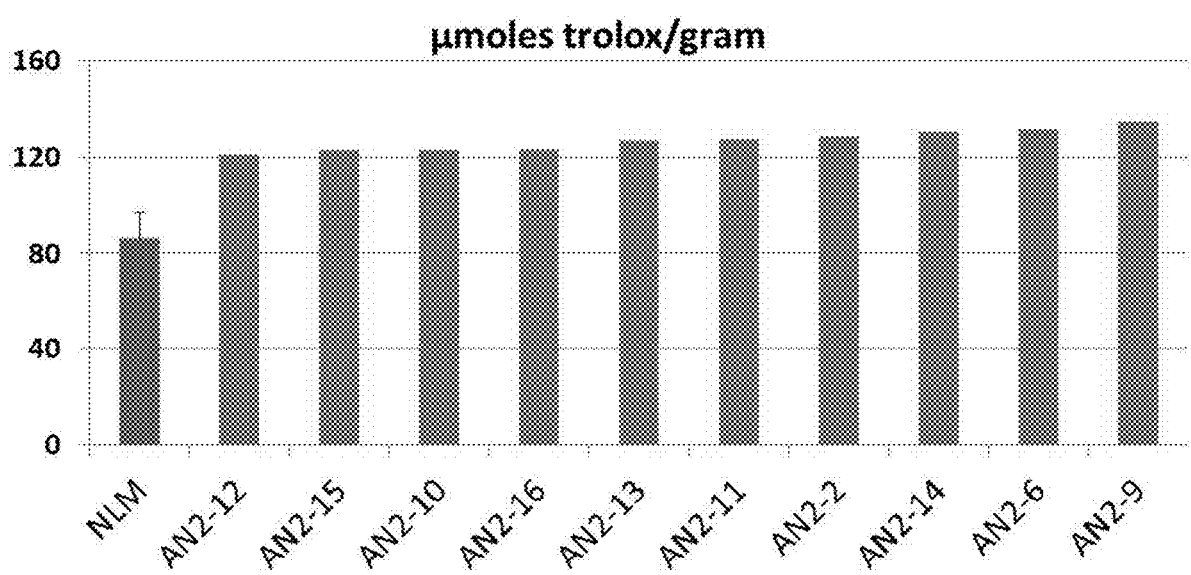
FIG. 14: Overexpression of NtAN2 (SEQ ID NO: 30) in NLM results in increased antioxidant capacity as measured using a FRAP assay. Greenhouse grown, individually tested T0 plants overexpressing NtAN2 show increased antioxidant capacity compared to the average antioxidant capacity determined for at least five unmodified NLM plants.

NtAN2, SEQ ID NO: 30, is incorporated into a p45-2-7 transformation vector, and modified tobacco plants are generated, according to Example 1. Modified NLM tobacco plants (T0 and T1 generation) and control tobacco plants are grown for 4-6 weeks after transplantation to soil, harvested, and cured in PGC chambers. Cured leaf samples are prepared for evaluation of TSNAs, oxidative degradation potential, alkaloids, and nitrites/nitrates as described in Examples 2 to 5. A FRAP assay is used to determine antioxidant capacity in T0 plants as described in Example 7. Increased antioxidant capacity is detected in individual field grown T0 plants compared to the average antioxidant capacity determined for at least five unmodified Narrow leaf Madole plants (FIG. 14).

Figure 15:
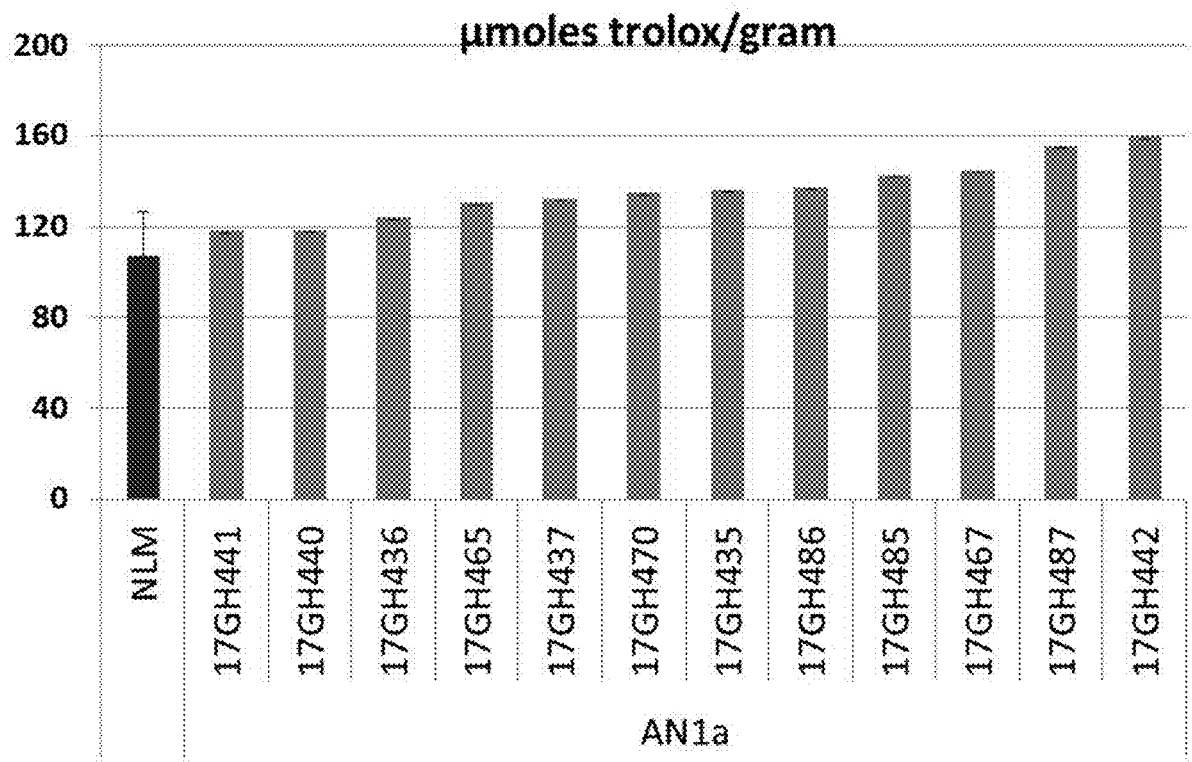
FIG. 15: Overexpression of NtAN1a (SEQ ID NO: 28) in NLM results in increased antioxidant capacity as measured using a FRAP assay. Greenhouse grown, individually tested T0 plants overexpressing NtAN1a show increased antioxidant capacity compared to the average antioxidant capacity determined for at least five unmodified NLM plants.

NtAN1a, SEQ ID NO: 28, is incorporated into a p45-2-7 transformation vector, and modified tobacco plants are generated, according to Example 1. Modified NLM tobacco plants (T0 and T1 generation) and control tobacco plants are grown for 4-6 weeks after transplantation to soil, harvested, and cured in PGC chambers. Cured leaf samples are prepared for evaluation of TSNAs, oxidative degradation potential, alkaloids, and nitrites/nitrates as described in Examples 2 to 5. A FRAP assay is used to determine antioxidant capacity in T0 plants as described in Example 7. Increased antioxidant capacity is detected in individual greenhouse grown T0 plants compared to the average antioxidant capacity determined for at least five unmodified Narrow leaf Madole plants (FIG. 15).

Figure 16:
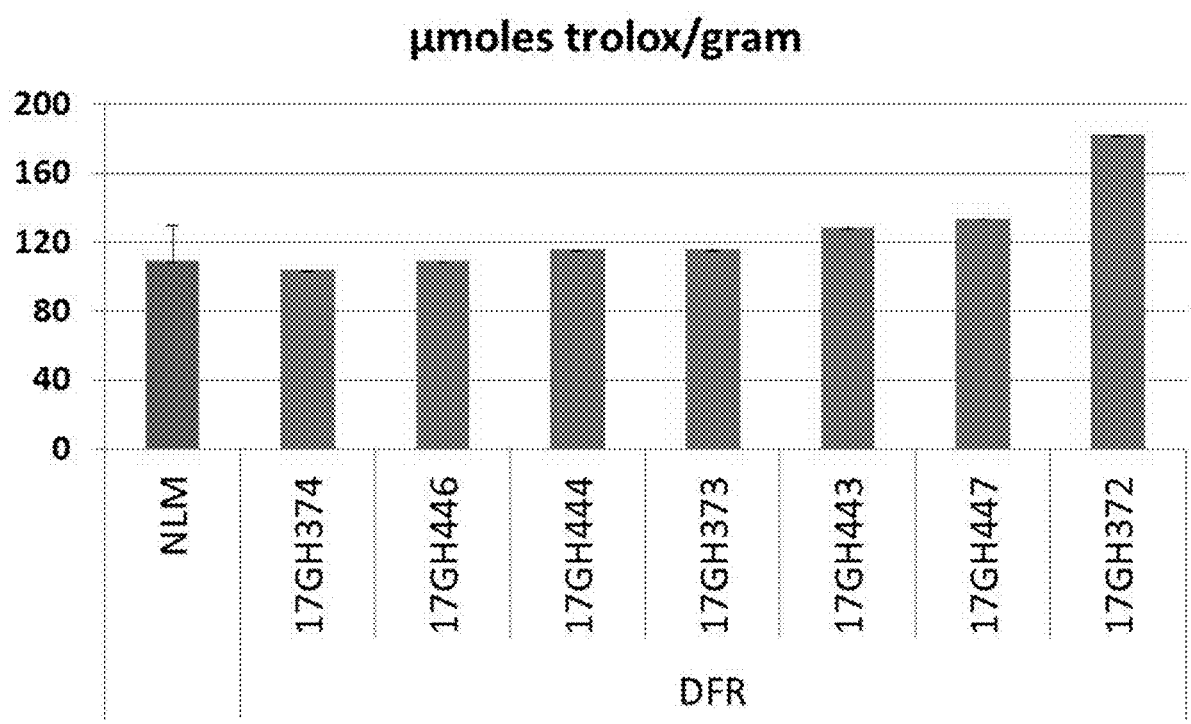
FIG. 16: Overexpression of NtDFR (SEQ ID NO: 37) in NLM results in increased antioxidant capacity as measured using a FRAP assay. Greenhouse grown, individually tested T0 plants overexpressing NtDFR show increased antioxidant capacity compared to the average antioxidant capacity determined for at least five unmodified NLM plants.

NtDFR, SEQ ID NO: 37, is incorporated into a p45-2-7 transformation vector, and modified tobacco plants are generated, according to Example 1. Modified NLM tobacco plants (T0 and T1 generation) and control tobacco plants are grown for 4-6 weeks after transplantation to soil, harvested, and cured in PGC chambers. Cured leaf samples are prepared for evaluation of TSNAs, oxidative degradation potential, alkaloids, and nitrites/nitrates as described in Examples 2 to 5. A FRAP assay is used to determine antioxidant capacity in T0 plants as described in Example 7. Increased antioxidant capacity is detected in individual greenhouse grown T0 plants compared to the average antioxidant capacity determined for at least five unmodified Narrow leaf Madole plants (FIG. 16).

Figure 17:
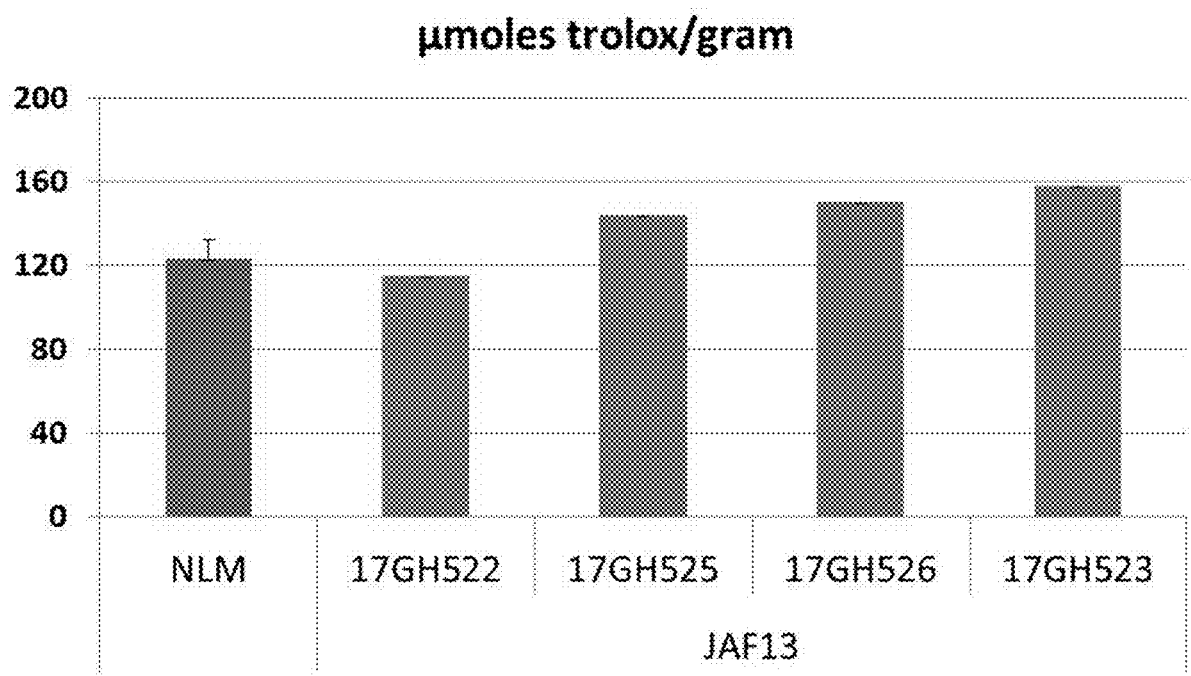
FIG. 17: Overexpression of NtJAF13 (SEQ ID NO: 33) in NLM results in increased antioxidant capacity as measured using a FRAP assay. Greenhouse grown, individually tested T0 plants overexpressing NtJAF13 show increased antioxidant capacity compared to the average antioxidant capacity determined for at least five unmodified NLM plants.

NtJAF13, SEQ ID NO: 33, is incorporated into a p45-2-7 transformation vector, and modified tobacco plants are generated, according to Example 1. Modified NLM tobacco plants (T0 and T1 generation) and control tobacco plants are grown for 4-6 weeks after transplantation to soil, harvested, and cured in PGC chambers. Cured leaf samples are prepared for evaluation of TSNAs, oxidative degradation potential, alkaloids, and nitrites/nitrates as described in Examples 2 to 5. A FRAP assay is used to determine antioxidant capacity in T0 plants as described in Example 7. Increased antioxidant capacity is detected in individual greenhouse grown T0 plants compared to the average antioxidant capacity determined for at least five unmodified Narrow leaf Madole plants (FIG. 17).

Figure 18:
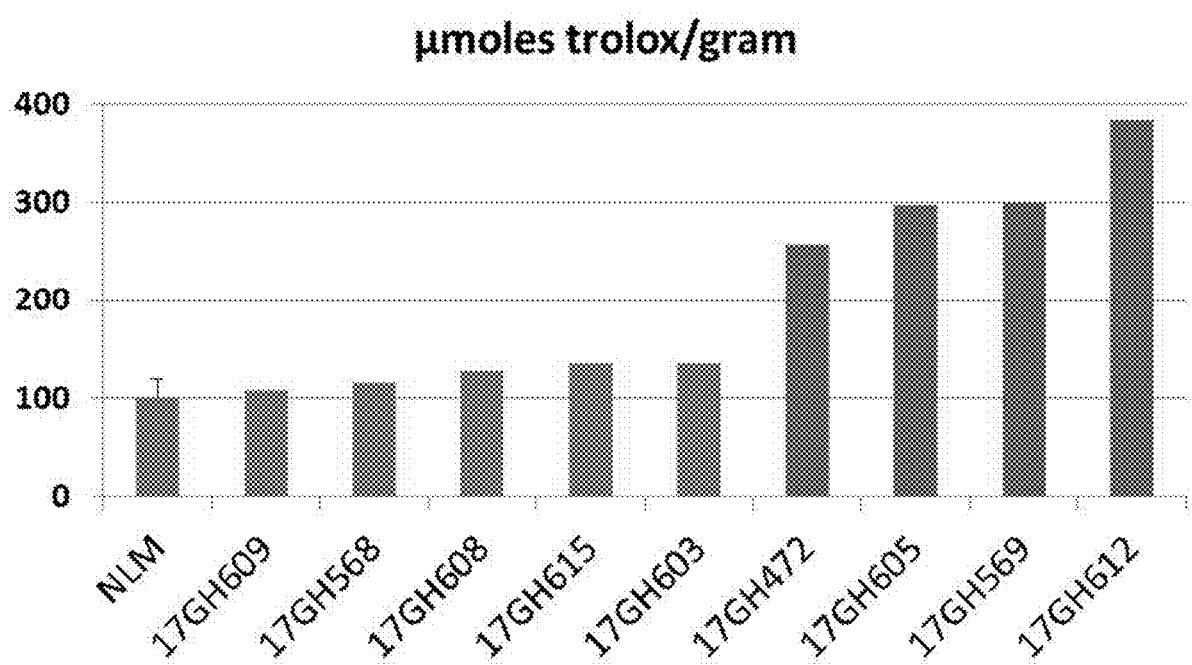
FIG. 18: Overexpression of NtMYB3 (SEQ ID NO: 36) in NLM results in increased antioxidant capacity as measured using a FRAP assay. Greenhouse grown, individually tested T0 plants overexpressing NtMYB3 show increased antioxidant capacity compared to the average antioxidant capacity determined for at least five unmodified NLM plants.
Figure 19:
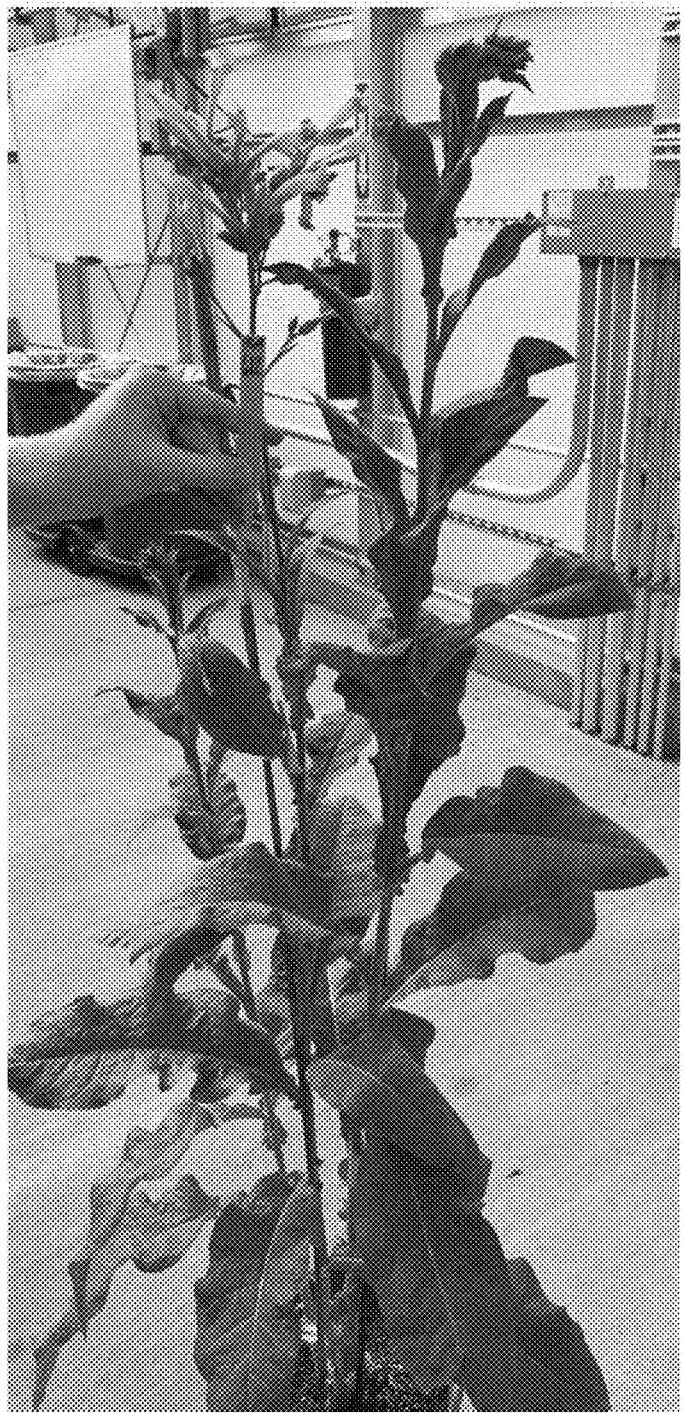
FIG. 19: Overexpression of NtMYB3 (SEQ ID NO: 36) in NLM results in tobacco plants with normal leaf color in T0 plants grown in the greenhouse.

NtMYB3, SEQ ID NO: 36, is incorporated into a p45-2-7 transformation vector, and modified tobacco plants are generated, according to Example 1. Modified tobacco plants (T0 and T1 generation) and control tobacco plants are grown for 4-6 weeks after transplantation to soil, harvested, and cured in PGC chambers. Cured leaf samples are prepared for evaluation of TSNAs, oxidative degradation potential, alkaloids, and nitrites/nitrates as described in Examples 2 to 5. A FRAP assay is used to determine antioxidant capacity in T0 plants as described in Example 7. Increased antioxidant capacity is detected in individual greenhouse grown T0 plants compared to the average antioxidant capacity determined for at least five unmodified Narrow leaf Madole plants (FIG. 18). Plants overexpressing NtMYB3 show a normal leaf color in the T0 generation (FIG. 19).

TABLE 6

A list of plant-origin antioxidants that can be used to reduce TSNAs.

| Chemical Classes | Compounds | Source of the Species |
|---|---|---|
| Anthocyanidin | Delphnidin | Tobacco, *Arabidopsis*. Cabbage, potato or *petunia* |
| | Cyanidin | Tobacco, *Arabidopsis*. Cabbage, potato or *petunia* |
| | Procyanidin | Tobacco, *Arabidopsis*. Cabbage, potato or *petunia* |
| | Prodelphinidin | Tobacco, *Arabidopsis*. Cabbage, potato or *petunia* |

TABLE 6-continued

A list of plant-origin antioxidants that can be used to reduce TSNAs.

| Chemical Classes | Compounds | Source of the Species |
|---|---|---|
| Flavanone | Hesperetin | *Citrus* or related species |
|  | Naringenin | *Citrus* or related species |
| Flavanol | Catechin | Tobacco or other related species |
|  | Epicatechin | Tobacco or other related species |
| Flavone | Apigenin | Parsley, tobacco or other related species |
|  | Luteonin | Parsley, tobacco or other related species |
| Flavonol | Quercetin | Red kidney bean or other related species |
|  | Myricetin | Red kidney bean or other related species |
|  | Rutin | Tobacco, Red kidney bean or other related species |
| Isoflavone | Genistein | Soybean or other related species |
|  | Daidzein | Soybean or other related species |
| HydroxybenzoicAcid | Gallic acid | Tobacco, oak or other related species |
|  | Vanillic acid | Tobacco, Acai or other related species |
|  | Protocatechuic acid | Tobacco, *Hibiscus* or other related species |
| Hydroxycinnamic acid | Ferunic acid | Tobacco or other related species |
|  | Cinnamic acid | Tobacco or other related species |
|  | Coumeric acid | Tobacco or other related species |
|  | Chlorogenic acid | Tobacco or other related species |
|  | Coffeic acid | Tobacco or other related species |
|  | Ferulic acid | Tobacco or other related species |
| Ellagitannin | Sanguiin | Raspberry or other related species |
| Stibene | Resveratrol | Grape or other related species |
| Lignan | Sesamin | Sesame or other related species |
| carotenoids | Caretonoids | Tobacco or carrots |
|  | Vitamin C | Tobacco or carrots |
| Glycyrrhzin |  | Licorice |

TABLE 7

Nucleotide sequence comparison between selected transcription factors. Percent identity is shown.
Nucleotide identity

|  | AtPAP1 | NtAN1 | NtAN2 | NtMYB3 | NtJAF13 |
|---|---|---|---|---|---|
| AtPAP1 |  | 15.12 | 49.35 | 46.99 | 17.72 |
| NtAN1 | 15.12 |  | 13.29 | 17.4 | 46.75 |
| NtAN2 | 49.35 | 13.29 |  | 39.98 | 14.24 |
| NtMYB3 | 46.99 | 17.4 | 39.98 |  | 19.4 |
| NtJAF13 | 17.72 | 46.75 | 14.24 | 19.4 |  |

TABLE 8

Amino acid sequence comparison between selected transcription factors. Percent identity is shown.
Amino Acid identity

|  | AtPAP1 | NtAN1 | NtAN2 | NtMYB3 | NtJAF13 |
|---|---|---|---|---|---|
| AtPAP1 |  | 6.8 | 46.3 | 33.67 | 7.5 |
| NtAN1 | 6.8 |  | 5.77 | 7.4 | 30.64 |
| NtAN2 | 46.3 | 5.77 |  | 32.78 | 7.19 |
| NtMYB3 | 33.67 | 7.4 | 32.78 |  | 9.25 |
| NtJAF13 | 7.5 | 30.64 | 7.19 | 9.25 |  |

TABLE 9

Nucleotide and protein sequences.

| Target Antioxidant | Gene Function annotation | Source | Protein SEQ ID No. | Coding SEQ ID No. |
|---|---|---|---|---|
| Anthocyanin | Putative alcohol dehydrogenase; [*Solanum lycopersicum* (Tomato) (*Lycopersicon esculentum*).] | tobacco | 1 | 24 |
| Anthocyanin | 1-O-acylglucose:anthocyanin-O-acyltransferase; [*Clitoria ternatea* (Butterfly pea).] | tobacco | 2 | 25 |
| Chlorogenic acid | 4-coumarate:CoA ligase; [*Ipomoea batatas* (Sweet potato) (*Convolvulus batatas*).]. Also called 4CL | tobacco | 3 | 26 |
| Chlorogenic acid | 4-coumarate:CoA ligase-like; [*Nicotiana sylvestris* (Wood tobacco) (South American tobacco).]. Also called 4CL. | tobacco | 4 | 27 |
| Anthocyanin | Anthocyanin 1a; [*Nicotiana tabacum* (Common tobacco).]. Also called AN1a. | tobacco | 5 | 28 |
| Anthocyanin | Anthocyanin 1b; [*Nicotiana tabacum* (Common tobacco).]. Also called AN1b. | tobacco | 6 | 29 |
| Anthocyanin | Anthocyanin 2; [*Nicotiana tomentosiformis* (Tobacco).] | tobacco | 7 | 30 |
| Anthocyanin | anthocyanidin synthase 2 [*Nicotiana tabacum*]. Also called ANS2. | tobacco | 8 | 31 |
| Anthocyanin | leucoanthocyanidin dioxygenase [*Nicotiana tabacum*] | tobacco | 9 | 32 |

TABLE 9-continued

Nucleotide and protein sequences.

| Target Antioxidant | Gene Function annotation | Source | Protein SEQ ID No. | Coding SEQ ID No. |
|---|---|---|---|---|
| Anthocyanin | BHLH transcription factor JAF13; [*Petunia hybrida* (*Petunia*).] | tobacco | 10 | 33 |
| Ferulic acid | *Nicotiana tabacum* caffeic acid O-methyltransferase II gene | tobacco | 11 | 34 |
| chlorogenic acid | trans-cinnamate 4-monooxygenase-like [*Nicotiana tomentosiformis*], Also called C4H. | tobacco | 12 | 35 |
| Anthocyanin | transcription factor MYB3-like [*Nicotiana tabacum*]; tobacco homolog of AtPAP1 | tobacco | 13 | 36 |
| Anthocyanin | *Nicotiana tabacum* dihydroflavonol-4-reductase (LOC107797232) | tobacco | 14 | 37 |
| Anthocyanin | *Nicotiana tabacum* NtDFR2 gene for dihydroflavonol-4-reductase | tobacco | 15 | 38 |
| Anthocyanin | *Nicotiana tabacum* myb-related protein 308-like (LOC107782378), mRNA-XM_016603259. | tobacco | 16 | 39 |
| Chlorogenic acid | *Nicotiana tabacum* shikimate O-hydroxycinnamoyltransferase-like; also called HCT. | tobacco | 17 | 40 |
| Chlorogenic acid | *Nicotiana tabacum* mRNA for hydroxycinnamoyl CoA quinate transferase (hqt gene); also called HQT. | tobacco | 18 | 41 |
| Anthocyanin, CGA, ferulic acid, cinnamate, coumarate caffeic acid | *Nicotiana tabacum* phenylalanine ammonia lyase (tpa1) gene; also called PAL. | tobacco | 19 | 42 |
| Anthocyanin | *Arabidopsis thaliana* ttg1 gene; WD40. | *Arabidopsis* | 20 | 43 |
| carotenoids | phytoene synthase 1 [*Nicotiana tabacum*] | tobacco | 21 | 44 |
| carotenoids | phytoene synthase 2, chloroplastic [*Nicotiana sylvestris*] | tobacco | 22 | 45 |
| Anthocyanin | Production of anthocyanin pigment 1; PAP1. | *Arabidopsis* | 23 | 46 |
| Flavonoids and anthocyanins | Phenylalanine ammonia-lyase 4 (NtPAL4) | tobacco | 47 | 53 |
| Flavonoids and anthocyanins | Phenylalanine ammonia-lyase 2 (NtPAL2) | tobacco | 48 | 54 |
| Flavonoids and anthocyanins | Chalcone synthase (NtCHS) | tobacco | 49 | 55 |
| Flavonoids and anthocyanins | Flavonol 3-hydratase (NtF3H) | tobacco | 50 | 56 |
|  | Arogenate dehydrogenase 1 (NtADT1) | tobacco | 51 | 57 |
| Chlorogenic acid, Flavonoids and anthocyanins | Arogenate dehydrogenase 2 (NtADT2) | tobacco | 52 | 58 |

Example 10: Creation of Cisgenic Constructs to Modulate TSNA Levels

Cisgenic constructs are created to constitutively express AtPAP1, NtAN2, and NtAN1a. Tobacco native Ubiquitin (Ubi-4) or Tubulin (Tub) promoters are used in conjunction with a tobacco native heat shock protein (HSP) terminator. Sequences are incorporated into a p45-2-7 transformation vector, and modified tobacco plants are generated, according to Example 1. Constructs encoding Ubi4-P:PAP1-HSP-T (SEQ ID NO:59), Ubi4-P:NtAN2-HSP-T (SEQ ID NO:60), Tub-P:NtAN2-HSP-T (SEQ ID NO:61), Ubi4-P:NtAN2-HSP-T:Tub-P:NtAN2-HSP-T (SEQ ID NO:62), and Ubi4-P:NtAN1a-HSP-T:Tub-P:NtAN2-HSP-T (SEQ ID NO:63) are transformed into tobacco plants. The presence of the cisgenic construct in a transformed plant is confirmed using amplicon sequencing. Modified tobacco plants (T0 and T1 generation) and control tobacco plants are grown for 4-6 weeks after transplantation to soil, harvested, and cured in PGC chambers. Cured leaf samples are prepared for evaluation of TSNAs, oxidative degradation potential, alkaloids, and nitrites/nitrates as described in Examples 2 to 7.

Example 11: A Combination Approach for Further Reduction of TSNAs

Three nicotine demethylase genes, known as CYP82E4, CYP82E5, and CYP82E10, mediate nornicotine biosynthesis in *Nicotiana tabacum*. Triple knockout mutants (cyp82e4, cyp82e5, cyp82e10) exhibit a dramatic reduction of nornicotine and consequently a reduction of NNN. A combination strategy is taken to combine nicotine demethylase mutants and the approach provided in Examples 2 to 7 to achieve a further TSNA reduction. A cyp82e4, cyp82e5, cyp82e10 triple mutant is transformed with one or more constructs described in Example 9 to increase antioxidant levels. Alternatively, cyp82e4, cyp82e5, cyp82e10 triple mutants are crossed with mutant or transgenic tobacco having elevated antioxidant levels described in Example 2.

What is claimed is:

1. A method for reducing the level of one or more tobacco-specific nitrosamines (TSNAs) in cured tobacco leaf or a tobacco product made therefrom, said method comprising
    a) increasing the level of one or more antioxidants in a tobacco plant via a transgene encoding a protein comprising a sequence having at least 90% identity to a sequence selected from the group consisting of SEQ ID No. 13 and 23; and
    b) reducing the level of said one or more TSNAs in cured tobacco leaf from said tobacco plant or a tobacco product made from said cured tobacco leaf.

2. The method of claim 1, wherein, prior to the increase of said one or more antioxidants, said tobacco plant is capable of producing cured tobacco leaf or tobacco product having a reduced level of one or more TSNAs compared to a control tobacco plant when grown and cured under comparable conditions.

3. The method of claim 2, wherein said tobacco plant comprises reduced nicotine demethylase activity compared to said control tobacco plant.

4. The method of claim 1, wherein the level of said one or more TSNAs is reduced by at least 50% compared to cured tobacco leaf or a tobacco product from a control tobacco plant not comprising said transgene or said genetic modification.

5. The method of claim 1, wherein said cured tobacco leaf comprises less than 2 ppm total TSNAs.

6. The method of claim 1, wherein said cured tobacco leaf comprises less than 0.08 ppm 4-methylnitrosoamino-1-(3-pyridyl)-1-butanone (NNK), wherein the level of said total TSNAs is measured based on a freeze-dried cured leaf sample using liquid chromatograph with tandem mass spectrometry (LC/MS/MS).

7. The method of claim 1, wherein said one or more antioxidants are selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin.

8. The method of claim 1, wherein said one or more tobacco-specific nitrosamines (TSNAs) are selected from the group consisting of N'-nitrosonornicotine (NNN), 4-methylnitrosoamino-1-(3-pyridyl)-1-butanone (NNK), N'-nitrosoanatabine (NAT), and any combination thereof.

9. The method of claim 1, wherein said transgene encodes a protein comprising a sequence having at least 95% identity to a sequence selected from the group consisting of SEQ ID No. 13 and 23.

10. The method of claim 1, wherein said tobacco plant is selected from the group consisting of a flue-cured variety, a Burley variety, a Maryland variety, a dark variety, and an Oriental variety.

11. A method for manufacturing a tobacco product having a reduced level of one or more TSNAs, said method comprising
    a) obtaining cured tobacco leaf comprising a transgene encoding a protein comprising a sequence having at least 90% identity to a sequence selected from the group consisting of SEQ ID No. 13 and 23, wherein the transgene provides an increased level of one or more antioxidants in said cured tobacco; and
    b) manufacturing a tobacco product comprising a reduced level of said one or more TSNAs using said cured tobacco leaf.

12. The method of claim 11, wherein the level of said one or more TSNAs is reduced by at least 50% compared to a control tobacco product not comprising said transgene.

13. The method of claim 11, wherein said tobacco product comprises less than 2 ppm total TSNAs.

14. The method of claim 11, wherein said cured tobacco leaf comprises less than 0.08 ppm 4-methylnitrosoamino-1-(3-pyridyl)-1-butanone (NNK), wherein the level of said total TSNAs is measured based on a freeze-dried cured leaf sample using liquid chromatograph with tandem mass spectrometry (LC/MS/MS).

15. The method of claim 11, wherein said one or more antioxidants are selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin.

16. The method of claim 11, wherein said one or more tobacco-specific nitrosamines (TSNAs) are selected from the group consisting of N'-nitrosonornicotine (NNN), 4-methylnitrosoamino-1-(3-pyridyl)-1-butanone (NNK), N'-nitrosoanatabine (NAT), and any combination thereof.

17. The method of claim 11, wherein said transgene encodes a protein comprising a sequence having at least 95% identity to a sequence selected from the group consisting of SEQ ID No. 13 and 23.

18. The method of claim 11, wherein said tobacco plant is selected from the group consisting of a flue-cured variety, a Burley variety, a Maryland variety, a dark variety, and an Oriental variety.

19. The method of claim 1, wherein the level of total TSNAs is reduced in said cured tobacco leaf or a tobacco product made therefrom.

20. The method of claim 1, wherein said transgene encodes a protein comprising a sequence having at least 97% identity to a sequence selected from the group consisting of SEQ ID No. 13 and 23.

21. The method of claim 1, wherein said transgene encodes a protein comprising a sequence having 100% identity to a sequence selected from the group consisting of SEQ ID No. 13 and 23.

22. The method of claim 3, wherein the tobacco plant comprises at least one mutation in a nicotine demethylase gene selected from the group consisting of CYP82E4, CYP82E5, CYP82E10, and a combination thereof.

23. The method of claim 11, wherein said transgene encodes a protein comprising a sequence having at least 97% identity to a sequence selected from the group consisting of SEQ ID No. 13 and 23.

24. The method of claim 11, wherein said transgene encodes a protein comprising a sequence having 100% identity to a sequence selected from the group consisting of SEQ ID No. 13 and 23.

25. The method of claim 1, wherein said tobacco plant does not contain a transgene encoding an antioxidant biosynthetic enzyme.

26. The method of claim 11, wherein said tobacco leaf does not contain a transgene encoding an antioxidant biosynthetic enzyme.

\* \* \* \* \*

SEQUENCE LISTING

<160> NUMBER OF SEQ ID NOS: 63

<210> SEQ ID NO 1
<211> LENGTH: 330
<212> TYPE: PRT
<213> ORGANISM: Nicotiana

<400> SEQUENCE: 1

| Met | Glu | Ser | Lys | Ser | Ser | Gly | Gly | Glu | Gly | Lys | Val | Val | Cys | Val |
|---|---|---|---|---|---|---|---|---|---|---|---|---|---|---|
| 1 | | | | 5 | | | | | 10 | | | | | 15 |

Thr Gly Ala Ser Gly Phe Ile Ala Ser Trp Leu Val Lys Met Leu Leu
                20                  25                  30

Gln Arg Gly Tyr Thr Val Asn Ala Thr Val Arg Asn Leu Lys Asp Ala
                35                  40                  45

Ser Lys Val Asp His Leu Leu Gly Leu Asp Gly Ala Lys Glu Arg Leu
    50                  55                  60

His Leu Phe Lys Ala Glu Leu Leu Gly Glu His Ser Phe Asp Pro Ala
65                  70                  75                  80

Val Asp Gly Cys Glu Gly Val Phe His Thr Ala Ser Pro Val Ser Leu
                85                  90                  95

Thr Ala Lys Ser Lys Glu Glu Leu Val Asp Pro Ala Val Ser Gly Thr
                100                105                110

Leu Asn Val Leu Arg Ser Cys Thr Lys Ser Thr Ser Val Arg Arg Val
                115                120                125

Val Ile Thr Ser Ser Thr Ala Ser Val Ile Cys Asn Lys Asn Met Ser
    130                  135                140

Thr Pro Gly Ala Val Ala Asp Glu Thr Trp Tyr Ser Asp Ala Glu Leu
145                  150                155              160

Cys Glu Glu Arg Lys Glu Trp Tyr Gln Leu Ser Lys Thr Leu Ala Glu
                165                170                175

Glu Ala Ala Trp Lys Phe Ala Lys Glu Asn Gly Leu Asp Leu Val Thr
            180                  185                190

Leu His Pro Gly Leu Val Ile Gly Pro Leu Leu Gln Pro Thr Leu Asn
            195                200                205

Phe Ser Cys Glu Ala Ile Val Asn Phe Ile Lys Glu Gly Lys Glu Ala
    210                  215                220

Trp Ser Gly Gly Ile Tyr Arg Phe Val Asp Val Arg Asp Val Ala Asn
225                  230                235              240

Ala His Ile Leu Ala Phe Glu Val Pro Ser Ala Asn Gly Arg Tyr Cys
                245                250                255

Leu Val Gly Val Asn Gly Tyr Ser Ser Leu Val Leu Lys Ile Val Gln
            260                  265                270

Lys Leu Tyr Pro Ser Ile Thr Leu Pro Glu Asn Phe Glu Asp Gly Leu
            275                280                285

Pro Leu Ile Pro Thr Phe Gln Val Ser Ser Glu Arg Ala Lys Ser Leu
    290                  295                300

Gly Val Asn Phe Thr Ser Leu Glu Leu Ser Val Lys Asp Thr Val Glu
305                  310                315              320

Ser Leu Ile Glu Lys Asn Phe Leu Lys Ile
            325                330

<210> SEQ ID NO 2
<211> LENGTH: 416
<212> TYPE: PRT
<213> ORGANISM: Nicotiana

<400> SEQUENCE: 2

```
Met Met Cys Asn Ile Ile Ser Leu Val Ser Ile Ile Asn Phe Phe Leu
1               5                   10                  15

Leu Phe Tyr Arg Val Val Leu Pro Gln His Ala Ala Ser His
            20                  25                  30

Ser Thr Val Glu Phe Leu Pro Gly Phe Glu Gly Pro Leu Pro Phe His
            35                  40                  45

Leu Glu Thr Gly Tyr Ile Gly Val Gly Glu Tyr Glu Val Gln Leu
    50                  55                  60

Phe Tyr Tyr Phe Leu Lys Ser Glu Ser Glu Pro Thr Lys Asp Pro Ile
65                  70                  75                  80

Leu Ile Trp Leu Ser Gly Pro Gly Cys Ser Ser Phe Thr Ala Leu
                85                  90                  95

Val Tyr Gln Ile Gly Pro Leu Tyr Phe Glu Pro Asn Glu Tyr Asn Gly
                100                 105                 110

Ser Leu Pro Lys Leu Thr Leu Asn Pro Asn Ser Trp Thr Lys Val Ala
            115                 120                 125

Asn Ile Ile Phe Leu Asp Gln Pro Val Asn Ser Gly Phe Ser Tyr Ala
130                 135                 140

Thr Thr Ser Thr Thr Phe Lys Ser Thr Asp Leu Gln Ala Cys His His
145                 150                 155                 160

Ile Tyr Gln Phe Leu Arg Lys Trp Leu Ile Lys His Gln Glu Phe Ile
                165                 170                 175

Arg Asn Pro Met Tyr Ile Gly Gly Asp Ser Tyr Ser Gly Ile Thr Val
            180                 185                 190

Pro Val Ile Thr Gln Leu Ile Ser Asn Gly Ile Glu Ala Gly His Lys
        195                 200                 205

Pro Ser Ile Asn Leu Lys Gly Tyr Ile Leu Gly Asn Pro Ser Thr Phe
210                 215                 220

Pro Leu Gln Tyr Asn Tyr Trp Val Pro Tyr Ala His Gly Met Gly Leu
225                 230                 235                 240

Ile Ser Asp Glu Leu Tyr Gln Ala Thr Thr Leu Ile Leu Tyr Phe Lys
                245                 250                 255

Ile Tyr His Ile Ile Asn Ala Ile Asn Leu Ala Tyr Met Val Glu Val
                260                 265                 270

His Arg Leu Ser Thr Tyr Trp Ala Asn Asp Pro Arg Val Gln Glu Ala
            275                 280                 285

Leu Asn Val Arg Lys Gly Ala Ile Thr Arg Trp Thr Arg Cys Arg Glu
        290                 295                 300

Ser Ile Val Asn Lys Thr Tyr Thr Ile Thr Phe Gln Asp Ser Ile Pro
305                 310                 315                 320

Tyr His Val Glu Leu Ser Lys Lys Leu Tyr Arg Ser Leu Ile Tyr Ser
                325                 330                 335

Gly Asp His Asp Met Gly Ile Pro Phe Gln Ser Thr Gln Phe Trp Ile
            340                 345                 350

Lys Ser Leu Asn Tyr Ser Ile Val Asp Glu Trp Arg Pro Trp Ser Phe
        355                 360                 365

Asp Gly Gln Val Ala Gly Tyr Thr Arg Ser Tyr Ser Asn Gln Met Thr
370                 375                 380

Phe Ala Thr Val Lys Gly Ala Gly His Val Ala Pro Glu Tyr Lys Pro
385                 390                 395                 400

Lys Glu Cys Phe Thr Met Phe Gln Arg Trp Leu Ser His Glu Pro Leu
                405                 410                 415
```

<210> SEQ ID NO 3
<211> LENGTH: 569
<212> TYPE: PRT
<213> ORGANISM: Nicotiana

<400> SEQUENCE: 3

Met Leu Ser Val Ala Ser Val Glu Ala Gln Lys Ala Glu Leu Ser Ser
1               5                   10                  15

Ser Val Ile Pro Pro Ser Asp Gln Ser Thr Glu Glu Ile His Val Phe
            20                  25                  30

Arg Ser Arg Leu Pro Asp Ile Gln Ile Ser Asn Asn Val Pro Leu His
        35                  40                  45

Val Tyr Leu Phe Glu Arg Leu Ser Glu Phe Gln Asp Arg Thr Cys Leu
    50                  55                  60

Ile Ala Gly Ser Ser Gly Gln Ser Tyr Thr Phe Ala Glu Thr His Leu
65                  70                  75                  80

Ile Cys Gln Lys Ile Ala Ala Gly Leu Thr Asn Ile Gly Ile Lys Lys
                85                  90                  95

Gly Asp Val Ile Met Thr Phe Leu Gln Asn Cys Ala Glu Phe Val Phe
            100                 105                 110

Thr Phe Leu Ser Ala Ser Met Ile Gly Ala Val Ile Thr Thr Ala Asn
        115                 120                 125

Pro Phe Tyr Thr Lys Ala Glu Ala Phe Lys Gln Leu Lys Ala Ser Asn
    130                 135                 140

Ala Lys Leu Ile Val Thr Gln Ser Gln Tyr Val Asp Lys Phe Arg Asp
145                 150                 155                 160

Ser Gly Glu Asn Asp Pro Lys Ile Gly Glu Asp Phe Ser Val Ile Thr
                165                 170                 175

Ile Asp Asp Pro Pro Glu Asn Cys Leu His Phe Ser Val Leu Ser Glu
            180                 185                 190

Ala Asn Glu Glu Glu Met Pro Lys Gly Ile Val Ile Gln Pro Asp Asp
        195                 200                 205

Pro Val Ala Leu Pro Phe Ser Ser Gly Thr Thr Gly Leu Pro Lys Gly
    210                 215                 220

Val Ile Leu Thr His Lys Ser Leu Ile Thr Gly Val Ala Gln Leu Val
225                 230                 235                 240

Asp Gly Asp Asn Pro Asn Leu Tyr Leu Lys Gln Asp Asp Val Val Leu
                245                 250                 255

Cys Val Leu Pro Leu Phe His Ile Phe Ala Leu Asn Ser Val Leu Leu
            260                 265                 270

Val Ser Leu Arg Ala Gly Ala Ser Val Leu Leu Met Gln Lys Phe Glu
        275                 280                 285

Ile Gly Ala Leu Leu Glu Leu Ile Gln Asn His Arg Val Ser Val Ala
    290                 295                 300

Ala Val Val Pro Pro Leu Val Leu Ala Leu Ala Lys Asn Pro Met Val
305                 310                 315                 320

Asp Ser Phe Asp Leu Ser Ser Ile Arg Leu Val Leu Ser Gly Ala Ala
                325                 330                 335

Pro Leu Gly Lys Glu Leu Glu Glu Ala Leu His Gln Arg Val Pro Gln
            340                 345                 350

Ala Ile Phe Gly Gln Gly Tyr Gly Met Thr Glu Ala Gly Pro Val Val
        355                 360                 365

Thr Met Cys Pro Ala Phe Ala Lys Gln Pro Phe Ser Thr Lys Ser Gly

-continued

```
              370                 375                 380
Ser Cys Gly Ser Val Val Arg Asn Ala Asp Leu Lys Val Val Asp Pro
385                 390                 395                 400

Glu Thr Gly Gly Ser Leu Gly Arg Asn Gln Pro Gly Glu Ile Cys Ile
                405                 410                 415

Arg Gly Ser Gln Ile Met Lys Gly Tyr Leu Asn Asp Asp Glu Ala Thr
                420                 425                 430

Ala Arg Thr Ile Asp Val Asp Gly Trp Leu His Thr Gly Asp Ile Gly
            435                 440                 445

Tyr Val Asp Asp Asp Glu Ile Tyr Ile Val Asp Arg Val Lys Glu
            450                 455                 460

Leu Ile Lys Phe Lys Gly Phe Gln Val Pro Ala Glu Leu Glu Ser
465                 470                 475                 480

Leu Leu Val Ser His Pro Asp Ile Ala Asp Ala Val Val Pro Gln
                485                 490                 495

Lys Asp Asp Ala Ala Gly Glu Val Pro Val Ala Phe Val Arg Ser
                500                 505                 510

Ala Asn Gly Phe Glu Ile Thr Glu Glu Ala Ile Lys Glu Phe Ile Ala
                515                 520                 525

Lys Gln Val Ile Phe Tyr Lys Arg Leu His Lys Val Tyr Phe Ile His
                530                 535                 540

Ala Ile Pro Lys Ser Pro Ser Gly Lys Ile Leu Arg Lys Glu Leu Arg
545                 550                 555                 560

Ala Lys Leu Ala Ala Pro Ser Thr Gln
                565
```

<210> SEQ ID NO 4
<211> LENGTH: 551
<212> TYPE: PRT
<213> ORGANISM: Nicotiana

<400> SEQUENCE: 4

```
Met Gly Thr Arg Ala Val Glu Ser Ser Gln Gln Gln Glu Cys Glu His
1               5                   10                  15

Ile Phe Arg Ser Arg Tyr Pro Pro Val Gln Val Pro Asp Asn Val Thr
                20                  25                  30

Leu Pro Asp Phe Val Leu His Asn Val Glu Leu Tyr Thr Asp Lys Met
            35                  40                  45

Ala Phe Val Asp Ala Thr Thr Gly Lys Gly Tyr Thr Tyr Gly Gln Val
        50                  55                  60

Ala Arg Asp Ile Arg Arg Phe Ala Lys Ala Leu Arg Ser Leu Gly Leu
65                  70                  75                  80

Arg Lys Gly Arg Val Val Val Val Leu Pro Asn Val Pro Glu Tyr
                85                  90                  95

Ala Ile Val Ala Leu Gly Ile Met Ala Ala Gly Gly Val Phe Ser Gly
                100                 105                 110

Ala Asn Pro Ala Ala His Ser Ser Glu Ile Val Lys Gln Val Glu Ser
                115                 120                 125

Ala Asp Gly Lys Leu Ile Val Ser Asp Leu Pro Thr Tyr His Lys Val
            130                 135                 140

Lys Asp Cys Gly Leu Pro Val Ile Leu Gly Glu Glu His Val Glu
145                 150                 155                 160

Gly Thr Ile His Trp Asp Glu Leu Leu Glu Ala Glu Arg Ala Gly
                165                 170                 175
```

```
Ser Arg Thr Asp His Ile Thr Asn His Glu Asp Glu Met Val Gln Gln
            180                 185                 190

Asn Asp Leu Cys Ala Leu Pro Phe Ser Ser Gly Thr Thr Gly Leu Ser
            195                 200                 205

Lys Gly Val Met Leu Thr His Arg Asn Leu Val Ala Asn Leu Cys Ser
        210                 215                 220

Thr Leu Phe Ser Val Ser Pro Glu Met Val Gly Gln Val Thr Thr Leu
225                 230                 235                 240

Gly Leu Ile Pro Phe Phe His Ile Tyr Gly Ile Thr Gly Ile Cys Cys
                245                 250                 255

Ala Thr Ile Arg Asn Lys Gly Lys Val Val Leu Arg Arg Tyr Glu
        260                 265                 270

Leu Arg Ala Phe Leu Asn Ala Leu Ile Thr His Glu Val Thr Phe Ala
        275                 280                 285

Pro Ile Val Pro Pro Ile Ile Leu Ala Leu Val Lys Asn Pro Ile Val
        290                 295                 300

Asp Glu Phe Asp Leu Ser Lys Leu Lys Leu Arg Ser Ile Met Thr Ala
305                 310                 315                 320

Ala Ala Pro Leu Ala Pro Glu Ile Leu Asn Glu Phe Glu Lys Lys Phe
                325                 330                 335

Pro Asp Val Gln Val Gln Glu Ala Tyr Gly Met Thr Glu His Ser Cys
            340                 345                 350

Ile Thr Leu Ser His Ser Asp Gln His Thr Ala Lys Arg Asn Ser Val
                355                 360                 365

Gly Phe Ile Leu Pro Asn Leu Glu Val Lys Phe Val Asp Pro Asp Thr
        370                 375                 380

Gly Arg Ser Leu Pro Lys Asn Lys Pro Gly Glu Ile Cys Val Lys Ser
385                 390                 395                 400

Gln Cys Val Met Lys Gly Tyr Tyr Lys Asn Glu Phe Glu Thr Cys Leu
                405                 410                 415

Thr Ile Asp Lys Asp Gly Trp Leu Gln Thr Gly Asp Ile Gly Tyr Ile
            420                 425                 430

Asp Asp Asp Gly Asp Ile Phe Leu Val Asp Arg Ile Lys Glu Leu Ile
            435                 440                 445

Lys Tyr Lys Gly Phe Gln Val Ala Pro Ala Glu Leu Glu Gly Ile Leu
        450                 455                 460

Leu Thr His Pro Ser Val Glu Asp Ala Ala Val Val Gly Leu Pro Asp
465                 470                 475                 480

Glu Glu Ala Gly Glu Ile Pro Val Ala Trp Val Val Leu Asn Ser Lys
                485                 490                 495

Ala Lys Glu Ser Glu Glu Asp Ile Ile Asn Tyr Ile Ala Ser Thr Val
            500                 505                 510

Ala Gln Tyr Lys Arg Val Arg Val Val Gln Phe Val Asp Ser Ile Pro
        515                 520                 525

Lys Ser Pro Ser Gly Lys Ile Leu Arg Arg Leu Ile Lys Asp Lys Met
        530                 535                 540

Leu Glu Arg Leu Lys Asn Ala
545                 550
```

<210> SEQ ID NO 5
<211> LENGTH: 671
<212> TYPE: PRT
<213> ORGANISM: Nicotiana

<400> SEQUENCE: 5

```
Met Thr Glu Ile Pro Pro Asn Ser Gln Met Lys Thr Met Leu Gln Lys
1               5                   10                  15

Ala Val Gln Ser Val Gln Trp Thr Tyr Thr Leu Phe Trp Gln Leu Cys
            20                  25                  30

Pro Gln Gln Gly Ala Leu Val Trp Arg Asp Gly Tyr Tyr Asn Gly Ala
        35                  40                  45

Ile Lys Thr Arg Lys Thr Val Gln Pro Met Glu Val Ser Ala Glu Glu
    50                  55                  60

Ala Ser Leu His Arg Ser Gln Gln Leu Arg Glu Leu Tyr Glu Ser Leu
65                      70                  75                  80

Ser Ala Gly Glu Ser Asn Gln Pro Ala Arg Arg Pro Ser Ala Ala Leu
                85                  90                  95

Ser Pro Glu Asp Leu Thr Glu Ser Glu Trp Phe Tyr Leu Met Cys Val
            100                 105                 110

Ser Phe Ser Phe Pro Pro Gly Ile Gly Leu Pro Gly Lys Ala Tyr Ser
        115                 120                 125

Lys Lys His His Ile Trp Ile Met Gly Ala Asn Glu Val Asp Ser Lys
    130                 135                 140

Val Phe Cys Arg Ala Ile Leu Ala Lys Ser Ala Arg Ile Gln Thr Val
145                 150                 155                 160

Val Gly Ile Pro Leu Leu Asp Gly Val Leu Glu Leu Gly Thr Thr Glu
                165                 170                 175

Arg Val Gln Glu Glu Ile Gly Phe Ile Asn His Val Lys Ser Phe Phe
            180                 185                 190

Thr Glu Gln Gln Gln Pro Gln Leu Pro Lys Pro Ala Leu Ser Glu His
        195                 200                 205

Ser Thr Ser Asn Pro Thr Thr Phe Ser Glu Pro His Phe Tyr Ser Gly
    210                 215                 220

Asn Thr Ser Pro Ser Ala Asn Val Asp Ile Ala His Gln Asp Gly Gly
225                 230                 235                 240

Ala Ala Gly Glu Glu Asp Glu Glu Glu Glu Glu Glu Asp Asp Asp
                245                 250                 255

Glu Ala Glu Leu Asp Ser Asp Ser Ile Ala Ile Gln Ser Ala Ala Asn
            260                 265                 270

Pro Ile Ala Val Glu Ala Ser Glu Leu Met Gln Leu Asp Val Ser Glu
        275                 280                 285

Ala Ile Gln Leu Gly Ser Pro Asp Asp Asp Ser Asp Asn Met Asp Ser
    290                 295                 300

Asp Phe His Leu Val Gly Ala Gly Asn Thr Ala His Asp Tyr Gln Arg
305                 310                 315                 320

Gln Ala Asp Ser Phe Lys Ala Glu Thr Ala Ile Ser Trp Pro His Phe
                325                 330                 335

Gln Asp Leu Gln Gln Leu Pro Gly Gly Ser Ser Tyr Asp Glu Leu Ser
            340                 345                 350

Gln Glu Asp Thr His Tyr Ser Gln Thr Val Ser Thr Ile Leu Glu His
        355                 360                 365

Arg Ser Ser Lys Phe Ser Ser Thr Thr Met Gly Cys Ile Ser His Asp
    370                 375                 380

Ser Ala Gln Ser Ala Phe Thr Leu Cys Pro Ser Thr Val Cys Ser
385                 390                 395                 400

Pro Asn Pro Ala His Cys Arg His Asp Asp Ser Leu Val Asp Gly Gly
                405                 410                 415
```

```
Gly Ala Ser Gln Trp Leu Leu Lys Ser Ile Leu Phe Thr Val Pro Phe
                420                 425                 430

Leu His Thr Lys Tyr Gln Ser Glu Ala Ser Pro Lys Ser Arg Asp Val
            435                 440                 445

Ala Thr Val Asp Ser Ser Thr Ala Ser Arg Phe Arg Lys Gly Cys
450                 455                 460

Ser Ile Thr Ser Gln Glu Glu Pro Ser Gly Asn His Val Leu Ala Glu
465                 470                 475                 480

Arg Arg Arg Arg Glu Lys Leu Asn Glu Arg Phe Ile Ile Leu Arg Ser
                485                 490                 495

Leu Val Pro Phe Val Thr Lys Met Asp Lys Ala Ser Ile Leu Gly Asp
            500                 505                 510

Thr Ile Glu Tyr Val Lys Gln Leu Arg Lys Lys Val Gln Asp Leu Glu
        515                 520                 525

Ala Arg Ala Arg Asp Thr Glu His Ser Arg Asp Ala Asp Lys Lys Gly
            530                 535                 540

Gly Thr Ala Thr Val Lys Val Leu Gln Gly Arg Gly Lys Arg Arg Met
545                 550                 555                 560

Asn Thr Val Asp Gly Ser Val Gly Gly Gln Ala Thr Ile Thr Ala
                565                 570                 575

Ser Pro Pro Ser Thr Thr Glu Asn Glu Glu Val Val Gln Val Gln Val
            580                 585                 590

Ser Ile Ile Glu Ser Asp Ala Leu Val Glu Leu Arg Cys Pro Tyr Lys
        595                 600                 605

Glu Gly Leu Leu Leu Asn Val Met Gln Met Leu Arg Glu Leu Lys Val
610                 615                 620

Glu Val Val Ala Ile Gln Ser Ala Leu Asn Asn Gly Val Phe Leu Ala
625                 630                 635                 640

Glu Leu Arg Ala Lys Val Lys Glu Asn Ile Cys Gly Arg Lys Ala Ser
                645                 650                 655

Ile Leu Glu Val Lys Arg Ser Ile His Gln Ile Ile Pro Arg Asp
            660                 665                 670

<210> SEQ ID NO 6
<211> LENGTH: 683
<212> TYPE: PRT
<213> ORGANISM: Nicotiana

<400> SEQUENCE: 6

Met Thr Glu Ile Pro Pro Asn Ser Gln Met Gln Thr Met Leu Gln Lys
1               5                   10                  15

Ala Val Gln Ser Val Gln Trp Thr Tyr Thr Leu Phe Trp Gln Leu Cys
                20                  25                  30

Ser Gln Gly Val Leu Val Trp Arg Asp Gly Tyr Tyr Asn Gly Ala
            35                  40                  45

Ile Lys Thr Arg Lys Thr Val Gln Pro Met Glu Val Ser Ala Glu Glu
50                  55                  60

Ala Ser Leu His Arg Ser Gln Gln Leu Arg Glu Leu Tyr Glu Ser Leu
65                  70                  75                  80

Ser Ala Gly Glu Ser Asn Gln Pro Ala Arg Arg Pro Ser Ala Ala Leu
                85                  90                  95

Ser Pro Glu Asp Leu Thr Glu Ser Glu Trp Phe Tyr Leu Met Cys Val
            100                 105                 110

Ser Phe Ser Phe Pro Pro Gly Ile Gly Leu Pro Gly Lys Ala Tyr Ser
        115                 120                 125
```

```
Lys Lys His His Ile Trp Ile Met Cys Ala Asn Glu Val Asp Ser Lys
    130                 135                 140

Val Phe Cys Arg Ala Ile Leu Ala Lys Ser Ala Arg Ile Gln Thr Val
145                 150                 155                 160

Val Cys Ile Pro Leu Leu Asp Gly Val Leu Glu Leu Gly Thr Thr Glu
                165                 170                 175

Arg Val Gln Glu Asp Ile Gly Phe Ile Asn His Val Lys Ser Phe Phe
            180                 185                 190

Thr Glu Gln Gln Gln Pro Gln Pro Pro Lys Pro Ala Leu Ser Glu His
        195                 200                 205

Ser Thr Ser Asn Ser Thr Thr Phe Ser Glu Pro His Phe Tyr Ser Gly
    210                 215                 220

Asn Thr Pro Pro Ser Gly Asn Ala Asp Ile Ala Gln Gln Asp Gly Gly
225                 230                 235                 240

Ala Ala Gly Glu Glu Asp Glu Glu Glu Glu Glu Asp Asp Glu
                245                 250                 255

Ala Glu Leu Asp Ser Asp Ser Ile Ala Ile Gln Ser Glu Val Gly Gly
            260                 265                 270

Ala Ala Asn Pro Ile Ala Ala Glu Ala Ser Glu Leu Met Gln Leu Asp
        275                 280                 285

Met Ser Glu Ala Ile Arg Leu Gly Ser Pro Asp Asp Gly Ser Asn Asn
    290                 295                 300

Met Asp Ser Asp Phe His Leu Val Gly Ala Gly Asn Thr Ala Asp Tyr
305                 310                 315                 320

Gln Arg Gln Pro Asp Ser Phe Lys Ala Glu Thr Ala Ile Ser Trp Ala
                325                 330                 335

His Phe Gln Asp Leu Gln His Leu Pro Gly Gly Ser Ser Tyr Glu Glu
            340                 345                 350

Leu Ser Gln Glu Asp Thr His Tyr Ser Gln Thr Val Ser Thr Ile Leu
        355                 360                 365

Glu His Phe Ser Asn Arg Ser Ser Lys Phe Ser Ser Thr Thr Met Gly
    370                 375                 380

Cys Ile Ser His Asp Ser Ala Gln Ser Ala Phe Thr Leu Cys Pro Ser
385                 390                 395                 400

Thr Thr Val Asp Cys Ser Pro Asn Pro Ala His Cys Arg Arg Arg His
                405                 410                 415

Asp Asp Ser Leu Leu Asp Gly Gly Ala Ser Pro Ser Ser Gln Trp
            420                 425                 430

Leu Leu Lys Ser Ile Leu Phe Thr Val Pro Phe Leu His Thr Lys Tyr
        435                 440                 445

Gln Ser Glu Ala Ser Pro Lys Ser Val Asp Val Ala Thr Val Asp Ser
    450                 455                 460

Ser Ser Thr Ala Ser Arg Phe Arg Lys Gly Cys Ser Ile Thr Ser Gln
465                 470                 475                 480

Glu Glu Pro Ser Gly Asn His Val Leu Ala Arg Arg Arg Glu
                485                 490                 495

Lys Leu Asn Glu Arg Phe Ile Ile Leu Arg Ser Leu Val Pro Phe Val
            500                 505                 510

Thr Lys Met Asp Lys Ala Ser Ile Leu Gly Asp Thr Ile Glu Tyr Val
        515                 520                 525

Lys Gln Leu His Lys Lys Val Gln Asp Leu Glu Ala Arg Ala Arg His
    530                 535                 540
```

```
Thr Glu Gln Ser Lys Asp Ala Asp Gln Lys Ser Gly Thr Ala Thr Val
545                 550                 555                 560

Lys Val Leu Gln Gly Arg Gly Lys Arg Arg Met Asn Thr Val Glu Ala
                565                 570                 575

Gly Asn Ile Gly Gly Gly Gln Ala Lys Met Thr Ala Phe Pro Leu Ser
            580                 585                 590

Thr Thr Glu Asp Glu Glu Val Gln Val Glu Val Ser Ile Ile Glu
        595                 600                 605

Ser Asp Ala Leu Leu Glu Leu Arg Cys Pro Tyr Lys Glu Gly Leu Leu
    610                 615                 620

Leu Asp Val Met Gln Met Leu Arg Glu Leu Lys Val Glu Val Val Ala
625                 630                 635                 640

Ile Gln Ser Ser Leu Asn Asn Gly Ile Phe Leu Ala Glu Leu Arg Ala
                645                 650                 655

Lys Val Lys Glu Asn Ile Tyr Gly Arg Lys Ala Ser Ile Val Glu Val
                660                 665                 670

Lys Lys Ser Ile His Gln Ile Ile Pro Arg Asp
                675                 680
```

<210> SEQ ID NO 7
<211> LENGTH: 220
<212> TYPE: PRT
<213> ORGANISM: Nicotiana

<400> SEQUENCE: 7

```
Met Asn Ile Cys Thr Asn Lys Ser Ser Gly Val Lys Lys Gly Ala
1               5                   10                  15

Trp Thr Glu Glu Asp Val Leu Leu Lys Lys Cys Ile Glu Lys Tyr
                20                  25                  30

Gly Glu Gly Lys Trp His Gln Val Pro Leu Arg Ala Gly Leu Asn Arg
            35                  40                  45

Cys Arg Lys Ser Cys Arg Leu Arg Trp Leu Asn Tyr Leu Arg Pro His
    50                  55                  60

Ile Lys Arg Gly Asp Phe Ser Phe Asp Glu Val Asp Leu Ile Leu Arg
65                  70                  75                  80

Leu His Lys Leu Leu Gly Asn Arg Trp Ser Leu Ile Ala Gly Arg Leu
                85                  90                  95

Pro Gly Arg Thr Ala Asn Asp Val Lys Asn Tyr Trp Asn Ser His Leu
            100                 105                 110

Arg Lys Lys Leu Ile Ala Pro His Asp Gln Lys Glu Ser Lys Gln Lys
        115                 120                 125

Ala Lys Lys Ile Thr Ile Phe Arg Pro Arg Pro Arg Thr Phe Ser Lys
    130                 135                 140

Thr Asn Thr Cys Val Lys Ser Asn Thr Asn Val Asp Lys Asp Ile
145                 150                 155                 160

Glu Gly Ser Ser Glu Ile Ile Arg Phe Asn Asp Asn Leu Lys Pro Thr
                165                 170                 175

Thr Glu Glu Leu Thr Asp Asp Gly Ile Gln Trp Trp Ala Asp Leu Leu
            180                 185                 190

Ala Asn Asn Tyr Asn Asn Asn Gly Ile Glu Glu Ala Asp Asn Ser Ser
        195                 200                 205

Pro Thr Leu Leu His Glu Glu Met Pro Leu Leu Ser
    210                 215                 220
```

<210> SEQ ID NO 8

<211> LENGTH: 419
<212> TYPE: PRT
<213> ORGANISM: Nicotiana

<400> SEQUENCE: 8

```
Met Val Ile Ser Ala Val Val Pro Thr Pro Ser Arg Val Glu Ser
1               5                   10                  15

Leu Ala Lys Ser Gly Ile Gln Ala Ile Pro Lys Glu Tyr Val Arg Pro
                20                  25                  30

Gln Glu Glu Leu Asn Gly Ile Gly Asn Ile Phe Glu Glu Lys Lys
            35                  40                  45

Asp Glu Gly Pro Gln Val Pro Thr Ile Asp Leu Lys Glu Ile Asp Ser
50                  55                  60

Glu Asp Lys Glu Ile Arg Glu Lys Cys His Lys Glu Leu Lys Lys Ala
65                  70                  75                  80

Ala Met Glu Trp Gly Val Met Tyr Leu Val Asn His Gly Ile Ser Asp
                85                  90                  95

Gln Leu Ile Asp Arg Val Lys Val Ala Gly Lys Thr Phe Phe Asp Gln
            100                 105                 110

Pro Val Glu Glu Lys Glu Lys Tyr Ala Asn Asp Gln Pro Ser Gly Asn
        115                 120                 125

Val Gln Gly Tyr Gly Ser Lys Leu Ala Asn Ser Ala Cys Gly Gln Leu
130                 135                 140

Glu Trp Glu Asp Tyr Phe Phe His Cys Val Phe Pro Glu Asp Lys Cys
145                 150                 155                 160

Asp Leu Ser Ile Trp Pro Lys Ile Pro Thr Asp Tyr Ile Pro Ala Thr
                165                 170                 175

Ser Glu Tyr Ala Lys Gln Ile Arg Asn Leu Ala Thr Lys Ile Leu Ala
            180                 185                 190

Val Leu Ser Ile Gly Leu Gly Leu Glu Glu Gly Arg Leu Glu Lys Glu
        195                 200                 205

Val Gly Gly Lys Glu Asp Leu Leu Leu Gln Met Lys Ile Asn Tyr Tyr
210                 215                 220

Pro Lys Cys Pro Gln Pro Glu Leu Ala Leu Gly Val Glu Ala His Thr
225                 230                 235                 240

Asp Val Ser Ala Leu Thr Phe Ile Leu His Asn Met Val Pro Gly Leu
                245                 250                 255

Gln Leu Phe Tyr Glu Gly Gln Trp Val Thr Ala Lys Cys Val Pro Asn
            260                 265                 270

Ser Ile Ile Met His Ile Gly Asp Thr Leu Glu Ile Leu Ser Asn Gly
        275                 280                 285

Lys Tyr Lys Ser Ile Leu His Arg Gly Val Val Asn Lys Glu Lys Val
290                 295                 300

Arg Ile Ser Trp Ala Ile Phe Cys Glu Pro Pro Lys Glu Lys Ile Ile
305                 310                 315                 320

Leu Lys Pro Leu Ser Glu Thr Ile Thr Glu Ala Glu Pro Pro Arg Phe
                325                 330                 335

Pro Pro Arg Thr Phe Ala Gln His Met Ala His Lys Leu Phe Lys Lys
            340                 345                 350

Asp Asp Gln Asp Ala Ala Ala Glu His Lys Val Ser Lys Lys Asp Asp
        355                 360                 365

Pro Asp Ser Ala Ala Gly His Lys Pro Phe Lys Asp Asp Gln Asp
370                 375                 380

Ala Val Val Gln Gln Lys Val Leu Lys Glu Asp Glu Gln Asp Ala Ala
```

-continued

```
                385                 390                 395                 400
Ala Glu His Lys Val Phe Lys Asp Asn Gln Asp Ala Ala Glu
                    405                 410                 415
Glu Ser Lys

<210> SEQ ID NO 9
<211> LENGTH: 419
<212> TYPE: PRT
<213> ORGANISM: Nicotiana

<400> SEQUENCE: 9

Met Val Val Ile Ser Ala Val Val Pro Thr Pro Ser Arg Val Glu Ser
1               5                   10                  15

Leu Ala Lys Ser Gly Ile Gln Ala Ile Pro Lys Glu Tyr Val Arg Pro
                20                  25                  30

Gln Glu Glu Leu Asn Gly Ile Gly Asn Ile Phe Glu Glu Lys Lys
            35                  40                  45

Asp Glu Gly Pro Gln Val Pro Thr Ile Asp Leu Thr Glu Ile Asp Ser
        50                  55                  60

Glu Asp Lys Glu Ile Arg Glu Lys Cys His Gln Glu Leu Lys Lys Ala
65                  70                  75                  80

Ala Ile Glu Trp Gly Val Met His Leu Val Asn His Gly Ile Ser Asp
                85                  90                  95

Glu Leu Ile Asp Arg Val Lys Val Ser Gly Asp Thr Phe Phe Asp Gln
            100                 105                 110

Pro Val Glu Glu Lys Glu Lys Tyr Ala Asn Asp Gln Pro Ser Gly Asn
        115                 120                 125

Val Gln Gly Tyr Gly Ser Lys Leu Ala Asn Ser Ala Cys Gly Gln Leu
130                 135                 140

Glu Trp Glu Asp Tyr Phe Phe His Cys Val Phe Pro Glu Asp Lys Cys
145                 150                 155                 160

Asn Leu Ser Ile Trp Pro Lys Thr Pro Thr Asp Tyr Ile Pro Ala Thr
                165                 170                 175

Ser Glu Tyr Ala Lys Gln Ile Arg Asn Leu Ala Thr Lys Ile Leu Ala
            180                 185                 190

Val Leu Ser Ile Gly Leu Arg Leu Glu Glu Gly Arg Leu Glu Lys Glu
        195                 200                 205

Val Gly Gly Met Glu Asp Leu Leu Gln Met Lys Ile Asn Tyr Tyr
210                 215                 220

Pro Lys Cys Pro Gln Pro Glu Leu Ala Leu Gly Val Glu Ala His Thr
225                 230                 235                 240

Asp Val Ser Ala Leu Thr Phe Ile Leu His Asn Met Val Pro Gly Leu
                245                 250                 255

Gln Leu Phe Tyr Glu Gly Gln Trp Val Thr Ala Lys Cys Val Pro Asn
            260                 265                 270

Ser Ile Ile Met His Ile Gly Asp Thr Leu Glu Ile Leu Ser Asn Gly
        275                 280                 285

Lys Tyr Lys Ser Ile Leu His Arg Gly Val Val Asn Lys Glu Lys Ile
290                 295                 300

Arg Ile Ser Trp Ala Ile Phe Cys Glu Pro Lys Glu Lys Ile Ile
305                 310                 315                 320

Leu Lys Pro Leu Pro Glu Thr Ile Thr Glu Ala Glu Pro Pro Arg Phe
                325                 330                 335

Pro Pro Arg Thr Phe Ala Gln His Met Ala His Lys Leu Phe Lys Lys
```

```
                340             345             350
Asp Asp Gln Asp Ala Ala Glu His Lys Val Ser Lys Lys Asp Asp
            355             360             365

Pro Asp Ser Ala Ala Glu His Lys Pro Phe Lys Lys Asp Asp Gln Asp
        370             375             380

Ala Val Ala Gln Gln Lys Val Leu Lys Glu Asp Glu Gln Asn Ala Ala
385             390             395             400

Ala Glu His Lys Val Phe Lys Lys Asp Asn Gln Asp Ala Ala Ala Glu
            405             410             415

Glu Ser Lys

<210> SEQ ID NO 10
<211> LENGTH: 622
<212> TYPE: PRT
<213> ORGANISM: Nicotiana

<400> SEQUENCE: 10

Met Ala Met Gly His Gln Asp Gln Asp Gly Val Pro Asn Asn Leu Arg
1               5               10              15

Lys Gln Leu Ala Leu Ala Val Arg Gly Ile Gln Trp Ser Tyr Ala Ile
            20              25              30

Phe Trp Ser Thr Pro Val Thr Gln Pro Gly Val Leu Glu Trp Ser Asp
        35              40              45

Gly Tyr Tyr Asn Gly Asp Ile Lys Thr Arg Lys Thr Val Gln Val Gly
    50              55              60

Glu Val Asn Glu Asp Gln Leu Gly Leu His Arg Thr Glu Gln Leu Arg
65              70              75              80

Glu Leu Tyr Ser Ser Leu Leu Thr Gly Glu Gly Glu Glu Asp Leu Gln
            85              90              95

Pro Gln Ala Lys Arg Pro Ser Ala Ala Leu Ser Pro Glu Asp Leu Thr
        100             105             110

Asp Thr Glu Trp Tyr Phe Leu Val Cys Met Ser Phe Val Phe Asn Val
    115             120             125

Gly Gln Gly Leu Pro Gly Lys Thr Ser Ala Thr Asn Gln Thr Ile Trp
130             135             140

Leu Cys Asn Ala His Gln Ala Glu Ser Arg Val Phe Ser Arg Ser Leu
145             150             155             160

Leu Ala Lys Ser Ala Ser Ile Gln Thr Val Val Cys Phe Pro Tyr Leu
            165             170             175

Gly Gly Val Ile Glu Leu Gly Val Thr Glu Leu Val Leu Glu Asp Pro
        180             185             190

Asn Leu Ile Gln Gln Ile Lys Asn Ser Phe Glu Val Asp His Ser Val
    195             200             205

Ile Ser Lys Arg Pro Asn Tyr Asn Ser Asn Asp Ala Lys Asp Asp Met
210             215             220

Asn Val Ala Ser Arg Lys Leu Asp His Asn Val Leu Glu Ser Asp Ala
225             230             235             240

Tyr Pro Val Glu Ile Asn Asn Ser Ser Pro His Asp Ser Ser Asn Gly
            245             250             255

Phe Val Ala Asn Gln Glu Ala Glu Asp Ser Leu Met Val Val Gly Val
        260             265             270

Ile Gly Glu Thr Ser Gln Ala Gln Ser Trp Lys Phe Val Asp Asp Asn
    275             280             285

Met Ser Asn Gly Val His Asn Ser Leu Asn Ser Ser Asp Cys Ile Ser
```

```
                290                 295                 300
Gln Asn Tyr Glu Lys Leu Ser Pro Leu Ser Asn Gly Glu Lys Glu Thr
305                 310                 315                 320

Lys Pro Cys Pro Ile Asp Arg Gln Glu His Asn Gln Asn Lys Leu His
                325                 330                 335

Leu Leu Asp His Gln Gly Asp Ala Gln Tyr Gln Ala Val Ile Ser
                340                 345                 350

Thr Leu Leu Lys Ser Ser Asp Gln Leu Thr Leu Gly Pro His Phe Arg
                355                 360                 365

Asn Ile Asn Lys Lys Ser Ser Phe Ala Gly Trp Lys Asn Asp Thr Glu
                370                 375                 380

Ala Pro Arg Ile Gly Thr Ala Gln Lys Leu Leu Lys Lys Val Leu Leu
385                 390                 395                 400

Glu Val Pro Arg Met His Gly Gly Val Thr His Lys Phe Ser Arg Glu
                405                 410                 415

Asn Arg Lys Lys Asn Gly Leu Trp Arg Pro Glu Val Asp Asp Ile Asp
                420                 425                 430

Arg Ser Arg Val Ile Ser Glu Arg Arg Arg Glu Lys Ile Asn Glu
                435                 440                 445

Arg Phe Met His Leu Ala Ser Met Leu Pro Thr Gly Gly Lys Val Asp
                450                 455                 460

Lys Ile Ser Leu Leu Asp Glu Thr Ile Glu Tyr Met Lys Glu Leu Glu
465                 470                 475                 480

Arg Arg Val Gln Glu Leu Glu Ala Arg Ser Gly Lys Lys Thr Asn Asp
                485                 490                 495

Thr Ala Glu Gln Thr Ser Asp Asn Cys Gly Thr Ser Lys Phe Asn Asp
                500                 505                 510

Val Asn Gly Ser Leu Lys Arg Lys Ala Cys Asp Met Asp Glu Met Glu
                515                 520                 525

Pro Glu Ser Cys Asn Glu Leu Leu Lys Gly Ser Ser Ala Asp Gly Ile
                530                 535                 540

Val Ile Ser Met Ile Asp Lys Glu Val Ser Ile Lys Met Arg Cys Leu
545                 550                 555                 560

Trp Ser Glu Gly Leu Leu Leu Lys Ile Met Glu Ala Leu Thr Asp Leu
                565                 570                 575

Gln Met Asp Cys His Thr Val Gln Ser Ser Lys Ile Asp Gly Ile Leu
                580                 585                 590

Ser Ile Ala Ile Glu Ser Lys Ser Asn Gly Leu Lys Thr Val Ser Val
                595                 600                 605

Gly Ala Ile Arg Glu Val Leu Gln Arg Val Val Trp Lys Ser
610                 615                 620

<210> SEQ ID NO 11
<211> LENGTH: 364
<212> TYPE: PRT
<213> ORGANISM: Nicotiana

<400> SEQUENCE: 11

Met Glu Ser Ser Thr Lys Ser Gln Ile Pro Thr Gln Ser Glu Glu
1               5                   10                  15

Arg Asn Cys Thr Tyr Ala Met Gln Leu Leu Ser Ser Val Leu Pro
                20                  25                  30

Phe Val Leu His Ser Thr Ile Gln Leu Glu Val Phe Glu Ile Leu Ala
                35                  40                  45
```

```
Lys Ser Asn Asp Thr Lys Leu Ser Ala Ser Gln Ile Val Ser Gln Ile
 50                  55                  60

Pro Asn Cys Thr Lys Pro Glu Ala Pro Thr Met Leu Asn Arg Met Leu
 65                  70                  75                  80

Tyr Val Leu Ala Ser Tyr Ser Leu Phe Thr Cys Ser Ile Val Glu Asp
                 85                  90                  95

Glu Lys Asn Asn Gly Gly Gln Lys Arg Val Tyr Gly Leu Ser Gln Val
                100                 105                 110

Gly Lys Phe Phe Val Lys Asn Glu Asn Gly Ala Ser Met Gly Pro Leu
                115                 120                 125

Leu Ala Leu Leu Gln Asn Lys Val Phe Ile Asn Ser Trp Phe Glu Leu
130                 135                 140

Lys Asp Ala Val Leu Glu Gly Val Pro Phe Asp Arg Val His Gly
145                 150                 155                 160

Val His Ala Phe Glu Tyr Pro Lys Ser Asp Pro Lys Phe Asn Asp Val
                165                 170                 175

Phe Asn Lys Ala Met Ile Asn His Thr Thr Val Val Met Lys Lys Ile
                180                 185                 190

Leu Glu Asn Tyr Lys Gly Phe Glu Asn Leu Lys Thr Leu Val Asp Val
                195                 200                 205

Gly Gly Gly Leu Gly Val Asn Leu Lys Met Ile Thr Ser Lys Tyr Pro
                210                 215                 220

Thr Ile Lys Gly Thr Asn Phe Asp Leu Pro His Val Val Gln His Ala
225                 230                 235                 240

Pro Ser Tyr Pro Gly Val Glu His Val Gly Gly Asp Met Phe Glu Ser
                245                 250                 255

Val Pro Glu Gly Asp Ala Ile Phe Met Lys Trp Ile Leu His Asp Trp
                260                 265                 270

Ser Asp Ser His Asn Leu Lys Leu Leu Lys Asn Cys Tyr Lys Ala Leu
                275                 280                 285

Pro Asp Asn Gly Lys Val Ile Val Val Glu Ala Ile Leu Pro Val Lys
                290                 295                 300

Pro Asp Ile Asp Thr Ala Val Val Gly Val Ser Gln Cys Asp Leu Ile
305                 310                 315                 320

Met Met Ala Gln Asn Pro Gly Gly Lys Glu Arg Ser Glu Glu Glu Phe
                325                 330                 335

Arg Ala Leu Ala Thr Glu Ala Gly Phe Lys Gly Val Asn Leu Ile Cys
                340                 345                 350

Cys Val Cys Asn Phe Trp Val Met Glu Phe Cys Lys
                355                 360

<210> SEQ ID NO 12
<211> LENGTH: 506
<212> TYPE: PRT
<213> ORGANISM: Nicotiana

<400> SEQUENCE: 12

Met Asp Leu Leu Leu Leu Glu Lys Thr Leu Ile Gly Leu Phe Phe Ala
 1               5                  10                  15

Ile Ile Val Ala Ile Val Val Ser Lys Leu Arg Ser Lys Asn Phe Lys
                 20                  25                  30

Leu Pro Pro Gly Pro Ile Pro Val Pro Val Phe Gly Asn Trp Leu Gln
                 35                  40                  45

Val Gly Asp Asp Leu Asn His Arg Asn Leu Thr Glu Tyr Ala Lys Lys
 50                  55                  60
```

-continued

```
Phe Gly Asp Met Phe Leu Leu Arg Met Gly Gln Arg Asn Leu Val Val
 65                  70                  75                  80

Val Ser Ser Pro Glu Leu Ala Lys Glu Val Leu His Thr Gln Gly Val
                 85                  90                  95

Glu Phe Gly Ser Arg Thr Arg Asn Val Val Phe Asp Ile Phe Thr Gly
                100                 105                 110

Lys Gly Gln Asp Met Val Phe Thr Val Tyr Gly Glu His Trp Arg Lys
                115                 120                 125

Met Arg Arg Ile Met Thr Val Pro Phe Phe Thr Asn Lys Val Val Gln
130                 135                 140

Gln Tyr Arg Arg Gly Trp Glu Asp Glu Val Ala His Val Val Glu Asp
145                 150                 155                 160

Val Lys Lys Asn Pro Glu Ser Ala Thr Asn Gly Ile Val Leu Arg Lys
                165                 170                 175

Arg Leu Gln Leu Met Met Tyr Asn Asn Met Tyr Arg Ile Met Phe Asp
                180                 185                 190

Arg Arg Phe Glu Ser Glu Asp Asp Pro Leu Phe Asn Lys Leu Lys Ala
                195                 200                 205

Leu Asn Gly Glu Arg Ser Arg Leu Ala Gln Ser Phe Glu Tyr Asn Tyr
210                 215                 220

Gly Asp Phe Ile Pro Ile Leu Arg Pro Phe Leu Arg Gly Tyr Leu Asn
225                 230                 235                 240

Ile Cys Lys Glu Ile Lys Gln Arg Arg Leu Gln Leu Phe Lys Asp Tyr
                245                 250                 255

Phe Val Asp Glu Arg Lys Lys Leu Ala Asn Thr Thr Lys Ser Met Asp
                260                 265                 270

Asn Asn Ser Leu Lys Cys Ala Ile Asp His Ile Leu Glu Ala Glu Gln
                275                 280                 285

Lys Gly Glu Ile Asn Glu Asp Asn Val Leu Tyr Ile Val Glu Asn Ile
290                 295                 300

Asn Val Ala Ala Ile Glu Thr Thr Leu Trp Ser Ile Glu Trp Gly Ile
305                 310                 315                 320

Ala Glu Leu Val Asn His Pro Glu Ile Gln Lys Lys Leu Arg Asp Glu
                325                 330                 335

Ile Asp Ser Val Leu Gly Val Gly Val Gln Ile Thr Glu Pro Glu Leu
                340                 345                 350

Asn Lys Leu Pro Tyr Leu Gln Ala Val Ile Lys Glu Thr Leu Arg Leu
                355                 360                 365

Arg Met Ala Ile Pro Leu Leu Val Pro His Met Asn Leu His Asp Ala
370                 375                 380

Lys Leu Ala Gly Tyr Asp Ile Pro Ala Glu Ser Lys Ile Leu Val Asn
385                 390                 395                 400

Ala Trp Trp Leu Ala Asn Asn Pro Ala Thr Trp Lys Lys Pro Glu Glu
                405                 410                 415

Phe Arg Pro Glu Arg Phe Phe Glu Glu Lys His Val Glu Ala Asn
                420                 425                 430

Gly Asn Asp Phe Arg Tyr Leu Pro Phe Gly Val Gly Arg Arg Ser Cys
                435                 440                 445

Pro Gly Ile Ile Leu Ala Leu Pro Ile Leu Gly Ile Thr Leu Gly Arg
                450                 455                 460

Leu Val Gln Asn Phe Glu Leu Leu Pro Pro Gly Gln Ser Lys Leu
465                 470                 475                 480
```

Asp Thr Thr Glu Lys Gly Gly Gln Phe Ser Leu His Ile Leu Lys His
            485                 490                 495

Ser Thr Ile Val Met Lys Pro Arg Ser Phe
        500                 505

<210> SEQ ID NO 13
<211> LENGTH: 298
<212> TYPE: PRT
<213> ORGANISM: Nicotiana

<400> SEQUENCE: 13

Met Gly Arg Lys Pro Cys Cys Val Lys Glu Gly Leu Arg Lys Gly Pro
1               5                   10                  15

Trp Ser Ser Lys Glu Asp Leu Leu Leu Thr Asn Tyr Ile Lys Glu Asn
            20                  25                  30

Gly Glu Gly Gln Trp Arg Ser Leu Pro Lys Asn Ala Gly Leu Leu Arg
        35                  40                  45

Cys Gly Lys Ser Cys Arg Leu Arg Trp Met Asn Tyr Leu Arg Pro Gly
50                  55                  60

Ile Lys Arg Gly Asn Phe Ser Gln Asp Glu Glu Asp Leu Ile Val Arg
65                  70                  75                  80

Leu His Ser Leu Leu Gly Asn Arg Trp Ser Leu Ile Ala Gly Arg Leu
                85                  90                  95

Pro Gly Arg Thr Asp Asn Glu Ile Lys Asn Tyr Trp Asn Thr His Leu
            100                 105                 110

Ile Lys Lys Leu Lys Asn Ala Gly Ile Glu Pro Lys Pro His Lys Asn
        115                 120                 125

Phe Ser Lys Cys Ser Lys Lys Glu Ser Arg Lys Gly Pro Gln Gln Gly
130                 135                 140

Lys Ser Arg Lys Ile Gln Gly Lys Lys Ser Asn Asn Lys Asn Asn Lys
145                 150                 155                 160

Gly Gln Ile Val Gln Val Glu Lys Thr Lys Val Phe Phe Pro Lys Pro
                165                 170                 175

Ile Arg Ile Ser Cys Gly Ile Ser Arg Asn Asn Ser Phe Glu Asn Val
            180                 185                 190

Thr Leu Ser Thr Thr Cys Ser Ser Asn Ser Asn Ser Gly Glu Ala Asn
        195                 200                 205

Leu Glu Asn Lys Glu Asn Glu Val Lys Leu Glu Glu Val Ser Phe Phe
210                 215                 220

Pro Arg Asp Leu Asp Phe Gly Lys Leu Leu Glu Gly Asp Ala Ile Tyr
225                 230                 235                 240

Asp Glu Phe Leu Met Glu Glu Ser Cys His Ile Ser Asn Lys Cys Ser
                245                 250                 255

Leu Pro Met Asn Glu Ser Met Leu Glu Lys Val Tyr Glu Glu Tyr Leu
            260                 265                 270

Leu Leu Leu Ser Glu Asn Cys Tyr Leu Gln Asp Asp His Gln Asn Glu
        275                 280                 285

Gln Asn Phe Pro Val Asn Val Ser Asp Gln
290                 295

<210> SEQ ID NO 14
<211> LENGTH: 381
<212> TYPE: PRT
<213> ORGANISM: Nicotiana

<400> SEQUENCE: 14

```
Met Ala Ser Glu Ala His Ala Val His Ala Pro Pro Val Ala
1               5                   10                  15

Pro Thr Val Cys Val Thr Gly Ala Ala Gly Phe Ile Gly Ser Trp Leu
            20                  25                  30

Val Met Arg Leu Leu Glu Arg Gly Tyr Asn Val His Ala Thr Val Arg
            35                  40                  45

Asp Pro Glu Asn Lys Lys Val Lys His Leu Phe Glu Leu Pro Lys
        50                  55                  60

Ala Asp Thr Asn Leu Thr Leu Trp Lys Ala Asp Leu Ser Val Glu Gly
65                  70                  75                  80

Ser Phe Asp Glu Ala Ile Gln Gly Cys Gln Gly Val Phe His Val Ala
                85                  90                  95

Thr Pro Met Asp Phe Glu Ser Glu Asp Pro Glu Asn Glu Val Ile Lys
            100                 105                 110

Pro Thr Val Arg Gly Met Leu Ser Ile Ile Glu Ser Cys Ala Lys Ala
            115                 120                 125

Asn Thr Val Lys Arg Leu Val Phe Thr Ser Ser Ala Gly Thr Leu Asp
        130                 135                 140

Ala Gln Glu His Gln Lys Leu Phe Tyr Asp Glu Thr Ser Trp Ser Asp
145                 150                 155                 160

Leu Asp Phe Ile Tyr Ala Lys Lys Met Thr Gly Trp Met Tyr Phe Val
                165                 170                 175

Ser Lys Ile Leu Ala Glu Lys Ala Ala Met Glu Ala Ala Lys Lys Lys
            180                 185                 190

Asn Phe Asp Phe Ile Ser Ile Ile Pro Pro Leu Val Val Gly Pro Phe
            195                 200                 205

Leu Thr Pro Thr Phe Pro Pro Ser Leu Ile Thr Ala Leu Ser Leu Ile
        210                 215                 220

Thr Gly Asn Glu Ala His Tyr Cys Ile Ile Lys Gln Gly Gln Tyr Val
225                 230                 235                 240

His Leu Asp Asp Leu Cys Glu Ala His Ile Phe Leu Tyr Glu Gln Pro
                245                 250                 255

Lys Ala Glu Gly Arg Phe Ile Cys Ala Ser His His Ala Ile Ile Tyr
            260                 265                 270

Asp Val Ala Lys Met Val Arg Glu Lys Trp Pro Glu Tyr Tyr Val Pro
        275                 280                 285

Thr Glu Phe Lys Gly Ile Asp Lys Asp Leu Pro Val Val Tyr Phe Ser
290                 295                 300

Pro Lys Lys Leu Thr Asp Met Gly Phe Gln Phe Lys Tyr Thr Leu Glu
305                 310                 315                 320

Asp Met Tyr Lys Gly Ala Ile Glu Thr Cys Arg Gln Lys Gln Leu Leu
                325                 330                 335

Pro Phe Ser Thr Gln Ser Thr Ala Asp Asn Gly Arg Asp Lys Glu Thr
            340                 345                 350

Ile Pro Leu Ser Ala Glu Asn Tyr Ala Ser Gly Lys Glu Asn Ser Pro
        355                 360                 365

Val Ala Asn Gly Thr Gly Lys Ser Thr Asn Gly Glu Ile
    370                 375                 380
```

<210> SEQ ID NO 15
<211> LENGTH: 382
<212> TYPE: PRT
<213> ORGANISM: Nicotiana

<400> SEQUENCE: 15

```
Met Ala Ser Glu Gly His Ala Ala Val His Ala Pro Ser Pro Pro Ala
1               5                   10                  15

Ala Pro Thr Val Cys Val Thr Gly Ala Ala Gly Phe Ile Gly Ser Trp
            20                  25                  30

Leu Val Met Arg Leu Leu Glu Arg Gly Tyr Asn Val His Ala Thr Val
        35                  40                  45

Arg Asp Pro Glu Asn Lys Lys Val Lys His Leu Leu Glu Leu Pro
    50                  55                  60

Lys Ala Asp Thr Asn Leu Thr Leu Trp Lys Ala Asp Leu Ser Val Glu
65                  70                  75                  80

Gly Ser Phe Asp Glu Ala Ile Gln Gly Cys Gln Gly Val Phe His Val
                85                  90                  95

Ala Thr Pro Met Asp Phe Glu Ser Glu Asp Pro Glu Asn Glu Val Ile
            100                 105                 110

Lys Pro Thr Val Arg Gly Met Leu Ser Ile Ile Glu Ser Cys Ala Lys
        115                 120                 125

Ala Asn Thr Val Lys Arg Leu Val Phe Thr Ser Ser Ala Gly Thr Val
130                 135                 140

Asp Val Gln Glu His Gln Lys Leu Leu Tyr Asp Glu Thr Ser Trp Ser
145                 150                 155                 160

Asp Leu Asp Phe Ile Tyr Ala Lys Lys Met Thr Gly Trp Met Tyr Phe
                165                 170                 175

Val Ser Lys Ile Leu Ala Glu Lys Ala Ala Met Glu Ala Ala Lys Lys
            180                 185                 190

Lys Asn Ile Asp Phe Ile Ser Ile Pro Pro Leu Val Val Gly Pro
        195                 200                 205

Phe Leu Ala Pro Thr Phe Pro Pro Ser Leu Ile Thr Ala Leu Ser Leu
210                 215                 220

Ile Thr Gly Asn Glu Ala His Tyr Ser Ile Ile Lys Gln Gly Lys Tyr
225                 230                 235                 240

Val His Leu Asp Asp Leu Cys Glu Ala His Ile Phe Leu Tyr Glu His
                245                 250                 255

Pro Lys Ala Glu Gly Arg Phe Ile Cys Ala Ser His His Ala Ile Ile
            260                 265                 270

Tyr Asp Val Ala Lys Met Val Gln Glu Lys Trp Pro Glu Tyr Tyr Val
        275                 280                 285

Pro Thr Glu Phe Lys Gly Ile Asp Lys Asp Leu Ser Val Val Tyr Phe
    290                 295                 300

Ser Ser Lys Lys Leu Thr Asp Met Gly Phe Gln Phe Lys Tyr Thr Leu
305                 310                 315                 320

Glu Asp Met Tyr Lys Gly Ala Ile Glu Thr Cys Arg Gln Lys Gln Leu
                325                 330                 335

Leu Pro Phe Ser Thr Arg Ser Thr Ala Asp Asn Val Arg Asp Lys Glu
            340                 345                 350

Ala Ile Pro Leu Ser Thr Glu Asn Tyr Ala Ser Gly Lys Glu Asn Ser
        355                 360                 365

Pro Val Ala Asn Gly Thr Gly Lys Ser Thr Asn Gly Glu Ile
    370                 375                 380

<210> SEQ ID NO 16
<211> LENGTH: 213
<212> TYPE: PRT
<213> ORGANISM: Nicotiana
```

<400> SEQUENCE: 16

```
Met Gly Arg Lys Pro Cys Cys Ser Lys Glu Gly Leu Arg Lys Gly Thr
1               5                   10                  15

Trp Thr Ala Lys Glu Asp Met Leu Leu Thr Asn Tyr Ile Asn Glu His
            20                  25                  30

Gly Glu Val Gly Trp Arg Ser Leu Pro Met Lys Ala Gly Ser Arg Trp
        35                  40                  45

Ser Leu Ile Ala Gly Arg Ile Pro Gly Arg Thr Asp Asn Glu Ile Lys
    50                  55                  60

Asn Tyr Trp Asn Thr His Leu Leu Lys Lys Leu Lys Ser Glu Gly Leu
65              70                  75                  80

Glu Pro Lys Ile His Lys Ser Leu Ala Lys Asn Thr Arg Arg Gln Lys
                85                  90                  95

Glu Lys Ala Asn Val Ser Ser Gln Ile Asn Gln Lys Gly Tyr Lys Glu
            100                 105                 110

Lys Lys Lys Arg Asn Lys Lys Gly Asn Ile Glu Glu Asn Cys Asn Asn
        115                 120                 125

Ile Glu Glu Lys Glu Gln Val Ala Lys Lys Ile Glu Glu Gln Trp His
    130                 135                 140

Thr Gln Asp Ser Val Gln Ala Met Ser Gly Phe Ser Ser Thr Ser Glu
145             150                 155                 160

Val Ala Ser Glu Lys Glu Thr Asn Cys Asn Asn Val His Cys Pro Ser
                165                 170                 175

Ser Gly Gln Ser Leu Glu Glu Asn Asp Asn Glu Ile Tyr Glu Lys Leu
            180                 185                 190

Gln Ala Ser Gly Asp Ser Lys Arg Cys Lys Leu Asn Phe Ser Ala Glu
        195                 200                 205

Val Asn Lys Thr Pro
    210
```

<210> SEQ ID NO 17
<211> LENGTH: 435
<212> TYPE: PRT
<213> ORGANISM: Nicotiana

<400> SEQUENCE: 17

```
Met Lys Ile Glu Val Lys Glu Ser Thr Met Val Lys Pro Ala Ala Glu
1               5                   10                  15

Thr Pro Gln Gln Arg Leu Trp Asn Ser Asn Val Asp Leu Val Val Pro
            20                  25                  30

Asn Phe His Thr Pro Ser Val Tyr Phe Tyr Arg Pro Thr Gly Ser Pro
        35                  40                  45

Asn Phe Phe Asp Gly Lys Val Leu Lys Glu Ala Leu Ser Lys Ala Leu
    50                  55                  60

Val Pro Phe Tyr Pro Met Ala Gly Arg Leu Cys Arg Asp Glu Asp Gly
65              70                  75                  80

Arg Ile Glu Ile Asp Cys Lys Gly Gln Gly Val Leu Phe Val Glu Ala
                85                  90                  95

Glu Ser Asp Gly Val Val Asp Asp Phe Gly Asp Phe Ala Pro Thr Leu
            100                 105                 110

Glu Leu Arg Gln Leu Ile Pro Ala Val Asp Tyr Ser Gln Gly Ile Gln
        115                 120                 125

Ser Tyr Ala Leu Leu Val Leu Gln Ile Thr His Phe Lys Cys Gly Gly
    130                 135                 140
```

```
Val Ser Leu Gly Val Gly Met Gln His His Ala Asp Gly Ala Ser
145                 150                 155                 160

Gly Leu His Phe Ile Asn Thr Trp Ser Asp Met Ala Arg Gly Leu Asp
                165                 170                 175

Leu Thr Ile Pro Pro Phe Ile Asp Arg Thr Leu Leu Arg Ala Arg Asp
            180                 185                 190

Pro Pro Gln Pro Gln Phe Pro His Val Glu Tyr Gln Pro Pro Thr
        195                 200                 205

Leu Lys Val Thr Pro Glu Asn Thr Pro Ile Ser Glu Ala Val Pro Glu
    210                 215                 220

Thr Ser Val Ser Ile Phe Lys Leu Thr Arg Asp Gln Ile Asn Thr Leu
225                 230                 235                 240

Lys Ala Lys Ser Lys Glu Asp Gly Asn Thr Val Asn Tyr Ser Ser Tyr
                245                 250                 255

Glu Met Leu Ala Gly His Val Trp Arg Ser Thr Cys Met Ala Arg Gly
            260                 265                 270

Leu Ala His Asp Gln Glu Thr Lys Leu Tyr Ile Ala Thr Asp Gly Arg
        275                 280                 285

Ser Arg Leu Arg Pro Ser Leu Pro Pro Gly Tyr Phe Gly Asn Val Ile
290                 295                 300

Phe Thr Thr Thr Pro Ile Ala Val Ala Gly Asp Ile Gln Ser Lys Pro
305                 310                 315                 320

Ile Trp Tyr Ala Ala Ser Lys Leu His Asp Ala Leu Ala Arg Met Asp
                325                 330                 335

Asn Asp Tyr Leu Arg Ser Ala Leu Asp Tyr Leu Glu Leu Gln Pro Asp
            340                 345                 350

Leu Lys Ala Leu Val Arg Gly Ala His Thr Phe Lys Cys Pro Asn Leu
        355                 360                 365

Gly Ile Thr Ser Trp Ser Arg Leu Pro Ile His Asp Ala Asp Phe Gly
370                 375                 380

Trp Gly Arg Pro Ile Phe Met Gly Pro Gly Ile Ala Tyr Glu Gly
385                 390                 395                 400

Leu Ser Phe Ile Leu Pro Ser Pro Thr Asn Asp Gly Ser Gln Ser Val
                405                 410                 415

Ala Ile Ser Leu Gln Ala Glu His Met Lys Leu Phe Glu Lys Phe Leu
            420                 425                 430

Tyr Asp Phe
        435

<210> SEQ ID NO 18
<211> LENGTH: 436
<212> TYPE: PRT
<213> ORGANISM: Nicotiana

<400> SEQUENCE: 18

Met Gly Ser Glu Lys Met Met Lys Ile Asn Ile Lys Glu Ser Thr Leu
1               5                   10                  15

Val Lys Pro Ser Lys Pro Thr Pro Thr Lys Arg Leu Trp Ser Ser Asn
            20                  25                  30

Leu Asp Leu Ile Val Gly Arg Ile His Leu Leu Thr Val Tyr Phe Tyr
        35                  40                  45

Lys Pro Asn Gly Ser Ser Asn Phe Phe Asp Ser Lys Ile Met Lys Glu
    50                  55                  60

Ala Leu Ser Asn Val Leu Val Ser Phe Tyr Pro Met Ala Gly Arg Leu
65                  70                  75                  80
```

```
Ala Arg Asp Glu Gln Gly Arg Ile Glu Ile Asn Cys Asn Gly Glu Gly
                85                  90                  95

Val Leu Phe Val Glu Ala Glu Ser Asp Ala Phe Val Asp Asp Phe Gly
            100                 105                 110

Asp Phe Thr Pro Ser Leu Glu Leu Arg Lys Leu Ile Pro Thr Val Asp
        115                 120                 125

Thr Ser Gly Asp Ile Ser Thr Phe Pro Leu Ile Ile Phe Gln Val Thr
    130                 135                 140

Arg Phe Lys Cys Gly Gly Val Ser Leu Gly Gly Val Phe His Thr
145                 150                 155                 160

Leu Ser Asp Gly Leu Ser Ser Ile His Phe Ile Asn Thr Trp Ser Asp
                165                 170                 175

Ile Ala Arg Gly Leu Ser Val Ala Ile Pro Pro Phe Ile Asp Arg Thr
            180                 185                 190

Leu Leu Arg Ala Arg Asp Pro Pro Thr Ser Ser Phe Glu His Val Glu
        195                 200                 205

Tyr His Pro Pro Pro Ser Leu Ile Ser Ser Ser Lys Ser Leu Glu Ser
    210                 215                 220

Thr Ser Pro Lys Pro Ser Thr Thr Thr Met Leu Lys Phe Ser Ser Asp
225                 230                 235                 240

Gln Leu Gly Leu Leu Lys Ser Lys Ser Lys His Asp Gly Ser Thr Tyr
                245                 250                 255

Glu Ile Leu Ala Ala His Ile Trp Arg Cys Thr Cys Lys Ala Arg Ala
            260                 265                 270

Leu Ser Asp Asp Gln Leu Thr Lys Leu His Val Ala Thr Asp Gly Arg
        275                 280                 285

Ser Arg Leu Cys Pro Pro Leu Pro Pro Gly Tyr Leu Gly Asn Val Val
    290                 295                 300

Phe Thr Gly Thr Pro Met Ala Lys Ser Ser Glu Leu Leu Gln Glu Pro
305                 310                 315                 320

Leu Thr Asn Ser Ala Lys Arg Ile His Ser Ala Leu Ser Lys Met Asp
                325                 330                 335

Asp Asn Tyr Leu Arg Ser Ala Leu Asp Tyr Leu Glu Leu Leu Pro Asp
            340                 345                 350

Leu Ser Ala Leu Ile Arg Gly Pro Thr Tyr Phe Ala Ser Pro Asn Leu
        355                 360                 365

Asn Ile Asn Ser Trp Thr Arg Leu Pro Val His Asp Ser Asp Phe Gly
    370                 375                 380

Trp Gly Arg Pro Ile His Met Gly Pro Ala Cys Ile Leu Tyr Glu Gly
385                 390                 395                 400

Thr Val Tyr Ile Leu Pro Ser Pro Asn Ser Lys Asp Arg Asn Leu Arg
                405                 410                 415

Leu Ala Val Cys Leu Asp Ala Asp His Met Pro Leu Phe Glu Lys Tyr
            420                 425                 430

Leu Tyr Glu Phe
        435

<210> SEQ ID NO 19
<211> LENGTH: 715
<212> TYPE: PRT
<213> ORGANISM: Nicotiana

<400> SEQUENCE: 19

Met Ala Ser Asn Gly His Val Asn Gly Gly Glu Asn Phe Glu Leu Cys
```

-continued

```
1               5                    10                   15
Lys Lys Ser Ala Asp Pro Leu Asn Trp Glu Met Ala Ala Glu Ser Leu
            20                  25                  30

Arg Gly Ser His Leu Asp Glu Val Lys Lys Met Val Ser Glu Phe Arg
            35                  40                  45

Lys Pro Met Val Lys Leu Gly Gly Glu Ser Leu Thr Val Ala Gln Val
            50                  55                  60

Ala Ala Ile Ala Val Arg Asp Lys Ser Ala Asn Gly Val Lys Val Glu
65                  70                  75                  80

Leu Ser Glu Glu Ala Arg Ala Gly Val Lys Ala Ser Ser Asp Trp Val
                85                  90                  95

Met Asp Ser Met Asn Lys Gly Thr Asp Ser Tyr Gly Val Thr Thr Gly
            100                 105                 110

Phe Gly Ala Thr Ser His Arg Thr Lys Asn Gly Gly Ala Leu Gln
            115                 120                 125

Lys Glu Leu Ile Arg Phe Leu Asn Ala Gly Val Phe Gly Asn Gly Thr
            130                 135                 140

Glu Thr Ser His Thr Leu Pro His Ser Ala Thr Arg Ala Ala Met Leu
145                 150                 155                 160

Val Arg Ile Asn Thr Leu Leu Gln Gly Tyr Ser Gly Ile Arg Phe Glu
                165                 170                 175

Ile Leu Glu Ala Ile Thr Lys Leu Ile Asn Ser Asn Ile Thr Pro Cys
            180                 185                 190

Leu Pro Leu Arg Gly Thr Ile Thr Ala Ser Gly Asp Leu Val Pro Leu
            195                 200                 205

Ser Tyr Ile Ala Gly Leu Leu Thr Gly Arg Pro Asn Ser Lys Ala Val
210                 215                 220

Gly Pro Asn Gly Glu Thr Leu Asn Ala Glu Ala Phe Arg Val Ala
225                 230                 235                 240

Gly Val Asn Gly Gly Phe Phe Glu Leu Gln Pro Lys Glu Gly Leu Ala
            245                 250                 255

Leu Val Asn Gly Thr Ala Val Gly Ser Gly Met Ala Ser Met Val Leu
            260                 265                 270

Phe Asp Ser Asn Ile Leu Ala Val Met Ser Glu Val Leu Ser Ala Ile
            275                 280                 285

Phe Ala Glu Val Met Asn Gly Lys Pro Glu Phe Thr Asp His Leu Thr
            290                 295                 300

His Lys Leu Lys His His Pro Gly Gln Ile Glu Ala Ala Ile Met
305                 310                 315                 320

Glu His Ile Leu Asp Gly Ser Ser Tyr Val Lys Ala Ala Gln Lys Leu
                325                 330                 335

His Glu Met Asp Pro Leu Gln Lys Pro Lys Gln Asp Arg Tyr Ala Leu
            340                 345                 350

Arg Thr Ser Pro Gln Trp Leu Gly Pro Gln Ile Glu Val Ile Arg Ala
            355                 360                 365

Ala Thr Lys Met Ile Glu Arg Glu Ile Asn Ser Val Asn Asp Asn Pro
            370                 375                 380

Leu Ile Asp Val Ser Arg Asn Lys Ala Leu His Gly Gly Asn Phe Gln
385                 390                 395                 400

Gly Thr Pro Ile Gly Val Ser Met Asp Asn Ala Arg Leu Ala Leu Ala
                405                 410                 415

Ser Ile Gly Lys Leu Met Phe Ala Gln Phe Ser Glu Leu Val Asn Asp
            420                 425                 430
```

Tyr Tyr Asn Asn Gly Leu Pro Ser Asn Leu Thr Ala Ser Arg Asn Pro
            435                 440                 445

Ser Leu Asp Tyr Gly Phe Lys Gly Ala Glu Ile Ala Met Ala Ser Tyr
    450                 455                 460

Cys Ser Glu Leu Gln Phe Leu Ala Asn Pro Val Thr Asn His Val Gln
465                 470                 475                 480

Ser Ala Glu Gln His Asn Gln Asp Val Asn Ser Leu Gly Leu Ile Ser
                485                 490                 495

Ala Arg Lys Thr Ala Glu Ala Val Asp Ile Leu Lys Leu Met Ser Ser
                500                 505                 510

Thr Tyr Leu Val Ala Leu Cys Gln Ala Ile Asp Leu Arg His Leu Glu
    515                 520                 525

Glu Asn Leu Lys Asn Ala Val Lys Asn Thr Val Ser Gln Val Ala Lys
530                 535                 540

Arg Thr Leu Thr Met Gly Ala Asn Gly Glu Leu His Pro Ala Arg Phe
545                 550                 555                 560

Cys Glu Lys Glu Leu Leu Arg Ile Val Asp Arg Glu Tyr Leu Phe Ala
                565                 570                 575

Tyr Ala Asp Asp Pro Cys Ser Cys Asn Tyr Pro Leu Met Gln Lys Leu
                580                 585                 590

Arg Gln Val Leu Val Asp His Ala Met Asn Asn Gly Glu Ser Glu Lys
                595                 600                 605

Asn Val Asn Ser Ser Ile Phe Gln Lys Ile Gly Ala Phe Glu Asp Glu
                610                 615                 620

Leu Lys Ala Val Leu Pro Lys Glu Val Glu Ser Ala Arg Ala Ala Leu
625                 630                 635                 640

Glu Ser Gly Asn Pro Ala Ile Pro Asn Arg Ile Thr Glu Cys Arg Ser
                645                 650                 655

Tyr Pro Leu Tyr Arg Phe Val Arg Lys Glu Leu Gly Thr Glu Leu Leu
                660                 665                 670

Thr Gly Glu Lys Val Arg Ser Pro Gly Glu Glu Cys Asp Lys Val Phe
                675                 680                 685

Thr Ala Met Cys Asn Gly Gln Ile Ile Asp Pro Met Leu Glu Cys Leu
                690                 695                 700

Lys Ser Trp Asn Gly Ala Pro Leu Pro Ile Cys
705                 710                 715

<210> SEQ ID NO 20
<211> LENGTH: 341
<212> TYPE: PRT
<213> ORGANISM: Nicotiana

<400> SEQUENCE: 20

Met Asp Asn Ser Ala Pro Asp Ser Leu Ser Arg Ser Glu Thr Ala Val
1               5                   10                  15

Thr Tyr Asp Ser Pro Tyr Pro Leu Tyr Ala Met Ala Phe Ser Ser Leu
                20                  25                  30

Arg Ser Ser Ser Gly His Arg Ile Ala Val Gly Ser Phe Leu Glu Asp
                35                  40                  45

Tyr Asn Asn Arg Ile Asp Ile Leu Ser Phe Asp Ser Asp Ser Met Thr
            50                  55                  60

Val Lys Pro Leu Pro Asn Leu Ser Phe Glu His Pro Tyr Pro Pro Thr
65              70                  75                  80

Lys Leu Met Phe Ser Pro Pro Ser Leu Arg Arg Pro Ser Ser Gly Asp

```
                85                  90                  95
Leu Leu Ala Ser Ser Gly Asp Phe Leu Arg Leu Trp Glu Ile Asn Glu
            100                 105                 110

Asp Ser Ser Thr Val Glu Pro Ile Ser Val Leu Asn Asn Ser Lys Thr
            115                 120                 125

Ser Glu Phe Cys Ala Pro Leu Thr Ser Phe Asp Trp Asn Asp Val Glu
        130                 135                 140

Pro Lys Arg Leu Gly Thr Cys Ser Ile Asp Thr Thr Cys Thr Ile Trp
145                 150                 155                 160

Asp Ile Glu Lys Ser Val Val Glu Thr Gln Leu Ile Ala His Asp Lys
                165                 170                 175

Glu Val His Asp Ile Ala Trp Gly Glu Ala Arg Val Phe Ala Ser Val
            180                 185                 190

Ser Ala Asp Gly Ser Val Arg Ile Phe Asp Leu Arg Asp Lys Glu His
        195                 200                 205

Ser Thr Ile Ile Tyr Glu Ser Pro Gln Pro Asp Thr Pro Leu Leu Arg
    210                 215                 220

Leu Ala Trp Asn Lys Gln Asp Leu Arg Tyr Met Ala Thr Ile Leu Met
225                 230                 235                 240

Asp Ser Asn Lys Val Val Ile Leu Asp Ile Arg Ser Pro Thr Met Pro
                245                 250                 255

Val Ala Glu Leu Glu Arg His Gln Ala Ser Val Asn Ala Ile Ala Trp
            260                 265                 270

Ala Pro Gln Ser Cys Lys His Ile Cys Ser Gly Gly Asp Asp Thr Gln
        275                 280                 285

Ala Leu Ile Trp Glu Leu Pro Thr Val Ala Gly Pro Asn Gly Ile Asp
    290                 295                 300

Pro Met Ser Val Tyr Ser Ala Gly Ser Glu Ile Asn Gln Leu Gln Trp
305                 310                 315                 320

Ser Ser Ser Gln Pro Asp Trp Ile Gly Ile Ala Phe Ala Asn Lys Met
                325                 330                 335

Gln Leu Leu Arg Val
            340

<210> SEQ ID NO 21
<211> LENGTH: 440
<212> TYPE: PRT
<213> ORGANISM: Nicotiana

<400> SEQUENCE: 21

Met Ser Met Ser Val Ala Leu Leu Trp Val Ser Pro Thr Ser Glu
1               5                   10                  15

Val Ser Asn Gly Thr Gly Leu Leu Asp Ser Val Arg Glu Gly Asn Arg
            20                  25                  30

Val Phe Val Ser Ser Arg Phe Leu Ala Arg Asp Arg Asn Leu Met Trp
        35                  40                  45

Asn Gly Arg Ile Lys Lys Gly Gly Arg Gln Arg Trp Asn Phe Gly Ser
    50                  55                  60

Leu Ile Ala Asp Pro Arg Tyr Ser Cys Leu Gly Gly Ser Arg Thr Glu
65                  70                  75                  80

Lys Gly Ser Ser Phe Ser Val Gln Ser Ser Leu Val Ala Ser Pro Ala
                85                  90                  95

Gly Glu Met Thr Val Ser Ser Glu Lys Lys Val Tyr Asp Val Val Leu
            100                 105                 110
```

```
Lys Gln Ala Ala Leu Val Lys Arg Gln Leu Arg Ser Thr Asp Glu Leu
            115                 120                 125

Glu Val Lys Pro Asp Ile Val Pro Gly Asn Leu Gly Leu Ser
    130                 135                 140

Glu Ala Tyr Asp Arg Cys Gly Glu Val Cys Ala Glu Tyr Ala Lys Thr
145                 150                 155                 160

Phe Tyr Leu Gly Thr Lys Leu Met Thr Pro Glu Arg Arg Ala Ile
                165                 170                 175

Trp Ser Ile Tyr Val Trp Cys Arg Arg Thr Asp Glu Leu Val Asp Gly
            180                 185                 190

Pro Asn Ala Ser His Ile Thr Pro Gln Ala Leu Asp Arg Trp Glu Ala
                195                 200                 205

Arg Leu Glu Asp Ile Phe Ser Gly Arg Pro Phe Asp Met Leu Asp Ala
            210                 215                 220

Ala Leu Ser Asp Thr Val Ser Arg Phe Pro Val Asp Ile Gln Pro Phe
225                 230                 235                 240

Arg Asp Met Ile Glu Gly Met Arg Met Asp Leu Trp Lys Ser Arg Tyr
                245                 250                 255

Asn Asn Phe Asp Glu Leu Tyr Leu Tyr Cys Tyr Tyr Val Ala Gly Thr
                260                 265                 270

Val Gly Leu Met Ser Val Pro Val Met Gly Ile Ala Pro Glu Ser Lys
            275                 280                 285

Ala Thr Thr Glu Ser Val Tyr Asn Ala Ala Leu Ala Leu Gly Leu Ala
            290                 295                 300

Asn Gln Leu Thr Asn Ile Leu Arg Asp Val Gly Glu Asp Ala Arg Arg
305                 310                 315                 320

Gly Arg Val Tyr Leu Pro Gln Asp Glu Leu Ala Gln Ala Gly Leu Ser
                325                 330                 335

Asp Glu Asp Ile Phe Ala Gly Arg Val Thr Asp Lys Trp Arg Asn Phe
                340                 345                 350

Met Lys Lys Gln Ile Gln Arg Ala Arg Lys Phe Phe Asp Glu Ser Glu
            355                 360                 365

Lys Gly Val Thr Glu Leu Asp Ser Ala Ser Arg Trp Pro Val Ser Thr
            370                 375                 380

Ala Leu Leu Leu Tyr Arg Lys Ile Leu Asp Glu Ile Glu Ala Asn Asp
385                 390                 395                 400

Tyr Asn Asn Phe Thr Arg Arg Ala Tyr Val Ser Lys Pro Lys Lys Leu
                405                 410                 415

Leu Thr Leu Pro Ile Ala Tyr Ala Lys Ser Leu Val Pro Pro Asn Arg
            420                 425                 430

Thr Ser Ser Pro Leu Ala Lys Thr
            435                 440

<210> SEQ ID NO 22
<211> LENGTH: 440
<212> TYPE: PRT
<213> ORGANISM: Nicotiana

<400> SEQUENCE: 22

Met Ser Met Ser Val Ala Leu Leu Trp Val Val Ser Pro Thr Ser Glu
1               5                   10                  15

Val Ser Asn Gly Thr Gly Leu Leu Asp Ser Val Arg Glu Gly Asn Arg
            20                  25                  30

Val Phe Val Ser Ser Arg Phe Leu Ala Arg Asp Arg Asn Leu Met Trp
        35                  40                  45
```

```
Asn Gly Arg Ile Lys Lys Gly Gly Arg Gln Arg Trp Asn Phe Gly Ser
 50                  55                  60

Leu Ile Ala Asp Pro Arg Tyr Ser Cys Leu Gly Ser Arg Thr Glu
 65                  70                  75                  80

Lys Gly Ser Ser Phe Ser Val Gln Ser Ser Leu Val Ala Ser Pro Ala
                 85                  90                  95

Gly Glu Met Thr Val Ser Ser Glu Lys Lys Val Tyr Asp Val Val Leu
                100                 105                 110

Lys Gln Ala Ala Leu Val Lys Arg Gln Leu Arg Ser Thr Asp Glu Leu
            115                 120                 125

Glu Val Lys Pro Asp Ile Val Pro Gly Asn Leu Gly Leu Leu Ser
    130                 135                 140

Glu Ala Tyr Asp Arg Cys Gly Glu Val Cys Ala Glu Tyr Ala Lys Thr
145                 150                 155                 160

Phe Tyr Leu Gly Thr Lys Leu Met Thr Pro Glu Arg Arg Ala Ile
                165                 170                 175

Trp Ala Ile Tyr Val Trp Cys Arg Arg Thr Asp Glu Leu Val Asp Gly
                180                 185                 190

Pro Asn Ala Ser His Ile Thr Pro Gln Ala Leu Asp Arg Trp Glu Ala
                195                 200                 205

Arg Leu Glu Asp Ile Phe Ser Gly Arg Pro Phe Asp Met Leu Asp Ala
    210                 215                 220

Ala Leu Ser Asp Thr Val Ser Arg Phe Pro Val Asp Ile Gln Pro Phe
225                 230                 235                 240

Arg Asp Met Ile Glu Gly Met Arg Met Asp Leu Trp Lys Ser Arg Tyr
                245                 250                 255

Asn Asn Phe Asp Glu Leu Tyr Leu Tyr Cys Tyr Tyr Val Ala Gly Thr
            260                 265                 270

Val Gly Leu Met Ser Val Pro Val Met Gly Ile Ala Pro Glu Ser Lys
                275                 280                 285

Ala Thr Thr Glu Ser Val Tyr Asn Ala Ala Leu Ala Leu Gly Leu Ala
            290                 295                 300

Asn Gln Leu Thr Asn Ile Leu Arg Asp Val Gly Glu Asp Ala Arg Arg
305                 310                 315                 320

Gly Arg Val Tyr Leu Pro Gln Asp Glu Leu Ala Gln Ala Gly Leu Ser
                325                 330                 335

Asp Glu Asp Ile Phe Ala Gly Arg Val Thr Asp Lys Trp Arg Asn Phe
            340                 345                 350

Met Lys Lys Gln Ile Gln Arg Ala Arg Lys Phe Phe Asp Glu Ser Glu
            355                 360                 365

Lys Gly Val Thr Glu Leu Asp Ser Ala Ser Arg Trp Pro Val Leu Ala
    370                 375                 380

Ala Leu Leu Leu Tyr Arg Lys Ile Leu Asp Glu Ile Glu Ala Asn Asp
385                 390                 395                 400

Tyr Asn Asn Phe Thr Arg Arg Ala Tyr Val Ser Lys Pro Lys Lys Leu
                405                 410                 415

Leu Thr Leu Pro Ile Ala Tyr Ala Lys Ser Leu Val Pro Pro Asn Arg
                420                 425                 430

Thr Ser Ser Pro Leu Ala Lys Thr
                435                 440

<210> SEQ ID NO 23
<211> LENGTH: 248
```

<212> TYPE: PRT
<213> ORGANISM: Nicotiana

<400> SEQUENCE: 23

```
Met Glu Gly Ser Ser Lys Gly Leu Arg Lys Gly Ala Trp Thr Thr Glu
1               5                   10                  15

Glu Asp Ser Leu Leu Arg Gln Cys Ile Asn Lys Tyr Gly Glu Gly Lys
            20                  25                  30

Trp His Gln Val Pro Val Arg Ala Gly Leu Asn Arg Cys Arg Lys Ser
        35                  40                  45

Cys Arg Leu Arg Trp Leu Asn Tyr Leu Lys Pro Ser Ile Lys Arg Gly
    50                  55                  60

Lys Leu Ser Ser Asp Glu Val Asp Leu Leu Leu Arg Leu His Arg Leu
65                  70                  75                  80

Leu Gly Asn Arg Trp Ser Leu Ile Ala Gly Arg Leu Pro Gly Arg Thr
                85                  90                  95

Ala Asn Asp Val Lys Asn Tyr Trp Asn Thr His Leu Ser Lys Lys His
            100                 105                 110

Glu Pro Cys Cys Lys Ile Lys Met Lys Lys Arg Asp Ile Thr Pro Ile
        115                 120                 125

Pro Thr Thr Pro Ala Leu Lys Asn Asn Val Tyr Lys Pro Arg Pro Arg
    130                 135                 140

Ser Phe Thr Val Asn Asn Asp Cys Asn His Leu Asn Ala Pro Pro Lys
145                 150                 155                 160

Val Asp Val Asn Pro Pro Cys Leu Gly Leu Asn Ile Asn Asn Val Cys
                165                 170                 175

Asp Asn Ser Ile Ile Tyr Asn Lys Asp Lys Lys Asp Gln Leu Val
            180                 185                 190

Asn Asn Leu Ile Asp Gly Asp Asn Met Trp Leu Glu Lys Phe Leu Glu
        195                 200                 205

Glu Ser Gln Glu Val Asp Ile Leu Val Pro Gly Ala Thr Thr Thr Glu
    210                 215                 220

Lys Gly Asp Thr Leu Ala Phe Asp Val Asp Gln Leu Trp Ser Leu Phe
225                 230                 235                 240

Asp Gly Glu Thr Val Lys Phe Asp
                245
```

<210> SEQ ID NO 24
<211> LENGTH: 992
<212> TYPE: DNA
<213> ORGANISM: Nicotiana

<400> SEQUENCE: 24

```
atggaaagca agagttccgg aggcggagaa ggaaaggttg tatgtgtaac agggggcctct    60 ggtttcatag cttcatggct tgttaagatg ctacttcaac gtggttacac tgtcaatgcc   120
actgttcgca acctcaagga tgcgagtaaa gtggatcacc tgttaggcct tgacggagct   180
aaagagaggc tgcatctttt caaagctgag ttacttggtg agcattcgtt tgatcctgcc   240
gttgatggtt gtgaaggtgt ctttcataca gcatcacctg tttctctcac agctaaatcc   300
aaggaggaac ttgtagaccc tgctgtgagc ggaacattaa acgtccttag gtcatgtacc   360
aaatcaacat ctgttagaag agtggtcata acctcttcta ccgcttctgt tatttgcaat   420
aaaaacatgt caaccctgg agctgtagct gatgagactt ggtattcaga tgcagaactc   480
tgtgaggaaa gaaggaatg gtatcaactc tccaaaacct tggctgagga agctgcttgg   540
```

```
aaatttgcaa aggagaatgg gttggacttg gttacacttc atccaggtct agtcatcggt     600
ccacttctgc agcctacgct caatttctcg tgcgaggcta tagtgaactt cataaaagaa     660
ggaaaagaag catggtctgg cggaatatat agatttgtcg atgttaggga tgttgctaat     720
gcacatatac tagcatttga ggtcccttca gcaaatggaa gatattgttt agttggggta     780
aatggatatt cttctttggt tttgaagatt gtacaaaagc tttacccttc catcactctc     840
cctgagaatt ttgaagatgg attacctctt atcccaacct tccaagtatc aagcgaaaga     900
gcaaaaagtt taggcgtcaa tttcacatct cttgagttga gcgtgaagga cactgttgaa     960
agcttgatag agaagaactt cctcaagatt tg                                  992

<210> SEQ ID NO 25
<211> LENGTH: 1251
<212> TYPE: DNA
<213> ORGANISM: Nicotiana

<400> SEQUENCE: 25
atgatgtgca atattatttc acttgtgtcc atcatcaact tcttttttgct gttttataga    60 gttgttgtcc taccacaaca tgctgctgct tctcactcta ccgttgaatt tcttcctgga   120
tttgaaggtc cacttccttt ccatcttgag actgggtata ttggagtagg tgaatatgaa   180
gaagtgcagc tcttttatta ttttcttaaa tcagaatcag aacccacaaa agatcctatt   240
ttgatttggc tctcaggagg acctggttgc tcttcctttta ctgcacttgt ttatcaaata   300
gggcccttgt atttttgagcc aaacgagtat aatgggagcc ttccaaagct aacattgaat   360
ccaaactcat ggaccaaggt agctaacata atattcttgg atcaacctgt gaatagtggc   420
ttctcttatg caacaacttc aacaacattc aagtctactg atctacaagc atgccaccat   480
atctaccagt ttttgcgaaa gtggttgatt aagcatcaag agttcattag gaatccaatg   540
tacattggtg gagattcata ttctggcatc actgttccag ttatcactca actaatatca   600
aatgaaattg aagcagggca caagccatcg attaatctta agggatatat acttgggaat   660
cctagcacgt ttcctcttca atataactac tgggttcctt atgctcatgg aatgggactt   720
atctccgacg aactttatca ggctactact cttatccttt actttaaaat ttatcatatc   780
ataaatgcaa ttaatttagc ttacatggtt gaggtacaca ggttgtctac ttactgggca   840
aatgatccaa gagtacaaga agctcttaat gttcgtaagg gagctataac aagatggaca   900
agatgtaggg aaagtatcgt gaataaaact tacactatta ctttccaaga tagcatacct   960
tatcatgtgg aactcagcaa aaaactttat cgatcactta tatacagtgg cgatcatgat  1020
atgggcattc cattccaatc aactcaattt tggataaaat ctctaaatta ttctattgtg  1080
gatgaatggc ggccatggag ttttgatggt caagttgcag gatatacaag atcctattcc  1140
aaccagatga catttgcaac tgtcaaggga gcaggacatg tagctcctga gtacaagcct  1200
aaagagtgct ttaccatgtt tcaaagatgg ttgtctcatg aaccactttg a            1251

<210> SEQ ID NO 26
<211> LENGTH: 1710
<212> TYPE: DNA
<213> ORGANISM: Nicotiana

<400> SEQUENCE: 26
atgttgagtg tagctagtgt tgaagcccag aaagcagagt tatcttcttc tgtaattcct    60
ccttctgatc aatctactga agagatacac gtgtttagat caagattacc agatatacaa   120
atttccaaca atgttcctct tcatgtttac ttgtttgaga ggctctctga atttcaagat   180
```

```
aggacatgtc ttatagcagg cagcagtgga caatcctaca cttttgctga aactcatctc      240
atttgccaga aaatagctgc tggcttaaca aatataggaa tcaaaagggg agatgtaatc      300 atgactttc  tccagaactg cgcggaattt gtgtttactt ttctctcggc ttctatgatt      360
ggcgccgtta taactacagc taatccattt tacacaaaag cagaggcgtt taagcaatta      420
aaagcgtcga atgcaaaact aatcgttact caatctcagt acgtggataa atttcgtgat      480
tctggagaga atgacccgaa aattggcgaa gattttcag  tcattacaat tgatgacccc      540
cctgaaaatt gcttacattt ctctgtactt tctgaagcta acgaagagga aatgccaaag      600
ggaattgtaa tccaaccaga tgatccagta gcttttaccat tttcttcagg aacaacaggg    660
ctaccaaaag gtgtgatttt aactcacaaa agtttaatca caggagtagc tcaattagtc     720
gacggagata atccaaattt gtacttaaaa caagacgacg tggtgctatg tgtgctacct     780
ttgtttcaca tatttgcgtt aaattcagtg cttttagtct cgttaagagc aggagctagt     840
gttttactaa tgcaaaaatt cgaaattggt gcattgctgg agctgataca aaaccaccgc     900
gtgtcagttg cagcagtagt tccgcccttg gttcttgcgt tggcgaaaaa tccgatggtt     960
gattcgttcg atttgagttc gattaggctc gtgttgtccg gggcggcgcc gctggggaaa    1020
gagttggagg aagcgctaca tcaaagagtc ccgcaagcta tatttggtca ggggtatggt    1080
atgacagagg caggaccagt agtaacaatg tgcccagcat ttgcaaagca accattttca    1140
accaaatctg gctcatgtgg ttcagtagtt cgaaatgcag acctcaaggt ggtcgacccc    1200
gaaactggtg gctccctcgg ccgcaaccaa cccggcgaaa tttgcatccg tggttcccaa    1260
atcatgaaag gttatctgaa tgatgatgag gccacggcac ggaccataga tgtcgatgga    1320
tggctccaca ctggtgatat aggatacgta gatgacgatg atgaaatata catcgtcgat    1380
agagtcaaag agcttatcaa gttcaaagga ttccaggtgc caccagctga gcttgagtcc    1440
cttctagtaa gccatccaga tattgcagat gctgctgttg taccgcaaaa agatgatgcg    1500
gcaggggaag tcccagttgc atttgtggtc cgctccgcca atggttttga aattactgaa    1560
gaagctataa aggaatttat tgccaaacag gtgatattct ataaaagatt gcacaaggtg    1620
tattttattc acgctattcc aaagtctccg tctggaaaga tactgaggaa agaactgaga    1680
gccaaactag ctgcgccctc cacccagtga                                     1710
```

<210> SEQ ID NO 27
<211> LENGTH: 1656
<212> TYPE: DNA
<213> ORGANISM: Nicotiana

<400> SEQUENCE: 27

```
atgggaactc gtgcagtaga aagctcacag cagcaagaat gtgaacatat tttccggagt      60
agatatcctc cggttcaagt accggacaat gtgaccctcc cggattttgt gcttcacaat     120
gtagagttat acactgacaa aatggcattt gtggatgcta ccactggcaa aggctacact    180
tatggccaag ttgcaagaga cataaggagg ttcgccaagg ccttgagatc ccttggctta     240
aggaaaggac gggtggtggt ggtagttctt ccaaatgtac cagaatatgc tattgttgct     300
cttggaatca tggctgctgg tggcgtcttc tccggtgcaa atccagcagc tcattcatca     360
gaaatcgtga aacaagttga atctgctgat ggcaagctta ttgtctctga tctaccaacc    420
tatcacaagg ttaaagattg tgggctgcca gtaataatac taggtgaaga acatgtagaa    480
ggaacaattc attgggatga attgcttgaa gctgcagagc gtgccggttc cagaactgat    540
```

-continued

| | |
|---|---|
| cacataacaa accatgaaga tgaaatggtg cagcaaaatg atttatgtgc actgcccttc | 600 |
| tcgtcaggca ctacgggct gtccaaggga gtgatgttaa cccacagaaa tctagtagca | 660 |
| aacctctgct ctacactctt cagtgttagc ccagaaatgg taggccaagt tacaacactg | 720 |
| ggtttgatac cattcttcca catttatggg ataactggaa tctgttgtgc aaccattaga | 780 |
| aacaaaggga agtggtagt cttgcgtagg tacgaactga gggcatttct aaatgcactc | 840 |
| attacacatg aagtcacatt tgcaccaatt gtgccaccta tcatcttggc acttgttaag | 900 |
| aatcctattg tggatgaatt tgatctcagc aagcttaagc ttagatccat catgacagcg | 960 |
| gcagccccac ttgcccctga gattcttaat gaatttgaaa agaaatttcc cgatgttcag | 1020 |
| gtccaagagg catatgggat gactgagcac agctgcatta ctctttctca tagtgaccag | 1080 |
| catactgcta aaagaaattc tgttggtttt attctaccta atttggaggt aaagttcgtt | 1140 |
| gatcctgata ccggtagatc tctccccaaa aacaaaccag gcgagatatg tgtcaaaagc | 1200 |
| caatgtgtta tgaagggtta ctacaaaaat gaatttgaga cttgccttac cattgataag | 1260 |
| gatggatggc ttcagactgg tgacattggc tacattgacg atgatggaga tatcttccta | 1320 |
| gtcgatcgta tcaaagagct tatcaagtac aagggattcc aagttgctcc agctgagtta | 1380 |
| gaagggatcc ttctcacaca tccttcagta gaagatgctg cagtagttgg gctgccagat | 1440 |
| gaagaagcag gagagatacc agtggcatgg gtagtcttga actcaaaagc aaaagaaagc | 1500 |
| gaagaggaca ttatcaacta cattgcatcg actgttgcac agtataaacg agtgagagtg | 1560 |
| gtgcagttcg ttgatagtat tccaaaatct ccttctggaa aaatactgag aagacttatc | 1620 |
| aaggataaga tgctagagag acttaagaat gcatag | 1656 |

<210> SEQ ID NO 28
<211> LENGTH: 2016
<212> TYPE: DNA
<213> ORGANISM: Nicotiana

<400> SEQUENCE: 28

| | |
|---|---|
| atgacggaga taccgcctaa cagccagatg aaaaccatgt tgcagaaggc agtgcaatcg | 60 |
| gttcaatgga catatactct tttctggcaa ttatgtcccc aacaagggc gttagtgtgg | 120 |
| agagatggat attacaatgg ggctataaag actagaaaga cagtgcagcc aatggaagtt | 180 |
| agcgctgagg aagcttctct tcacagaagc caacagctta gagaacttta cgaatcactt | 240 |
| tccgccggcg agtcaaatca gccagcgaga aggccgtcgg cagctttgtc accggaggac | 300 |
| ttgacggagt ccgagtggtt ttatctcatg tgtgtttctt tctcttttcc tcctggcatc | 360 |
| ggattacctg gcaaggctta ttcgaagaaa catcacatat ggatcatggg cgcaaacgag | 420 |
| gttgatagca aagtcttctg tagagctatt cttgccaaga gcgcccgcat acagacggtc | 480 |
| gttggtattc ctctcttgga tggtgtactg gaactgggaa ctacagaaag ggttcaagaa | 540 |
| gagattggat tcataaacca tgtaaagagc tttttcactg agcaacaaca acctcagcta | 600 |
| ccaaagccag ccttatctga gcactccact tccaatccca ccaccttttc cgagccacat | 660 |
| ttttactccg gcaatacttc gccatctgct aatgttgata ttgcgcatca agatggcgga | 720 |
| gctgccggcg aagaagatga ggaggaggaa gaagaagaag atgatgatga agccgagttg | 780 |
| gactcggata gtatagcgat tcaaagcgcg gctaatccta ttgccgttga ggctagtgaa | 840 |
| ctcatgcagc ttgatgtgtc cgaggctata cagctcggct cgcccgatga tgactctgat | 900 |
| aatatgggact ctgattttca tttggttggc gctggaaaca cggctcatga ctaccagcgc | 960 |
| caagctgact ctttcaaagc cgagaccgcc attagctggc cgcacttcca agaccttcaa | 1020 |

```
caattaccag gtggctctag ttatgatgaa ttatcacaag aagacacaca ctattctcaa   1080
acagtgtcaa ccattctcga acaccgaagc tccaaatttt cctctacaac aatgggctgt   1140
atttctcatg actcggccca atctgccttc acattgtgcc ctagcaccac cgtctgcagc   1200
ccgaatcccg cccactgccg ccacgacgac tcacttgtcg acggtggcgg cgcctcccag   1260
tggctgctca aaagcatact cttcactgtc ccatttcttc acactaaata ccaatctgaa   1320
gcttctccaa agtcacgtga cgtcgccact gttgattcct ccagtactgc ttctcgcttt   1380
cgcaaaggct gtagtataac gtcgcaagaa gagccaagtg gaaaccatgt acttgcagaa   1440
cgacgtcgta gagagaagct aaatgagcgt tttatcatat taaggtctct tgtacctttt   1500
gtaacgaaaa tggacaaagc ctccattttg ggtgacacca tagagtatgt caagcagtta   1560
cgtaagaaag ttcaggatct tgaagctcgt gctcgcgaca cggagcactc cagagatgca   1620
gataaaaaag gtggcacagc tacagtgaag gtgttgcaag gaagggggtaa gaggagaatg   1680 aatacggtag atggaagtgt tggtggaggg caggcaacga taacggcgtc cccaccgtca   1740
acgacggaaa atgaggaggt tgtgcaagta caagtatcaa ttatcgaaag cgatgcattg   1800
gtggagctcc ggtgtccgta caaagagggg ttgctgttaa atgtaatgca gatgctaagg   1860
gaactcaaag tggaagttgt agccattcaa tcagctctta ataatggcgt cttcttggct   1920
gagttaagag ctaaggtaaa agagaatata tgtggaagga aagcaagcat tttggaagta   1980
aaaaggtcaa tacatcagat aatccctaga gattaa                             2016

<210> SEQ ID NO 29
<211> LENGTH: 2052
<212> TYPE: DNA
<213> ORGANISM: Nicotiana

<400> SEQUENCE: 29
atgacggaga taccgcctaa cagccagatg caaaccatgt tgcagaaggc tgtgcaatcg     60
gttcaatgga catatactct tttctggcaa ttatgttccc aacaagggt gttagtgtgg    120 agagatggat attacaatgg ggctataaag actagaaaga ctgtgcagcc aatggaagtt    180
agcgctgagg aagcttctct tcacagaagc caacagctta gagaacttta cgaatcactt    240
tccgccggcg agtcaaatca gccggcgaga aggccgtcgg cagctttgtc accggaggac    300
ttgacggaat ccgagtggtt ttatctcatg tgtgtttctt tctcttttcc tcctggcatc    360
ggattacctg gcaaggctta ttcaaagaaa catcacatat ggattatgtg cgcaaacgag    420
gttgatagca aagtcttctg tagagctatt cttgccaaga gtgcccgcat acagacggtc    480
gtctgtattc ctctcttgga tggtgtactg gaactgggaa ctacagaaag ggttcaagaa    540
gacattggat tcataaacca tgtaaagagc tttttcactg agcaacaaca acctcagcca    600
ccaaagccag ccttatctga gcactccact tccaattcca ccacctttc cgagccacac     660 tttttactccg gcaatactcc gccatctggc aatgctgata ttgcgcagca agatggcgga    720
gctgccggag aagaagatga ggaggaggaa gaagaagaag acgatgaagc cgagttggat    780
tcggatagta tagcaattca aagtgaggtt ggtggcgcgg ctaatcctat agcggctgag    840
gctagtgaac tcatgcagct tgatatgtct gaggctatac ggcttggctc gcccgatgat    900
ggctctaata atatggactc tgattttcat ttggttggcg ctggaaatac ggctgactac    960
cagcgtcaac ctgactcttt caaagccgag actgccatta gctgggctca cttccaagac   1020
cttcaacatt taccaggtgg ctctagttat gaagaattat cacaagaaga cacacattat   1080
```

| tctcaaacag tgtcaaccat tcttgaacac ttctcaaacc gaagctccaa atttcctct | 1140 |
| accacaatgg gctgtatttc tcatgactca gcccaatctg ccttcacatt gtgccctagc | 1200 |
| accaccgtcg actgcagccc gaatcccgcc cactgccgcc gccgccacga cgattcactt | 1260 |
| ctcgacggtg gcggcgcctc ccctcctcc cagtggctgc tcaaaagcat actcttcact | 1320 |
| gtcccatttc ttcacactaa ataccaatct gaagcttctc cgaaatcagt tgacgtcgcc | 1380 |
| actgttgatt cctccagtac tgcttctcgc tttcgcaaag gctgtagtat aacgtcgcaa | 1440 |
| gaagagccca gtggaaacca tgtacttgca gaacgacgtc gtagagaaaa gctaaatgag | 1500 |
| cgttttatca tattaaggtc tcttgtacct tttgttacga aaatggataa agcctccatt | 1560 |
| ttgggtgaca ccatagagta tgtcaagcag ttacataaga aagttcagga tcttgaagct | 1620 |
| cgtgctcgtc acacggagca gtccaaagat gcagaccaaa aaagtggcac agctacagtg | 1680 |
| aaggtgttgc aagggagggg taagaggaga atgaatacgg tggaggccgg aaatattggt | 1740 |
| ggagggcagg caaagatgac ggcttttccg ctatcaacaa cggaggatga agaggttgtg | 1800 |
| caagtagaag tatcaattat tgaaagcgat gcattgttgg agctccgatg tccgtacaaa | 1860 |
| gaggggctgc tgttagatgt aatgcagatg ctaagggaac tcaaggtgga agttgtagcc | 1920 |
| attcaatcat ctcttaataa tggcatcttc ttggctgagt taagagctaa ggtaaaagag | 1980 |
| aatatatatg gaaggaaagc aagcattgtg gaagtaaaaa agtcaataca tcagataatc | 2040 |
| cctagagatt aa | 2052 |

<210> SEQ ID NO 30
<211> LENGTH: 663
<212> TYPE: DNA
<213> ORGANISM: Nicotiana

<400> SEQUENCE: 30

| atgaatattt gtactaataa gtcgtcgtca ggagtgaaga aggtgcatg gactgaagaa | 60 |
| gaagatgttc tattgaaaaa atgcatcgag aaatatggag aaggaaagtg gcatcaagtt | 120 |
| cctcttagag ctggtttgaa tagatgcaga aagagctgca gattaaggtg gctaaattat | 180 |
| ctaaggccac atataaagag aggagacttc tcttttgatg aagtagatct cattttgagg | 240 |
| cttcataagc tgttaggcaa cagatggtca cttattgctg gtagacttcc tggaaggacg | 300 |
| gcaaacgatg tcaaaaacta ctggaacagc catcttcgca agaagttaat tgctcctcat | 360 |
| gatcaaaagg agagcaagca aaaagcaaag aagatcacca tattcagacc tcggcctcga | 420 |
| accttctcaa agacaaatac ttgtgttaaa agtaacacaa atactgtaga taaggatatt | 480 |
| gaaggcagca gcgaaataat tagattcaac gataatttga agccaacaac tgaagaattg | 540 |
| acggatgatg gaattcaatg gtgggccgat ttactagcta acaattacaa caataatggg | 600 |
| attgaggaag ctgataattc atcaccaact ttgttgcatg aggaaatgcc acttctcagt | 660 |
| tga | 663 |

<210> SEQ ID NO 31
<211> LENGTH: 1260
<212> TYPE: DNA
<213> ORGANISM: Nicotiana

<400> SEQUENCE: 31

| atggtggtga tcagtgcagt agttccaact ccttcaagag ttgaaagctt ggctaaaagt | 60 |
| ggaatccagg ctatccctaa agagtatgtg aggccacaca aagagttaaa tggaatagga | 120 |
| aacatatttg aggaagagaa gaaagatgaa ggaccctcaag taccgacgat tgatctgaaa | 180 |

```
gaaatcgact cagaggacaa ggaaattcgc gagaaatgcc acaaagagtt gaagaaagca      240
gctatggagt ggggtgttat gtaccttgtt aaccatggca tatcagatca gctaattgat      300
cgtgtcaagg ttgctggaaa gaccttcttt gatcaacctg ttgaagaaaa ggagaagtat      360
gctaatgacc aaccctctgg caatgtccaa ggctatggca gcaagttagc aaatagtgct      420
tgtggtcagc ttgaatggga ggattatttc ttccattgcg ttttccccga ggacaagtgc      480
gacttatcca tctggcctaa aatccctact gactacattc cagcaacaag tgaatatgcc      540
aaacagatta ggaacctagc aacaaagatt ttggcagtgc tttctattgg gctgggacta      600
gaagaaggaa gactagagaa ggaagtcgga ggcaaggagg acctactgct tcaaatgaag      660
attaactact accccaaatg tccccaacca gaactagcac ttggcgttga agctcatact      720
gatgtgagtg cactgacttt tatcctccac aatatggtgc ctgggttaca acttttctat      780
gaaggacagt gggtaacggc aaagtgtgtg cctaattcca taatcatgca tattggggac      840
acccttgaaa tcctaagcaa tggaaagtac aaaagcattc ttcacagagg ggttgtgaat      900
aaagagaaag taagaatctc atgggctatt ttctgtgagc cgccaaagga agatcatc       960 cttaagcccc tatctgagac tatcactgag gctgaaccac ctcgattccc acctcgcacc     1020
tttgcacagc atatggccca taagctcttc aagaaggatg atcaggatgc tgctgctgaa     1080
cacaaagtct ccaagaagga tgacccggat tctgctgctg acacaaaacc cttcaagaag     1140
gatgatcagg atgctgttgt tcagcaaaaa gtcctcaagg aggatgaaca ggatgccgct     1200
gctgagcaca agtcttcaa gaaggataat caggatgctg ctgctgaaga atctaaatag     1260

<210> SEQ ID NO 32
<211> LENGTH: 1260
<212> TYPE: DNA
<213> ORGANISM: Nicotiana

<400> SEQUENCE: 32
atggtggtga tcagtgcagt agttccaact ccttcaagag ttgaaagctt ggctaaaagt       60
ggaatccagg ctatccctaa agagtatgtg aggccacaag aagagttaaa tggaatagga      120
aacatatttg aggaagagaa gaaagatgaa ggacctcaag taccgacgat tgatctaaca      180
gaaatcgact cagaggacaa ggaaattcga gagaaatgcc accaagagtt gaagaaagca      240
gctatagaat ggggtgttat gcaccttgtt aaccatggca tatcagatga gctaattgat      300
cgtgtcaagg tttctggaga taccttcttt gatcaacctg ttgaagaaaa ggagaagtat      360
gctaatgacc aaccctctgg caatgtccaa ggctatggca gcaagctagc aaatagtgct      420
tgtggtcagc ttgagtggga ggattatttc ttccattgtg ttttccctga ggacaagtgc      480
aacttatcca tctggccgaa aaccccctaca gactacattc cagcaacaag tgaatatgcc      540
aagcagatca ggaacctagc aacaaagatt ttggcagtgc tttctattgg gctgagacta      600
gaagaaggaa gactagagaa ggaagtcgga ggcatggagg acctgctgct tcaaatgaag      660
attaactact atcccaaatg cccccaacca gaactagcac ttggtgtcga agctcatact      720
gatgtcagtg cactgacttt tatcctccac aatatggtgc ctggcttgca acttttctac      780
gaaggacagt gggtaacggc aaagtgtgtg cctaattcca taatcatgca tattggggac      840
acccttgaaa ttctaagcaa tggaaagtac aagagcattc ttcacagagg ggttgtgaat      900
aaagagaaaa taagaatctc atgggctatt ttctgtgagc cgccgaagga agatcatc       960 cttaagcccc tacctgagac tataactgag gctgagccac ctcgattccc acctcgcacc     1020
```

```
tttgcacagc atatggccca taagctcttc aagaaggatg atcaggatgc tgctgctgaa    1080
cacaaagtct ccaagaagga tgacccggat tctgctgctg aacacaaacc cttcaagaag    1140
gatgatcagg atgctgttgc tcagcaaaaa gtcctcaagg aggatgaaca gaatgccgct    1200
gctgagcaca aagtcttcaa gaaggataat caggatgctg ctgctgaaga atctaaatag    1260
```

<210> SEQ ID NO 33
<211> LENGTH: 1869
<212> TYPE: DNA
<213> ORGANISM: Nicotiana

<400> SEQUENCE: 33

```
atggctatgg gacaccaaga ccaagatgga gttccaaaca acttgagaaa gcaacttgct      60
cttgctgtta gaggtattca atggagctat gcaatcttct ggtcaactcc agttacacag     120 ccagggggtgt tggaatggag tgatgggtac tataatgggg atatcaagac taggaagaca     180
gttcaggtgg gggaagttaa tgaagaccaa cttgggttgc acagaactga gcaattgcga     240
gaactttata gttcactctt aacaggtgaa ggtgaagaag acttacaacc tcaggctaaa     300
aggccctcag ctgcattatc tcctgaagat ctcactgata cggagtggta tttcttagta     360
tgcatgtctt tcgtcttcaa tgttggacaa gggttgccag gaagacctc agcgacgaat      420 caaacaatct ggctatgcaa tgctcaccaa gcagagagta gagtattttc tcgctctctg     480
ctagcaaaga gtgcatctat ccagactgtc gtatgctttc catatttagg aggcgttatt     540
gagctgggag tcaccgagct tgtcttagaa gatcccaacc tcattcagca aataaaaaat     600
tcctttgagg ttgatcactc tgttatttcg aagaggccta attacaactc caatgatgca     660
aaagatgaca tgaatgttgc tagccgaaag cttgatcata atgtacttga agtgatgct     720 tatccagttg aaataaacaa cagttcaccg catgatagtt caaacggttt tgtggccaat     780
caagaggcag aagattcttt aatggtggta ggcgttatag gggaaacttc acaagctcaa     840
agctggaagt tcgtggatga taatatgagt aacggtgtgc ataattcttt gaattccagt     900
gactgcatct ctcaaaatta tgaaaagttg tcccctcttt cgaatggaga aaagaaact      960 aagccttgcc aatagaccg tcaagagcac aatcagaata aactgcatct tttagatcac    1020
caaggagatg acgctcaata tcaagctgtc atttctaccc ttttaaaaag ctctgaccaa    1080
ttaactttgg gaccacattt tagaaatatt aacaaaaagt caagctttgc tggttggaag    1140
aatgatactg aagcgccaag aataggaact gcacaaaaac tattgaagaa ggtacttctt    1200
gaagttccta gaatgcatgg tggtgttaca cataaattca gcagagagaa tcgtaaaaag    1260
aacggccttt ggagaccgga ggttgatgac attgatagaa gccgtgttat ttcagagaga    1320
aggcgaagag aaaagataaa cgagagattt atgcatcttg catcaatgct gccgactggt    1380
ggcaaggttg acaaaatatc actacttgac gagacaatag aatacatgaa agagcttgag    1440
aggagagttc aagagctgga agctagatca ggaaaaaaaa caaatgatac tgcagagcag    1500
acatctgata attgtggcac tagtaaattc aatgacgtca atggatcgtt aaagaggaaa    1560
gcatgtgata tggatgaaat ggaacctgaa agctgtaatg aattactgaa aggcagttca    1620
gctgatggta ttgtcatcag tatgatcgat aaggaagtct cgatcaagat gaggtgtctt    1680
tggagcgagg gcttgttact taagattatg gaggcactaa ccgacctaca aatggattgc    1740
catacggttc aatcttccaa gattgatggg attttatcca ttgctattga atcaaagtca    1800
aatggattga aaactgtatc agttggagca attagagaag tacttcagcg agtagtctgg    1860
aaatcttga                                                           1869
```

<210> SEQ ID NO 34
<211> LENGTH: 1095
<212> TYPE: DNA
<213> ORGANISM: Nicotiana

<400> SEQUENCE: 34

```
atggaatcct caaccaaaag ccaaatacca acacaatcag aagaagagcg taactgcaca      60
tatgccatgc aactattgtc atcttcagtc ctcccctttg tgttgcattc aacaattcaa     120
ttggaagttt ttgagatatt agccaaatct aatgacacta aactttctgc ttctcaaatt     180
gtttctcaaa ttcctaactg cacaaaacct gaagcaccta ctatgttaaa taggatgctt     240
tatgtcttgg ctagttactc cttgtttact tgttccattg ttgaagatga aaaaaataat     300
gggggccaaa aaagagtgta tggtttgtca caagtgggaa aattctttgt taaaaatgaa     360
aatggtgcat caatggggcc acttttggct ttgcttcaaa ataaagtatt cataaacagc     420
tggtttgaac taaagatgc agttcttgaa ggaggagttc catttgacag ggtacacggt     480
gtgcatgcat ttgaatatcc aaaatcggac ccaaaattca tgatgttttt caacaaggca     540
atgatcaatc acacaactgt agtcatgaaa aaaatacttg aaaattacaa aggttttgag     600
aaccttaaaa ctttggttga tgttggaggt ggtcttggag ttaacctcaa gatgattaca     660
tctaaatacc ccacaattaa gggcactaat tttgatttgc acatgttgt tcaacatgcc     720
ccttcctatc ctggggtgga acatgttggg ggagatatgt ttgaaagtgt tccagaagga     780
gatgctattt ttatgaagtg gattcttcat gactggagtg atagtcacaa cctcaagttg     840
ctaaagaact gctacaaggc tctaccagac aatggaaagg tgattgttgt tgaggccatt     900
ttaccagtga aaccagacat tgacaccgca gtggttggcg tttcgcaatg tgatttgatc     960
atgatggctc aaaatcctgg aggcaaagag cgatcggaag aggagtttcg agccttggct    1020
actgaagctg gattcaaagg cgttaactta atatgttgtg tctgtaattt ttgggtcatg    1080
gaattctgca agtag                                                    1095
```

<210> SEQ ID NO 35
<211> LENGTH: 1521
<212> TYPE: DNA
<213> ORGANISM: Nicotiana

<400> SEQUENCE: 35

```
atggatcttc tccttctaga gaagacccct atagggttat tctttgctat cattgtagct      60
atagttgttt ctaagctacg tagcaagaat tttaagttgc ccccaggtcc gattcctgtg     120
ccagttttg gcaattggct tcaagttggt gatgacttga atcacagaaa cctcactgaa     180
tatgccaaga aatttggtga catgttcttg ctaagaatgg acagaggaa tcttgtggtg     240
gtgtcatccc ctgaactagc caaagaagtt ttgcatacac aaggggttga atttggatca     300
agaacaagga atgtggtctt tgatattttc actggaaaag ccaagatat ggttttaca     360
gtatatggtg aacactggag gaaaatgagg aggattatga ctgttccatt ttttacaaac     420
aaagtggtgc agcagtatag gcgtgggtgg gaagatgaag tggcacatgt tgttgaggat     480
gtgaagaaaa atccagagtc agcaactaat gggattgtgt tgaggaaaag gttgcagctt     540
atgatgtaca ataacatgta caggattatg tttgatagga ggtttgagag tgaggatgat     600
cctttgtttt acaagcttaa ggctttgaat ggggagagga gtagattggc tcagagtttt     660
gagtacaatt atggtgattt tatccctata ttgagacctt tcttgagagg ttacttgaac     720
```

```
atctgtaagg aaattaagca gaggaggttg cagcttttca aagattactt tgttgatgaa      780
agaaagaaac ttgcaaacac gacgaagagc atggacaata attcgctaaa gtgtgccatt      840
gatcacattc ttgaggctga acagaaggga gagatcaatg aggataatgt cctttacatt      900
gttgagaaca tcaatgttgc tgcaatagaa actacactgt ggtcaatcga gtggggtatt      960
gctgaactag tgaaccaccc tgaaatccag aagaaactcc gtgacgagat tgacagtgtt     1020
cttggagtag gagtgcaaat cactgagcca gaactcaaca agcttcctta ccttcaggct     1080
gtgatcaagg agacccttcg tctccgtatg gcaatccctc ttttagtccc acacatgaac     1140
cttcacgatg cgaagcttgc tggatatgac attcccgcgg agagcaagat cctggtaaac     1200
gcttggtggc tggctaacaa ccctgctacc tggaagaagc ccgaagagtt taggccagag     1260
aggttctttg aagaggagaa gcacgttgag gctaatggca atgacttcag atatcttcca     1320
tttggtgttg gtaggaggag ctgccctgga attatccttg cactgccaat tcttggcatt     1380
accttgggac gcttggtgca gactttgag ttgttgcctc ctccaggaca gtcaaagctt     1440
gacacaacag agaaaggcgg gcaattcagt ctgcacattt tgaagcattc caccattgtg     1500
atgaaaccaa gatcttttta a                                              1521

<210> SEQ ID NO 36
<211> LENGTH: 897
<212> TYPE: DNA
<213> ORGANISM: Nicotiana

<400> SEQUENCE: 36
atgggaagaa aaccatgttg tgtaaaagag ggattgagaa aaggtccatg gtcttctaaa       60
gaagatttat tacttactaa ttatatcaag gaaaatggtg aaggacaatg gagatctttg      120
cctaagaatg ctgggttgct taggtgtgga aaaagttgta gactaagatg gatgaactat      180
ttaagaccag ggattaaaag aggaaatttc agtcaagatg aagaagatct tatagtgaga      240
ctacattctc ttttgggtaa tcgttggtca ctaattgctg gaagattacc aggtcgtaca      300
gacaatgaaa tcaagaatta ttggaacaca catttaatca agaagctcaa aaatgctgga      360
attgaaccaa aacccacaa aaatttctcc aaatgttcca aaaaggaatc aagaaaagga      420
ccccaacaag ggaaatcaag aaaaatacaa ggcaaaaaga gcaacaacaa aaacaataag      480
ggtcaaattg tacaagttga gaagaccaaa gtattttcc caaaacccat caggatttct      540
tgtggaattt caaggaacaa tagttttgaa atgttacat tgagtactac ttgttcctca      600
aatagtaatt ctggagaagc taatcttgaa aacaaggaaa atgaggtgaa attagaagaa      660
gtttcattct ttccaaggga cttagatttt ggtaaattac ttgaagggga tgcaattat      720 gatgaatttc taatggaaga agttgccac atttcaaaca aatgttcatt gccaatgaat      780
gagagcatgt tggagaaagt atatgaagaa tatctttac ttctttctga aaattgttac      840
cttcaagatg atcatcaaaa tgagcaaaat ttccctgtaa atgtttctga tcagtga       897

<210> SEQ ID NO 37
<211> LENGTH: 1146
<212> TYPE: DNA
<213> ORGANISM: Nicotiana

<400> SEQUENCE: 37
atggcaagtg aagctcatgc agctgttcat gctcctcctc cggtagcacc gacggtttgc       60
gtcactggag cagctggatt tattggctct tggcttgtca tgagactcct tgaacgtggt      120
tataatgttc acgctactgt tcgtgatcct gagaacaaga gaaggtaaa gcatctattc      180
```

```
gaattgccaa aagctgacac aaacttaacg ctgtggaaag cggacttgtc agtggaagga      240
agctttgatg aagccattca aggctgtcaa ggagtattcc atgtggcaac acctatggat      300
ttcgagtccg aggaccctga gaatgaagta attaaaccaa cagtcagggg aatgttaagc      360
atcatagaat catgtgctaa agcaaacaca gtgaagaggc tggttttcac ttcatcggct      420
ggaactctcg atgcccaaga acaccaaaag cttttctatg acgagaccag ctggagcgac      480
ttggacttca tatatgctaa gaagatgaca ggatggatga ttttgtttc caagatactg       540 gcagagaagg ccgcaatgga agcagctaaa aagaagaact tgatttttat tagcatcata      600
ccgccgctgg ttgttggtcc attcctcacg cctacattcc cacctagctt aatcactgca      660 cttctcactaa ttactgggaa tgaagctcac tactgcatca ttaaacaagg tcaatatgtg     720
catttggatg atctttgtga ggctcatatt ttcctatatg agcagccaaa ggcagaggga      780
agattcatct gcgcgtccca tcatgctatc atctatgatg tggcaaagat ggtccgagag      840
aaatggccag agtactacgt ccctactgag tttaaaggca tcgataagga cttgcccgtg      900
gtgtattttt cgccaaagaa gctgacggat atggggtttc aattcaagta cactttggag      960
gatatgtata aaggggccat tgagacttgt cgacagaagc agttgcttcc cttttctacc     1020
caaagcacag cagataatgg acgtgacaaa gaaaccattc cccttttctgc tgaaaactat    1080 gcaagtggca aagagaattc accagttgca aatggtacag gaaagtcaac caatggggaa    1140
atctag                                                                1146

<210> SEQ ID NO 38
<211> LENGTH: 1149
<212> TYPE: DNA
<213> ORGANISM: Nicotiana

<400> SEQUENCE: 38
atggcaagtg aaggtcatgc agctgttcat gccccttctc ctccggcagc gccgacagtt       60
tgcgtcactg gagcagctgg atttattggc tcttggcttg tcatgagact ccttgaacgt      120
ggttataatg ttcacgctac tgttcgtgat cctgagaaca agaagaaggt aaagcatcta      180
ttggaattgc caaaagctga cacgaactta acgttgtgga agcagacttt gtcagtggaa      240
ggaagctttg atgaagccat tcaaggctgt caaggagtat tccatgtggc aacgcctatg      300
gatttcgagt ccgaggatcc tgagaatgaa gtaattaaac aacagtcag ggaatgtta      360 agcatcatag aatcatgtgc taaagcaaac acagtgaaga ggctggtttt cacttcatct      420
gctggaactg tcgatgtcca agagcaccaa aagctcttat atgacgagac cagctggagt      480
gacttggact ttatatatgc taagaagatg acaggatgga tgtattttgt ttccaagata      540
ctggcagaga aggccgcaat ggaagcagct aaaaagaaga catcgatttt cattagcatc      600
ataccgccac tggttgttgg tccattcctc gcgcctacat tcccacctag cttaatcact      660
gccctttcac taattactgg gaatgaagct cactacagca tcattaaaca aggtaaatat      720
gtgcatttgg atgatctttg tgaggctcat attttcctat atgagcaccc aaaggcagag      780
gggagattca tctgcgcgtc ccatcatgct atcatctatg atgtggcaaa gatggtccaa      840
gagaaatggc cggagtacta cgtccctact gagtttaaag catcgataa ggacttgtcc      900 gtggtgtatt tttcgtcaaa gaagctgacg gatatggggt ttcaattcaa gtacactttg      960
gaggatatgt ataaaggggc cattgagact tgtcgacaga agcagttgct tccctttttct    1020 acccgaagca ctgcagataa tgtacgtgac aaagaagcca ttcctctttc tactgaaaac    1080
```

| | |
|---|---:|
| tatgcaagtg gcaaagaaaa ttcaccagtt gcaaatggta cgggaaagtc aaccaatggt | 1140 |
| gaaatctag | 1149 |

<210> SEQ ID NO 39
<211> LENGTH: 642
<212> TYPE: DNA
<213> ORGANISM: Nicotiana

<400> SEQUENCE: 39

| | |
|---|---:|
| atgggaagaa aaccctgttg ttctaaagaa ggtctgagga aaggtacatg gactgcaaaa | 60 |
| gaagatatgc tacttactaa ttatattaat gaacatggag aagttggatg gagatctctt | 120 |
| cctatgaaag ctggaagtcg ttggtctctc attgctggaa gaatacctgg tcgaacagac | 180 |
| aacgaaataa agaattattg gaacacacat cttctcaaga aactcaaatc cgaaggactt | 240 |
| gagccaaaaa tacacaaatc tcttgcaaaa aacactagaa gacaaaagga gaaagcaaat | 300 |
| gtttcttccc aaattaacca aaaaggttaa aggaaaaga agaagaggaa taaaaagggc | 360 |
| aatatcgaag aaaattgtaa caatattgaa gagaaagaac aagtagctaa gagatagag | 420 |
| gagcagtggc atacgcagga ttccgtgcaa gcgatgtcag ggttttcaag tactagtgaa | 480 |
| gttgctagta gaaggaaac taattgcaat aatgtccatt gtccttcttc tggtcaaagt | 540 |
| cttgaagaaa atgacaatga aatttatgag aagcttcagg ctagcggaga ttctaaacgt | 600 |
| tgcaaattga atttcagtgc agaggttaat aagacccctt aa | 642 |

<210> SEQ ID NO 40
<211> LENGTH: 1308
<212> TYPE: DNA
<213> ORGANISM: Nicotiana

<400> SEQUENCE: 40

| | |
|---|---:|
| atgaagatcg aggtgaaaga atcgacgatg gtaaagccgg cggcggagac gccacaacag | 60 |
| aggctgtgga actctaatgt ggatttggtg gtgccgaatt ccacacgcc aagtgtttat | 120 |
| ttttacaggc cgacgggatc cccaaatttc ttcgacggaa aagtgctgaa ggaagctcta | 180 |
| agcaaagcac ttgtgccgtt ttatcctatg gcggggaggc tgtgtaggga cgaagatggt | 240 |
| cgtattgaga ttgactgtaa aggtcagggg gtgcttttg tggaagctga gtcggatggt | 300 |
| gtggtggatg attttggtga ttttgccccg acgttagaac tccgtcaact catccccgcc | 360 |
| gttgattact cacaaggaat tcaatcgtat gctctcttag tgttgcagat aacacatttt | 420 |
| aaatgtgggg gagtttccct tggtgtgggc atgcaacatc atgcagcaga tggagcttct | 480 |
| ggtcttcact tcatcaacac atggtctgat atggctcgtg gtctggacct caccatccca | 540 |
| cctttcattg accggaccct cctccgtgct cgtgatccac ctcagcctca gtttccccat | 600 |
| gtcgagtacc agccacctcc cactctcaag gtaactccag aaaacacccc tatatctgaa | 660 |
| gctgttcctg aaaccagcgt gtccatcttc aaattaaccc gtgatcaaat caataccctc | 720 |
| aaagcgaagt ccaaggaaga tggaaatacc gttaactaca gctcctacga gatgttggca | 780 |
| ggacatgtgt ggcgctccac gtgcatggca cgaggactcg ctcatgatca agaaaccaaa | 840 |
| ttgtacatag caacagatgg acgttccagg cttcggccct ctctcccacc aggctatttc | 900 |
| ggtaatgtga tatttactac cactcctatt gcagtcgcag gtgatatcca atcgaagcct | 960 |
| atttggtatg ctgccagtaa attacatgat gcattggcta gaatggacaa cgattactta | 1020 |
| agatcagctc ttgattattt ggagttgcag cctgacttaa aggctcttgt tcgtggtgca | 1080 |
| catacgttta agtgcccgaa tttaggaata actagttggt ctaggctgcc aatccatgat | 1140 |

```
gctgattttg gctggggtag gcctatattt atgggacctg gtggtattgc ttatgaaggt    1200
ttaagcttta tattgccaag tcctacaaat gatggcagtc aatctgttgc aatctctcta    1260
caagcagaac acatgaaact tttcgagaag ttcttgtatg acttttga                 1308
```

<210> SEQ ID NO 41
<211> LENGTH: 1311
<212> TYPE: DNA
<213> ORGANISM: Nicotiana

<400> SEQUENCE: 41

```
atgggaagtg aaaaatgat  gaaaattaat atcaaggaat caacattagt aaaaccatca     60
aaaccaacac caacaaaaag actttggagt tctaacttag atttaatagt gggaagaatt    120
catcttttaa cagtatattt ctataaacca aatggatctt caaatttctt tgattcaaaa    180
ataatgaaag aagcattaag taatgttctt gtttcatttt acccaatggc tggaagatta    240
gctagagata acaaggaag  aattgagata aattgtaatg agaaggagt  tttatttgtt    300 gaagctgaaa gtgatgcttt tgttgatgat tttggtgatt ttactccaag tttggaactt    360
aggaaactta ttcctactgt tgacacttct ggtgatattt ctactttccc cctcatcatc    420
tttcaggtta ctcgtttcaa atgtggtgga gtttcacttg gtggaggagt attccacact    480
ttatcagatg gtctctcatc aattcacttc atcaacacat ggtccgatat agcccgaggc    540
ctctccgtcg ccatcccgcc gttcatcgac cggaccctcc tccgtgcacg ggacccacca    600
acatcgtctt tcgagcacgt cgagtatcat cctcctccat ctctaatttc atcatcaaaa    660
agcttagaat ccactagccc aaagcctagt accacaacca tgttaaaatt ctctagtgac    720
caacttgggc ttctaaagtc caagtccaaa catgatggta gcacttacga atcctcgcg    780 gcccatattt ggcgttgcac gtgcaaggca cgtgcactgt ccgacgatca attgaccaaa    840
ttacatgtgg ccactgatgg taggtctagg ctttgccctc ctttgccacc aggttactta    900
ggaaatgttg tgttcacagg cacacctatg gcaaaatcaa gtgaactttt acaagaacca    960
ttgacaaatt cagccaagag aattcatagt gcattatcaa aaatggatga caattaccta   1020
agatcagctc tcgattacct cgaattactg cccgatttat cggctttaat ccgtggaccg   1080
acgtactttg ctagccctaa tcttaatatt aatagttgga ctagattgcc tgttcatgat   1140
tcagattttg gatggggaag gccaattcat atgggaccag cttgcatttt atatgaaggg   1200
acagtttata tattgccaag tccaaatagt aaagatagga acttgcgttt ggctgttgt    1260 ttagatgctg atcacatgcc actatttgag aagtatttgt atgaattttg a            1311
```

<210> SEQ ID NO 42
<211> LENGTH: 2148
<212> TYPE: DNA
<213> ORGANISM: Nicotiana

<400> SEQUENCE: 42

```
atggcatcaa atggtcatgt taatggagga gaaaactttg agttgtgcaa aaaatcagct     60
gatccattga attgggaaat ggcagctgaa tccttaagag ggagtcattt ggatgaagtg    120
aaaaaaatgg tgagtgaatt tagaaaacca atggtaaaac ttggtggtga agtttaaca    180 gtggcacaag tggctgctat tgctgttagg gacaaaagtg caaatggtgt taaagttgaa    240
ctttctgaag aggcaagagc tggtgttaaa gctagtagtg attgggttat ggacagtatg    300
aataaaggaa ctgatagtta tggtgttact actggttttg gtgctacatc tcataggaga    360
```

```
accaagaatg gtggtgctct tcaaaaagaa cttattaggt tcttgaatgc tggtgttttt    420
ggcaatggaa cagaaacaag ccacacattg ccacattcag caacaagggc agctatgctt    480
gttaggatca acacactcct acaaggctac tctggcatca gatttgaaat cttggaagct    540
attacaaaat tgattaacag caacatcact ccatgtttac ctctccgtgg aacgatcact    600
gcctcgggtg atcttgtccc tttatcctac attgctggtt tgctcactgg taggcctaat    660
tccaaggctg ttggtcccaa tggtgagaca cttaatgctg aagaagcgtt ccgcgttgct    720
ggtgttaacg gtggatttt cgagttgcag cctaaggaag acttgcact tgtgaatggt    780
acagctgttg gttctggtat ggcatcaatg gtcctctttg attccaacat tcttgctgta    840
atgtctgaag ttttatcagc aattttcgct gaagtaatga acggaaagcc cgaattcact    900
gaccatttga cacacaagtt gaagcaccac cctggtcaaa ttgaggctgc tgctattatg    960
gaacatattt tggatggaag ctcttatgtg aaggcggctc aaaagctaca tgaaatggat   1020
cctctacaaa aaccaaagca agatcgttat gctctccgaa catctccaca atggcttggc   1080
cctcaaattg aagtcattcg cgctgcaact aagatgattg agaggagat taactcagtg   1140
aacgataacc ctttgatcga tgtttcaaga acaaggcgt tacatggtgg caacttccaa   1200
ggcactccta tcggtgtttc catggataat gcaagattgg ctcttgcatc aattgggaaa   1260
ttgatgtttg ctcaattctc ggaacttgtc aacgactatt acaacaacgg tttgccctct   1320
aatctcactg catcaaggaa tccaagcttg gactatggtt tcaagggagc tgaaatcgcc   1380
atggcttctt actgctcaga acttcaattc ttggcaaatc cagtgacaaa ccatgtccaa   1440
agtgctgaac aacacaacca agatgtcaac tccttaggct taatctcagc aaggaaaaca   1500
gctgaagctg ttgatatctt aaagctcatg tcatcaactt atctcgtggc actttgccaa   1560
gctatagact tgaggcattt ggaagaaaac ttaaagaatg cagtcaagaa cacagttagc   1620
caagtagcta agagaactct tacaatgggt gctaatggtg aacttcatcc agcaagattc   1680
tgtgaaaagg aattgcttcg aatcgtggat agggaatact tgttcgccta cgctgatgat   1740
ccttgcagtt gcaactaccc tttaatgcag aaactgagac aagtacttgt tgatcatgca   1800
atgaataatg gtgaaagtga aagaatgtg aacagctcaa tctttcaaaa gattggagct   1860
ttcgaagatg aattgaaggc tgtttttacca aaggaagttg agagtgcaag agctgcatta   1920
gaaagtggaa accctgctat tcctaacagg attacagaat gcagatctta tccattgtac   1980
aggtttgtga aaaggagct tggaacagaa ttattgacag gagaaaaagt ccgatcaccg   2040
ggcgaggagt gtgacaaagt gttcacagca atgtgcaatg acaaatcat tgatccaatg   2100
ttggagtgtc tcaagagctg gaatggtgct cctcttccta tctgttag              2148
```

<210> SEQ ID NO 43
<211> LENGTH: 1026
<212> TYPE: DNA
<213> ORGANISM: Nicotiana

<400> SEQUENCE: 43

```
atggataatt cagctccaga ttcgttatcc agatcggaaa ccgccgtcac atacgactca     60
ccatatccac tctacgccat ggctttctct tctctccgct catcctccgg tcacagaatc    120
gccgtcggaa gcttcctcga agattacaac aaccgcatcg acattctctc tttcgattcc    180
gattcaatga ccgttaagcc tctcccgaat ctctccttcg agcatcctta tcctccaaca    240
aagctaatgt tcagtcctcc ttctctccgt cgtccttcct ccgagatct cctgcttcc    300
tccggcgatt tcctccgtct ttgggaaatt aacgaagatt catcaaccgt cgagccaatc    360
```

```
tcggttctca acaacagcaa aacgagcgag ttttgtgcgc cgttgacttc cttcgattgg      420
aacgatgtag agccgaaacg tctcggaact tgtagtattg atacgacgtg tacgatttgg      480
gatattgaga agtctgttgt tgagactcag cttatagctc atgataaaga ggttcatgac      540
attgcttggg gagaagctag ggttttcgca tcagtctctg ctgatggatc cgttaggatc      600
tttgatttac gtgataagga acattctaca atcatttacg agagtcctca gcctgatacg      660
cctttgttaa gacttgcttg gaacaaacaa gatcttagat atatggctac gattttgatg      720
gattctaata aggttgtgat tctcgatatt cgttcgccga ctatgcctgt tgctgagctt      780
gaaagacatc aggctagtgt gaatgctata gcttgggcgc ctcagagctg taaacatatt      840
tgttctggtg gtgatgatac acaggctctt atttgggagc ttcctactgt tgctggaccc      900
aatgggattg atccgatgtc ggtttattcg gctggttcgg agattaatca gttgcagtgg      960
tcttcttcgc agcctgattg gattggtatt gcttttgcta acaaaatgca gctccttaga     1020
gtttga                                                                1026

<210> SEQ ID NO 44
<211> LENGTH: 1323
<212> TYPE: DNA
<213> ORGANISM: Nicotiana

<400> SEQUENCE: 44
atgagcatgt ctgttgcttt gttgtgggtt gtttctccca cttccgaggt ctcgaatggg       60
acaggattgt tggattcagt ccgagaagga aaccgcgtct ttgtatcatc caggttccta      120
gctcgagata ggaatttgat gtggaatggg agaatcaaga aaggtgggag acaaaggtgg      180
aattttggct cttaattgc tgatccaaga tattcatgct tgggtggatc aagaactgaa       240
aagggaagca gtttctctgt acagtccagt ttggtggcta gcccagctgg agaaatgaca      300
gtgtcatcag agaaaaaggt ctatgatgtg gtattgaagc aagcagcttt agtgaagagg      360
cagctgagat ctaccgatga attagaagtg aaacctgata tagttgttcc agggaatttg      420
ggcttgttga gtgaagcata tgatcgttgt ggcgaagtat gtgcagagta tgcaaagaca      480
ttttacttag gaacaaagct aatgactcca gagagaagaa gagctatctg gtcaatatat      540
gtgtggtgca ggagaacgga tgagctagtc gatggcccta acgcatcaca cataactcca      600
caagctttag acaggtggga ggccaggctg gaagatattt tcagtgggcg gccatttgat      660
atgcttgatg ctgctttatc cgatactgtc tccagatttc ctgttgatat tcagccattc      720
agagatatga tagaaggaat gcgtatggac ttgtggaaat ccagatataa caacttcgat      780
gagctatatc tctattgtta ttatgttgct ggtacagtag gactgatgag tgttccagtt      840
atgggtattg cacctgaatc aaaggcaaca acagagagtg tatataatgc tgctttggct      900
ttagggcttg caaatcaact aaccaatata ctcagagatg taggagaaga tgccagaaga      960
ggacgagtat acttacctca agatgaatta gcacaggcag gctttctga tgaagatata     1020 tttgctggaa gagtgaccga taagtggagg aactttatga agaaacaaat tcagagggcg     1080
aggaaattct tgatgagtc agagaaaggt gtcacagaac tggactctgc tagtagatgg     1140
cctgtaagta cagcgctgct gttgtatcgc aagatattgg acgagattga agccaatgac     1200
tacaataact tcacaaggag ggcttatgtt agcaagccaa agaagcttct caccttgccc     1260
attgcttatg caaatctctc tgtgcccct aatagaactt cctctccact agcaaaaaca     1320
tga                                                                  1323
```

<210> SEQ ID NO 45
<211> LENGTH: 1323
<212> TYPE: DNA
<213> ORGANISM: Nicotiana

<400> SEQUENCE: 45

| | | | | | | |
|---|---|---|---|---|---|---|
| atgagcatgt | ctgttgcttt | gttgtgggtt | gtttctccca | cttccgaggt | ctcgaatggg | 60 |
| acaggattgt | tggattcagt | ccgagaagga | aaccgcgtct | ttgtatcatc | caggttccta | 120 |
| gctcgagata | ggaatttgat | gtggaatggg | agaatcaaga | aaggtgggag | acaaaggtgg | 180 |
| aattttggct | ctttaattgc | tgatccaaga | tattcatgct | tgggtggatc | aagaactgaa | 240 |
| aagggaagca | gtttctctgt | acagtccagt | ttggtggcta | gcccagctgg | agaaatgaca | 300 |
| gtgtcatcag | agaaaaaggt | ctatgatgtg | gtattgaagc | aagcagcttt | agtgaagagg | 360 |
| cagctgagat | ctaccgatga | attagaagtg | aaacctgata | ttgttgttcc | agggaatttg | 420 |
| ggcttgttga | gtgaagcata | tgatcgttgt | ggcgaagtat | gtgcagagta | tgcaaagaca | 480 |
| ttttacttag | aacaaagct | aatgactcca | gagaagaaga | gagctatctg | gcaatatat | 540 |
| gtgtggtgca | ggagaacgga | tgagctagtc | gatggcccta | acgcatcaca | cataactcca | 600 |
| caagctttag | acaggtggga | ggccaggctg | aagatattt | tcagtgggcg | gccatttgat | 660 |
| atgcttgatg | ctgctttatc | cgatactgtc | tccagatttc | ctgttgatat | tcagccattc | 720 |
| agagatatga | tagaaggaat | gcgtatggac | ttgtggaaat | ccagatataa | caacttcgat | 780 |
| gagctatatc | tctattgtta | ttatgttgct | ggtacagtag | gactgatgag | tgttccagtt | 840 |
| atgggtattg | cacctgaatc | aaaggcaaca | acagagagtg | tatataatgc | tgctttggct | 900 |
| ttagggcttg | caaatcaact | aaccaatata | ctcagagatg | taggagaaga | tgccagaaga | 960 |
| ggacgagtat | acttacctca | agatgaatta | gcacaggcag | ggctttctga | tgaagatata | 1020 |
| tttgctggaa | gagtgaccga | taagtggagg | aactttatga | agaaacaaat | tcagagggcg | 1080 |
| aggaaattct | ttgatgagtc | agagaaaggt | gtcacagaac | tggactctgc | tagtagatgg | 1140 |
| cctgtgttag | cagcgctgct | gttgtatcgc | aagatattgg | acgagattga | agccaatgac | 1200 |
| tacaataact | tcacaaggag | ggcttatgtt | agcaagccaa | agaagcttct | caccttgccc | 1260 |
| attgcttatg | caaaatctct | tgtgcccct | aatagaactt | cctctccact | agcaaaaaca | 1320 |
| tga | | | | | | 1323 |

<210> SEQ ID NO 46
<211> LENGTH: 747
<212> TYPE: DNA
<213> ORGANISM: Nicotiana

<400> SEQUENCE: 46

| | | | | | | |
|---|---|---|---|---|---|---|
| atggagggtt | cgtccaaagg | gctgcgaaaa | ggtgcttgga | ctactgaaga | agatagtctc | 60 |
| ttgagacagt | gcattaataa | gtatggagaa | ggcaaatggc | accaagttcc | tgtaagagct | 120 |
| gggctaaacc | ggtgcaggaa | aagttgtaga | ttaagatggt | tgaactattt | gaagccaagt | 180 |
| atcaagagag | gaaaacttag | ctctgatgaa | gtcgatcttc | ttcttcgcct | tcataggctt | 240 |
| ctagggaata | ggtggtcttt | aattgctgga | agattacctg | tcggaccgc | aaatgacgtc | 300 |
| aagaattact | ggaacactca | tctgagtaag | aaacatgaac | cgtgttgtaa | gataaagatg | 360 |
| aaaaagagag | acattacgcc | cattcctaca | acaccggcac | taaaaaacaa | tgtttataag | 420 |
| cctcgacctc | gatccttcac | agttaacaac | gactgcaacc | atctcaatgc | cccaccaaaa | 480 |
| gttgacgtta | atcctccatg | ccttggactt | aacatcaata | atgtttgtga | caatagtatc | 540 |

```
atatacaaca aagataagaa gaaagaccaa ctagtgaata atttgattga tggagataat      600
atgtggttag agaaattcct agaggaaagc caagaggtag atattttggt tcctgaagcg      660
acgacaacag aaaaggggga caccttggct tttgacgttg atcaactttg gagtcttttc      720
gatggagaga ctgtgaaatt tgattag                                         747

<210> SEQ ID NO 47
<211> LENGTH: 717
<212> TYPE: PRT
<213> ORGANISM: Nicotiana

<400> SEQUENCE: 47
```

Met Ala Ser Asn Gly His Val Asn Gly Gly Glu Asn Phe Glu Leu Cys
1               5                   10                  15

Lys Lys Ser Ser Ala Thr Asp Pro Leu Asn Trp Glu Met Ala Ala Glu
            20                  25                  30

Ser Leu Arg Gly Ser His Leu Asp Glu Val Lys Lys Met Val Ser Glu
        35                  40                  45

Phe Arg Lys Pro Met Val Lys Leu Gly Gly Glu Thr Leu Thr Val Ala
    50                  55                  60

Gln Val Ala Ala Ile Ala Val Arg Asp Lys Ser Ala Asn Gly Val Lys
65                  70                  75                  80

Val Glu Leu Ser Glu Glu Ala Arg Ala Gly Val Lys Ala Ser Ser Asp
                85                  90                  95

Trp Val Met Asp Ser Met Asn Lys Gly Thr Asp Ser Tyr Gly Val Thr
            100                 105                 110

Thr Gly Phe Gly Ala Thr Ser His Arg Arg Thr Lys Asn Gly Gly Ala
        115                 120                 125

Leu Gln Lys Glu Leu Ile Arg Phe Leu Asn Ala Gly Val Phe Gly Asn
    130                 135                 140

Gly Thr Glu Thr Ser His Thr Leu Pro His Ser Ala Thr Arg Ala Ala
145                 150                 155                 160

Met Leu Val Arg Ile Asn Thr Leu Leu Gln Gly Tyr Ser Gly Ile Arg
                165                 170                 175

Phe Glu Ile Leu Glu Ala Ile Ala Lys Leu Ile Asn Ser Asn Ile Thr
            180                 185                 190

Pro Cys Leu Pro Leu Arg Gly Thr Ile Thr Ala Ser Gly Asp Leu Val
        195                 200                 205

Pro Leu Ser Tyr Ile Ala Gly Leu Leu Thr Gly Arg Pro Asn Ser Lys
    210                 215                 220

Ala Val Ser Pro Asn Gly Glu Thr Leu Asn Ala Glu Glu Ala Phe Arg
225                 230                 235                 240

Val Ala Gly Val Asn Gly Gly Phe Phe Glu Leu Gln Pro Lys Glu Gly
                245                 250                 255

Leu Ala Leu Val Asn Gly Thr Ala Val Gly Ser Gly Met Ala Ser Met
            260                 265                 270

Val Leu Phe Asp Ser Asn Ile Leu Ala Val Met Ser Glu Val Leu Ser
        275                 280                 285

Ala Ile Phe Ala Glu Val Met Asn Gly Lys Pro Glu Phe Thr Asp His
    290                 295                 300

Leu Thr His Lys Leu Lys His His Pro Gly Gln Ile Glu Ala Ala Ala
305                 310                 315                 320

Ile Met Glu His Ile Leu Asp Gly Ser Ser Tyr Val Lys Ala Ala Gln
                325                 330                 335

Lys Leu His Glu Met Asp Pro Leu Gln Lys Pro Lys Gln Asp Arg Tyr
            340                 345                 350

Ala Leu Arg Thr Ser Pro Gln Trp Leu Gly Pro Gln Ile Glu Val Ile
            355                 360                 365

Arg Ala Ala Thr Lys Met Ile Glu Arg Glu Ile Asn Ser Val Asn Asp
            370                 375                 380

Asn Pro Leu Ile Asp Val Ser Arg Asn Lys Ala Leu His Gly Gly Asn
385                 390                 395                 400

Phe Gln Gly Thr Pro Ile Gly Val Ser Met Asp Asn Ala Arg Leu Ala
            405                 410                 415

Leu Ala Ser Ile Gly Lys Leu Met Phe Ala Gln Phe Ser Glu Leu Val
            420                 425                 430

Asn Asp Tyr Tyr Asn Asn Gly Leu Pro Ser Asn Leu Thr Ala Ser Arg
            435                 440                 445

Asn Pro Ser Leu Asp Tyr Gly Phe Lys Gly Ala Glu Ile Ala Met Ala
            450                 455                 460

Ser Tyr Cys Ser Glu Leu Gln Phe Leu Ala Asn Pro Val Thr Asn His
465                 470                 475                 480

Val Gln Ser Ala Glu Gln His Asn Gln Asp Val Asn Ser Leu Gly Leu
            485                 490                 495

Ile Ser Ala Arg Lys Thr Ala Glu Ala Val Asp Ile Leu Lys Leu Met
            500                 505                 510

Ser Ser Thr Tyr Leu Val Ala Leu Cys Gln Ala Ile Asp Leu Arg His
            515                 520                 525

Leu Glu Glu Asn Leu Lys Asn Ala Val Lys Asn Thr Val Ser Gln Val
            530                 535                 540

Ala Lys Arg Thr Leu Thr Met Gly Ala Asn Gly Glu Leu His Pro Ala
545                 550                 555                 560

Arg Phe Cys Glu Lys Glu Leu Leu Arg Val Val Asp Arg Glu Tyr Leu
            565                 570                 575

Phe Ala Tyr Ala Asp Asp Pro Cys Ser Cys Asn Tyr Pro Leu Met Gln
            580                 585                 590

Lys Leu Arg Gln Val Leu Val Asp His Ala Met Asn Asn Gly Glu Ser
            595                 600                 605

Glu Lys Asn Val Asn Ser Ser Ile Phe Gln Lys Ile Gly Ala Phe Glu
            610                 615                 620

Asp Glu Leu Lys Ala Val Leu Pro Lys Glu Val Glu Ser Ala Arg Ala
625                 630                 635                 640

Ala Leu Glu Cys Gly Asn Pro Ala Ile Ala Asn Arg Ile Thr Glu Cys
            645                 650                 655

Arg Ser Tyr Pro Leu Tyr Arg Phe Val Arg Lys Glu Leu Gly Thr Glu
            660                 665                 670

Leu Leu Thr Gly Glu Arg Val Arg Ser Pro Gly Glu Glu Cys Glu Lys
            675                 680                 685

Val Phe Thr Ala Met Cys Asn Gly Gln Ile Ile Asp Pro Met Leu Glu
            690                 695                 700

Cys Leu Lys Ser Trp Asn Gly Ala Pro Leu Pro Ile Cys
705                 710                 715

<210> SEQ ID NO 48
<211> LENGTH: 712
<212> TYPE: PRT
<213> ORGANISM: Nicotiana

-continued

```
<400> SEQUENCE: 48

Met Ala Gly Val Ala Gln Asn Gly His Gln Glu Met Asp Phe Cys Met
1               5                   10                  15

Lys Val Asp Pro Leu Asn Trp Glu Met Ala Asp Ser Leu Lys Gly
            20                  25                  30

Ser His Leu Asp Glu Val Lys Lys Met Val Ala Glu Phe Arg Lys Pro
        35                  40                  45

Val Val Lys Leu Gly Gly Glu Thr Leu Thr Val Ala Gln Val Ala Ala
    50                  55                  60

Ile Ala Ala Lys Asp Asn Val Lys Thr Val Lys Val Glu Leu Ser Glu
65                  70                  75                  80

Gly Ala Arg Ala Gly Val Lys Ala Ser Ser Asp Trp Val Met Asp Ser
                85                  90                  95

Met Gly Lys Gly Thr Asp Ser Tyr Gly Val Thr Thr Gly Phe Gly Ala
            100                 105                 110

Thr Ser His Arg Arg Thr Lys Asn Gly Gly Ala Leu Gln Lys Glu Leu
        115                 120                 125

Ile Arg Phe Leu Asn Ala Gly Val Phe Gly Asn Gly Thr Glu Ser Cys
130                 135                 140

His Thr Leu Pro Gln Ser Gly Thr Arg Ala Ala Met Leu Val Arg Ile
145                 150                 155                 160

Asn Thr Leu Leu Gln Gly Tyr Ser Gly Ile Arg Phe Glu Ile Leu Glu
                165                 170                 175

Ala Ile Thr Lys Leu Leu Asn His Asn Val Thr Pro Cys Leu Pro Leu
            180                 185                 190

Arg Gly Thr Ile Thr Ala Ser Gly Asp Leu Val Pro Leu Ser Tyr Ile
        195                 200                 205

Ala Gly Leu Leu Thr Gly Arg Pro Asn Ser Lys Ala Val Gly Pro Asn
    210                 215                 220

Gly Glu Thr Leu Asn Ala Glu Glu Ala Phe Arg Val Ala Gly Val Asn
225                 230                 235                 240

Gly Gly Phe Phe Glu Leu Gln Pro Lys Glu Gly Leu Ala Leu Val Asn
                245                 250                 255

Gly Thr Ala Val Gly Ser Gly Leu Ala Ser Met Val Leu Phe Asp Ala
            260                 265                 270

Asn Val Leu Ala Val Phe Ser Glu Val Leu Ser Ala Ile Phe Ala Glu
        275                 280                 285

Val Met Asn Gly Lys Pro Glu Phe Thr Asp His Leu Thr His Lys Leu
    290                 295                 300

Lys His His Pro Gly Gln Ile Glu Ala Ala Ile Met Glu His Ile
305                 310                 315                 320

Leu Asp Gly Ser Ser Tyr Val Lys Ala Ala Gln Lys Leu His Glu Thr
                325                 330                 335

Asp Pro Leu Gln Lys Pro Lys Gln Asp Arg Tyr Ala Leu Arg Thr Ser
            340                 345                 350

Pro Gln Trp Leu Gly Pro Gln Ile Glu Val Ile Arg Ser Ala Thr Lys
        355                 360                 365

Met Ile Glu Arg Glu Ile Asn Ser Val Asn Asp Asn Pro Leu Ile Asp
    370                 375                 380

Val Ser Arg Asn Lys Ala Leu His Gly Gly Asn Phe Gln Gly Thr Pro
385                 390                 395                 400

Ile Gly Val Ser Met Asp Asn Ala Arg Leu Ala Leu Ala Ser Ile Gly
                405                 410                 415
```

```
Lys Leu Met Phe Ala Gln Phe Ser Glu Leu Val Asn Asp Tyr Tyr Asn
                420                 425                 430

Asn Gly Leu Pro Ser Asn Leu Thr Ala Gly Arg Asn Pro Ser Leu Asp
            435                 440                 445

Tyr Gly Phe Lys Gly Ser Glu Ile Ala Met Ala Ser Tyr Cys Ser Glu
        450                 455                 460

Leu Gln Phe Leu Ala Asn Pro Val Thr Asn His Val Gln Ser Ala Glu
465                 470                 475                 480

Gln His Asn Gln Asp Val Asn Ser Leu Gly Leu Ile Ser Ala Arg Lys
                485                 490                 495

Thr Ala Glu Ala Val Asp Ile Leu Lys Leu Met Ser Ser Thr Tyr Leu
            500                 505                 510

Val Ala Leu Cys Gln Ala Ile Asp Leu Arg His Leu Glu Glu Asn Leu
        515                 520                 525

Arg Asn Ala Val Lys Asn Thr Val Ser Gln Val Ala Lys Arg Thr Leu
530                 535                 540

Thr Met Gly Thr Asn Gly Glu Leu His Pro Ser Arg Phe Cys Glu Lys
                550                 555                 560
545

Asp Leu Leu Arg Val Val Asp Arg Glu Tyr Val Phe Ala Tyr Ala Asp
                565                 570                 575

Asp Ala Cys Ser Ala Asn Tyr Pro Leu Met Gln Lys Leu Arg Gln Val
        580                 585                 590

Leu Val Asp His Ala Leu Gln Asn Gly Glu Asn Glu Lys Asn Ala Asn
                595                 600                 605

Ser Ser Ile Phe Gln Lys Ile Leu Ala Phe Glu Asp Glu Leu Lys Ala
610                 615                 620

Val Leu Pro Lys Glu Val Glu Ser Ala Arg Ala Ala Leu Glu Ser Gly
625                 630                 635                 640

Asn Pro Ala Ile Ala Asn Arg Ile Lys Glu Cys Arg Ser Tyr Pro Leu
                645                 650                 655

Tyr Arg Phe Val Arg Gly Glu Leu Gly Ala Glu Leu Leu Thr Gly Glu
            660                 665                 670

Lys Val Arg Ser Pro Gly Glu Glu Cys Asp Lys Val Phe Thr Ala Met
        675                 680                 685

Cys Asn Gly Gln Ile Ile Asp Ser Leu Leu Glu Cys Leu Lys Glu Trp
    690                 695                 700

Asn Gly Ala Pro Leu Pro Ile Cys
705                 710

<210> SEQ ID NO 49
<211> LENGTH: 389
<212> TYPE: PRT
<213> ORGANISM: Nicotiana

<400> SEQUENCE: 49

Met Val Thr Val Glu Glu Phe Arg Arg Ala Gln Arg Ala Glu Gly Pro
1               5                   10                  15

Ala Thr Val Met Ala Ile Gly Thr Ala Thr Pro Ser Asn Cys Val Asp
            20                  25                  30

Gln Ser Thr Tyr Pro Asp Tyr Tyr Phe Arg Ile Thr Asn Ser Glu His
        35                  40                  45

Lys Thr Glu Leu Lys Glu Lys Phe Lys Arg Met Cys Glu Lys Ser Met
    50                  55                  60

Ile Lys Lys Arg Tyr Met His Leu Thr Glu Glu Ile Leu Lys Glu Asn
```

```
                65                  70                  75                  80
        Pro Asn Ile Cys Ala Tyr Met Ala Pro Ser Leu Asp Ala Arg Gln Asp
                        85                  90                  95

Ile Val Val Glu Val Pro Lys Leu Gly Lys Glu Ala Ala Gln Lys
                    100                 105                 110

Ala Ile Lys Glu Trp Gly Gln Pro Lys Ser Lys Ile Ser His Leu Val
                    115                 120                 125

Phe Cys Thr Thr Ser Gly Val Asp Met Pro Gly Cys Asp Tyr Gln Leu
                130                 135                 140

Thr Lys Leu Leu Gly Leu Arg Pro Ser Val Lys Arg Phe Met Met Tyr
        145                 150                 155                 160

Gln Gln Gly Cys Phe Ala Gly Gly Thr Val Leu Arg Met Ala Lys Asp
                        165                 170                 175

Leu Ala Glu Asn Asn Lys Gly Ala Arg Val Leu Val Val Cys Ser Glu
                    180                 185                 190

Ile Thr Ala Val Thr Phe Arg Gly Pro Asn Asp Thr His Leu Asp Ser
                    195                 200                 205

Leu Val Gly Gln Ala Leu Phe Gly Asp Gly Ala Ala Ala Val Ile Val
                210                 215                 220

Gly Ser Asp Pro Ile Pro Asp Val Glu Arg Pro Leu Phe Glu Leu Val
        225                 230                 235                 240

Ser Ala Ala Gln Thr Leu Leu Pro Asp Ser Glu Gly Ala Ile Asp Gly
                        245                 250                 255

His Leu Arg Glu Val Gly Leu Thr Phe His Leu Leu Lys Asp Val Pro
                    260                 265                 270

Gly Leu Ile Ser Lys Asn Ile Glu Lys Ser Leu Val Glu Ala Phe Gln
                    275                 280                 285

Pro Leu Gly Ile Ser Asp Trp Asn Ser Leu Phe Trp Ile Ala His Pro
                290                 295                 300

Gly Gly Pro Ala Ile Leu Asp Gln Val Glu Leu Lys Leu Gly Leu Lys
        305                 310                 315                 320

Gln Glu Lys Leu Lys Ala Thr Arg Asn Val Leu Ser Asn Tyr Gly Asn
                        325                 330                 335

Met Ser Ser Ala Cys Val Leu Phe Ile Leu Asp Glu Met Arg Lys Ala
                    340                 345                 350

Ser Ala Lys Glu Gly Leu Gly Thr Thr Gly Glu Gly Leu Glu Trp Gly
                    355                 360                 365

Val Leu Phe Gly Phe Gly Pro Gly Leu Thr Val Glu Thr Val Val Leu
                370                 375                 380

His Ser Val Ala Thr
        385

<210> SEQ ID NO 50
<211> LENGTH: 369
<212> TYPE: PRT
<213> ORGANISM: Nicotiana

<400> SEQUENCE: 50

Met Ala Pro Ser Thr Leu Thr Ala Leu Ala Glu Glu Lys Thr Leu Gln
        1               5                   10                  15

Thr Ser Phe Ile Arg Asp Glu Asp Glu Arg Pro Lys Val Ala Tyr Asn
                    20                  25                  30

Gln Phe Ser Asp Glu Ile Pro Ile Ile Ser Leu Lys Gly Ile Asp Asp
                35                  40                  45
```

Glu Gly Gly Ile Asn Gly Arg Arg Gly Glu Ile Cys Glu Lys Ile Val
    50                  55                  60

Lys Ala Cys Glu Asp Trp Gly Val Phe Gln Val Val Asp His Gly Val
 65              70                  75                  80

Asp Ala Gln Leu Ile Ser Gln Met Thr Thr Leu Ala Lys Gln Phe Phe
                85                  90                  95

Ala Leu Pro Ala Glu Glu Lys Leu Arg Phe Asp Met Ser Gly Gly Lys
            100                 105                 110

Lys Gly Gly Phe Ile Val Ser Ser His Leu Gln Gly Glu Val Val Gln
            115                 120                 125

Asp Trp Arg Glu Ile Val Thr Tyr Phe Ser Tyr Pro Ile Arg Ala Arg
130                 135                 140

Asp Tyr Ser Arg Trp Pro Asp Lys Pro Glu Gly Trp Ile Asp Val Thr
145                 150                 155                 160

Gln Lys Tyr Ser Glu Lys Leu Met Glu Leu Ala Cys Lys Leu Leu Glu
                165                 170                 175

Val Leu Ser Glu Ala Met Gly Leu Glu Lys Glu Ala Leu Thr Lys Ala
            180                 185                 190

Cys Val Asp Met Asp Gln Lys Val Val Asn Phe Tyr Pro Lys Cys
            195                 200                 205

Pro Gln Pro Asp Leu Thr Leu Gly Leu Lys Arg His Thr Asp Pro Gly
            210                 215                 220

Thr Ile Thr Leu Leu Leu Gln Asp Gln Val Gly Gly Leu Gln Ala Thr
225                 230                 235                 240

Lys Asp Asn Gly Lys Thr Trp Ile Thr Val Gln Pro Val Val Gly Ala
                245                 250                 255

Phe Val Val Asn Leu Gly Asp His Gly His Phe Leu Ser Asn Gly Arg
            260                 265                 270

Phe Lys Asn Ala Asp His Gln Ala Val Val Asn Ser Asn Ser Ser Arg
            275                 280                 285

Leu Ser Ile Ala Thr Phe Gln Asn Pro Ala Pro Glu Ala Ile Val Tyr
            290                 295                 300

Pro Leu Lys Ile Arg Glu Gly Glu Lys Ala Val Met Asp Glu Pro Val
305                 310                 315                 320

Ala Phe Ala Glu Met Tyr Arg Arg Lys Met Ser Lys Asp Leu Glu Leu
                325                 330                 335

Ala Arg Leu Lys Lys Leu Ala Lys Glu Gln Ile Gln Ala Glu Glu
            340                 345                 350

Ala Ala Glu Lys Ala Lys Ser Glu Thr Lys Pro Ile Asp Glu Ile Leu
            355                 360                 365

Ala

<210> SEQ ID NO 51
<211> LENGTH: 145
<212> TYPE: PRT
<213> ORGANISM: Nicotiana

<400> SEQUENCE: 51

Met Phe Gly Pro Gln Ser Gly Lys Asp Gly Trp Thr Asp Leu Thr Phe
 1               5                  10                  15

Met Tyr Asp Met Ile Arg Ile Arg Asp Lys Ser Leu Cys Ser Ser Phe
                20                  25                  30

Leu Gln Ile Phe Ser Ser Glu Gly Cys Lys Met Leu Glu Met Thr Cys
            35                  40                  45

```
Glu Glu His Asp Lys Leu Ala Ala Arg Ser Gln Phe Leu Thr His Thr
 50                  55                  60
Ile Gly Arg Ile Leu Ser Glu Met Glu Val Glu Pro Thr Pro Ile Asp
 65                  70                  75                  80
Thr Lys Gly Phe Gln Lys Leu Val Gln Val Lys Glu Ser Ser Val Arg
                 85                  90                  95
Asp Ser Phe Asp Leu Phe Ser Gly Leu Phe Ile His Asn Arg Phe Ala
                100                 105                 110
Arg Gln Gln Met Lys Asn Leu Glu Val Ala Val Glu Lys Thr Lys Gln
                115                 120                 125
Lys Leu Glu Glu Arg Ser Lys Glu Leu Gln Asp Pro Ile Ile Ser Lys
130                 135                 140
Phe
145

<210> SEQ ID NO 52
<211> LENGTH: 376
<212> TYPE: PRT
<213> ORGANISM: Nicotiana

<400> SEQUENCE: 52

Met Leu Ser Phe Thr Pro Leu Gln Ser Lys Pro Thr Pro Thr Pro Pro
 1               5                  10                  15
Thr Ser Asn Pro Thr Arg Trp Ser Trp Ser His Leu Thr His His His
                 20                  25                  30
Pro Thr Thr Arg Arg His Phe Ser Ala Ser Ser Pro Ser Lys Val Ser
                 35                  40                  45
Tyr Arg Arg Leu Ser Ile Asn Ala Ile Asp Ala Ala Gln Pro Tyr Asp
 50                  55                  60
Tyr Glu Ala Leu Val Ser Asn Gln Tyr Ala Gln Ser Thr Arg Leu Lys
 65                  70                  75                  80
Ile Ala Ile Val Gly Phe Gly Asn Phe Gly Gln Phe Leu Ala Lys Ala
                 85                  90                  95
Phe Val Arg Gln Gly His Val Val Phe Ala His Ser Arg Thr Asp Tyr
                100                 105                 110
Ser His Ile Ala Asn Ser Leu Gly Val Leu Phe Phe Gln Asp Pro His
                115                 120                 125
Asp Leu Cys Glu Gln His Pro Asp Val Ile Leu Leu Cys Thr Ser Ile
130                 135                 140
Ile Ser Thr Glu Pro Val Leu Arg Ser Leu Pro Ile Gln Arg Leu Lys
145                 150                 155                 160
Arg Asn Thr Leu Phe Val Asp Val Leu Ser Val Lys Glu Phe Pro Lys
                165                 170                 175
Asn Ile Phe Leu Gln Val Leu Pro Ser His Phe Asp Ile Leu Cys Thr
                180                 185                 190
His Pro Met Phe Gly Pro Glu Ser Gly Lys Asp Ser Trp Lys Asp Leu
                195                 200                 205
Ala Phe Val Phe Asp Lys Val Arg Ile Gly Glu Gly Glu Ser Arg Lys
210                 215                 220
Gly Arg Val Asp Arg Phe Leu Asp Ile Phe Glu Lys Glu Gly Cys Arg
225                 230                 235                 240
Met Val Gln Met Thr Cys Ala Glu His Asp Arg Tyr Ala Ala Gly Ser
                245                 250                 255
Gln Phe Ile Thr His Thr Met Gly Arg Val Leu Glu Lys Leu Asp Leu
                260                 265                 270
```

```
Glu Thr Thr Pro Ile Asn Thr Lys Gly Tyr Glu Thr Leu Leu Asn Leu
        275                 280                 285

Val Glu Asn Thr Ser Ser Asp Ser Phe Asp Leu Tyr Tyr Gly Leu Phe
    290                 295                 300

Met Tyr Asn Lys Asn Ala Met Glu Gln Leu Glu Arg Leu Asp Leu Ala
305                 310                 315                 320

Phe Glu Ala Leu Lys Lys Glu Leu Phe Gly His Leu His Glu Val Leu
                325                 330                 335

Arg Lys Gln Leu Phe Gly Lys Ala Glu Glu Ala Gly Gln Arg Arg Ile
                340                 345                 350

Leu Thr Lys Leu Pro Lys Asn Gly Tyr Ala Leu Pro Ala Pro Ser Ser
            355                 360                 365

Glu Ala Val Lys Ser Glu Asn Asn
    370                 375

<210> SEQ ID NO 53
<211> LENGTH: 2154
<212> TYPE: DNA
<213> ORGANISM: Nicotiana

<400> SEQUENCE: 53
atggcatcaa atggtcatgt taatggagga gaaaactttg agttgtgcaa gaaatcatca      60
gccactgatc cattgaattg ggaaatggca gctgaatctt aagagggag tcatttggat     120 gaagtgaaaa aaatggtgag tgaatttaga aaaccaatgg taaaacttgg tggtgaaact     180
ttaacagtgg cacaagtggc tgctattgct gttaggggaca aaagtgcaaa tggtgttaaa     240
gttgaacttt ctgaagaggc aagagctggt gttaaagcta gtagtgattg ggttatggat     300
agtatgaata aggaacaga tagttatggt gttactactg gttttggtgc tacatctcat     360 aggagaaacca agaatggtgg tgctcttcaa aaagaactta ttaggttctt gaatgctggt     420 gttttttggca atggaacaga acaagccac acattgccac attcagcaac aagggcagct     480
atgcttgtta ggatcaacac actcctacaa ggctactctg gcatcagatt tgaaatcttg     540
gaagcaattg caaaattgat taacagcaac attactccat gtttacctct ccgtggcacg     600
atcactgcct cgggcgatct tgttccttta tcctacattg ctggtttgct cactggtagg     660
cctaattcca aggctgttag tcccaatggt gagacccta atgctgaaga agcgttccgc     720
gttgctggtg ttaacggtgg attttttcgag ttgcagccta aggaaggact tgcacttgtg     780
aatggtacag cagttggttc tggtatggca tcaatggtcc tctttgattc caacattctt     840
gctgttatgt ctgaagtttt atcagcaatt tcgctgaag ttatgaacgg aaagcccgaa     900
tttactgacc atttgacaca caagttgaag caccaccctg gtcaaattga gctgctgct     960 attatggaac atattttgga tggaagctct tatgtgaagg cggctcaaaa gctacatgaa    1020
atggatcctc tccaaaaacc aaagcaagat cgttatgctc tccgaacatc tccacaatgg    1080
cttggccctc aaattgaagt cattcgcgct gcaactaaga tgattgagag ggagattaac    1140
tcagtgaacg ataacccctt gatcgatgtt tcaagaaaca aggcattaca tggtggcaac    1200
ttccaaggca cccctatcgg tgtgtccatg gataatgcaa gattggctct tgcatcaatt    1260
gggaaattga tgtttgctca attctcggaa cttgtcaacg actattacaa caacggtttg    1320
ccatctaacc tcaccgcatc aaggaatcca agcttggact atggtttcaa gggagctgaa    1380
atcgccatgg catcttactg ctcagaactt caattcttgg caaatccagt gacaaaccat    1440
gtccaaagtg ctgagcaaca caaccaagat gtcaactcct tgggcttaat ctcagcaagg    1500
```

| | |
|---|---|
| aaaacagctg aagctgtcga tatcttaaag ctcatgtcat caacttatct agtggcactt | 1560 |
| tgccaagcta tcgacttgag gcatttggag gaaaacttaa agaatgcagt caagaacaca | 1620 |
| gttagccaag tagctaagag aactcttaca atgggtgcta acggtgaact tcatccagca | 1680 |
| agattctgtg aaaaggaatt gctacgagtc gtggacaggg aatacttgtt cgcctacgct | 1740 |
| gatgatcctt gcagttgcaa ctacccttta atgcagaaac tgagacaagt acttgttgat | 1800 |
| catgcaatga ataatggtga aagtgagaag aatgtgaaca gctcaatctt ccaaaagatt | 1860 |
| ggagctttcg aagacgaatt aaaggctgtt ttaccaaagg aagttgagag tgcaagagct | 1920 |
| gcattggaat gtggcaaccc tgctattgct aacaggatta cagaatgcag atcttatcca | 1980 |
| ttgtacaggt ttgtgagaaa ggagcttgga acagaactac taacaggaga aagagtccga | 2040 |
| tcaccgggcg aggagtgtga aaagtgttc acagcaatgt gcaatggaca gattattgat | 2100 |
| ccaatgttgg agtgtctcaa gagctggaat ggtgctcctc tacctatctg ttag | 2154 |

<210> SEQ ID NO 54
<211> LENGTH: 2139
<212> TYPE: DNA
<213> ORGANISM: Nicotiana

<400> SEQUENCE: 54

| | |
|---|---|
| atggctggtg ttgcacaaaa tggtcaccaa gaaatggatt tttgcatgaa agtggatcca | 60 |
| ttaaactggg aaatggcagc tgattcattg aaaggaagcc atttagatga agtgaagaaa | 120 |
| atggtggctg agtttaggaa accagtagtg aaacttggag gtgagacttt gacagtggct | 180 |
| caagttgcgg ctattgctgc aaaagataat gttaaaactg ttaaagtgga gctttctgaa | 240 |
| ggggcaagag ctggtgttaa agctagcagt gattgggtta tggacagtat gggtaaagga | 300 |
| actgatagtt atggtgttac aactggcttt ggtgctactt cacataggag gaccaagaat | 360 |
| ggtggtgctc ttcaaaagga acttattagg ttcttgaatg ctggagtttt tggcaatgga | 420 |
| acagagtcat gtcacacatt accacaatca gggacaaggg cagctatgtt agttaggatc | 480 |
| aacactctcc ttcaagggta ctctggcatc agatttgaaa tcttagaagc aatcactaaa | 540 |
| ttgcttaacc acaatgttac tccatgtttg ccccttcgcg gcaccatcac cgcctctggt | 600 |
| gatctcgtcc ccttgtccta cattgccggt ttactcactg gtcggcctaa ttctaaagca | 660 |
| gttggaccta atggcgaaac cctcaacgct gaagaagcgt ttcgtgttgc tggagttaac | 720 |
| ggtggatttt tcgagttgca gcctaaggaa ggccttgctc ttgtgaatgg tactgcagtt | 780 |
| ggttctggtt tggcctcaat ggttctcttt gatgctaatg ttctcgcggt ctttctgaa | 840 |
| gttctctcag ctattttgc tgaggtaatg aatggaaagc ccgagttcac tgaccacttg | 900 |
| acacacaagt tgaagcatca ccccggacaa attgaggctc tgctattat ggaacacatt | 960 |
| ttggatggta gctcttatgt gaaggcggct cagaagcttc acgaaacgga tcctctccaa | 1020 |
| aaaccaaagc aagatcgtta tgctcttaga acgtcgcccc aatggcttgg ccctcaaatt | 1080 |
| gaggtcatcc gttctgcaac caagatgatt gagagggaga ttaattcagt gaacgacaac | 1140 |
| cctttgatcg atgtttcaag aaacaaggca ttacacggtg gcaacttcca gggcactcca | 1200 |
| attggtgtct ctatgacaa tgctagatta gcccttgcat caatagggaa attgatgttt | 1260 |
| gcccaattct ccgagcttgt caacgattac acaacaacg gattgccatc taatctgaca | 1320 |
| gcaggaagga atcctagctt ggactatggt ttcaagggat ctgagattgc catggcttca | 1380 |
| tactgttcag aacttcaatt cttggcaaat ccagtgacta ccacgtaca aagcgccgag | 1440 |

| | |
|---|---|
| caacacaacc aagatgtgaa ctccttgggc ttaatctcag ctagaaaaac agctgaagcc | 1500 |
| gtggacatct taaagctaat gtcatccaca tatctagttg cactttgcca agcaatagac | 1560 |
| ttgaggcatt tggaagaaaa tctgaggaat gcagtcaaga acacggtgag ccaagtcgca | 1620 |
| aagagaactt taacaatggg taccaatgga gaacttcatc catcaagatt ctgtgaaaag | 1680 |
| gacttgcttc gagtcgtgga cagggaatac gtcttcgcct atgctgacga cgcctgcagc | 1740 |
| gctaactacc cactgatgca gaaactaagg caagtcctcg tcgaccacgc cttgcaaaat | 1800 |
| ggcgaaaatg agaagaacgc aaacagctca atcttccaaa agatactagc ttttgaagac | 1860 |
| gagctaaagg ccgtgttgcc aaaagaagtc gagagtgcaa gagccgcgct ggaaagtggg | 1920 |
| aaccctgcaa ttgccaacag gataaaagaa tgcagatctt atccacttta caggtttgtt | 1980 |
| agaggagaac ttggagctga attattgacg ggagaaaaag tcaggtcacc aggtgaagaa | 2040 |
| tgtgacaaag tgttcacagc aatgtgcaat ggacaaatta ttgattcatt gttagaatgt | 2100 |
| ctcaaggaat ggaatggtgc acctcttcca atctgttag | 2139 |

<210> SEQ ID NO 55
<211> LENGTH: 1170
<212> TYPE: DNA
<213> ORGANISM: Nicotiana

<400> SEQUENCE: 55

| | |
|---|---|
| atggtgacgg tcgaggagtt tcgtagggca caacgtgccg agggtccggc cacggtcatg | 60 |
| gccatcggaa cagccacacc ttccaactgt gttgatcaaa gcacttaccc cgattactat | 120 |
| tttcgtatca ctaatagcga gcataagact gagcttaagg agaaatttaa gcgcatgtgt | 180 |
| gaaaaatcaa tgattaagaa aaggtacatg cacttaacag aggaaatctt gaaagagaat | 240 |
| cctaatattt gtgcatacat ggcacccttcc cttgatgcta acaagacat agtggtggtt | 300 |
| gaagtgccaa aacttggcaa agaggcagcc caaaaggcca tcaaagaatg gggccagccc | 360 |
| aagtccaaaa ttagtcattt ggtcttttgt acaactagtg gtgtagacat gcccgggtgt | 420 |
| gactaccaac tcactaagct actcgggctc cgtccttcgg tcaagcggtt catgatgtac | 480 |
| caacaaggtt gctttgccgg tgggacggta ctccggatgg ctaaggactt ggccgaaaac | 540 |
| aacaagggcg ctcgagtcct tgttgtttgc tcagagatca ccgctgtcac gttccgtggg | 600 |
| cccaatgaca cccacttgga tagtttggtt gggcaagccc ttttggtga tggggcagcc | 660 |
| gcggtcattg taggttctga tccaattcca gatgtcgaga ggccttttgtt cgagcttgtt | 720 |
| tccgcagccc aaaccctact ccccgatagc gaaggcgcta tcgacggtca tctccgtgaa | 780 |
| gttgggctta cattccactt actcaaagat gttcctgggc ttatctcgaa aaacattgag | 840 |
| aaaagccttg tggaagcatt ccaaccttttg ggaattctg attggaactc ttttattttgg | 900 |
| attgctcacc ctggtgggcc tgccattttg gaccaagttg aactaaaatt gggcctaaag | 960 |
| caagagaaac ttaaggctac aagaaatgta ttaagtaact atggcaatat gtcaagtgct | 1020 |
| tgtgtgttgt ttattttgga tgaaatgagg aaagcctctg caaagaagg tttaggaact | 1080 |
| actggtgaag gcttgaatg gggtgtgctt tttggatttg ggcctgggct tacagttgag | 1140 |
| actgttgtcc ttcacagtgt tgctacttag | 1170 |

<210> SEQ ID NO 56
<211> LENGTH: 1110
<212> TYPE: DNA
<213> ORGANISM: Nicotiana

<400> SEQUENCE: 56

```
atggcacctt cgacattgac agctctagca gaggaaaaga cacttcaaac aagtttcata    60
agagatgaag atgagcgacc aaaagtggcg tacaaccaat tcagcgatga gattccgatc   120
atatcgttga agggtattga tgatgagggt ggaattaatg aagaagagg tgaaatatgt   180 gaaaagattg tcaaggcatg tgaagattgg ggcgttttcc aggtagttga tcatggtgtt   240
gatgctcaac ttatctcaca aatgacaact ctcgctaaac aattcttcgc tttgcctgct   300
gaggaaaagc tacggtttga catgtcgggt ggcaagaaag tggcttcat tgtctctagc   360 catctacagg gtgaagtggt ccaagattgg cgtgaaatag tgacctactt ctcatacca   420 attcgggcta gagactactc tagatggcca gacaaaccag agggatggat agatgtgact   480
caaaagtaca gtgaaaagtt aatggagttg gcttgcaaat tattggaagt actatcagag   540
gctatgggct tagagaagga ggccttaacc aaggcatgtg tggatatgga ccaaaaagtg   600
gttgtcaatt tttacccaaa gtgtccacag cctgacctta cccttgggct gaaacgacac   660
actgatccag gaaccatcac cctcttgtta caagaccaag ttggtgggct tcaagccact   720
aaagataatg gcaaaacttg gattactgtt cagcccgttg ttggcgcttt tgttgtcaat   780
cttggtgacc atggtcattt tttgagcaat ggaaggttta agaacgctga tcatcaagca   840
gtggtgaact cgaatagcag cagattatcg atagctacgt ttcagaatcc agcaccagag   900
gcaatagtgt atcctttgaa aattagggaa ggagagaagg cagtgatgga cgagcccgta   960
gcatttgcag aaatgtatag gaggaaaatg agtaaggacc ttgagcttgc taggctcaag  1020
aaactagcca aggagcagca atacaagct gaagaagctg ctgagaaggc caagtcggaa  1080
accaagccta ttgatgaaat tcttgcttaa                                   1110
```

<210> SEQ ID NO 57
<211> LENGTH: 438
<212> TYPE: DNA
<213> ORGANISM: Nicotiana

<400> SEQUENCE: 57

```
atgtttggac cacaaagtgg aaaagatgga tggactgatt tgacttttat gtacgacatg    60
attcgaatta gagataaatc tctgtgttcc agttttctgc aaatattctc aagtgagggg   120
tgcaaaatgc tggaaatgac ttgtgaagag catgacaaat tggctgctcg aagtcaattt   180
ctgactcaca caattggcag gatcttatcc gaaatggagg ttgaacccac ccccatagac   240
acgaagggat ttcagaaact tgttcaagtg aaggagagct cagttagaga tagttttgat   300
ctattcagcg ggctattcat acacaatagg tttgccaggc aacagatgaa aaatttagaa   360
gtagcagtgg agaaaactaa acagaagctt gaagagaggt cgaaggagct gcaggatcct   420
atcatatcta agttctag                                                  438
```

<210> SEQ ID NO 58
<211> LENGTH: 1131
<212> TYPE: DNA
<213> ORGANISM: Nicotiana

<400> SEQUENCE: 58

```
atgttgtctt tcacccctct tcaatccaag ccaacaccac ccaccccac ctcaaacccc    60 acccgttggt cttggtctca tctcacccac caccacccca ctcccgccg ccacttctct   120 gcctcttcac cctccaaagt cagttaccgc cgccttagca ttaatgccat tgatgcagca   180
cagccatatg attatgaagc attagtttca aatcaatatg ctcagtcaac aagactcaag   240
```

-continued

```
attgctatag tgggttttgg caacttcggt cagtttcttg ctaaagcctt tgttcgtcaa      300
ggtcatgttg ttttttgctca ttcaagaact gattactcac acattgcaaa ttctttaggt    360
gttttgtttt ttcaagatcc acatgacctt tgtgagcaac atcctgatgt tattctactt    420
tgtacttcaa ttatatctac tgaacctgtc cttagatcac tccctattca aaggctaaaa    480
agaaacacat tatttgttga tgttttgtct gttaaagagt ttccaaagaa catttctctt    540
caagttttgc cttcccattt tgatattttg tgtactcatc ctatgtttgg acctgaaagt    600
ggtaaggata gttggaaaga tttggccttt gtgtttgata aagttagaat tggtgaaggg    660
gaatcgagaa aaggaagggt tgataggttt cttgatatat ttgagaaaga agggtgtagg    720
atggtgcaga tgacgtgtgc ggagcatgat aggtatgctg caggttcgca gtttattaca    780
catacaatgg ggagagtatt ggagaagttg gatttggaga caactcctat taatacgaaa    840
gggtacgaga ctttgttgaa tttggttgag aatacttcta gtgatagctt tgacttgtac    900
tatgggttgt ttatgtacaa taagaatgcg atggagcagt tggaaagact tgatttggct    960
ttcgaggctt tgaagaagga gttatttggg catttgcatg aagtcttgag gaagcaattg   1020
ttcgggaagg cggaggaagc gggacagaga cgtatcttaa ccaagttgcc caagaatggg   1080
tatgcactac cagctccttc atcggaggct gttaaatctg agaacaattg a            1131
```

<210> SEQ ID NO 59
<211> LENGTH: 2623
<212> TYPE: DNA
<213> ORGANISM: Artificial Sequence
<220> FEATURE:
<223> OTHER INFORMATION: comprises plant native sequences only

<400> SEQUENCE: 59

```
cccgggttag tattcaaacc gaataaatca aagttaccaa accgaataaa tcgaaaccga      60
aaggagaaac cgcaccatac cgaatttaat taggtacgat attgatattg tattttaaaa    120
aatcgaatac caaaaatacc gaattaaaat atctaaatat cgtacagtac cgaccgataa    180
atactctata agcatcatca tgtcaccatt cctgcttgga aatagatgta ataatgtaat    240
tcaaggtgaa gatcattgaa aatgagatat ttggactctt agataattgt gcaactgata    300 ttttttattta cttttttttct ttcatccaat aattgcgtta cattaaaaat gagatatttg    360
gattaatatt cttctccttg accacaaagc aaggaaagcc taaggaccga tagtaaagtt    420
gtattcgtgt ggttgcgtgt tagttttgag cggcaaaata aattatgtta aggtaaatta    480 ttttttggaac aataataaaa ttatttctgt ataatatata aatcatatat ttgaaccgta    540
gaattatcag ttaatacttg tatatgagga ggctaactac gttagagcgc taacgagaat    600
acttcatata ccgtattttt tacgataata ataatgtaat gtgaaattgc tatccaaaag    660
gcacctaatt ttgtccaccg ttcaaaggaa aggacaagga agtagtagcg tgtaggtttg    720
gtgctgtaca aaataagcaa gacacgtgtt gccttattat aggataatcc ataaggcaat    780
ttcgtcttaa gtcggccatt gcacctttaa aaggagcctc tttgttccca aaatcttcat    840
cctttgattt ctctattctc aatatctcct caatttttct ctagtcttca aacacttctc    900
aaggtacatt aacttcttct ttcttttttgt tcctcttatt ttatgctact tttatttaat    960
ttcgatctat attttttagga tctaaatact catttttgat ttgtttaatc gctctgtata   1020
tatgcaccaa gttgaaattt ttgtaagttt attttgttcg gtctatattt taagatctga   1080
aatacccttt actgagaaaa aaaaaactca accttgattt tgttgtacct ggttgaattt   1140
gttattgttg tgtatacagt taaaaaactc aagtcttgat tttattgttt ccctttttgta   1200
```

```
gtttgtatat acatagagct gaattggtgt tctaattttg gttgatttt atgtatacag    1260 tataaaatcg atcttagttt tgttcattga tttgtatttg cacaaagttg gaattttgcg    1320
tttgttattt tgatgattga aacctttct gtatatacag ctcgagatgg agggttcgtc    1380
caaagggctg cgaaaggtg cttggactac tgaagaagat agtctcttga gacagtgcat    1440
taataagtat ggagaaggca atggccacca agttcctgta agagctgggc taaaccggtg    1500
caggaaaagt tgtagattaa gatggttgaa ctatttgaag ccaagtatca agagaggaaa    1560
acttagctct gatgaagtcg atcttcttct tcgccttcat aggcttctag gaataggtg    1620 gtctttaatt gctggaagat tacctggtcg gaccgcaaat gacgtcaaga attactggaa    1680
cactcatctg agtaagaaac atgaaccgtg ttgtaagata aagatgaaaa agagagacat    1740
tacgcccatt cctacaacac cggcactaaa aaacaatgtt tataagcctc gacctcgatc    1800
cttcacagtt aacaacgact gcaaccatct caatgcccca ccaaaagttg acgttaatcc    1860
tccatgcctt ggacttaaca tcaataatgt tgtgacaat agtatcatat acaacaaaga    1920
taagaagaaa gaccaactag tgaataattt gattgatgga gataatatgt ggttagagaa    1980
attcctagag gaaagccaag aggtagatat tttggttcct gaagcgacga caacagaaaa    2040
gggggacacc ttggcttttg acgttgatca actttggagt cttttcgatg gagagactgt    2100
gaaatttgat tagtctagaa ataacagagg gcgcgcgagc ggtggctact gatcgcctat    2160
gagttctgtg attctacttg taatttcaga agtgttttca gtgtcttgtt ttctggaagt    2220
ccgtctggtt tttagtaact tttagctcaa aaatgtgtct gtacgatggt atttgtatgt    2280
ttgtgggtct tttacatata cgcttgtaat cgatcaatgt agaatgctgt gtgccttttc    2340
cgtcaacagc ttatttagtg tttactctgt atacgtatat ctaatatata gtactgattc    2400
tttcatctgg tgatttgttt tcctaaagag attattatca tagctttaat tgaatgatac    2460
aaagaggtgt tgcctggctt caccagagca gaaattttca ttgatatagg gtacaaatgt    2520
cattcacata atgttaagag ataagttttt caatgtcctc aagagcccac caagagtttc    2580
ttccgggaat tgcttaaatt atcttaaatt taaattgtaa aac    2623

<210> SEQ ID NO 60
<211> LENGTH: 2539
<212> TYPE: DNA
<213> ORGANISM: Artificial Sequence
<220> FEATURE:
<223> OTHER INFORMATION: plant native sequences only

<400> SEQUENCE: 60
cccgggttag tattcaaacc gaataaatca agttaccaa accgaataaa tcgaaaccga      60
aaggagaaac cgcaccatac cgaatttaat taggtacgat attgatattg tattttaaaa     120
aatcgaatac caaaaatacc gaattaaaat atctaaatat cgtacagtac cgaccgataa     180
atactctata agcatcatca tgtcaccatt cctgcttgga aatagatgta ataatgtaat     240
tcaaggtgaa gatcattgaa aatgagatat ttggactctt agataattgt gcaactgata     300 ttttattta ctttttttct ttcatccaat aattgcgtta cattaaaaat gagatatttg     360
gattaatatt cttctccttg accacaaagc aaggaaagcc taaggaccga tagtaaagtt     420
gtattcgtgt ggttgcgtgt tagttttgag cggcaaaata aattatgtta aggtaaatta     480
tttttggaac aataataaaa ttattctgt ataatatata aatcatatat ttgaaccgta     540
gaattatcag ttaatacttg tatatgagga ggctaactac gttagagcgc taacgagaat     600
```

| | | | | | |
|---|---|---|---|---|---|
| acttcatata | ccgtattttt | tacgataata | ataatgtaat | gtgaaattgc | tatccaaaag | 660
| gcacctaatt | ttgtccaccg | ttcaaaggaa | aggacaagga | agtagtagcg | tgtaggtttg | 720
| gtgctgtaca | aaataagcaa | gacacgtgtt | gccttattat | aggataatcc | ataaggcaat | 780
| ttcgtcttaa | gtcggccatt | gcacctttaa | aaggagcctc | tttgttccca | aaatcttcat | 840
| cctttgattt | ctctattctc | aatatctcct | caattttttct | ctagtcttca | aacacttctc | 900
| aaggtacatt | aacttcttct | ttcttttttgt | tcctcttatt | ttatgctact | tttatttaat | 960
| ttcgatctat | attttttagga | tctaaatact | cattttttgat | ttgtttaatc | gctctgtata | 1020
| tatgcaccaa | gttgaaattt | ttgtaagttt | attttgttcg | gtctatattt | taagatctga | 1080
| aatacccttt | actgagaaaa | aaaaaactca | accttgattt | tgttgtaccct | ggttgaattt | 1140
| gttattgttg | tgtatacagt | taaaaaactc | aagtcttgat | tttattgttt | ccctttttgta | 1200
| gtttgtatat | acatagagct | gaattggtgt | tctaattttg | gttgattttt | atgtatacag | 1260
| tataaaatcg | atcttagttt | tgttcattga | tttgtatttg | cacaaagttg | gaattttgcg | 1320
| tttgttattt | tgatgattga | aacctttttct | gtatatacag | ctcgagatga | atatttgtac | 1380
| taataagtcg | tcgtcaggag | tgaagaaagg | tgcatggact | gaagaagaag | atgttctatt | 1440
| gaaaaaatgc | atcgagaaat | atggagaagg | aaagtggcat | caagttcctc | ttagagctgg | 1500
| tttgaataga | tgcagaaaga | gctgcagatt | aaggtggcta | aattatctaa | ggccacatat | 1560
| aaagagagga | gacttctctt | tgatgaagt | agatctcatt | tgaggcttc | ataagctgtt | 1620
| aggcaacaga | tggtcactta | ttgctggtag | acttcctgga | aggacggcaa | acgatgtcaa | 1680
| aaactactgg | aacagccatc | ttcgcaagaa | gttaattgct | cctcatgatc | aaaaggagag | 1740
| caagcaaaaa | gcaagaaga | tcaccatatt | cagacctcgg | cctcgaacct | tctcaaagac | 1800
| aaatacttgt | gttaaaagta | acacaaatac | tgtagataag | gatattgaag | gcagcagcga | 1860
| aataattaga | ttcaacgata | atttgaagcc | aacaactgaa | gaattgacgg | atgatggaat | 1920
| tcaatggtgg | gccgatttac | tagctaacaa | ttacaacaat | aatgggattg | aggaagctga | 1980
| taattcatca | ccaactttgt | tgcatgagga | aatgccactt | ctcagttgat | ctagaaataa | 2040
| cagagggcgc | gcgagcggtg | gctactgatc | gcctatgagt | tctgtgattc | tacttgtaat | 2100
| ttcagaagtg | ttttcagtgt | cttgttttct | ggaagtccgt | ctggttttta | gtaacttta | 2160
| gctcaaaaat | gtgtctgtac | gatggtattt | gtatgtttgt | gggtctttta | catatacgct | 2220
| tgtaatcgat | caatgtagaa | tgctgtgtgc | cttttccgtc | aacagcttat | ttagtgttta | 2280
| ctctgtatac | gtatatctaa | tatatagtac | tgattctttc | atctggtgat | ttgttttcct | 2340
| aaagagatta | ttatcatagc | tttaattgaa | tgatacaaag | aggtgttgcc | tggcttcacc | 2400
| agagcagaaa | ttttcattga | tatagggtac | aaatgtcatt | cacataatgt | taagagataa | 2460
| gtttttcaat | gtcctcaaga | gcccaccaag | agtttcttcc | gggaattgct | taaattatct | 2520
| taaatttaaa | ttgtaaaac | | | | | 2539

<210> SEQ ID NO 61
<211> LENGTH: 3701
<212> TYPE: DNA
<213> ORGANISM: Artificial Sequence
<220> FEATURE:
<223> OTHER INFORMATION: comprises plant native sequences only

<400> SEQUENCE: 61

| | | | | | |
|---|---|---|---|---|---|
| cccgggaaac | taataagaac | aagcaatata | agagaattcg | taaaaaactt | tctagttctt | 60
| gaacatctac | ccatgtgaat | tctcttttat | ttttgtacac | tataattaaa | ttaacatggc | 120

```
taaaccaatt atgccaactg aataaattat caatattgat aaacttcagg tttacaccat    180
gacgtgtgca attatgaata aactccaagt ttattatgat atgagttttt atatcaataa    240
acttctactt tactgtgaca ttcttttgtt tgtgtagtac aaattggaga ataaagcgtg    300
taacttttca catacatatt accccgctat aagttgtagt aatagaagat attaaatctt    360
tcctttcttt atagtctcaa tataaccaat cgcttttgcg aatactttag aaactaaata    420
agtttctttg agacttacta caacataatg ccttattgat aatcaatttt gttccttcaa    480
aatagtaata attggctctt ccagagctct caattaattt tgtactacca catattcatc    540
aacatccata tggtgaatat ctcttttaaa gagaaagtta taccattatg gttatggtca    600
aaattatatg caatatttgt ttcttgcatt accgttgcct tttagtaatc acattgccaa    660
aatattttgg cctacaataa gtacgtgacc aatgaccatt tatgccataa tgacattatt    720
ttcttatttt ctctcaaacc tccttcaaga gatgagtgtg gtatatacta ctagcacgct    780
catattcttc caaaaatgaa tatgtattca taaatcacat attgtcacat tcacatcatg    840
aatggaccat aatcatctat atgtgcttta caaaatctca tgtcaaatcg atgataaata    900
ttactttcac atagtgaatg attattttga gaatacttat tattctcatt accacaatga    960
aaatgattat aatttcgtct attgtcacat ccacatccat tgatacattc atggtaataa   1020
ttttatcttc tttcagacgt atcatatatt gctatcacat tctcgtaagg gaatgagaat   1080
aaagcaaatt caatgggacg agtttccact ttttgtgctc acaatcatac atgaatttga   1140
tcatggcaat acatagaaat tttatcactt tggtggtta aatttctta caaactctat    1200 tagagttata ataaaaattt attgtctttg cttgtattta aaatcaaatt ataaaatttt   1260
aaaaattcaa aagagaaaaa taagtaaaa tacttacttt aaatccagaa tttaatcacg    1320
aaggaagttc atgaataat tgacgatcat tatgctcaat cccaaagctt ctactcaatt    1380
ggttacagtc tcgtgccgat aacgtgttat aaaacaataa aagaagaaca atattgcaga   1440
gaaagagaga gagggaattc ttattgaatt ttaggatgaa ttacaatgga ataggacccc   1500
tctatttata gggaaagagt gacttagcca ccaagtaaaa tccctaaaat ctctctaaaa   1560
tatagacatt caccttaaat aaaactctat ttataacaaa aacaaaattg ttctagacga   1620
gaatcatttt cacttttaa tgttttctt ctactccttt agttttcct taaaccaaaa      1680 taaaaaaaa gtctatattt ttctatcctt tttcttctct agttttaata cattccataa    1740
aatttgtggt gaaattgtac tttctccttt tttttcctct ttagtttcat agaaattaaa   1800
caataaaacg aaaacatcaa aatatatcaa caaatagtaa atttcattac atttattttt    1860
ttgctcaaag tgctcttttg ttgaatactc aaagtatata gtatattaca gttctaatca   1920
ggaattattc actgaaatat tgactgattt taggttcgtg tgatcgatta aatacctctt   1980
gaaccactac aaatttaacg aattaataac ttttacctaa cattttgtta cccatgtatt   2040
aatttgaatt tatactatta cttcctattt atgagtaata taacataatt tctgtgtaaa   2100
ggacagaaaa tacagaattt gattaattca aaattaatta tacttcaaaa aatatcacaa   2160
ggatatcaaa atttatcaaa taaaggagca acgtcatttt cggctctccc acacaattca   2220
aaataattca aaacagaacc ggctagacct aacctaacca aaccatggtt aatacaaatc   2280
taaatcaccg aaaaacaatc ttaaccatag ttaataaccc gtattaatta acccgatatc   2340
catttcgcct tgcccttatt cattctccta taaaacagag gcccttcagt atagcgaaga   2400
ctcacaattc gaatttcgaa aactcatctc tttctgtttt aacggcgtct tgataaacgc   2460
```

```
cgctccttct ctcctcctct ttgaaatttg aattttagg gtttcgtgaa actcgagaac    2520
aatgaatatt tgtactaata agtcgtcgtc aggagtgaag aaaggtgcat ggactgaaga    2580
agaagatgtt ctattgaaaa aatgcatcga gaaatatgga gaaggaaagt ggcatcaagt    2640
tcctcttaga gctggtttga atagatgcag aaagagctgc agattaaggt ggctaaatta    2700
tctaaggcca catataaaga gaggagactt ctcttttgat gaagtagatc tcattttgag    2760
gcttcataag ctgttaggca acagatggtc acttattgct ggtagacttc ctggaaggac    2820
ggcaaacgat gtcaaaaact actggaacag ccatcttcgc aagaagttaa ttgctcctca    2880
tgatcaaaag gagagcaagc aaaaagcaaa gaagatcacc atattcagac tcggcctcg     2940 aaccttctca aagacaaata cttgtgttaa agtaacaca aatactgtag ataaggatat      3000
tgaaggcagc agcgaaataa ttagattcaa cgataatttg aagccaacaa ctgaagaatt    3060
gacggatgat ggaattcaat ggtgggccga tttactagct aacaattaca acaataatgg    3120
gattgaggaa gctgataatt catcaccaac tttgttgcat gaggaaatgc cacttctcag    3180
ttgatctaga ataacagag ggcgcgcgag cggtggctac tgatcgccta tgagttctgt      3240
gattctactt gtaatttcag aagtgttttc agtgtcttgt tttctggaag tccgtctggt    3300
ttttagtaac ttttagctca aaaatgtgtc tgtacgatgg tatttgtatg tttgtgggtc    3360
ttttacatat acgcttgtaa tcgatcaatg tagaatgctg tgtgcctttt ccgtcaacag    3420
cttatttagt gtttactctg tatacgtata tctaatatat agtactgatt ctttcatctg    3480
gtgatttgtt ttcctaaaga gattattatc atagctttaa ttgaatgata caaagaggtg    3540
ttgcctggct tcaccagagc agaaattttc attgatatag ggtacaaatg tcattcacat    3600
aatgttaaga gataagtttt tcaatgtcct caagagccca ccaagagttt cttccgggaa    3660
ttgcttaaat tatcttaaat ttaaattgta cccgtttaaa c                        3701

<210> SEQ ID NO 62
<211> LENGTH: 6230
<212> TYPE: DNA
<213> ORGANISM: Artificial Sequence
<220> FEATURE:
<223> OTHER INFORMATION: comprises plant native sequences only

<400> SEQUENCE: 62 cccggttag tattcaaacc gaataaatca aagttaccaa accgaataaa tcgaaaccga      60
aaggagaaac cgcaccatac cgaatttaat taggtacgat attgatattg tatttaaaa    120 aatcgaatac caaaatacc gaattaaaat atctaaatat cgtacagtac cgaccgataa    180
atactctata agcatcatca tgtcaccatt cctgcttgga aatagatgta ataatgtaat    240
tcaaggtgaa gatcattgaa aatgagatat ttggactctt agataattgt gcaactgata    300
tttttattta cttttttct ttcatccaat aattgcgtta cattaaaaat gagatatttg    360
gattaatatt cttctccttg accacaaagc aaggaaagcc taaggaccga tagtaaagtt    420
gtattcgtgt ggttgcgtgt tagttttgag cggcaaaata aattatgtta aggtaaatta    480
tttttggaac aataataaaa ttatttctgt ataatatata aatcatatat ttgaaccgta    540
gaattatcag ttaatacttg tatatgagga ggctaactac gttagagcgc taacgagaat    600
acttcatata ccgtattttt tacgataata ataatgtaat gtgaaattgc tatccaaaag    660
gcacctaatt ttgtccaccg ttcaaaggaa aggacaagga agtagtagcg tgtaggtttg    720
gtgctgtaca aaataagcaa gacacgtgtt gccttattat aggataatcc ataaggcaat    780
ttcgtcttaa gtcggccatt gcaccttta aaggagcctc tttgttccca aaatcttcat     840
```

```
cctttgattt ctctattctc aatatctcct caattttct ctagtcttca aacacttctc       900
aaggtacatt aacttcttct ttcttttgt tcctcttatt ttatgctact tttatttaat       960
ttcgatctat attttagga tctaaatact cattttgat tgtttaatc gctctgtata        1020 tatgcaccaa gttgaaattt ttgtaagttt attttgttcg gtctatattt taagatctga     1080
aatacccttt actgagaaaa aaaaaactca accttgattt tgttgtacct ggttgaattt     1140
gttattgttg tgtatacagt taaaaaactc aagtcttgat tttattgttt ccctttgta     1200 gtttgtatat acatagagct gaattggtgt tctaattttg gttgattttt atgtatacag     1260
tataaaatcg atcttagttt tgttcattga tttgtatttg cacaaagttg gaattttgcg     1320
tttgttattt tgatgattga aaccttttct gtatatacag ctcgagatga atatttgtac     1380
taataagtcg tcgtcaggag tgaagaaagg tgcatggact gaagaagaag atgttctatt     1440 gaaaaatgc atcgagaaat atggagaagg aaagtggcat caagttcctc ttagagctgg     1500
tttgaataga tgcagaaaga gctgcagatt aaggtggcta aattatctaa ggccacatat     1560
aaagagagga gacttctctt tgatgaagt agatctcatt ttgaggcttc ataagctgtt     1620
aggcaacaga tggtcactta ttgctggtag acttcctgga aggacggcaa acgatgtcaa     1680
aaactactgg aacagccatc ttcgcaagaa gttaattgct cctcatgatc aaaaggagag     1740
caagcaaaaa gcaaagaaga tcaccatatt cagacctcgg cctcgaacct tctcaaagac     1800
aaatacttgt gttaaaagta acacaaatac tgtagataag gatattgaag cagcagcga     1860 aataattaga ttcaacgata atttgaagcc aacaactgaa gaattgacgg atgatggaat     1920
tcaatggtgg gccgatttac tagctaacaa ttacaacaat aatgggattg aggaagctga     1980
taattcatca ccaactttgt tgcatgagga aatgccactt ctcagttgat ctagaaataa     2040
cagagggcgc gcgagcggtg gctactgatc gcctatgagt tctgtgattc tacttgtaat     2100
ttcagaagtg ttttcagtgt cttgttttct ggaagtccgt ctggttttta gtaacttta     2160 gctcaaaaat gtgtctgtac gatggtattt gtatgtttgt gggtctttta catatacgct     2220
tgtaatcgat caatgtagaa tgctgtgtgc cttttccgtc aacagcttat ttagtgttta     2280
ctctgtatac gtatatctaa tatatagtac tgattctttc atctggtgat tgttttcct     2340 aaagagatta ttatcatagc tttaattgaa tgatacaaag aggtgttgcc tggcttcacc     2400
agagcagaaa ttttcattga tagggtac aaatgtcatt cacataatgt taagagataa      2460 gttttcaat gtcctcaaga gcccaccaag agtttcttcc gggaattgct taaattatct     2520
taaatttaaa ttgtaaaact aataagaaca agcaatataa gagaattcgt aaaaaacttt     2580
ctagttcttg aacatctacc catgtgaatt ctcttttatt tttgtacact ataattaaat     2640
taacatggct aaaccaatta tgccaactga ataaattatc aatattgata aacttcaggt     2700
ttacaccatg acgtgtgcaa ttatgaataa actccaagtt tattatgata tgagttttta     2760
tatcaataaa cttctacttt actgtgacat tcttttgttt gtgtagtaca aattggagaa     2820
taaagcgtgt aacttttcac atacatatta ccccgctata agttgtagta atagaagata     2880
ttaaatcttt cctttcttta tagtctcaat ataaccaatc gcttttgcga atactttaga     2940 aactaaaataa gttctttga gacttactac aacataatgc cttattgata tcaatttg     3000 ttccttcaaa atagtaataa ttggctcttc cagagctctc aattaatttt gtactaccac     3060
atattcatca acatccatat ggtgaatatc tcttttaaag agaaagttat accattatgg     3120
ttatggtcaa aattatatgc aatatttgtt tcttgcatta ccgttgcctt ttagtaatca     3180
```

```
cattgccaaa atattttggc ctacaataag tacgtgacca atgaccattt atgccataat    3240
gacattattt tcttattttc tctcaaacct ccttcaagag atgagtgtgg tatatactac    3300
tagcacgctc atattcttcc aaaaatgaat atgtattcat aaatcacata ttgtcacatt    3360
cacatcatga atggaccata atcatctata tgtgctttac aaaatctcat gtcaaatcga    3420
tgataaatat tactttcaca tagtgaatga ttattttgag aatacttatt attctcatta    3480
ccacaatgaa aatgattata atttcgtcta ttgtcacatc cacatccatt gatacattca    3540
tggtaataat tttatcttct ttcagacgta tcatatattg ctatcacatt ctcgtaaggg    3600
aatgagaata aagcaaattc aatgggacga gtttccactt tttgtgctca caatcataca    3660
tgaatttgat catggcaata catagaaatt ttatcacttt tggtggttat aatttcttac    3720
aaactctatt agagttataa taaaaattta ttgtctttgc ttgtatttaa aatcaaatta    3780 taaaattttta aaaattcaaa agagaaaaat aaagtaaaat acttacttta aatccagaat    3840
ttaatcacga aggaagttca tggaataatt gacgatcatt atgctcaatc ccaaagcttc    3900
tactcaattg gttacagtct cgtgccgata acgtgttata aaacaataaa agaagaacaa    3960
tattgcagag aaagagagag agggaattct tattgaattt taggatgaat tacaatggaa    4020
taggacccct ctatttatag ggaaagagtg acttagccac caagtaaaat ccctaaaatc    4080
tctctaaaat atagacattc acctttaaata aaactctatt tataacaaaa acaaaattgt    4140
tctagacgag aatcattttc acttttttaat gttttttcttc tactcctttta gttttttcctt    4200 aaaccaaaat aaaaaaaaag tctatatttt tctatccttt tcttctcta gttttaatac    4260 attccataaa atttgtggtg aaattgtact ttctcctttt ttttcctctt tagtttcata    4320
gaaattaaac aataaaacga aacatcaaa atatatcaac aaatagtaaa tttcattaca    4380
tttatttttt tgctcaaagt gctctttttgt tgaatactca aagtatatag tatattacag    4440
ttctaatcag gaattattca ctgaaatatt gactgatttt aggttcgtgt gatcgattaa    4500
atacctcttg aaccactaca aatttaacga attaataact tttacctaac attttgttac    4560
ccatgtatta atttgaattt atactattac ttcctatttta tgagtaatat aacataattt    4620
ctgtgtaaag gacagaaaat acagaatttg attaattcaa aattaattat acttcaaaaa    4680
atatcacaag gatatcaaaa tttatcaaat aaaggagcaa cgtcattttc ggctctccca    4740
cacaattcaa ataattcaa aacagaaccg gctagaccta acctaaccaa accatggtta    4800
atacaaatct aaatcaccga aaaacaatct taaccatagt taataacccg tattaattaa    4860
cccgatatcc atttcgcctt gcccttattc attctcctat aaaacagagg cccttcagta    4920
tagcgaagac tcacaattcg aatttcgaaa actcatctct ttctgttta acggcgtctt    4980 gataaacgcc gctccttctc tcctcctctt tgaaatttga attttttaggg tttcgtgaaa    5040 ctcgagaaca atgaatattt gtactaataa gtcgtcgtca ggagtgaaga aaggtgcatg    5100
gactgaagaa gaagatgttc tattgaaaaa atgcatcgag aaatatggag aaggaaagtg    5160
gcatcaagtt cctcttagag ctggtttgaa tagatgcaga aagagctgca gattaaggtg    5220
gctaaattat ctaaggccac atataaagag aggagacttc tcttttgatg aagtagatct    5280 catttttgagg cttcataagc tgttaggcaa cagatggtca cttattgctg gtagacttcc    5340
tggaaggacg gcaaacgatg tcaaaaacta ctggaacagc catcttcgca agaagttaat    5400
tgctcctcat gatcaaaagg agagcaagca aaaagcaaag aagatcacca tattcagacc    5460
tcggcctcga accttctcaa agacaaatac ttgtgttaaa agtaacacaa atactgtaga    5520
taaggatatt gaaggcagca gcgaaataat tagattcaac gataatttga agccaacaac    5580
```

```
tgaagaattg acggatgatg gaattcaatg gtgggccgat ttactagcta acaattacaa    5640
caataatggg attgaggaag ctgataattc atcaccaact ttgttgcatg aggaaatgcc    5700
acttctcagt tgatctagaa ataacagagg gcgcgcgagc ggtggctact gatcgcctat    5760
gagttctgtg attctacttg taatttcaga agtgttttca gtgtcttgtt ttctggaagt    5820
ccgtctggtt tttagtaact tttagctcaa aaatgtgtct gtacgatggt atttgtatgt    5880
ttgtgggtct tttacatata cgcttgtaat cgatcaatgt agaatgctgt gtgccttttc    5940
cgtcaacagc ttatttagtg tttactctgt atacgtatat ctaatatata gtactgattc    6000
tttcatctgg tgatttgttt tcctaaagag attattatca tagctttaat tgaatgatac    6060
aaagaggtgt tgcctggctt caccagagca gaaattttca ttgatatagg gtacaaatgt    6120
cattcacata atgttaagag ataagttttt caatgtcctc aagagcccac caagagtttc    6180
ttccgggaat tgcttaaatt atcttaaatt taaattgtac ccgtttaaac               6230
```

<210> SEQ ID NO 63
<211> LENGTH: 7583
<212> TYPE: DNA
<213> ORGANISM: Artificial Sequence
<220> FEATURE:
<223> OTHER INFORMATION: comprises plant native sequences only

<400> SEQUENCE: 63

```
cccgggttag tattcaaacc gaataaatca aagttaccaa accgaataaa tcgaaaccga      60
aaggagaaac cgcaccatac cgaatttaat taggtacgat attgatattg tattttaaaa    120
aatcgaatac caaaaatacc gaattaaaat atctaaatat cgtacagtac cgaccgataa    180
atactctata agcatcatca tgtcaccatt cctgcttgga aatagatgta ataatgtaat    240
tcaaggtgaa gatcattgaa aatgagatat ttggactctt agataattgt gcaactgata    300
tttttattta cttttttttct ttcatccaat aattgcgtta cattaaaaat gagatatttg    360
gattaatatt cttctccttg accacaaagc aaggaaagcc taaggaccga tagtaaagtt    420
gtattcgtgt ggttgcgtgt tagttttgag cggcaaaata aattatgtta aggtaaatta    480
tttttggaac aataataaaa ttattctgtg ataatatata aatcatatat ttgaaccgta    540
gaattatcag ttaatacttg tatatgagga ggctaactac gttagagcgc taacgagaat    600
acttcatata ccgtattttt tacgataata ataatgtaat gtgaaattgc tatccaaaag    660
gcacctaatt ttgtccaccg ttcaaggaa aggacaagga agtagtagcg tgtaggtttg    720
gtgctgtaca aaataagcaa gacacgtgtt gccttattat aggataatcc ataaggcaat    780
ttcgtcttaa gtcggccatt gcacctttaa aaggagcctc tttgttccca aaatcttcat    840
cctttgattt ctctattctc aatatctcct caattttttct ctagtcttca aacacttctc    900
aaggtacatt aacttcttct ttcttttgt tcctcttatt ttatgctact tttatttaat    960
ttcgatctat attttttagga tctaaatact catttttgat ttgtttaatc gctctgtata   1020
tatgcaccaa gttgaaattt ttgtaagttt atttttgttcg gtctatattt taagatctga   1080 aataccccttt actgagaaaa aaaaaactca accttgattt tgttgtacct ggttgaattt   1140
gttattgttg tgtatacagt taaaaaactc aagtcttgat tttattgttt cccttttgta   1200
gtttgtatat acatagagct gaattggtgt tctaattttg gttgattttt atgtatacag   1260
tataaaatcg atcttagttt tgttcattga tttgtatttg cacaaagttg gaattttgcg   1320
tttgttattt tgatgattga aaccttttct gtatatacag ctcgagatga cggagatacc   1380
```

```
gcctaacagc cagatgaaaa ccatgttgca gaaggcagtg caatcggttc aatggacata    1440
tactcttttc tggcaattat gtccccaaca agggcgtta gtgtggagag atggatatta    1500
caatggggct ataaagacta gaaagacagt gcagccaatg gaagttagcg ctgaggaagc    1560
ttctcttcac agaagccaac agcttagaga actttacgaa tcactttccg ccggcgagtc    1620
aaatcagcca gcgagaaggc cgtcggcagc tttgtcaccg gaggacttga cggagtccga    1680
gtggttttat ctcatgtgtg tttctttctc ttttcctcct ggcatcggat tacctggcaa    1740
ggcttattcg aagaaacatc acatatggat catgggcgca aacgaggttg atagcaaagt    1800
cttctgtaga gctattcttg ccaagagcgc ccgcatacag acggtcgttg gtattcctct    1860
cttggatggt gtactggaac tgggaactac agaaagggtt caagaagaga ttggattcat    1920
aaaccatgta aagagctttt tcactgagca acaacaacct cagctaccaa agccagcctt    1980
atctgagcac tccacttcca atcccaccac cttttccgag ccacattttt actccggcaa    2040
tacttcgcca tctgctaatg ttgatattgc gcatcaagat ggcggagctg ccggcgaaga    2100
agatgaggag gaggaagaag aagaagatga tgatgaagcc gagttggact cggatagtat    2160
agcgattcaa agcgcggcta atcctattgc cgttgaggct agtgaactca tgcagcttga    2220
tgtgtccgag gctatacagc tcggctcgcc cgatgatgac tctgataata tggactctga    2280
ttttcatttg gttggcgctg gaaacacggc tcatgactac cagcgccaag ctgactcttt    2340
caaagccgag accgccatta gctggccgca cttccaagac cttcaacaat taccaggtgg    2400
ctctagttat gatgaattat cacaagaaga cacacactat tctcaaacag tgtcaaccat    2460
tctcgaacac cgaagctcca aattttcctc tacaacaatg gctgtatttt ctcatgactc    2520
ggcccaatct gccttcacat tgtgccctag caccaccgtc tgcagcccga atcccgccca    2580
ctgccgccac gacgactcac ttgtcgacgt tggcggcgcc tcccagtggc tgctcaaaag    2640
catactcttc actgtcccat ttcttcacac taaataccaa tctgaagctt ctccaaagtc    2700
acgtgacgtc gccactgttg attcctccag tactgcttct cgctttcgca aaggctgtag    2760
tataacgtcg caagaagagc caagtggaaa ccatgtactt gcagaacgac gtcgtagaga    2820
gaagctaaat gagcgtttta tcatattaag gtctcttgta ccttttgtaa cgaaaatgga    2880
caaagcctcc attttgggtg acaccataga gtatgtcaag cagttacgta agaaagttca    2940
ggatcttgaa gctcgtgctc gcgacacgga gcactccaga gatgcagata aaaaaggtgg    3000
cacagctaca gtgaaggtgt tgcaaggaag gggtaagagg agaatgaata cggtagatgg    3060
aagtgttggt ggagggcagg caacgataac ggcgtcccca ccgtcaacga cggaaaatga    3120
ggaggttgtg caagtacaag tatcaattat cgaaagcgat gcattggtgg agctccggtg    3180
tccgtacaaa gaggggttgc tgttaaatgt aatgcagatg ctaagggaac tcaaagtgga    3240
agttgtagcc attcaatcag ctcttaataa tggcgtcttc ttggctgagt taagagctaa    3300
ggtaaaagag aatatatgtg gaaggaaagc aagcattttg gaagtaaaaa ggtcaataca    3360
tcagataatc cctagagatt aatctagaaa taacagaggg cgcgcgagcg gtggctactg    3420
atcgcctatg agttctgtga ttctacttgt aatttcagaa gtgttttcag tgtcttgttt    3480
tctggaagtc cgtctggttt ttagtaactt ttagctcaaa aatgtgtctg tacgatggta    3540
tttgtatgtt tgtgggtctt ttacatatac gcttgtaatc gatcaatgta gaatgctgtg    3600
tgccttttcc gtcaacagct tatttagtgt ttactctgta tacgtatatc taatatatag    3660
tactgattct ttcatctggt gatttgtttt cctaaagaga ttattatcat agctttaatt    3720
gaatgataca aagaggtgtt gcctggcttc accagagcag aaattttcat tgatataggg    3780
```

```
tacaaatgtc attcacataa tgttaagaga taagttttc aatgtcctca agagcccacc    3840
aagagtttct tccgggaatt gcttaaatta tcttaaattt aaattgtaaa actaataaga   3900
acaagcaata taagagaatt cgtaaaaaac tttctagttc ttgaacatct acccatgtga   3960
attctctttt atttttgtac actataatta aattaacatg gctaaaccaa ttatgccaac   4020
tgaataaatt atcaatattg ataaacttca ggtttacacc atgacgtgtg caattatgaa   4080
taaactccaa gttattatg atatgagttt ttatatcaat aaacttctac tttactgtga    4140
cattcttttg tttgtgtagt acaaattgga gaataaagcg tgtaacttt cacatacata    4200
ttaccccgct ataagttgta gtaatagaag atattaaatc tttcctttct ttatagtctc   4260
aatataacca atcgcttttg cgaatacttt agaaactaaa taagtttctt tgagacttac   4320
tacaacataa tgccttattg ataatcaatt ttgttccttc aaaatagtaa taattggctc   4380
ttccagagct ctcaattaat tttgtactac cacatattca tcaacatcca tatggtgaat   4440
atctctttta aagagaaagt tataccatta tggttatggt caaaattata tgcaatattt   4500
gtttcttgca ttaccgttgc cttttagtaa tcacattgcc aaaatatttt ggcctacaat   4560
aagtacgtga ccaatgacca tttatgccat aatgacatta ttttcttatt ttctctcaaa   4620
cctccttcaa gagatgagtg tggtatatac tactagcacg ctcatattct tccaaaaatg   4680
aatatgtatt cataaatcac atattgtcac attcacatca tgaatggacc ataatcatct   4740
atatgtgctt tacaaaatct catgtcaaat cgatgataaa tattactttc acatagtgaa   4800
tgattatttt gagaatactt attattctca ttaccacaat gaaaatgatt ataatttcgt   4860
ctattgtcac atccacatcc attgatacat tcatggtaat aatttatct tctttcagac    4920
gtatcatata ttgctatcac attctcgtaa gggaatgaga ataaagcaaa ttcaatggga   4980
cgagtttcca cttttttgtgc tcacaatcat acatgaattt gatcatggca atacatgaa    5040
attttatcac ttttggtggt tataatttct tacaaactct attagagtta taataaaaat   5100
ttattgtctt tgcttgtatt taaaatcaaa ttataaaatt ttaaaaattc aaaagagaaa   5160
aataaagtaa aatacttact ttaaatccag aatttaatca cgaaggaagt tcatggaata   5220
attgacgatc attatgctca atcccaaagc ttctactcaa ttggttacag tctcgtgccg   5280
ataacgtgtt ataaaacaat aaaagaagaa caatattgca gagaaagaga gagagggaat   5340
tcttattgaa ttttaggatg aattacaatg gaataggacc cctctatta tagggaaaga    5400
gtgacttagc caccaagtaa aatccctaaa atctctctaa aatatagaca ttcaccttaa   5460
ataaaactct atttataaca aaaacaaaat tgttctagac gagaatcatt ttcacttttt   5520
aatgtttttc ttctactcct ttagtttttc cttaaaccaa aataaaaaaa agtctatat    5580
ttttctatcc ttttctttct ctagttttaa tacattccat aaaatttgtg gtgaaattgt   5640
actttctcct ttttttcct ctttagtttc atagaaatta aacaataaaa cgaaaacatc    5700
aaaatatatc aacaaatagt aaatttcatt acatttattt ttttgctcaa agtgctcttt   5760
tgttgaatac tcaaagtata tagtatatta cagttctaat caggaattat tcactgaaat   5820
attgactgat tttaggttcg tgtgatcgat taaatacctc ttgaaccact acaaatttaa   5880
cgaattaata acttttacct aacatttgt tacccatgta ttaatttgaa tttatactat    5940
tacttcctat ttatgagtaa tataacataa tttctgtgta aaggacagaa aatacagaat   6000
ttgattaatt caaaattaat tatacttcaa aaaatatcac aaggatatca aaatttatca   6060
aataaaggag caacgtcatt ttcggctctc ccacacaatt caaataatt caaaacagaa    6120
```

```
ccggctagac ctaacctaac caaaccatgg ttaatacaaa tctaaatcac cgaaaaacaa    6180
tcttaaccat agttaataac ccgtattaat taacccgata tccatttcgc cttgccctta    6240
ttcattctcc tataaaacag aggcccttca gtatagcgaa gactcacaat tcgaatttcg    6300
aaaactcatc tctttctgtt ttaacggcgt cttgataaac gccgctcctt ctctcctcct    6360
ctttgaaatt tgaattttta gggtttcgtg aaactcgaga acaatgaata tttgtactaa    6420
taagtcgtcg tcaggagtga agaaaggtgc atggactgaa gaagaagatg ttctattgaa    6480
aaaatgcatc gagaaatatg gagaaggaaa gtggcatcaa gttcctctta gagctggttt    6540
gaatagatgc agaaagagct gcagattaag gtggctaaat tatctaaggc cacatataaa    6600
gagaggagac ttctcttttg atgaagtaga tctcattttg aggcttcata agctgttagg    6660
caacagatgg tcacttattg ctggtagact tcctggaagg acggcaaacg atgtcaaaaa    6720
ctactggaac agccatcttc gcaagaagtt aattgctcct catgatcaaa aggagagcaa    6780
gcaaaaagca aagaagatca ccatattcag acctcggcct cgaaccttct caaagacaaa    6840
tacttgtgtt aaaagtaaca caaatactgt agataaggat attgaaggca gcagcgaaat    6900
aattagattc aacgataatt tgaagccaac aactgaagaa ttgacggatg atggaattca    6960
atggtgggcc gatttactag ctaacaatta caacaataat gggattgagg aagctgataa    7020
ttcatcacca actttgttgc atgaggaaat gccacttctc agttgatcta gaaataacag    7080
agggcgcgcg agcggtggct actgatcgcc tatgagttct gtgattctac ttgtaatttc    7140
agaagtgttt tcagtgtctt gttttctgga agtccgtctg gtttttagta acttttagct    7200
caaaaatgtg tctgtacgat ggtatttgta tgtttgtggg tcttttacat atacgcttgt    7260
aatcgatcaa tgtagaatgc tgtgtgcctt ttccgtcaac agcttattta gtgtttactc    7320
tgtatacgta tatctaatat atagtactga ttctttcatc tggtgatttg ttttcctaaa    7380
gagattatta tcatagcttt aattgaatga tacaaagagg tgttgcctgg cttcaccaga    7440
gcagaaattt tcattgatat agggtacaaa tgtcattcac ataatgttaa gagataagtt    7500
tttcaatgtc ctcaagagcc caccaagagt ttcttccggg aattgcttaa attatcttaa    7560
atttaaattg tacccgttta aac                                            7583
```